(12) United States Patent
Dousson et al.

(10) Patent No.: US 7,932,240 B2
(45) Date of Patent: Apr. 26, 2011

(54) PHOSPHADIAZINE HCV POLYMERASE INHIBITORS IV

(75) Inventors: Cyril Dousson, Canet (FR); Dominique Surleraux, Wauthier-Braine (BE); Jean-Laurent Paparin, Vendemian (FR); Claire Pierra, Montarnaud (FR); Arlène Roland, Marsillargues (FR)

(73) Assignee: Idenix Pharmaceuticals, Inc., Cambridge, MA (US)

( * ) Notice: Subject to any disclaimer, the term of this patent is extended or adjusted under 35 U.S.C. 154(b) by 317 days.

(21) Appl. No.: 12/198,895

(22) Filed: Aug. 27, 2008

(65) Prior Publication Data

US 2009/0081158 A1   Mar. 26, 2009

Related U.S. Application Data

(60) Provisional application No. 60/967,237, filed on Aug. 31, 2007.

(51) Int. Cl.
*A61K 31/675* (2006.01)
*C07D 239/70* (2006.01)

(52) U.S. Cl. .......................................... 514/80; 544/253

(58) Field of Classification Search .................... 514/80; 544/253
See application file for complete search history.

(56) References Cited

FOREIGN PATENT DOCUMENTS

| EP | 1 634 886 A2 | 3/2006 |
|---|---|---|
| EP | 1634886 | 3/2006 |

OTHER PUBLICATIONS

PCT ISA/EP International Search Report dated Jan. 21, 2009, for International Application No. PCT/US2008/010225. filed Aug. 28, 2008.
PCT ISA/EP International Written Opinion dated Jan. 21, 2009, for International Application No. PCT/US2008/010225. filed Aug. 28, 2008.
Palacios et al., Tetrahedron (1999), 55(10), 3091-3104.
Palacios et al., Tetrahedron (2005), 61(5), 1087-1094.
Palacios et al., Tetrahedron Letters (2002), 43(34), 5917-5919.
Yu et al., Zhurnal Obshchei Khimii (1993), 63(9), 1976-89.
English abstract of C4, 1993.
Alcaraz, G.; Baceiredo, A.; Nieger, M.; Schoeller, W. W.; Bertrand, G. Inorg. Chem. 1996, 35, 2458-2462.
Dmitrichenko et al., Russian Journal of General Chemistry, (1995), vol. 65, No. 3, Part 1.
Ashley, G. W.; Bartlett, P. A. Biochem. Biophys. Res. Commun. 1982, 108, 1467-1474.
Barluenga, J.; Lo'pez, F.; Palacios, F. Tetrahedron Lett. 1987, 28, 2875-2878.
Ried, W.; Fulde, M.; Bats, J. W. Helv. Chim. Acta 1990, 73, 1888-1893.
Pushechnikov et al., Khimiya Geterotsiklicheskikh Soedinenii (2001), No. 5, pp. 708-710.
English equivalent of C11, 2001.

*Primary Examiner* — Rei-tsang Shiao
(74) *Attorney, Agent, or Firm* — Jones Day

(57) ABSTRACT

Provided herein are phosphadiazine polymerase inhibitor, for example, of any of Formulas IV, IV', I'', II'', or IVa, pharmaceutical compositions comprising the compounds, and processes of preparation thereof. Also provided are methods of their use for the treatment of an HCV infection in a host in need thereof.

61 Claims, No Drawings

PHOSPHADIAZINE HCV POLYMERASE INHIBITORS IV

CROSS-REFERENCE TO RELATED APPLICATIONS

This application claims the benefit of U.S. provisional application No. 60/967,237, filed Aug. 31, 2007, the content of which is hereby incorporated by reference in its entirety.

FIELD

Provided herein are phosphadiazine polymerase inhibitor compounds, pharmaceutical compositions comprising the compounds, and processes of preparation thereof. Also provided are methods of their use for the treatment of an HCV infection in a host in need thereof.

BACKGROUND

Hepatitis C virus (HCV) is known to cause at least 80% of posttransfusion hepatitis and a substantial proportion of sporadic acute hepatitis (Houghton et al., *Science* 1989, 244, 362-364; Thomas, *Curr. Top. Microbiol. Immunol.* 2000, 25-41). Preliminary evidence also implicates HCV in many cases of "idiopathic" chronic hepatitis, "cryptogenic" cirrhosis, and probably hepatocellular carcinoma unrelated to other hepatitis viruses, such as hepatitis B virus (Di Besceglie et al., *Scientific American,* 1999, October, 80-85; Boyer et al., *J. Hepatol.* 2000, 32, 98-112).

HCV is an enveloped virus containing a positive-sense single-stranded RNA genome of approximately 9.4 kb (Kato et al., *Proc. Natl. Acad. Sci. USA* 1990, 87, 9524-9528; Kato, *Acta Medica Okayama,* 2001, 55, 133-159). The viral genome consists of a 5' untranslated region (UTR), a long open reading frame encoding a polyprotein precursor of approximately 3011 amino acids, and a short 3' UTR. The 5' UTR is the most highly conserved part of the HCV genome and is important for the initiation and control of polyprotein translation. Translation of the HCV genome is initiated by a cap-independent mechanism known as internal ribosome entry. This mechanism involves the binding of ribosomes to an RNA sequence known as the internal ribosome entry site (IRES). An RNA pseudoknot structure has recently been determined to be an essential structural element of the HCV IRES. Viral structural proteins include a nucleocapsid core protein (C) and two envelope glycoproteins, E1 and E2. HCV also encodes two proteinases, a zinc-dependent metalloproteinase encoded by the NS2-NS3 region and a serine proteinase encoded in the NS3 region. These proteinases are required for cleavage of specific regions of the precursor polyprotein into mature peptides. The carboxyl half of nonstructural protein 5, NS5B, contains the RNA-dependent RNA polymerase. The function of the remaining nonstructural proteins, NS4A and NS4B, and that of NS5A (the amino-terminal half of nonstructural protein 5) remain unknown.

Presently, the most effective HCV therapy employs a combination of alpha-interferon and ribavirin, leading to sustained efficacy in about 40% of patients (Poynard et al., *Lancet* 1998, 352, 1426-1432). Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load (Manns et al, *Lancet* 2001, 358, 958-965; Fried et al., *N. Engl. J. Med.* 2002, 347, 975-982; Hadziyannis et al., *Ann. Intern. Med.* 2004, 140, 346-355). Furthermore, research shows that using pegylated interferon and ribavirin to treat patients with HCV can cause significant side effects, such as alopecia, anorexia, depression, fatigue, myalgia, nausea and prunitus (Ward et al., *American Family Physician.* 2005, Vol. 72, No. 4; Al-Huthail, *The Saudi Journal of Gastroenterology.* 2006, Vol. 12, No. 2, 59-67). Severe weight loss is also reported as a side effect in the interferon-based therapy in combination with ribavirin (Bani-Sadr et al., *Journal of Viral Hepatitis.* 2008, 15(4): 255-260). Thus, there is a clear and unmet need to develop effective therapeutics for treatment of HCV infection.

SUMMARY OF THE DISCLOSURE

Provided herein are phosphadiazine polymerase inhibitor compounds, pharmaceutical compositions comprising the compounds, and processes of preparation thereof. Also provided are methods of the use of the compounds for the treatment of an HCV infection in a host in need thereof.

In one aspect, provided herein is a compound of Formula IV':

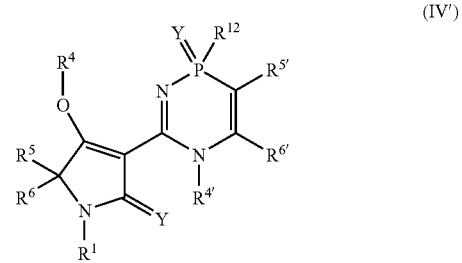

(IV')

or a single enantiomer, a mixture of an enantiomeric pair, an individual diastereomer, a mixture of diastereomers, or any tautomeric form thereof; or a pharmaceutically acceptable salt, solvate, or prodrug thereof, wherein:

$R^1$ is H, alkyl, arylalkyl, heteroarylalkyl, halogen, $-NR^{10}SO_2R^8$, $-OR^8$, $-NR^8R^9$, $-C(O)R^8$, $-C(O)NR^8R^9$, $-C(O)OR^8$, aryl, arylalkyl, alkenyl, alkynyl, heterocyclylalkyl, sulfonyl, or heteroaryl;

$R^4$ is H, alkyl, aryl-$CH_2$—, $-NR^8R^9$, $-C(O)R^8$, $-C(O)NR^8R^9$, $-C(O)OR^8$, sulfonyl, aryl, arylalkyl, alkenyl, alkynyl, heterocyclylalkyl or heteroaryl;

$R^{4'}$ is H, alkyl, aryl-$CH_2$—, $-NR^8R^9$, $-C(O)R^8$, $-C(O)NR^8R^9$, $-C(O)OR^8$, sulfonyl, aryl, arylalkyl, alkenyl, alkynyl, heterocyclylalkyl or heteroaryl;

$R^5$ is H, halogen, $-NR^{10}SO_2R^8$, $-OR^8$, $-NR^8R^9$, $-C(O)R^8$, $-C(O)NR^8R^9$, $-C(O)OR^8$, alkyl, aryl, or heteroaryl, or $R^4$ and $R^5$ together form a part of a 3-8 membered heterocycloalkyl ring;

$R^6$ is H, halogen, $-NR^{10}SO_2R^8$, $-OR^8$, $-NR^8R^9$, $-C(O)R^8$, $-C(O)NR^8R^9$, $-C(O)OR^8$, alkyl, aryl, or heteroaryl, or $R^5$ and $R^6$ together form a part of a 3-8 membered cycloalkyl or heterocycloalkyl ring;

$R^{5'}$ is H, halogen, cyano, nitro, $-NR^{10}SO_2R^8$, $-OR^8$, $-NR^8R^9$, $-C(O)R^8$, $-C(O)NR^8R^9$, $-C(O)OR^8$, alkyl, aryl, heteroaryl, $-NR^8R^{10}$, alkenyl, or alkynl;

$R^{6'}$ is H, halogen, cyano, nitro, $-NR^{10}SO_2R^8$, $-OR^8$, $-NR^8R^9$, $-C(O)R^8$, $-C(O)NR^8R^9$, $-C(O)OR^8$, alkyl, aryl, or heteroaryl; $R^{5'}$ and $R^{6'}$ together form a part of a 3-8 membered cycloalkyl, aryl, heterocycloalkyl, or heteroaryl ring;

$R^{12}$ is F, —$OR^8$, —$SR^8$, —$NR^8R^9$, alkyl, or aryl;

each $R^8$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, $C_{1-6}$ alkyl-$C_{3-7}$ cycloalkylene, or $C_{1-10}$ alkylsiloxyl;

each $R^9$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or $R^8$ and $R^9$ together with the N atom to which they are attached form heterocyclyl;

each $R^{10}$ is independently H, alkyl, aryl, sulfonyl, $C(O)R^8$, $C(O)OR^8$ or $C(O)NR^8R^9$; and each Y is independently O or S, wherein each alkyl, aryl, arylalkyl, heteroaryl, alkenyl, alkynyl, cycloalkyl, heterocyclyl, sulfonyl, or alkyl-cycloalkyl is optionally substituted.

In another aspect, provided herein is a compound of Formula IV:

(IV)

or a single enantiomer, a mixture of an enantiomeric pair, an individual diastereomer, a mixture of diastereomers, or any tautomeric form thereof; or a pharmaceutically acceptable salt, solvate, or prodrug thereof, wherein $R^1$ is H, alkyl, arylalkyl, heteroarylalkyl, halogen, —$NR^{10}SO_2R^8$, —$OR^8$, —$NR^8R^9$, —$C(O)R^8$, —$C(O)NR^8R^9$, —$C(O)OR^8$, aryl, arylalkyl, alkenyl, alkynyl, heterocyclylalkyl, sulfonyl, or heteroaryl;

$R^5$ is independently H, halogen, —$NR^{10}SO_2R^8$, —$OR^8$, —$NR^8R^9$, —$C(O)R^8$, —$C(O)NR^8R^9$, —$C(O)OR^8$, alkyl, aryl, or heteroaryl;

$R^6$ is independently H, halogen, —$NR^{10}SO_2R^8$, —$OR^8$, —$NR^8R^9$, —$C(O)R^8$, —$C(O)NR^8R^9$, —$C(O)OR^8$, alkyl, aryl, or heteroaryl, or $R^5$ and $R^6$ together form a part of a 3-8 membered cycloalkyl or heterocycloalkyl ring;

$R^{12}$ is F, —$OR^8$, —$SR^8$, —$NR^8R^9$, alkyl, or aryl;

each $R^{14}$ is independently H, halogen, alkyl, alkenyl, alkynyl, aryl, heterocyclyl, heteroaryl, cyano, nitro, OH, —$NR^{10}SO_2R^8$, —$OR^8$, —$NR^8R^9$, —$C(O)R^8$, $C(O)NR^8R^9$, —$OCH_2C(O)NR^8R^9$, —$C(O)OR^8$, —O—($C_1$-$C_6$ hydroxyalkyl), —O—($C_1$-$C_6$ alkoxy), —O—($C_1$-$C_6$ alkylene)-cyano, —O—($C_1$-$C_6$ alkylene)-$C(O)R^{9'}$, —$OCHR^{9'}C(O)O$—$R^8$, —$OCHR^{9'}C(O)NHOH$, —O—($C_1$-$C_6$ alkyl)-$C(O)NR^8R^9$, —O—($C_1$-$C_6$ alkylene)-$NR^{9'}C(O)R^8$, —O—($C_1$-$C_6$ alkylene)-$NR^{9'}C(O)OR^8$, —O—($C_1$-$C_6$ alkylene)-$NR^{9'}C(O)NR^8R^9$, $OCHR^{9'}C(O)NR^8R^9$, —O—($C_1$-$C_6$ alkylene)-$S(O)R^{9'}$, —O—($C_1$-$C_6$ alkyl)-$S(O)_2R^{9'}$, —O—($C_1$-$C_6$ alkylene)-$S(O)_2NR^8R^9$, —O—($C_1$-$C_6$ alkylene)-$NR^{9'}S(O)_2NR^8R^9$, —O—($C_1$-$C_6$ alkylene)-$NR^{9'}S(O)R^8$—O—($C_1$-$C_6$ alkylene)-$S(O)_2R^{9'}$—O—($C_1$-$C_6$ alkylene)-$NR^8R^9$, —($C_1$-$C_6$ alkylene)-$S(O)_2R^8$, —($C_1$-$C_6$ alkylene)-$S(O)_2NR^8R^9$, —($C_1$-$C_6$ alkylene)-$S(O)R^8$, —($C_1$-$C_6$ alkylene)-$C(O)R^9$, —($C_1$-$C_6$ alkylene)-$C(O)NR^8R^9$, —($C_1$-$C_6$ alkylene)-$NR^{9'}C(O)R^8$, —($C_1$-$C_6$ alkylene)-$NR^{9'}S(O)_2R^8$, —($C_1$-$C_6$ alkylene)-$NR^{9'}C(O)OR^8$, —($C_1$-$C_6$ alkylene)-$NR^{9'}C(O)NR^8R^9$, —($C_1$-$C_6$ alkylene)-$NR^{9'}S(O)_2NR^8R^9$, —($C_1$-$C_6$ alkylene)-

$C(O)OR^8$, —($C_1$-$C_6$ alkylene)-$NR^8R^9$, —$NR^8C(O)R^9$, —$NR^{9'}S(O)_2NR^8R^9$, —$S(O)R^{9'}$, —$S(O)_2R^{9'}$, or —$S(O)_2NR^8R^9$;

n is an integer from 1 to 4;

each $R^8$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, $C_{1-6}$ alkyl-$C_{3-7}$ cycloalkylene, or $C_{1-10}$ alkylsiloxyl;

each $R^9$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or $R^8$ and $R^9$ together with the N atom to which they are attached form heterocyclyl;

each $R^{9'}$ is independently hydrogen, $C_{1-6}$ alkyl, $C_{2-6}$ alkenyl, $C_{2-6}$-alkynyl, $C_{3-7}$ cycloalkyl, $C_{6-14}$ aryl, heteroaryl, or heterocyclyl; and each $R^{10}$ is independently H, alkyl, aryl, sulfonyl, $C(O)R^8$, $C(O)OR^8$ or $C(O)NR^8$, $R^9$, wherein each alkyl, aryl, arylalkyl, heteroaryl, alkenyl, alkynyl, cycloalkyl, heterocyclyl, sulfonyl, or alkyl-cycloalkyl is optionally substituted.

In some embodiments, provided herein is a compound of Formula IVa:

(IVa)

or a single enantiomer, a mixture of an enantiomeric pair, an individual diastereomer, a mixture of diastereomers, or any tautomeric form thereof, or a pharmaceutically acceptable salt, solvate, or prodrug thereof, wherein $R^1$ is H, alkyl, arylalkyl, heteroarylalkyl, halogen, —$NR^{10}SO_2R^8$, —$OR^8$, —$NR^8R^9$, —$C(O)R^8$, —$C(O)NR^8R^9$, —$C(O)OR^8$, aryl, arylalkyl, alkenyl, alkynyl, heterocyclylalkyl, sulfonyl, or heteroaryl;

$R^6$ is H, halogen, —$NR^{10}SO_2R^8$, —$OR^8$, —$NR^8R^9$, —$C(O)R^8$, —$C(O)NR^8R^9$, —$C(O)OR^8$, alkyl, aryl, or heteroaryl;

$R^{12}$ is F, —$OR^8$, —$SR^8$, —$NR^8R^9$, alkyl, or aryl;

each $R^{14}$ is independently H, halogen, alkyl, alkenyl, alkynyl, aryl, heterocyclyl, heteroaryl, cyano, nitro, OH, —$NR^{10}SO_2R^8$, —$OR^8$, —$NR^8R^9$, —$C(O)R^8$, $C(O)NR^8R^9$, —$OCH_2C(O)NR^8R^9$, —$C(O)OR^8$, —O—($C_1$-$C_6$ hydroxyalkyl), —O—($C_1$-$C_6$ alkoxy), —O—($C_1$-$C_6$ alkylene)-cyano, —O—($C_1$-$C_6$ alkylene)-$C(O)R^{9'}$, —$OCHR^{9'}C(O)O$—$R^8$, —$OCHR^{9'}C(O)NHOH$, —O—($C_1$-$C_6$ alkyl)-$C(O)NR^8R^9$, —O—($C_1$-$C_6$ alkylene)-$NR^{9'}C(O)R^8$, —O—($C_1$-$C_6$ alkylene)-$NR^{9'}C(O)OR^8$, —O—($C_1$-$C_6$ alkylene)-$NR^{9'}C(O)NR^8R^9$, —$OCHR^{9'}C(O)NR^8R^9$, —O—($C_1$-$C_6$ alkylene)-$S(O)R^{9'}$, —O—($C_1$-$C_6$ alkyl)-$S(O)_2R^{9'}$, —O—($C_1$-$C_6$ alkylene)-$S(O)_2NR^8R^9$, —O—($C_1$-$C_6$ alkylene)-$NR^{9'}S(O)_2NR^8R^9$, —O—($C_1$-$C_6$ alkylene)-$NR^{9'}S(O)_2R^8$—O—($C_1$-$C_6$ alkylene)-$S(O)_2R^{9'}$—O—($C_1$-$C_6$ alkylene)-$NR^8R^9$, —($C_1$-$C_6$ alkylene)-$S(O)_2R^8$, —($C_1$-$C_6$ alkylene)-$S(O)_2$ $NR^8R^9$, —($C_1$-$C_6$ alkylene)-$S(O)R^8$, —($C_1$-$C_6$ alkylene)-$C(O)R^9$, —($C_1$-$C_6$ alkylene)-$C(O)NR^8R^9$, —($C_1$-$C_6$ alkylene)-$NR^{9'}C(O)R^8$, —($C_1$-$C_6$ alkylene)-$NR^{9'}S(O)_2R^8$, —($C_1$-$C_6$ alkylene)-$NR^{9'}C(O)OR^8$, —($C_1$-$C_6$ alkylene)-$NR^{9'}C(O)NR^8R^9$, —(C$_1$-C$_6$ alkylene)-NR$^{9'}$S(O)$_2$NR$^8$R$^9$, —(C$_1$-C$_6$ alkylene)-C(O)OR$^8$, —(C$_1$-C$_6$ alkylene)-NR$^8$R$^9$, —NR$^8$C(O)R$^9$, —NR$^9$S(O)$_2$NR$^8$R$^9$, —S(O)R$^{9'}$, —S(O)$_2$R$^{9'}$, or —S(O)$_2$NR$^8$R$^9$;

each R$^8$ is independently hydrogen, C$_{1-6}$ alkyl, C$_{2-6}$ alkenyl, C$_{2-6}$ alkynyl, C$_{3-7}$ cycloalkyl, C$_{6-14}$ aryl, heteroaryl, heterocyclyl, C$_{1-6}$ alkyl-C$_{3-7}$ cycloalkylene, or C$_{1-10}$ alkylsiloxyl; and each R$^9$ is independently hydrogen, C$_{1-6}$ alkyl, C$_{2-6}$ alkenyl, C$_{2-6}$ alkynyl, C$_{3-7}$ cycloalkyl, C$_{6-14}$ aryl, heteroaryl, or heterocyclyl, or R$^8$ and R$^9$ together with the N atom to which they are attached form heterocyclyl; and each R$^{9'}$ is independently hydrogen, C$_{1-4}$ alkyl, C$_{2-6}$ alkenyl, C$_{2-6}$ alkynyl, C$_{3-7}$ cycloalkyl, C$_{6-14}$ aryl, heteroaryl, or heterocyclyl; and each R$^{10}$ is independently H, alkyl, aryl, sulfonyl, C(O)R$^8$, C(O)OR$^8$ or C(O)NR$^8$R$^9$, wherein each alkyl, aryl, arylalkyl, heteroaryl, alkenyl, alkynyl, cycloalkyl, heterocyclyl, sulfonyl, or alkyl-cycloalkyl is optionally substituted.

Also provided herein are pharmaceutical compositions comprising a compound disclosed herein, e.g., a compound of Formula IV, IV', I", II", or IVa, including a single enantiomer, a mixture of an enantiomeric pair, an individual diastereomer, or a mixture of diastereomers thereof, or a pharmaceutically acceptable salt, solvate, or prodrug thereof; in combination with one or more pharmaceutically acceptable excipients or carriers.

Also provided herein is a method for treating or preventing an HCV infection, which comprises administering to a subject a therapeutically effective amount of a compound disclosed herein, e.g., a compound of Formula IV, IV', I", II", or IVa, including a single enantiomer, a mixture of an enantiomeric pair, an individual diastereomer, or a mixture of diastereomers thereof; or a pharmaceutically acceptable salt, solvate, or prodrug thereof.

Also provided herein is a method for treating, preventing, or ameliorating one or more symptoms of a liver disease or disorder associated with an HCV infection, comprising administering to a subject a therapeutically effective amount of a compound disclosed herein, e.g., a compound of Formula IV, IV', I", II", or IVa including a single enantiomer, a mixture of an enantiomeric pair, an individual diastereomer, or a mixture of diastereomers thereof, or a pharmaceutically acceptable salt, solvate, or prodrug thereof.

Also provided herein is a method for inhibiting replication of a virus in a host, which comprises contacting the host with a therapeutically effective amount of a compound disclosed herein, e.g., a compound of Formula IV, IV', I", II", or IVa, including a single enantiomer, a mixture of an enantiomeric pair, an individual diastereomer, or a mixture of diastereomers thereof; or a pharmaceutically acceptable salt, solvate, or prodrug thereof.

Also provided herein is a method for inhibiting replication of a virus, which comprises contacting the virus with a therapeutically effective amount of a compound disclosed herein, e.g., a compound of Formula IV, IV', I", II", or IVa, including a single enantiomer, a mixture of an enantiomeric pair, an individual diastereomer, or a mixture of diastereomers thereof; or a pharmaceutically acceptable salt, solvate, or prodrug thereof.

Provided herein is a method for inhibiting the activity of a polymerase, which comprises contacting the polymerase with a compound disclosed herein, e.g., a compound of Formula IV, IV', I", II", or IVa, including a single enantiomer, a mixture of an enantiomeric pair, an individual diastereomer, or a mixture of diastereomers thereof, or a pharmaceutically acceptable salt, solvate, or prodrug thereof.

Provided is a compound disclosed herein, e.g., a compound of Formula IV, IV', I", II", or IVa, or a pharmaceutical composition thereof, for use in therapy. Also provided is a compound disclosed herein, e.g., a compound of Formula IV, IV', I", II", or IVa, or a pharmaceutical composition thereof, for use in treating or preventing an HCV infection. Also provided is a compound disclosed herein, e.g., a compound of Formula IV, IV', I", II", or IVa, or a pharmaceutical composition thereof, for use in treating, preventing, or ameliorating one or more symptoms of a liver disease or disorder associated with an HCV infection. Also provided is a compound disclosed herein, e.g., a compound of Formula IV, IV', I", II", or IVa, or a pharmaceutical composition thereof, for use in inhibiting replication of a virus in a host. Also provided is the use of a compound disclosed herein, e.g., a compound of Formula IV, IV', I", II", or IVa, or a pharmaceutical composition thereof, for manufacture of a medicament for treating or preventing an HCV infection. Also provided is the use of a compound disclosed herein, e.g., a compound of Formula IV, IV', I", II", or IVa, or a pharmaceutical composition thereof, for manufacture of a medicament for treating, preventing, or ameliorating one or more symptoms of a liver disease or disorder associated with an HCV infection. Also provided is the use of a compound disclosed herein, e.g., a compound of Formula IV, IV', I", II", or IVa, or a pharmaceutical composition thereof, for manufacture of a medicament for inhibiting replication of a virus in a host.

DETAILED DESCRIPTION

To facilitate understanding of the disclosure set forth herein, a number of terms are defined below.

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs. In the event that there is a plurality of definitions for a term used herein, those in this section prevail unless stated otherwise.

The term "subject" refers to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject.

The term "host" refers to a unicellular or multicellular organism in which a virus can replicate, including, but not limited to, a cell, cell line, and animal, such as human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disease; or reducing a subject's risk of acquiring a disorder, disease, or condition.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a cell, tissue, system, animal, or human, which is being sought by a researcher, veterinarian, medical doctor, or clinician.

The term "IC$_{50}$" refers an amount, concentration, or dosage of a compound that is required for 50% inhibition of a maximal response in an assay that measures such response.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy*, 21st Edition; Lippincott Williams & Wilkins: Philadelphia, Pa., 2005; *Handbook of Pharmaceutical Excipients*, 5th Edition; Rowe et al., Eds., The Pharmaceutical Press and the American Pharmaceutical Association: 2005; and *Handbook of Pharmaceutical Additives*, 3rd Edition; Ash and Ash Eds., Gower Publishing Company: 2007; *Pharmaceutical Preformulation and Formulation*, Gibson Ed., CRC Press LLC: Boca Raton, Fla., 2004).

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a disorder or disease. As used herein, "active ingredient" and "active substance" may be an optically active isomer of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

The term "release controlling excipient" refers to an excipient whose primary function is to modify the duration or place of release of an active substance from a dosage form as compared with a conventional immediate release dosage form.

The term "nonrelease controlling excipient" refers to an excipient whose primary function do not include modifying the duration or place of release of an active substance from a dosage form as compared with a conventional immediate release dosage form.

The term "alkyl" refers to a linear or branched saturated monovalent hydrocarbon radical. The term "alkyl" also encompasses both linear and branched alkyl, unless otherwise specified. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. In certain embodiments, the alkyl is a linear or branched saturated monovalent hydrocarbon radical that has at least 1, 2, 3, 4, 5, 6, 7, 8, 9, or 10 carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, t-butyl, pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl may be substituted.

The term "alkylene" refers to a linear or branched saturated divalent hydrocarbon radical, wherein the alkylene may optionally be substituted. The term "alkylene" encompasses both linear and branched alkylene, unless otherwise specified. In certain embodiments, the alkylene is a linear saturated divalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. In certain embodiments, the alkylene is a linear or branched saturated divalent hydrocarbon radical that has at least 1, 2, 3, 4, 5, 6, 7, 8, 9, or 10 carbon atoms. As used herein, linear $C_{1-6}$ and branched $C_{3-6}$ alkylene groups are also referred as "lower alkylene." Examples of alkylene groups include, but are not limited to, methylene, ethylene, propylene (including all isomeric forms), n-propylene, isopropylene, butylene (including all isomeric forms), n-butylene, isobutylene, t-butylene, pentylene (including all isomeric forms), and hexylene (including all isomeric forms). For example, $C_{2-6}$ alkylene refers to a linear saturated divalent hydrocarbon radical of 2 to 6 carbon atoms or a branched saturated divalent hydrocarbon radical of 3 to 6 carbon atoms.

The term "alkenyl" refers to a linear or branched monovalent hydrocarbon radical, which contains one or more carbon-carbon double bonds. The alkenyl may be optionally substituted, e.g., as described herein. The term "alkenyl" also embraces radicals having "cis" and "trans" configurations, or alternatively, "E" and "Z" configurations, as appreciated by those of ordinary skill in the art. As used herein, the term "alkenyl" encompasses both linear and branched alkenyl, unless otherwise specified. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propenyl, allyl, propenyl, butenyl, and 4-methylbutenyl.

The term "alkenylene" refers to a linear or branched divalent hydrocarbon radical, which contains one or more carbon-carbon double bonds. The alkenylene may be optionally substituted, e.g., as described herein. Similarly, the term "alkenylene" also embraces radicals having "cis" and "trans" configurations, or alternatively, "E" and "Z" configurations. As used herein, the term "alkenylene" encompasses both linear and branched alkenylene, unless otherwise specified. For example, $C_{2-6}$ alkenylene refers to a linear unsaturated divalent hydrocarbon radical of 2 to 6 carbon atoms or a branched unsaturated divalent hydrocarbon radical of 3 to 6 carbon atoms. In certain embodiments, the alkenylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenylene groups include, but are not limited to, ethenylene, propenylene, allylene, propenylene, butenylene, and 4-methylbutenylene.

The term "alkynyl" refers to a linear or branched monovalent hydrocarbon radical, which contains one or more carbon-carbon triple bonds. The alkynyl may be optionally substituted, e.g., as described herein. The term "alkynyl" also encompasses both linear and branched alkynyl, unless otherwise specified. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynyl groups include, but are not limited to, ethynyl (—C≡CH) and propargyl (—CH$_2$C≡CH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms.

The term "alkynylene" refers to a linear or branched divalent hydrocarbon radical, which contains one or more carbon-carbon triple bonds. The alkynylene may be optionally substituted, e.g., as described herein. The term "alkynylene" also encompasses both linear and branched alkynylene, unless otherwise specified. In certain embodiments, the alkynylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynylene groups include, but are not limited to, ethynylene (—C≡C—) and propargylene (—CO$_2$C≡C—). For example, $C_{2-4}$ alkynyl refers to a linear unsaturated divalent hydrocarbon radical of 2 to 6 carbon atoms or a branched unsaturated divalent hydrocarbon radical of 3 to 6 carbon atoms.

The term "cycloalkyl" refers to a cyclic saturated bridged or non-bridged monovalent hydrocarbon radical, which may be optionally substituted, e.g., as described herein. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, decalinyl, and adamantyl.

The term "cycloalkylene" refers to a cyclic saturated bridged or non-bridged divalent hydrocarbon radical, which may be optionally substituted, e.g., as described herein. In certain embodiments, the cycloalkylene has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkylene groups include, but are not limited to, cyclopropylene, cyclobutylene, cyclopentylene, cyclohexylene, cycloheptylene, decalinylene, and adamantylene.

The term "aryl" refers to a monocyclic or multicyclic monovalent aromatic group. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). All such aryl groups may also be optionally substituted, e.g., as described herein.

The term "arylene" refers to a monocyclic or multicyclic divalent aromatic group. In certain embodiments, the arylene has from 6 to 20 ($C_{6-20}$), from 6 to 15 ($C_{6-15}$), or from 6 to 10 ($C_{6-10}$) ring atoms. Examples of arylene groups include, but are not limited to, phenylene, naphthylene, fluorenylene, azulenylene, anthrylene, phenanthrylene, pyrenylene, biphenylene, and terphenylene. Arylene also refers to bicyclic or tricyclic carbon rings, where one of the rings is aromatic and the others of which may be saturated, partially unsaturated, or aromatic, for example, dihydronaphthylene, indenylene, indanylene, or tetrahydro-naphthylene (tetralinyl). All such aryl groups may also be optionally substituted, e.g., as described herein.

The term "heteroaryl" refers to a monocyclic or multicyclic aromatic group, wherein at least one ring contains one or more heteroatoms independently selected from O, S, and N. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, and triazinyl. Examples of bicyclic heteroaryl groups include, but are not limited to, indolyl, benzothiazolyl, benzoxazolyl, benzothienyl, quinolinyl, tetrahydroisoquinolinyl, isoquinolinyl, benzimidazolyl, benzopyranyl, indolizinyl, benzofuranyl, isobenzofuranyl, chromonyl, coumarinyl, cinnolinyl, quinoxalinyl, indazolyl, purinyl, pyrrolopyridinyl, furopyridinyl, thienopyridinyl, dihydroisoindolyl, and tetrahydroquinolinyl. Examples of tricyclic heteroaryl groups include, but are not limited to, carbazolyl, benzindolyl, phenanthrollinyl, acridinyl, phenanthridinyl, and xanthenyl. All such heteroaryl groups may also be optionally substituted, e.g., as described herein.

The term "heterocyclyl" or "heterocyclic" refers to a monocyclic or multicyclic non-aromatic ring system, wherein one or more of the ring atoms are heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. Examples of heterocyclyl groups include, but are not limited to, pyrrolidinyl, piperidinyl, 2-oxopyrrolidinyl, 2-oxopiperidinyl, morpholinyl, piperazinyl, tetrahydropyranyl, and thiomorpholinyl. All such heterocyclic groups may also be optionally substituted, e.g., as described herein.

The term "alkoxy" refers to an —OR radical, wherein R is, for example, alkyl, alkenyl, alkynyl, cycloalkyl, aryl, heteroaryl, or heterocyclyl, each as defined herein. Examples of alkoxy groups include, but are not limited to, methoxy, ethoxy, propoxy, n-propoxy, 2-propoxy, n-butoxy, isobutoxy, tert-butoxy, cyclohexyloxy, phenoxy, benzoxy, and 2-naphthyloxy.

The term "acyl" refers to a —C(O)R radical, wherein R is, for example, alkyl, alkenyl, alkynyl, cycloalkyl, aryl, heteroaryl, or heterocyclyl, each as defined herein. Examples of acyl groups include, but are not limited to, acetyl, propionyl, butanoyl, isobutanoyl, pentanoyl, hexanoyl, heptanoyl, octanoyl, nonanoyl, decanoyl, dodecanoyl, tetradecanoyl, hexadecanoyl, octadecanoyl, eicosanoyl, docosanoyl, myristoleoyl, palmitoleoyl, oleoyl, linoleoyl, arachidonoyl, benzoyl, pyridinylcarbonyl, and furoyl.

The term "halogen", "halide" or "halo" refers to fluorine, chlorine, bromine, or iodine.

The term "arylaklyl" refers to an aryl group appended to an alkyl radical, such as aryl-(CH$_2$)—, aryl-CH$_2$—CH$_2$—, and aryl-CH$_2$—CH$_2$—CH$_2$—.

The term "heteroarylalkyl" refers to an heteroaryl group appended to an alkyl radical, such as heteroaryl-(CH$_2$)—, heteroaryl-CH$_2$—CH$_2$—, and heteroaryl-CH$_2$—CH$_2$—CH$_2$—.

The term "optionally substituted" is intended to mean that a group, such as an alkyl, alkylene, alkenyl, alkenylene, alkynyl, alkynylene, alkoxyl, cycloalkyl, cycloalkylene, aryl, arylene, heteroaryl, or heterocyclyl group, may be substituted with one or more substituents independently selected from, e.g., halo, cyano (—CN), nitro (—NO$_2$), —SR$^a$, —S(O)R$^a$, —S(O)$_2$R$^a$, —R$^a$, —C(O)R$^a$, —C(O)OR$^a$, C(O)NR$^b$R$^c$, —OCH$_2$C(O)NR$^b$R$^c$, —C(NR$^a$)NR$^b$R$^c$, —OR$^a$, —OC(O) R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$(O)R$^b$, —NR$^a$C(O)OR$^b$, —NR$^a$C(O)NR$^b$R$^c$, —NR$^a$C(=NR$^a$)NR$^b$R$^c$, —NR$^a$S(O)R$^b$, —NR$^a$S(O)$_2$R$^b$, —NR$^a$S(O)R$^b$R$^c$, —NR$^a$S(O)$_2$R$^b$R$^c$, or OSi—R$^a$R$^b$R$^c$; wherein R$^a$, R$^b$, R$^c$, and R$^d$ are each independently, e.g., hydrogen, alkyl, alkenyl, alkynyl, cycloalkyl, aryl, heteroaryl, or heterocyclyl, each optionally substituted, e.g., as described herein; or R$^b$ and R$^c$ together with the N atom to which they are attached form heterocyclyl or heteroaryl, each optionally substituted, e.g., as described herein. The group can be substituted with any described moiety, including, but not limited to, one or more moieties selected from the group consisting of halogen (fluoro, chloro, bromo, or iodo), hydroxyl, amino, alkylamino (e.g., monoalkylamino, dialkylamino, or trialkylamino), arylamino (e.g., monoarylamino, diarylamino, or triarylamino), alkoxy, aryloxy, nitro, cyano, sulfonic acid, sulfate, phosphonic acid, phosphate, or phosphonate, either unprotected or protected as necessary, as known to those skilled in the art, for example, as taught in Greene, et al., *Protective Groups in Organic Synthesis*, John Wiley and Sons, Second Edition, 1991. As used herein, all groups that can be substituted in one embodiment are "optionally substituted," unless otherwise specified.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, or no less than about 94% no less than about 95%, no less than about 96%, no less than about 97%, no less than about 98%, no less than about 99%, or no less than about 99.5%, no less than about 99.8%. In certain embodiments, the compound comprises about 95% or more of the desired enantiomer and about 5% or less of the less preferred enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The term "solvate" refers to a compound provided herein or a salt thereof, which further includes a stoichiometric or non-stoichiometric amount of solvent bound by non-covalent intermolecular forces. Where the solvent is water, the solvate is a hydrate.

Compounds

Provided herein are compounds which are useful for the treatment of HCV infection, which, in one embodiment, can have activity as HCV polymerase inhibitors. Also provided herein are pharmaceutical compositions that comprise the compounds, methods of manufacture of the compounds, and methods of use of the compounds for the treatment of HCV infection in a host in need of treatment.

In one aspect, provided herein is a compound of Formula IV':

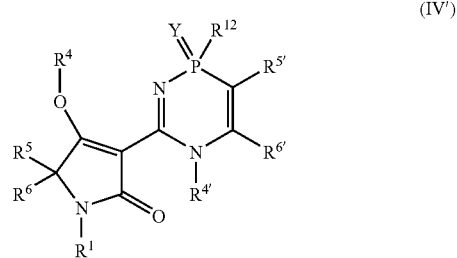

(IV')

or a single enantiomer, a mixture of an enantiomeric pair, an individual diastereomer, a mixture of diastereomers, or any tautomeric form thereof; or a pharmaceutically acceptable salt, solvate, or prodrug thereof, wherein:

R$^1$ is H, alkyl, arylalkyl, heteroarylalkyl, halogen, —NR$^{10}$SO$_2$R$^8$, —OR$^8$, —NR$^8$R$^9$, —C(O)R$^8$, —C(O)NR$^8$R$^9$, —C(O)OR$^8$, aryl, arylalkyl, alkenyl, alkynyl, heterocyclylalkyl, sulfonyl, or heteroaryl;

each R$^4$ is H, alkyl, aryl-CH$_2$—, —NR$^8$R$^9$, —C(O)R$^8$, —C(O)NR$^8$R$^9$, —C(O)OR$^8$, sulfonyl, aryl, arylalkyl, alkenyl, alkynyl, heterocyclylalkyl or heteroaryl;

each R$^{4'}$ is H, alkyl, aryl-CH$_2$—, —NR$^8$R$^9$, —C(O)R$^8$, —C(O)NR$^8$R$^9$, —C(O)OR$^8$, sulfonyl, aryl, arylalkyl, alkenyl, alkynyl, heterocyclylalkyl or heteroaryl;

R$^5$ is H, halogen, —NR$^{10}$SO$_2$R$^8$, —OR$^8$, —NR$^8$R$^9$, C(O)R$^8$, —C(O)NR$^8$R$^9$, —C(O)OR$^8$, alkyl, aryl, or heteroaryl, or R$^4$ and R$^5$ together form a part of a 3-8 membered heterocycloalkyl ring;

R$^6$ is H, halogen, —NR$^{10}$SO$_2$R$^8$, —OR$^8$, —NR$^8$R$^9$, C(O)R$^8$, —C(O)NR$^8$R$^9$, —C(O)OR$^8$, alkyl, aryl, or heteroaryl, or R$^5$ and R$^6$ together form a part of a 3-8 membered cycloalkyl or heterocycloalkyl ring;

R$^{5'}$ is H, halogen, cyano, nitro, —NR$^{10}$SO$_2$R$^8$, —OR$^8$, —NR$^8$R$^9$, —C(O)R$^8$, —C(O)NR$^8$R$^9$, —C(O)OR$^8$, alkyl, aryl, heteroaryl, —NR$^8$R$^{10}$, alkenyl, or alkynl;

R$^{6'}$ is H, halogen, cyano, nitro, —NR$^{10}$SO$_2$R$^8$, —OR$^8$, —NR$^8$R$^9$, —C(O)R$^8$, —C(O)NR$^8$R$^9$, —C(O)OR$^8$, alkyl, aryl, or heteroaryl, or R$^{5'}$ and R$^{6'}$ together form a part of a 3-8 membered cycloalkyl, aryl, heterocycloalkyl or heteroaryl ring;

each R$^{12}$ is independently F, —OR$^8$, —SR$^8$, —NR$^8$R$^9$, alkyl, or aryl;

each R$^8$ is independently hydrogen, C$_{1-6}$ alkyl, C$_{2-6}$ alkenyl, C$_{2-6}$ alkynyl, C$_{3-7}$ cycloalkyl, C$_{6-14}$ aryl, heteroaryl, heterocyclyl, C$_{1-6}$ alkyl-C$_{3-7}$ cycloalkylene, or C$_{1-10}$ alkyl-siloxyl;

each $R^9$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or $R^8$ and $R^9$ together with the N atom to which they are attached form heterocyclyl; and each $R^{10}$ is independently H, alkyl, aryl, sulfonyl, $C(O)R^8$, $C(O)OR^8$ or $C(O)NR^8R^9$, wherein each alkyl, aryl, arylalkyl, heteroaryl, alkenyl, alkynyl, cycloalkyl, heterocyclyl, sulfonyl, or alkyl-cycloalkyl is optionally substituted.

In some embodiments, each pair of $R^{5'}$ and $R^{6'}$ together independently form a part of a 3-8 membered cycloalkyl, aryl, heterocycloalkyl or heteroaryl ring. In some embodiments, each pair of $R^{5'}$ and $R^{6'}$ together independently form a benzo group having formula (A):

(A)

where
each * is a bond;
each $R^{14}$ is independently H, halogen, alkyl, alkenyl, alkynyl, aryl, heterocyclyl, heteroaryl, cyano, nitro, OH, $-NR^{10}SO_2R^8$, $-OR^8$, $-NR^8R^9$, $-C(O)R^8$, $C(O)NR^8R^9$, $-OCH_2C(O)NR^8R^9$, $-C(O)OR^8$, $-O-(C_1-C_6$ hydroxyalkyl), $-O-(C_1-C_6$ alkoxy), $-O-(C_1-C_6$ alkylene)-cyano, $-O-(C_1-C_6$ alkylene)-$C(O)R^{9'}$, $-OCHR^{9'}C(O)O-R^8$, $-OCHR^{9'}C(O)NHOH$, $-O-(C_1-C_6$ alkyl)-$C(O)NR^8R^9$, $-O-(C_1-C_6$ alkylene)-$NR^{9'}C(O)R^8$, $-O-(C_1-C_6$ alkylene)-$NR^{9'}C(O)OR^8$, $-O-(C_1-C_6$ alkylene)-$NR^{9'}C(O)NR^8R^9$, $-OCHR^{9'}C(O)NR^8R^9$, $-O-(C_1-C_6$ alkylene)-$S(O)R^{9'}$, $-O-(C_1-C_6$ alkyl)-$S(O)_2R^{9'}$, $-O-(C_1-C_6$ alkylene)-$S(O)_2NR^8R^9$, $-O-(C_1-C_6$ alkylene)-$NR^{9'}S(O)_2NR^8R^9$, $-O-(C_1-C_6$ alkylene)-$NR^{9'}S(O)_2R^8-O-(C_1-C_6$ alkylene)-$S(O)_2R^{9'}-O-(C_1-C_6$ alkylene)-$NR^8R^9$, $-(C_1-C_6$ alkylene)-$S(O)_2R^8$, $-(C_1-C_6$ alkylene)-$S(O)_2$ $NR^8R^9$, $-(C_1-C_6$ alkylene)-$S(O)R^8$, $-(C_1-C_6$ alkylene)-$C(O)R^8$, $-(C_1-C_6$ alkylene)-$C(O)NR^8R^9$, $-(C_1-C_6$ alkylene)-$NR^{9'}C(O)R^8$, $-(C_1-C_6$ alkylene)-$NR^{9'}S(O)_2R^8$, $-(C_1-C_6$ alkylene)-$NR^{9'}C(O)OR^8$, $-(C_1-C_6$ alkylene)-$NR^{9'}C(O)NR^8R^9$, $-(C_1-C_6$ alkylene)-$NR^{9'}S(O)_2NR^8R^9$, $-(C_1-C_6$ alkylene)-$C(O)OR^8$, $-(C_1-C_6$ alkylene)-$NR^8R^9$, $-NR^8C(O)R^9$, $-NR^{9'}S(O)_2NR^8R^9$, $-S(O)R^{9'}$, $-S(O)_2R^{9'}$, or $-S(O)_2NR^8R^9$;

and n is an integer from 1 to 4, wherein each alkyl, aryl, arylalkyl, heteroaryl, alkenyl, alkynyl, cycloalkyl, heterocyclyl, sulfonyl, or alkyl-cycloalkyl is optionally substituted.

In some embodiments, each pair of $R^{5'}$ and $R^{6'}$ together independently form a part of a ring having one of formulae C-L:

(C)

(D)

(E)

(F)

(G)

(H)

(I)

(J)

(K)

(L)

where
each * is a bond;
each $R^{14}$ is independently H, halogen, alkyl, alkenyl, alkynyl, aryl, heterocyclyl, heteroaryl, cyano, nitro, OH, $-NR^{10}SO_2R^8$, $-OR^8$, $NR^8R^9$, $-C(O)R^8$, $C(O)NR^8R^9$, $-OCH_2C(O)NR^8R^9$, $-C(O)OR^8$, $-O-(C_1-C_6$ hydroxyalkyl), $-O-(C_1-C_6$ alkoxy), $-O-(C_1-C_6$ alkylene)-cyano, $-O-(C_1-C_6$ alkylene)-$C(O)R^{9'}$, $-OCHR^{9'}C(O)O-R^8$, $-OCHR^{9'}C(O)NHOH$, $-O-(C_1-C_6$ alkyl)-$C(O)NR^8R^9$, $-O-(C_1-C_6$ alkylene)-$NR^{9'}C(O)R^8$, $-O-(C_1-C_6$ alkylene)-$NR^{9'}C(O)OR^8$, $-O-(C_1-C_6$ alkylene)-$NR^{9'}C(O)NR^8R^9$, $-OCHR^{9'}C(O)NR^8R^9$, $-O-(C_1-C_6$ alkylene)-$S(O)R^{9'}$, $-O-(C_1-C_6$ alkyl)-$S(O)_2R^{9'}$, $-O-(C_1-C_6$ alkylene)-$S(O)_2NR^8R^9$, $-O-(C_1-C_6$ alkylene)-$NR^{9'}S(O)_2NR^8R^9$, $-O-(C_1-C_6$ alkylene)-$NR^{9'}S(O)_2R^8-O-(C_1-C_6$ alkylene)-$S(O)_2R^{9'}-O-(C_1-C_6$ alkylene)-$NR^8R^9$, $-(C_1-C_6$ alkylene)-$S(O)_2R^8$, $-(C_6-C_6$ alkylene)-$S(O)_2$ $NR^8R^9$, $-(C_1-C_6$ alkylene)-$S(O)R^8$, $-(C_1-C_6$ alkylene)-$C(O)R^8$, $-(C_1-C_6$ alkylene)-$C(O)NR^8R^9$, $-(C_1-C_6$ alkylene)-$NR^{9'}C(O)R^8$, $-(C_1-C_6$ alkylene)-$NR^{9'}S(O)_2R^8$, $-(C_1-C_6$ alkylene)-$NR^{9'}C(O)OR^8$, $-(C_6-C_6$ alkylene)-$NR^{9'}C(O)NR^8R^9$, $-(C_1-C_6$ alkylene)-$NR^{9'}S(O)_2NR^8R^9$, $-(C_1-C_6$ alkylene)-$C(O)OR^8$, $-(C_1-C_6$ alkylene)-$NR^8R^9$, $-NR^8C(O)R^9$, $-NR^{9'}S(O)_2NR^8R^9$, $-S(O)R^{9'}$, $-S(O)_2R^{9'}$, or $-S(O)_2NR^8R^9$;

each $R^8$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, $C_{1-6}$ alkyl-$C_{3-7}$ cycloalkylene, or $C_{1-10}$ alkyl-siloxyl;

each R⁹ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or R⁸ and R⁹ together with the N atom to which they are attached form heterocyclyl;

each R⁹' is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl;

each R¹⁰ is independently H, alkyl, aryl, sulfonyl, C(O)R⁸, C(O)OR⁸ or C(O)NR⁸R⁹;

each n is independently an integer from 1 to 3; and each X is independently S, O, NH, or $N(C_1-C_6$ alkyl), wherein each alkyl, aryl, arylalkyl, heteroaryl, alkenyl, alkynyl, cycloalkyl, heterocyclyl, sulfonyl, or alkyl-cycloalkyl is optionally substituted.

In certain embodiments, each n is independently an integer from 1 to 2. In certain embodiments, each n is 1.

In certain embodiments, the compound of Formula IV' has the following formula I" or II":

(I")

(II")

where compounds of formula I" can exist in the following resonance structures I"-a, or I"-b:

(I"-a)

(I"-b)

and compounds of formula II" can exist in the following resonance structures II"-a, II"-b, or II"-c:

(II"-a)

(II"-b)

(II"-c)

where
   each Y is independently O or S;
   each A is independently CR¹⁸ or N;
   each A' is independently $CR^{15}R^{16}$, NR¹⁷, CR¹⁵, N,N-oxide, N—OR⁸—, S or O;
   each of R¹² is independently F, —OR⁸, —SR⁸, —NR⁸R⁹, alkyl, or aryl;
   each R¹⁴ is independently H, halogen, alkyl, alkenyl, alkynyl, aryl, heterocyclyl, heteroaryl, cyano, nitro, OH, —NR¹⁰SO₂R⁸, —OR⁸, —NR⁸R⁹, —C(O)R⁸, C(O)NR⁸R⁹, OCH₂C(O)NR⁸R⁹, —C(O)OR⁸, —O—($C_1$-$C_6$ hydroxyalkyl), —O—($C_1$-$C_6$ alkoxy), —O—($C_1$-$C_6$ alkylene)-cyano, —O—($C_1$-$C_6$ alkylene)-C(O)R⁹', —OCHR⁹'C(O)O—R⁸, —OCHR⁹'C(O)NHOH, —O—($C_1$-$C_6$ alkyl)-C(O)NR⁸R⁹, —O—($C_1$-$C_6$ alkylene)-NR⁹'C(O)R⁸, —O—($C_1$-$C_6$ alkylene)-NR⁹'C(O)OR⁸, —O—($C_1$-$C_6$ alkylene)-NR⁹'C(O)NR⁸R⁹, —OCHR⁹'C(O)NR⁸R⁹, —O—($C_1$-$C_6$ alkylene)-S(O)R⁹', —O—($C_1$-$C_6$ alkyl)-S(O)₂R⁹', —O—($C_1$-$C_6$ alkylene)-S(O)₂NR⁸R⁹, —O—($C_1$-$C_6$ alkylene)-NR⁹'S(O)₂NR⁸R⁹, —O—($C_1$-$C_6$ alkylene)-NR⁹'S(O)₂R⁸—O—($C_1$-$C_6$ alkylene)-S(O)₂R⁹'—O—($C_1$-$C_6$ alkylene)-NR⁸R⁹, —($C_1$-$C_6$ alkylene)-S(O)₂R⁸, —($C_1$-$C_6$ alkylene)-S(O)₂ NR⁸R⁹, —($C_1$-$C_6$ alkylene)-S(O)R⁸, —($C_1$-$C_6$ alkylene)-C(O)R⁸, —($C_1$-$C_6$ alkylene)-C(O)NR⁸R⁹, —($C_1$-$C_6$ alkylene)-NR⁹'C(O)R⁸, —($C_1$-$C_6$ alkylene)-NR⁹'S(O)₂R⁸, —($C_1$-$C_6$ alkylene)-NR⁹'C(O)OR⁸, —($C_1$-$C_6$ alkylene)-NR⁹'C(O)NR⁸R⁹, —($C_1$-$C_6$ alkylene)-NR⁹'S(O)₂NR⁸R⁹, —($C_1$-$C_6$ alkylene)-C(O)OR⁸, —($C_1$-$C_6$ alkylene)-NR⁸R⁹, —NR⁸C(O)R⁹, —NR⁹'S(O)₂NR⁸R⁹, —S(O)R⁹', —S(O)₂R⁹', or —S(O)₂NR⁸R⁹; each R⁹' is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl;

each R⁸ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, $C_{1-6}$ alkyl-$C_{3-7}$ cycloalkylene, or $C_{1-10}$ alkylsiloxyl;

each R⁹ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or R⁸ and R⁹ together with the N atom to which they are attached form heterocyclyl;

each R⁹' is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl;

each R¹⁰ is independently H, alkyl, aryl, sulfonyl, C(O)R⁸, C(O)OR⁸ or C(O)NR⁸R⁹;

each $R^{15}$ is independently a bond, H, halogen, —$NR^{10}SO_2R^8$, —($C_1$-$C_6$ alkylene)-$NR^{9'}S(O)NR^8R^9$, ($C_1$-$C_6$ alkylene)-$NR^{9'}S(O)_2NR^8R^{10}$, —($C_1$-$C_6$ alkylene)-$NR^{9'}S(O)_2R^8$, —$OR^8$, —$NR^8R^9$, —$C(O)R^8$, —$C(O)NR^8R^9$, —$C(O)OR^8$, alkyl, aryl, or heteroaryl;

$R^{16}$ is independently a bond, H, halogen, —$NR^{10}SO_2R^8$, —($C_1$-$C_6$ alkyl)-$NR^{9'}S(O)_2NR^8R^9$, —($C_1$-$C_6$ alkyl)-$NR^{9'}S(O)_2NR^8R^{10}$, —($C_1$-$C_6$ alkyl)-$NR^{9'}S(O)_2R^8$, —$OR^8$, —$NR^8R^9$, —$C(O)R^8$, —$C(O)NR^8R^9$, —$C(O)OR^8$, alkyl, aryl, or heteroaryl;

$R^{17}$ is independently a bond, H, alkyl, aryl-$CH_2$—, —$NR^8R^9$, —$C(O)R^8$, —$C(O)NR^8R^9$, —$C(O)OR^8$, sulfonyl, aryl, arylalkyl, alkenyl, alkynyl, heterocyclylalkyl or heteroaryl; and $R^{18}$ is a bond, H, halogen, —$NR^{10}SO_2R^8$, —($C_1$-$C_6$ alkylene)-$NR^{9'}S(O)_2NR^8R^9$, —($C_1$-$C_6$ alkylene)-$NR^{9'}S(O)_2NR^8R^{10}$, —($C_1$-$C_6$ alkylene)-$NR^{9'}S(O)_2R^8$, —$OR^8$, —$NR^8R^9$, —$C(O)R^8$, —$C(O)NR^8R^9$, —$C(O)OR^8$, alkyl, aryl, or heteroaryl;

each n is independently an integer from 1 to 4;

each m is independently an integer from 1 to 3; and

Z has the following structure:

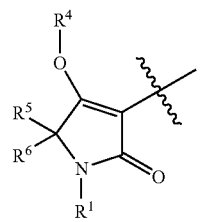

where each $R^1$ is independently H, alkyl, arylalkyl, heteroarylalkyl, halogen, —$NR^{10}SO_2R^8$, —$OR^8$, —$NR^8R^9$, —$C(O)R^8$, —$C(O)NR^8R^9$, —$C(O)OR^8$, aryl, arylalkyl, alkenyl, alkynyl, heterocyclylalkyl, sulfonyl, or heteroaryl;

each $R^4$ is independently H, alkyl, aryl-$CH_2$—, —$NR^8R^9$, —$C(O)R^8$, —$C(O)NR^8R^9$, —$C(O)OR^8$, sulfonyl, aryl, arylalkyl, alkenyl, alkynyl, heterocyclylalkyl or heteroaryl;

each $R^5$ is independently H, halogen, —$NR^{10}SO_2R^8$, —$OR^8$, —$NR^8R^9$, —$C(O)R^8$, —$C(O)NR^8R^9$, —$C(O)OR^8$, alkyl aryl, or heteroaryl, or $R^4$ and $R^5$ together form a part of a 3-8 membered heterocycloalkyl ring; and $R^6$ is H, halogen, —$NR^{10}SO_2R^8$, —$OR^8$, —$NR^8R^9$, —$C(O)R^8$, —$C(O)NR^8R^9$, —$C(O)OR^8$, alkyl, aryl, or heteroaryl, or $R^5$ and $R^6$ together form a part of a 3-8 membered cycloalkyl or heterocycloalkyl ring, wherein each alkyl, aryl, arylalkyl, heteroaryl, alkenyl, alkynyl, cycloalkyl, heterocyclyl, sulfonyl, or alkyl-cycloalkyl is optionally substituted.

In certain embodiments, each n is independently an integer from 1 to 3. In certain embodiments, each n is independently an integer from 1 to 2. In certain embodiments, each n is 1.

Each compound of Formula IV', where each of $R^4$ and $R^{4'}$ is H, may exist in various tautomeric forms. Provided herein are tautomeric forms of compounds of Formula IV', for example, when $R^4$ is H, when $R^{4'}$ is H, or when $R^4$ and $R^{4'}$ are H. For example, compounds having formula VI where $R^4$ and $R^{4'}$ are H may exist in, but not limited to, the following tautomeric forms IV'$_a$, IV'$_b$ or IV'$_c$:

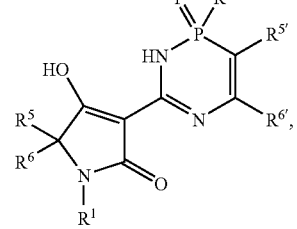

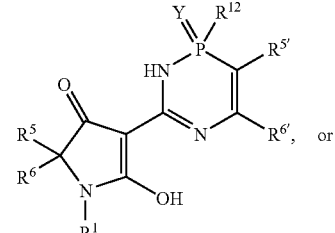

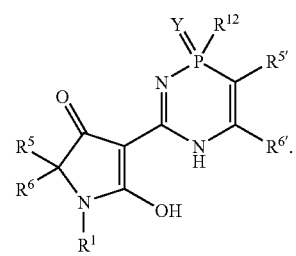

In one aspect, provided herein is a compound of Formula IV:

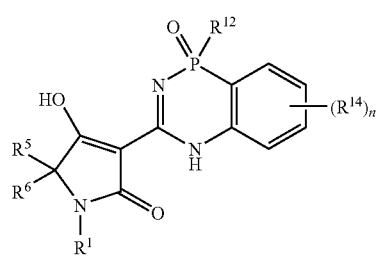

or a single enantiomer, a mixture of an enantiomeric pair, an individual diastereomer, a mixture of diastereomers, or any tautomeric form thereof; or a pharmaceutically acceptable salt, solvate, or prodrug thereof, wherein $R^1$ is H, alkyl, aryl-$CH_2$—, halogen, —$NR^{10}SO_2R^8$, —$OR^8$, —$NR^8R^9$, —$C(O)R^8$, —$C(O)NR^8R^9$, —$C(O)OR^8$, aryl, arylalkyl, alkenyl, alkynyl, heterocyclylalkyl, sulfonyl, or heteroaryl;

$R^5$ is H, halogen, —$NR^{10}SO_2R^8$, —$OR^8$, —$NR^8R^9$, —$C(O)R^8$, —$C(O)NR^8R^9$, —$C(O)OR^8$, alkyl, aryl, or heteroaryl;

$R^6$ is H, halogen, —$NR^{10}SO_2R^8$, —$OR^8$, —$NR^8R^9$, —$C(O)R^8$, —$C(O)NR^8R^9$, —$C(O)OR^8$, alkyl, aryl, or heteroaryl, or $R^5$ and $R^6$ together form a part of a 3-8 membered cycloalkyl or heterocycloalkyl ring;

$R^{12}$ is F, —$OR^8$, —$SR^8$, —$NR^8R^9$, alkyl, or aryl;

each $R^{14}$ is independently H, halogen, alkyl, alkenyl, alkynyl, aryl, heterocyclyl, heteroaryl, cyano, nitro, OH, —NR$^{10}$SO$_2$R$^8$, —OR$^8$, —NR$^8$R$^9$, —C(O)R$^8$, C(O)NR$^8$R$^9$, —OCH$_2$C(O)NR$^8$R$^9$, —C(O)OR$^8$, —O—(C$_1$-C$_6$ hydroxyalkyl), —O—(C$_1$-C$_6$ alkoxy), —O—(C$_1$-C$_6$ alkylene)-cyano, —O—(C$_1$-C$_6$ alkylene)-C(O)R$^{9'}$, —OCHR$^{9'}$C(O)O—R$^8$, —OCHR$^{9'}$C(O)NHOH, —O—(C$_1$-C$_6$ alkyl)-C(O)NR$^8$R$^9$, —O—(C$_1$-C$_6$ alkylene)-NR$^{9'}$C(O)R$^8$, —O—(C$_1$-C$_6$ alkylene)-NR$^{9'}$C(O)OR$^8$, —O—(C$_1$-C$_6$ alkylene)-NR$^{9'}$C(O)NR$^8$R$^9$, —OCHR$^{9'}$C(O)NR$^8$R$^9$, —O—(C$_1$-C$_6$ alkylene)-S(O)R$^{9'}$, —O—(C$_1$-C$_6$ alkyl)-S(O)$_2$R$^{9'}$, —O—(C$_1$-C$_6$ alkylene)-S(O)$_2$NR$^8$R$^9$, —O—(C$_1$-C$_6$ alkylene)-NR$^{9'}$S(O)$_2$NR$^8$R$^9$, —O—(C$_1$-C$_6$ alkylene)-NR$^{9'}$S(O)$_2$R$^8$—O—(C$_1$-C$_6$ alkylene)-S(O)$_2$R$^{9'}$—O—(C$_1$-C$_6$ alkylene)-NR$^8$R$^9$, —(C$_1$-C$_6$ alkylene)-S(O)$_2$R$^8$, —(C$_1$-C$_6$ alkylene)-S(O)$_2$ NR$^8$R$^9$, —(C$_1$-C$_6$ alkylene)-S(O)R$^8$, —(C$_1$-C$_6$ alkylene)-C(O)R$^8$, —(C$_1$-C$_6$ alkylene)-C(O)NR$^8$R$^9$, —(C$_1$-C$_6$ alkylene)-NR$^{9'}$C(O)R$^8$, —(C$_1$-C$_6$ alkylene)-NR$^{9'}$S(O)$_2$R$^8$, —(C$_1$-C$_6$ alkylene)-NR$^{9'}$C(O)OR$^8$, —(C$_1$-C$_6$ alkylene)-NR$^{9'}$C(O)NR$^8$R$^9$, —(C$_1$-C$_6$ alkylene)-NR$^{9'}$S(O)$_2$NR$^8$R$^9$, —(C$_1$-C$_6$ alkylene)-C(O)OR$^8$, —(C$_1$-C$_6$ alkylene)-NR$^8$R$^9$, —NR$^8$C(O)R$^{9'}$, —NR$^{9'}$S(O)$_2$NR$^8$R$^9$, —S(O)R$^{9'}$, —S(O)$_2$R$^{9'}$, or —S(O)$_2$NR$^8$R$^9$;

n is an integer from 1 to 4;

each R$^8$ is independently hydrogen, C$_{1-6}$ alkyl, C$_{2-6}$ alkenyl, C$_{2-6}$ alkynyl, C$_{3-7}$ cycloalkyl, C$_{6-14}$ aryl, heteroaryl, heterocyclyl, C$_{1-6}$ alkyl-C$_{3-7}$ cycloalkylene, or C$_{1-10}$ alkyl-siloxyl;

each R$^9$ is independently hydrogen, C$_{1-6}$ alkyl, C$_{2-6}$ alkenyl, C$_{2-6}$ alkynyl, C$_{3-7}$ cycloalkyl, C$_{6-14}$ aryl, heteroaryl, or heterocyclyl; or R$^8$ and R$^9$ together with the N atom to which they are attached form heterocyclyl;

each R$^{9'}$ is independently hydrogen, C$_{1-6}$ alkyl, C$_{2-6}$ alkenyl, C$_{2-6}$ alkynyl, C$_{3-7}$ cycloalkyl, C$_{6-14}$ aryl, heteroaryl, or heterocyclyl; or R$^8$ and R$^9$ together with the N atom to which they are attached form heterocyclyl;

each R$^{10}$ is independently H, alkyl, aryl, sulfonyl, C(O)R$^8$, C(O)OR$^8$ or C(O)NR$^8$R$^9$;

wherein each alkyl, aryl, arylalkyl, heteroaryl, alkenyl, alkynyl, cycloalkyl, heterocyclyl, sulfonyl, or alkyl-cycloalkyl is optionally substituted.

In some embodiments, provided herein is a compound according to any of Formulas IV, IV', I'', II'', or IVa as described herein, or a single enantiomer, a mixture of an enantiomeric pair, an individual diastereomer, or a mixture of diastereomers thereof; or a pharmaceutically acceptable salt, solvate, or prodrug thereof In one aspect, provided herein is a compound of Formula IVa:

(IVa)

or a single enantiomer, a mixture of an enantiomeric pair, an individual diastereomer, a mixture of diastereomers, or any tautomeric form thereof; or a pharmaceutically acceptable salt, solvate, or prodrug thereof;

wherein R$^1$ is H, alkyl, arylalkyl, heteroarylalkyl, halogen, —NR$^{10}$SO$_2$R$^8$, —OR$^8$, —NR$^8$R$^9$, —C(O)R$^8$, —C(O)NR$^8$R$^9$, —C(O)OR$^8$, aryl, arylalkyl, alkenyl, alkynyl, heterocyclylalkyl, sulfonyl, or heteroaryl;

R$^6$ is H, halogen, —NR$^{10}$SO$_2$R$^8$, —OR$^8$, NR$^8$R$^9$, —C(O)R$^8$, —C(O)NR$^8$R$^9$, —C(O)OR$^8$, alkyl, aryl, or heteroaryl;

R$^{12}$ is F, —OR$^8$, —SR$^8$, —NR$^8$R$^9$, alkyl, or aryl; and each R$^{14}$ is independently H, halogen, alkyl, alkenyl, alkynyl, aryl, heterocyclyl, heteroaryl, cyano, nitro, OH, —NR$^{10}$SO$_2$R$^8$, —OR$^8$, —NR$^8$R$^9$, —C(O)R$^8$, C(O)NR$^8$R$^9$, —OCH$_2$C(O)NR$^8$R$^9$, —C(O)OR$^8$, —O—(C$_1$-C$_6$ hydroxyalkyl), —O—(C$_1$-C$_6$ alkoxy), —O—(C$_1$-C$_6$ alkylene)-cyano, —O—(C$_1$-C$_6$ alkylene)-C(O)R$^{9'}$, —OCHR$^{9'}$C(O)O—R$^8$, —OCHR$^{9'}$C(O)NHOH, —O—(C$_1$-C$_6$ alkyl)-C(O)NR$^8$R$^9$, —O—(C$_1$-C$_6$ alkylene)-NR$^{9'}$C(O)R$^8$, —O—(C$_1$-C$_6$ alkylene)-NR$^{9'}$C(O)OR$^8$, —O—(C$_1$-C$_6$ alkylene)-NR$^{9'}$C(O)NR$^8$R$^9$, —OCHR$^{9'}$C(O)NR$^8$R$^9$, —O—(C$_1$-C$_6$ alkylene)-S(O)R$^{9'}$, —O—(C$_1$-C$_6$ alkyl)-S(O)$_2$R$^{9'}$, —O—(C$_1$-C$_6$ alkylene)-S(O)$_2$NR$^8$R$^9$, —O—(C$_1$-C$_6$ alkylene)-NR$^{9'}$S(O)$_2$NR$^8$R$^9$, —O—(C$_1$-C$_6$ alkylene)-NR$^{9'}$S(O)$_2$R$^8$—O—(C$_1$-C$_6$ alkylene)-S(O)$_2$R$^{9'}$—O—(C$_1$-C$_6$ alkylene)-NR$^8$R$^9$, —(C$_1$-C$_6$ alkylene)-S(O)R$^8$, —(C$_1$-C$_6$ alkylene)-S(O)$_2$ NR$^8$R$^9$, —(C$_1$-C$_6$ alkylene)-S(O)R$^8$, —(C$_1$-C$_6$ alkylene)-C(O)R$^8$, —(C$_1$-C$_6$ alkylene)-C(O)NR$^8$R$^9$, —(C$_1$-C$_6$ alkylene)-NR$^{9'}$C(O)R$^8$, —(C$_1$-C$_6$ alkylene)-NR$^{9'}$S(O)$_2$R$^8$, —(C$_1$-C$_6$ alkylene)-NR$^{9'}$C(O)OR$^8$, —(C$_1$-C$_6$ alkylene)-NR$^{9'}$C(O)NR$^8$R$^9$, —(C$_1$-C$_6$ alkylene)-NR$^{9'}$S(O)$_2$NR$^8$R$^9$, —(C$_1$-C$_6$ alkylene)-C(O)OR$^8$, —(C$_1$-C$_6$ alkylene)-NR$^8$R$^9$, —NR$^8$C(O)R$^{9'}$, —NR$^{9'}$S(O)$_2$NR$^8$R$^9$, —S(O)R$^{9'}$, —S(O)$_2$R$^{9'}$, or —S(O)$_2$NR$^8$R$^9$;

each R$^8$ is independently hydrogen, C$_{1-6}$ alkyl, C$_{2-6}$ alkenyl, C$_{2-6}$ alkynyl, C$_{3-7}$ cycloalkyl, C$_{6-14}$ aryl, heteroaryl, heterocyclyl, C$_{1-6}$ alkyl-C$_{3-7}$ cycloalkylene, or C$_{1-10}$ alkyl-siloxyl;

each R$^9$ is independently hydrogen, C$_{1-6}$ alkyl, C$_{2-6}$ alkenyl, C$_{2-6}$ alkynyl, C$_{3-7}$ cycloalkyl, C$_{6-14}$ aryl, heteroaryl, or heterocyclyl; or R$^8$ and R$^9$ together with the N atom to which they are attached form heterocyclyl;

each R$^{9'}$ is independently hydrogen, C$_{1-6}$ alkyl, C$_{2-6}$ alkenyl, C$_{2-6}$ alkynyl, C$_{3-7}$ cycloalkyl, C$_{6-14}$ aryl, heteroaryl, or heterocyclyl; and each R$^{10}$ is independently H, alkyl, aryl, sulfonyl, C(O)R$^8$, C(O)OR$^8$ or C(O)NR$^8$R$^9$.

In certain embodiments according to Formula IV, IV', I'', II'', or IVa, each alkyl, aryl, arylalkyl, heteroaryl, alkenyl, alkynyl, cycloalkyl, heterocyclyl, or alkyl-cycloalkyl is unsubstituted.

In certain embodiments according to Formula IV, IV', I'', II'', or IVa, R$^1$ is alkyl, arylalkyl, or heteroarylalkyl. In certain embodiments according to Formula IV, IV', I'', II'', or IVa, R$^1$ is C$_{1-6}$ alkyl. In certain embodiments according to Formula IV, IV', I'', II'', or IVa, R$^1$ is 2-cyclopropylethyl. In certain embodiments according to Formula IV, IV', I'', II'', or IVa, R$^1$ is 3,3-dimethylbutyl. In further embodiments, R$^1$ has one of the following structures:

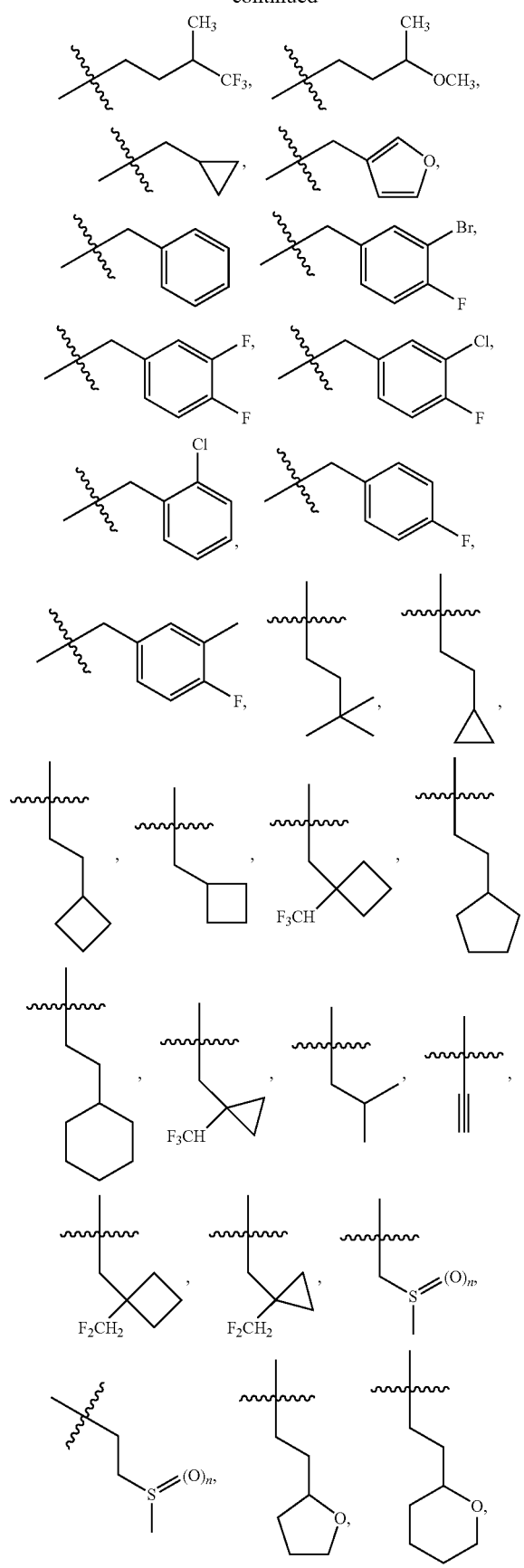
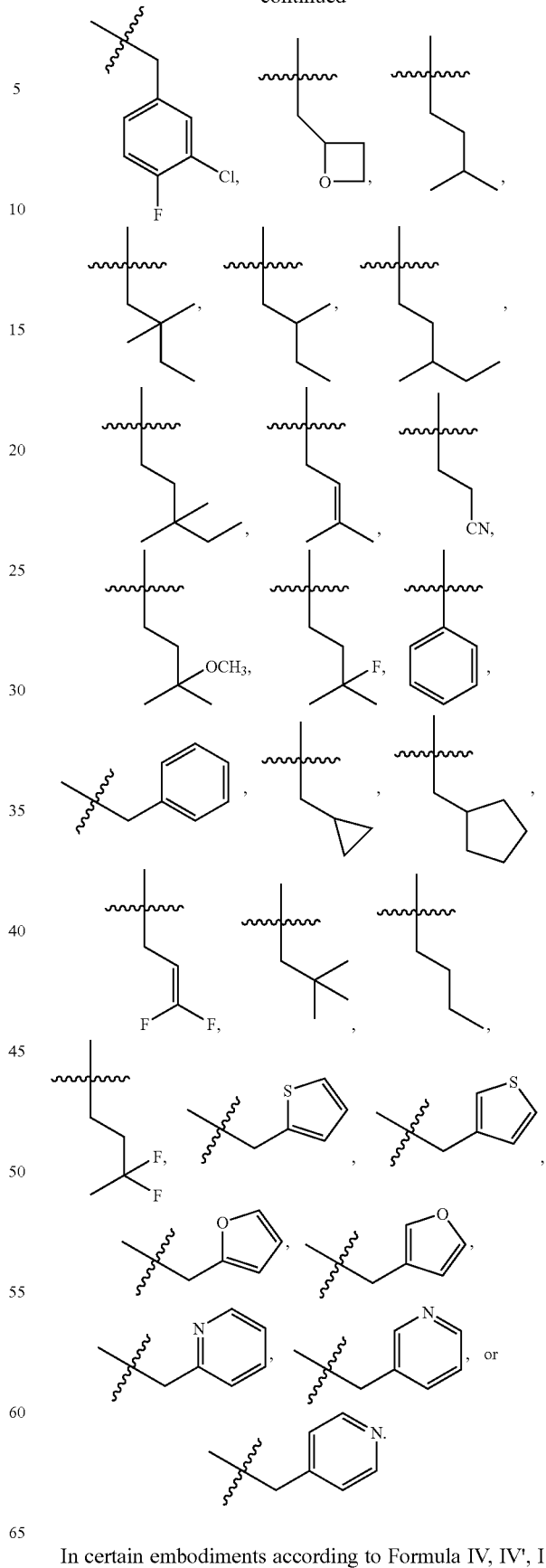
In certain embodiments according to Formula IV, IV', I", II", or IVa, $R^6$ is H, halo, —$OR^8$, —$NR^8R^9$, —$C(O)R^8$, alkyl arylalkyl, aryl, or heteroaryl. In other embodiments according to Formula IV or IVa, $R^6$ is hydrogen or halogen. In some embodiments according to Formula IV or IVa, $R^6$ is H, I, Cl, F, methyl, isobutyl, t-butyl, phenyl or benzyl. In other embodiments according to Formula IV or IVa, $R^6$ is tert-butyl. In certain embodiments according to Formula IV or IVa, $R^6$ is (S)-tert-butyl. In certain embodiments according to Formula IV or IVa, $R^6$ is heteroaryl. In further embodiments, $R^6$ is heteroaryl having one of the following structures:

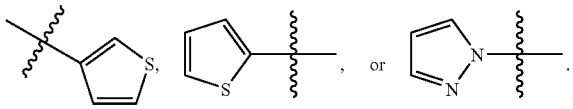

In certain embodiments according to Formula IV, IV', I", II", or IVa, $R^{12}$ is F, $-OR^8$, $-SR^8$, $-NR^8R^9$, alkyl, or aryl. In certain embodiments according to Formula I, IV, IV', I", II", or IVa, $R^{12}$ is $C_{1-6}$ alkoxy. In certain embodiments according to Formula IV, IV', I", II", or IVa, $R^{12}$ is methoxy. In certain embodiments according to Formula IV, IV', I", II", or IVa, $R^{12}$ is ethoxy. In certain embodiments according to Formula IV, IV', I", II", or IVa, $R^{12}$ is OH. In certain embodiments according to Formula IV, IV', I", II", or IVa, $R^{12}$ is $NH_2$. In certain embodiments according to Formula IV, IV', I", II", or IVa, $R^{12}$ is $-CH2$-cyclopropyl, isopropyl, $-CH_2CH_2CH_2-C(O)NHCH_3$, $-CH_2CH_2CH_2-C(O)NH_2$, or $-CH_2CH_2OCH_3$.

In certain embodiments according to Formula IV, IV', I", II", or IVa, $R^{14}$ is H, halogen, $-NR^{10}SO_2R^8$, $-OR^8$, $-NR^8R^9$, $-C(O)R^8$, $-C(O)NR^8R^9$, $-OCH_2C(O)NR^8R^9$, $-C(O)OR^8$, alkyl, aryl, or heteroaryl where $R^8$, $R^9$ and $R^{10}$ are as defined herein. In other embodiments according to Formula IV, IV', I", II", or IVa, $R^{14}$ is hydrogen. In some embodiments according to Formula IV, IV', I", II", or IVa, $R^{14}$ is $-NR^{10}SO_2R^8$ where $R^8$ is methyl and $R^{10}$ is H or alkyl such as methyl or ethyl. In some embodiments according to Formula IV, IV', I", II", or IVa, $R^{14}$ is $OCH_2C(O)NR^8R^9$ where each of $R^8$ and $R^9$ is independently H or alkyl.

In certain embodiments according to Formula IV, IV', I", II", or IVa, $R^8$ is $C_{1-6}$ alkyl, $C_{3-7}$ cycloalkyl, $C_{6-14}$ aryl, heteroaryl, heterocyclyl, or $C_{1-6}$ alkyl-$C_{3-7}$ cycloalkylene, each optionally substituted as described herein. In certain embodiments, $R^8$ is $C_{1-6}$ alkyl, optionally substituted as described herein. In certain embodiments, $R^8$ is $C_{3-7}$ cycloalkyl, optionally substituted as described herein. In certain embodiments, $R^8$ is cyclopropyl, 1-methylcyclopropyl, cyclobutyl, cyclopentyl, or cyclohexyl. In certain embodiments, $R^8$ is $C_{6-14}$ aryl, optionally substituted as described herein. In certain embodiments, $R^8$ is heteroaryl, optionally substituted as described herein. In certain embodiments, $R^8$ is heterocyclyl, optionally substituted as described herein.

In certain embodiments according to Formula IV, IV', I", II", or IVa, $R^8$ is $C_{1-6}$ alkyl. In certain embodiments according to Formula IV, IV', I", II", or IVa, $R^8$ is methyl.

In certain embodiments according to Formula IV, IV', I", II", or IVa, $R^9$ is hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl.

In certain embodiments according to Formula IV, IV', I", II", or IVa, $R^8$ and $R^9$ together with the N atom to which they are attached form heterocyclyl.

In certain embodiments according to Formula IV, IV', I", II", or IVa, $R^1$ is alkyl; $R^6$ is H, alkyl or halogen; $R^{12}$ is $-OR^8$; $R^{14}$ is H or $-NHSO_2R^8$; and each $R^8$ is independently H or alkyl. In certain embodiments according to Formula IV, IV', I", II", or IVa, $R^1$ is alkyl; $R^6$ is halogen; $R^{12}$ is $-OR^8$; $R^{14}$ is H or $-NHSO_2R^8$; and each $R^8$ is independently H or alkyl. In certain embodiments according to Formula IV, IV', I", II", or IVa, $R^1$ is alkyl; $R^6$ is tert-butyl; $R^{12}$ is $-OR^8$; $R^{14}$ is H or $-NHSO_2R^8$; and each $R^8$ is independently H or alkyl. In certain embodiments according to Formula IV, IV', I", II", or IVa, $R^1$ is alkyl; $R^6$ is tert-butyl; $R^{12}$ is $-OR^8$; $R^{14}$ is H or $-NHSO_2Me$; and $R^8$ is H, methyl or ethyl. In certain embodiments according to Formula IV, IV', I", II", or IVa, $R^6$ is (S)-tert-butyl. In certain embodiments according to Formula IV, IV', I", II", or IVa, $R^1$ is $C_{1-6}$ alkyl; $R^6$ is $C_{1-6}$ alkyl; $R^{12}$ is $-OR^8$; $R^{14}$ is $-NHSO_2R^8$; and each $R^8$ is independently methyl or ethyl. In certain embodiments according to this paragraph, each alkyl, aryl, arylalkyl, heteroaryl, alkenyl, alkynyl, cycloalkyl, heterocyclyl, or alkyl-cycloalkyl is unsubstituted.

In certain embodiments according to Formula IV, IV', I", II", or IVa, $R^1$ is 3,3-dimethylbutyl; $R^6$ is H, alkyl or halogen; $R^{12}$ is $-OR^8$; $R^{14}$ is H or $-NHSO_2R^8$; and each $R^8$ is independently H or alkyl. In certain embodiments according to Formula IV, IV', I", II", or IVa, $R^1$ is 3,3-dimethylbutyl; $R^6$ is halogen; $R^{12}$ is $-OR^8$; $R^{14}$ is H or $-NHSO_2R^8$; and each $R^8$ is independently H or alkyl. In certain embodiments according to Formula IV, IV', I", II", or IVa, $R^1$ is 3,3-dimethylbutyl; $R^6$ is tert-butyl; $R^{12}$ is $-OR^8$; $R^{14}$ is H or $-NHSO_2R^8$; and each $R^8$ is independently H or alkyl. In certain embodiments according to Formula IV, IV', I", II", or IVa, $R^1$ is 3,3-dimethylbutyl; $R^6$ is tert-butyl; $R^{12}$ is $-OR^8$; $R^{14}$ is H or $-NHSO_2Me$; and $R^8$ is H, methyl or ethyl. In certain embodiments according to this paragraph, each alkyl, aryl, arylalkyl, heteroaryl, alkenyl, alkynyl, cycloalkyl, heterocyclyl, or alkyl-cycloalkyl is unsubstituted. In certain embodiments according to this paragraph, $R^6$ is (S)-tert-butyl.

In certain embodiments according to Formula IV, IV', I", II", or IVa, $R^1$ is alkyl; $R^6$ is H, alkyl or halogen; $R^{12}$ is $-OR^8$; $R^{14}$ is H; and $R^8$ is H or alkyl. In certain embodiments according to Formula IV, IV', I", II", or IVa, $R^1$ is alkyl; $R^6$ is halogen; $R^{12}$ is $-OR^8$; $R^{14}$ is H; and $R^8$ is H or alkyl. In certain embodiments according to Formula IV, IV', I", II", or IVa, $R^1$ is alkyl; $R^6$ is tert-butyl; $R^{12}$ is $-OR^8$; $R^{14}$ is H; and $R^8$ is H or alkyl. In certain embodiments according to Formula IV, IV', I", II", or IVa, $R^1$ is alkyl; $R^6$ is tert-butyl; $R^{12}$ is $-OR^8$; $R^{14}$ is H; and $R^8$ is H, methyl or ethyl. In certain embodiments according to this paragraph, each alkyl, aryl, arylalkyl, heteroaryl, alkenyl, alkynyl, cycloalkyl, heterocyclyl, or alkyl-cycloalkyl is unsubstituted.

In certain embodiments according to Formula IV, IV', I", II", or IVa, $R^1$ is 2-cyclopropylethyl; $R^6$ is H, alkyl or halogen; $R^{12}$ is $-OR^8$; $R^{14}$ is $-NHSO_2R^8$; and each $R^8$ is independently H or alkyl. In certain embodiments according to Formula IV, IV', I", II", or IVa, $R^1$ is 2-cyclopropylethyl; $R^6$ is halogen; $R^{12}$ is $-OR^8$; $R^{14}$ is $-NHSO_2R^8$; and each $R^8$ is independently H or alkyl. In certain embodiments according to Formula IV, IV', I", II", or IVa, $R^1$ is 2-cyclopropylethyl; $R^6$ is tert-butyl; $R^{12}$ is $-OR^8$; $R^{14}$ is $-NHSO_2R^8$; and each $R^8$ is independently H or alkyl. In certain embodiments according to Formula IV, IV', I", II", or IVa, $R^1$ is 2-cyclopropylethyl; $R^6$ is tert-butyl; $R^{12}$ is $-OR^8$; $R^{14}$ is $-NHSO_2Me$; and $R^8$ is H, methyl or ethyl. In certain embodiments according to this paragraph, each alkyl, aryl, arylalkyl, heteroaryl, alkenyl, alkynyl, cycloalkyl, heterocyclyl, or alkyl-cycloalkyl is unsubstituted.

In one embodiment, provided herein is compound 1:

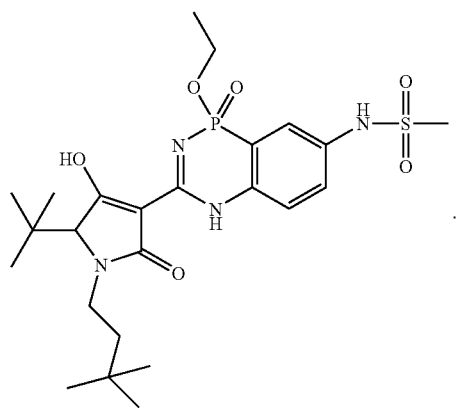

(1)

In yet another embodiment, provided herein is compound 2:

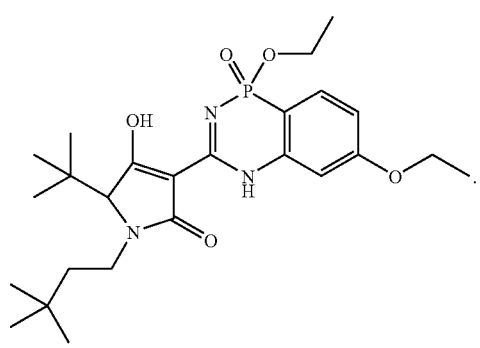

(2)

In yet another embodiment, provided herein is compound 3:

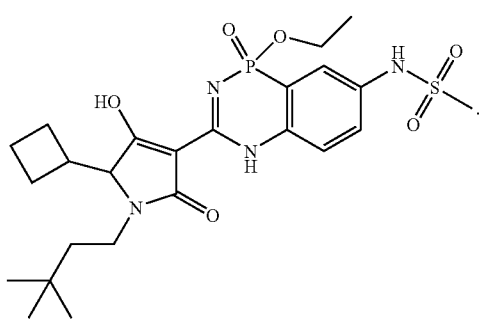

(3)

In yet another embodiment, provided herein is compound 4:

(4)

In yet another embodiment, provided herein is compound 5:

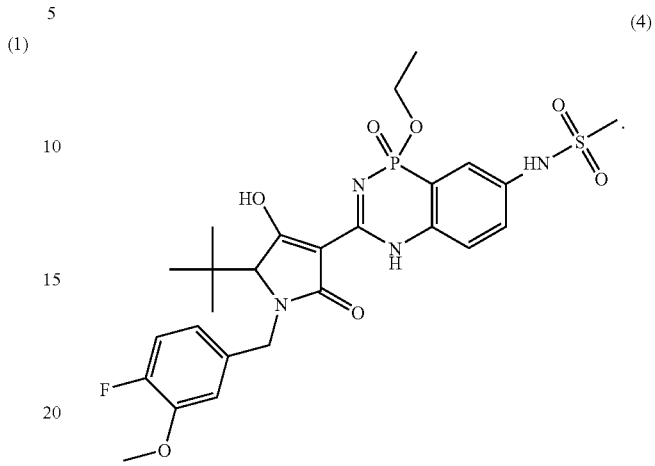

(5)

In certain embodiments, provided herein are the following compounds according to formulae IV-1 to IV-21:

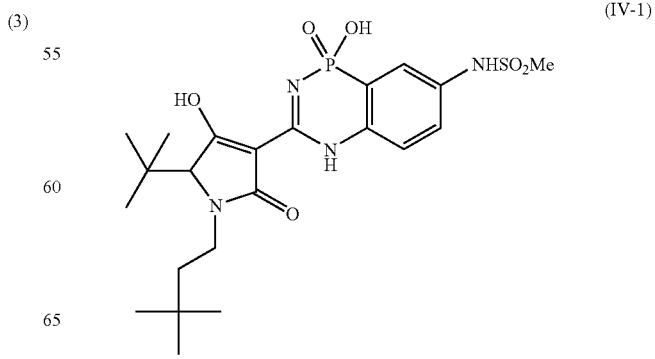

(IV-1)

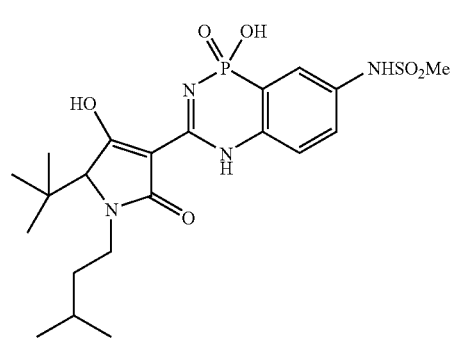
(IV-2)
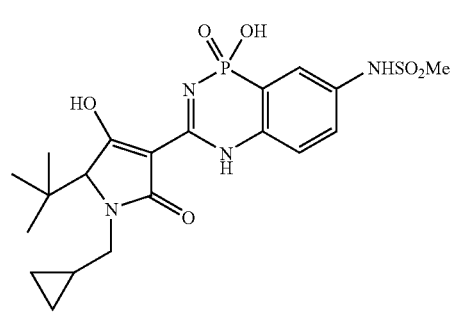
(IV-3)
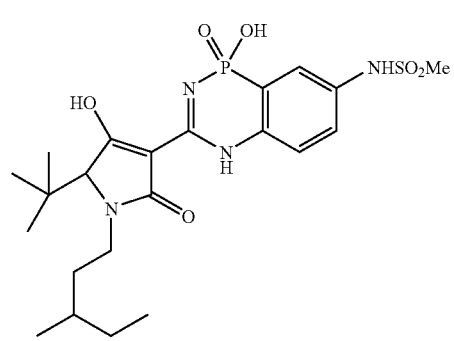
(IV-4)
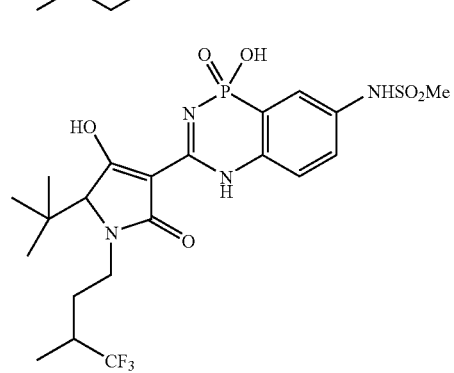
(IV-5)
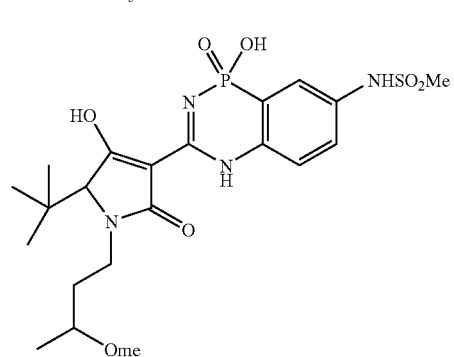
(IV-6)
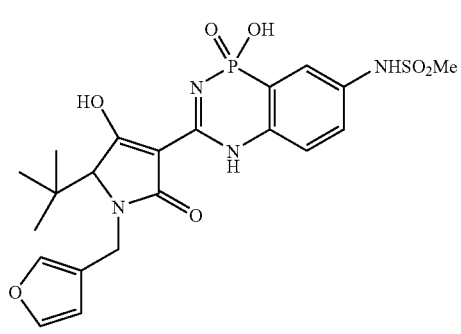
(IV-7)
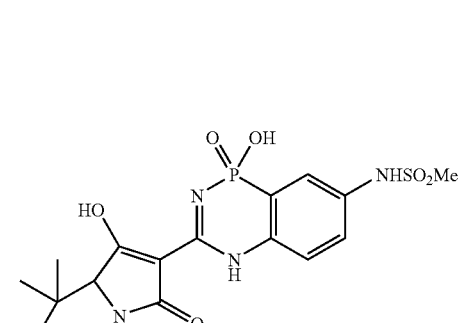
(IV-8)
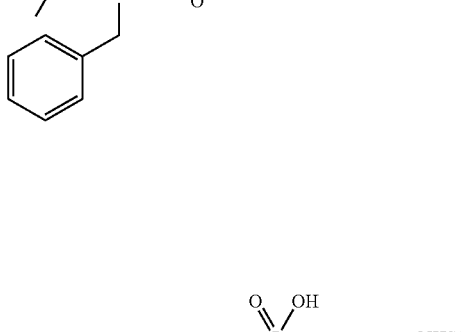
(IV-9)
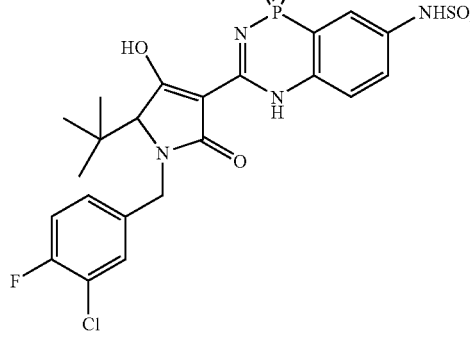
(IV-10)
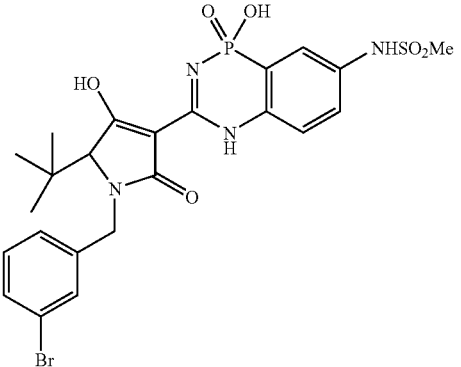

(IV-11) 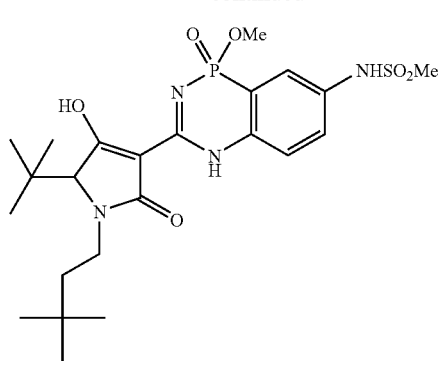
(IV-12) 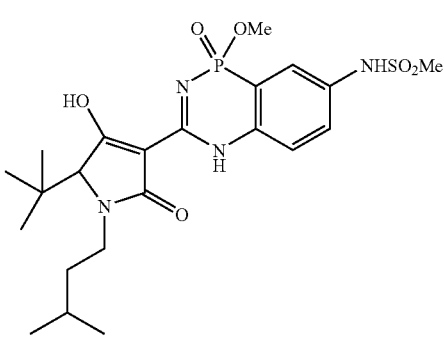
(IV-13) 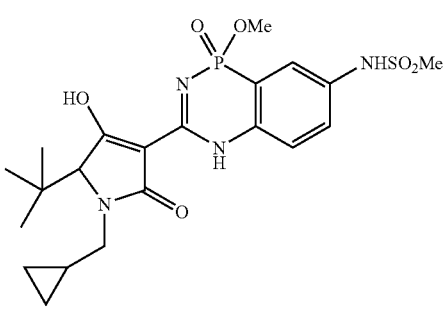
(IV-14) 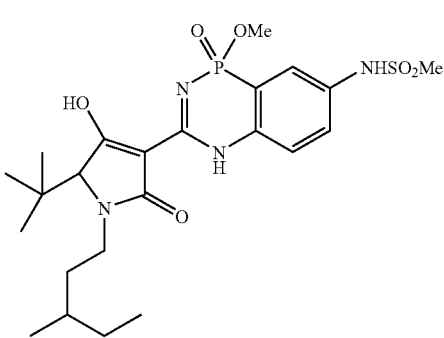
(IV-15) 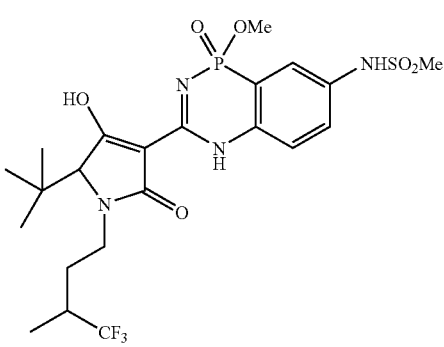
(IV-16) 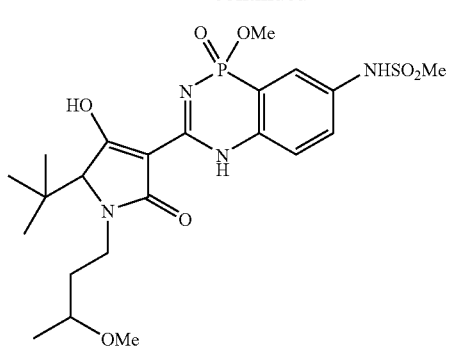
(IV-17)
(IV-18)
(IV-19)

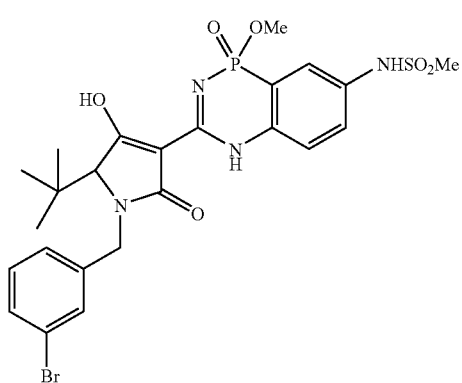
(IV-20)
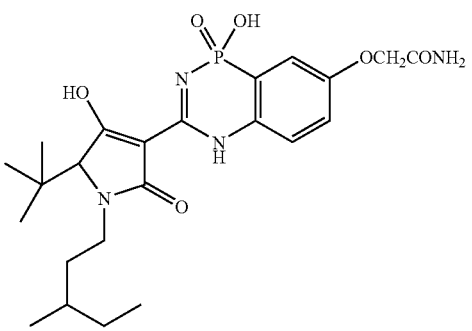
(IV-24)
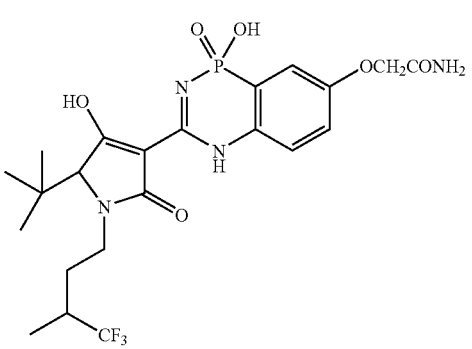
(IV-25)
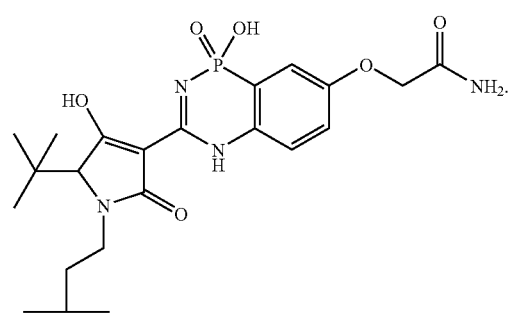
(IV-21)
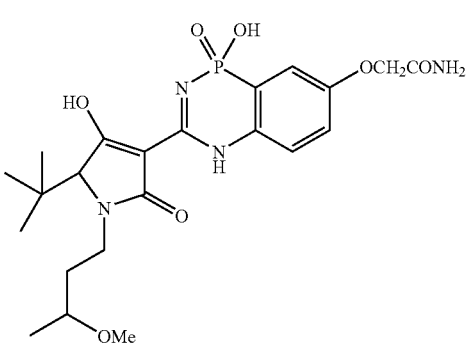
(IV-26)
In certain embodiments, provided herein are the following compounds according to formulae IV-22 to IV-42:
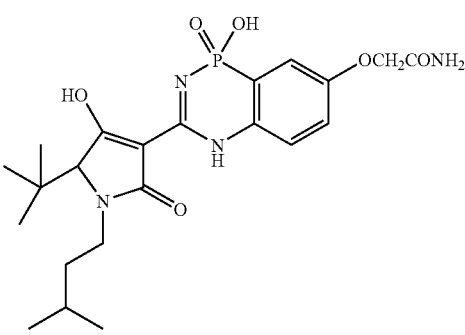
(IV-22)
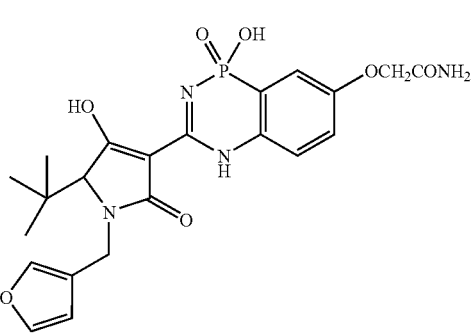
(IV-27)
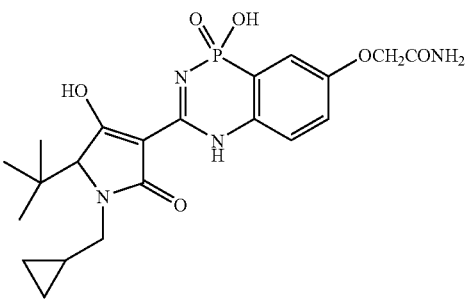
(IV-23)
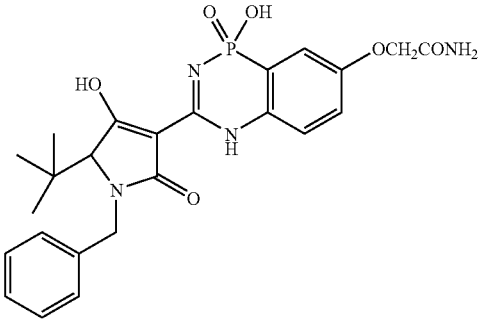
(IV-28)

(IV-29)
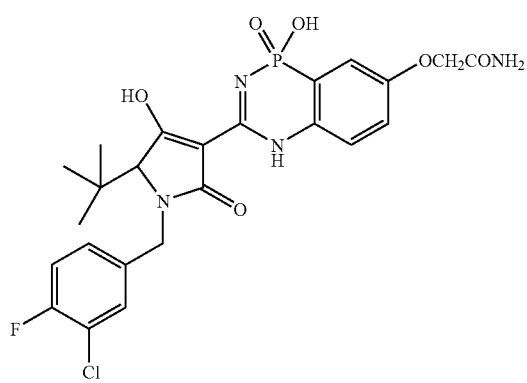
(IV-30)
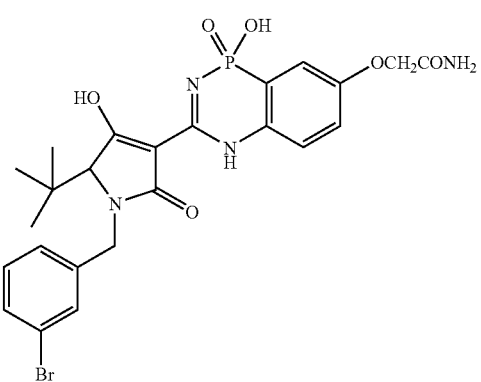
(IV-31)
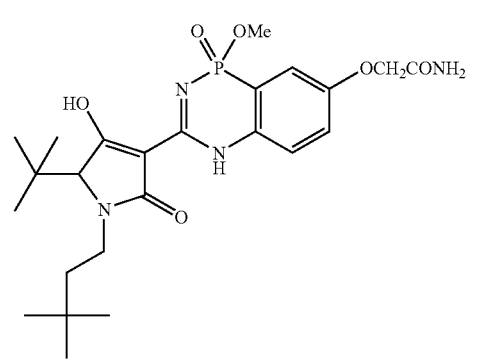
(IV-32)
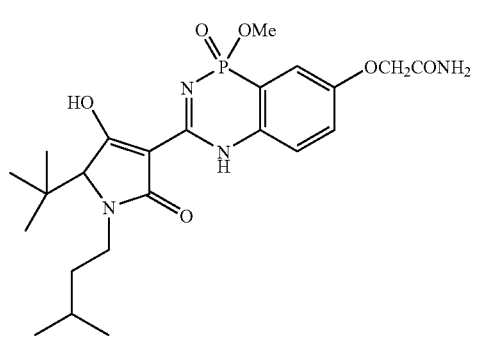
(IV-33)
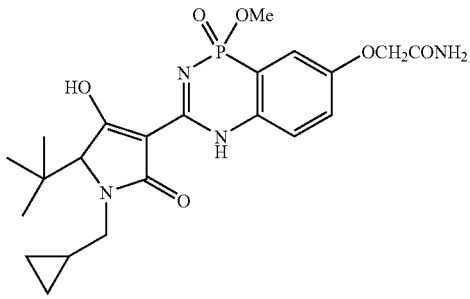
(IV-34)
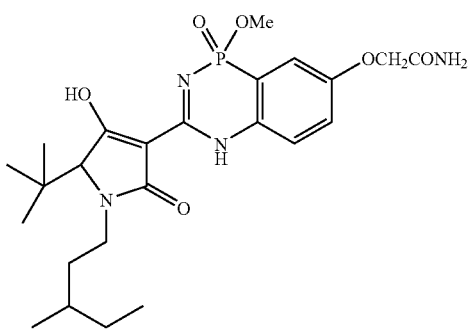
(IV-35)
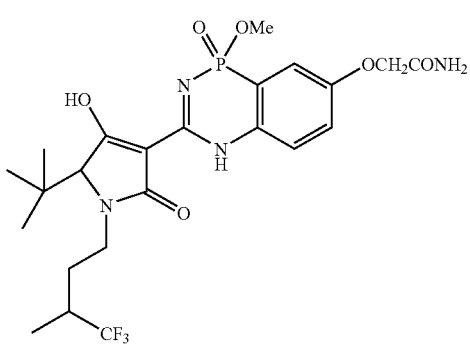
(IV-36)
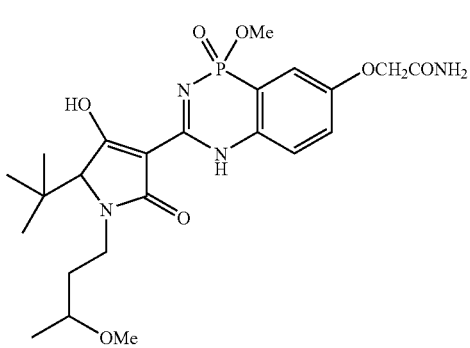
(IV-37)
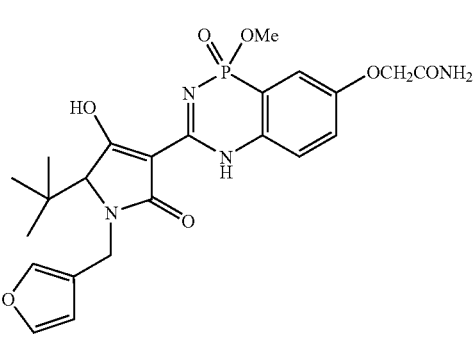

(IV-38)
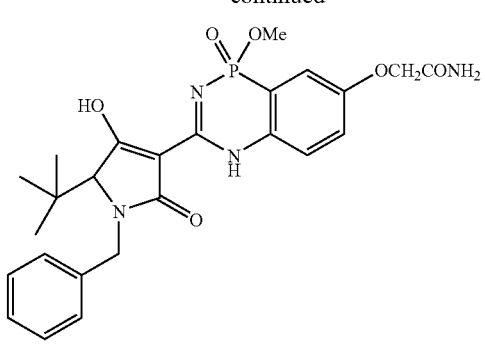
(IV-39)
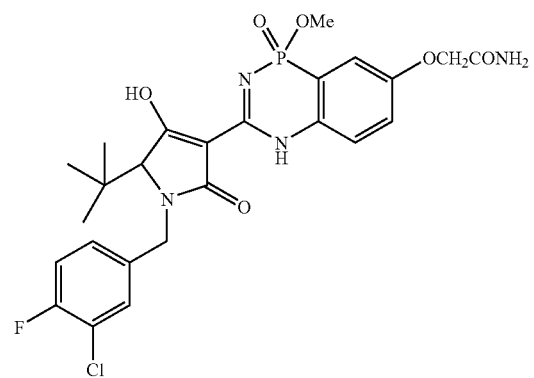
(IV-40)
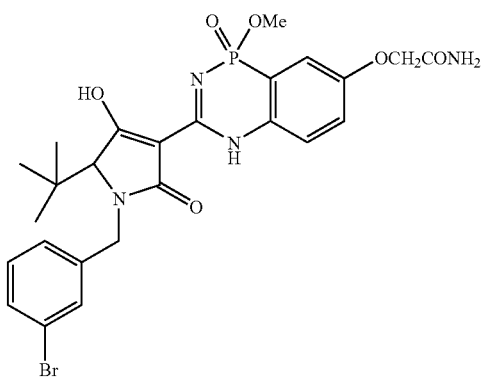
(IV-41)
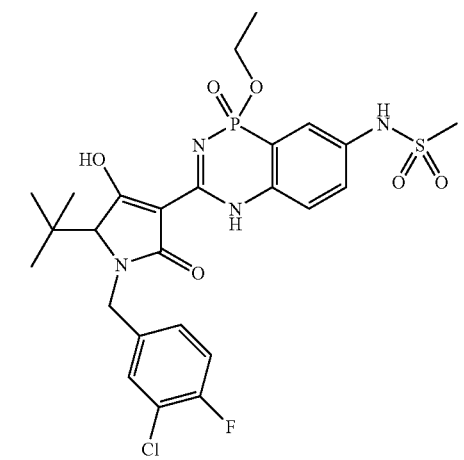
(IV-42)
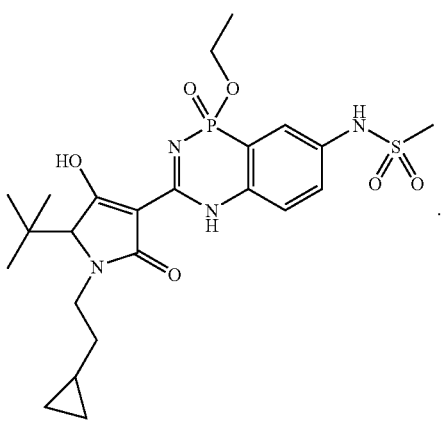
In certain embodiments, provided herein are the following compounds according to formulae IV-43 to IV-59:
(IV-43)
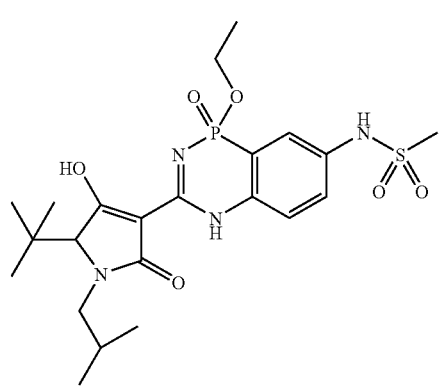
(IV-44)
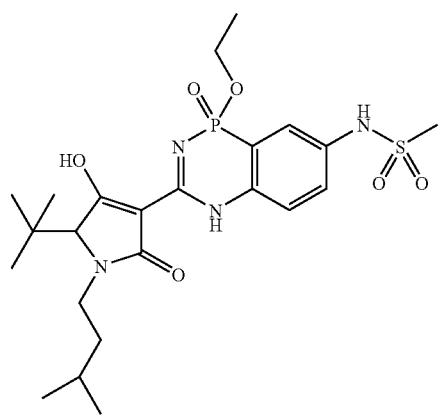

(IV-45)
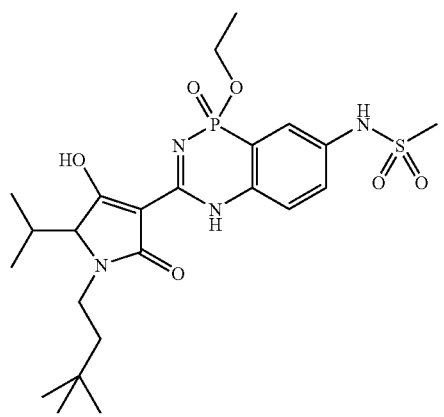
(IV-46)
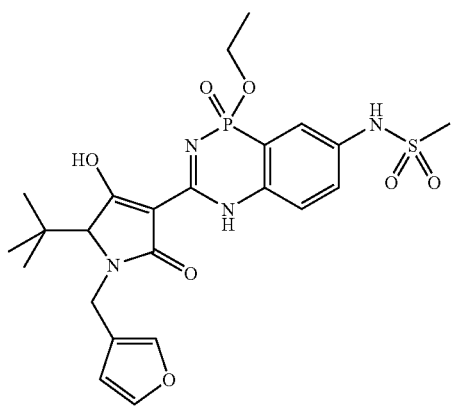
(IV-47)
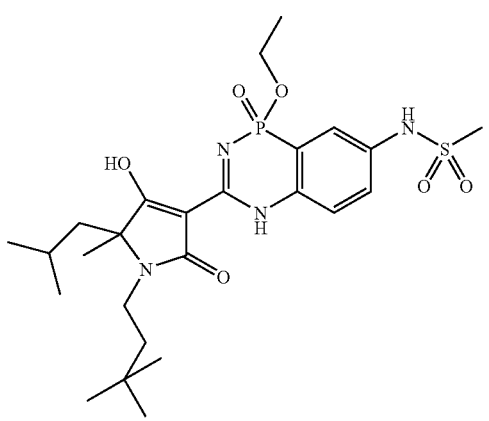
(IV-48)
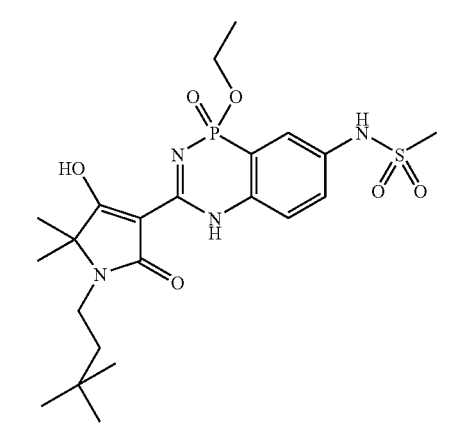
(IV-49)
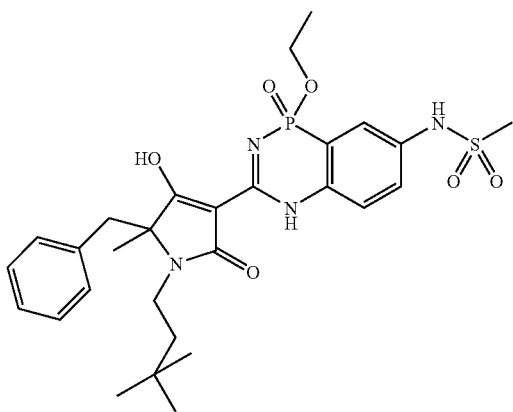
(IV-50)
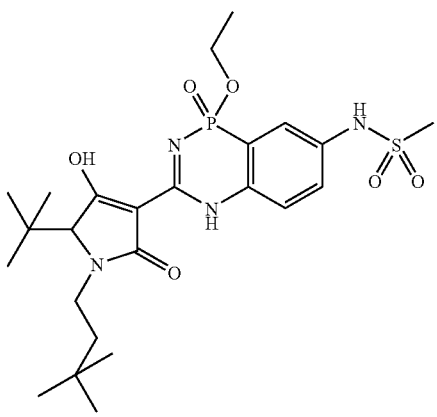
(IV-51)
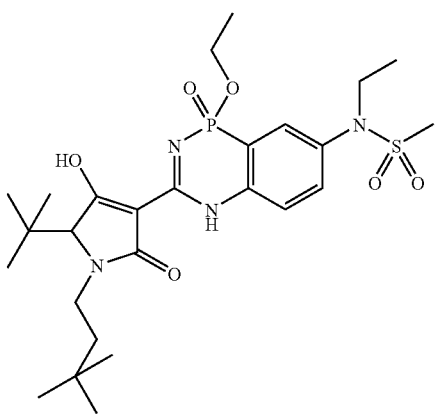

(IV-52)
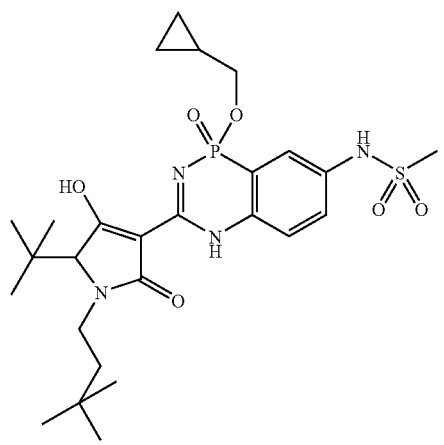
(IV-53)
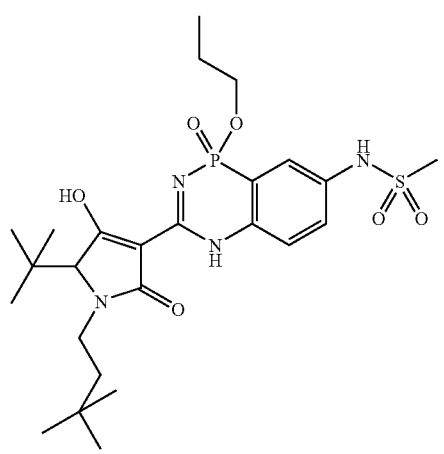
(IV-54)
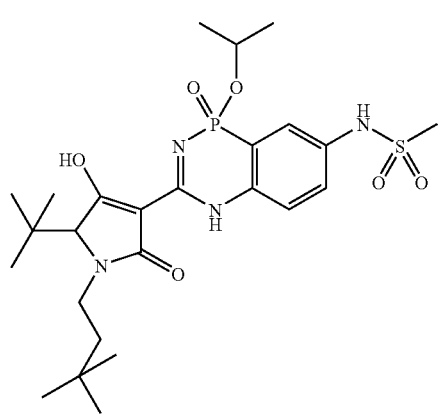
(IV-55)
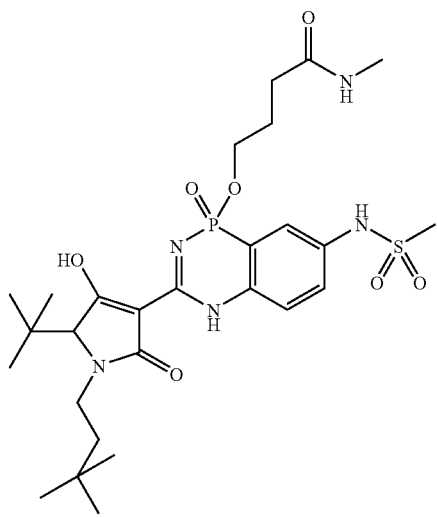
(IV-56)
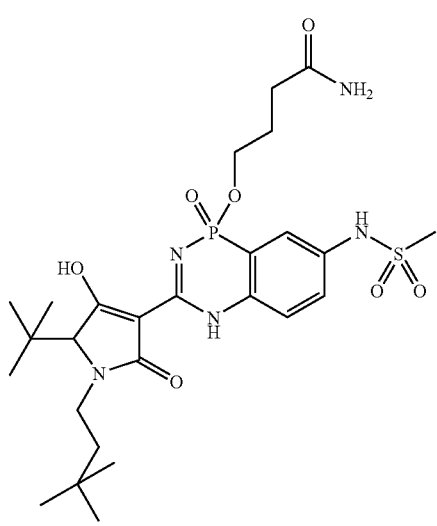
(IV-57)
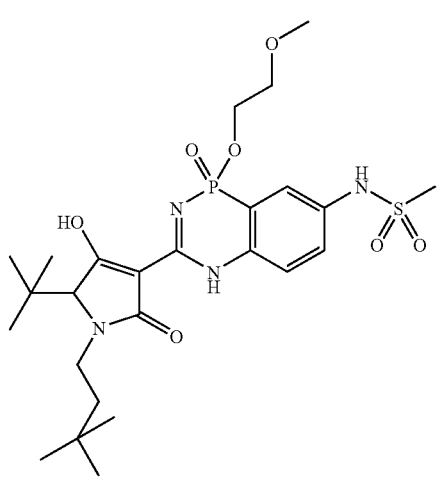

(IV-58)
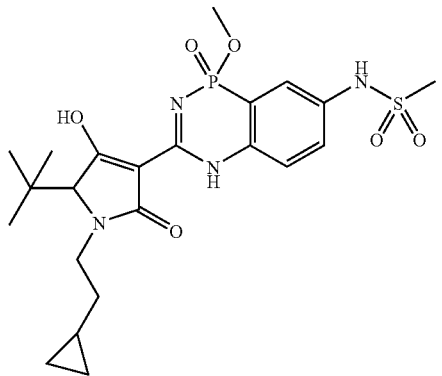
(IV-59)
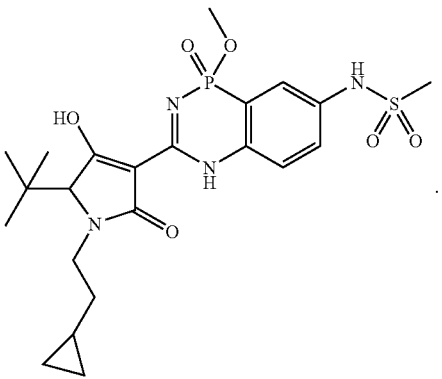
In certain embodiments, provided herein are the following compounds according to formulae IV-60 to IV-75:
(IV-60)
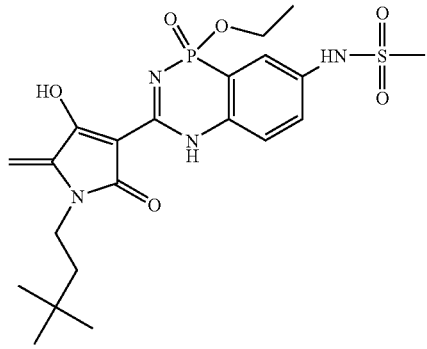
(IV-61)
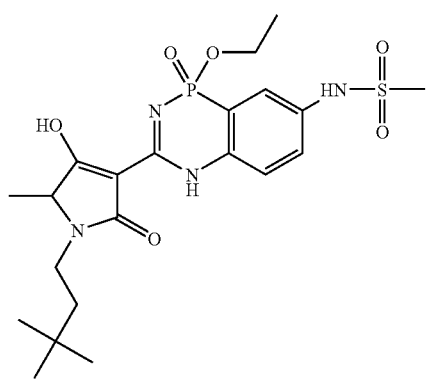
(IV-62)
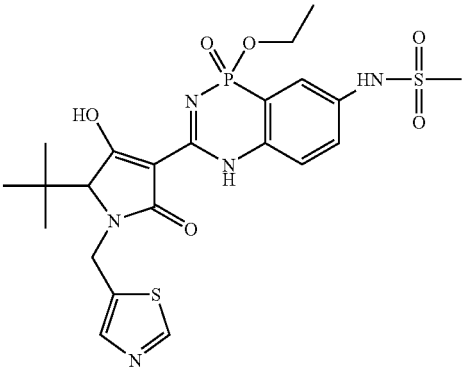
(IV-63)
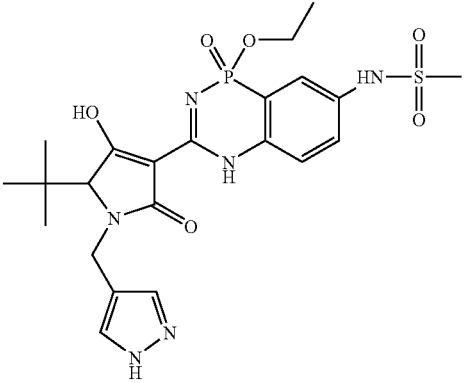
(IV-64)
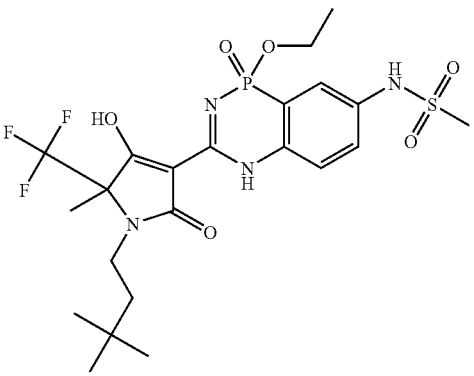
(IV-65)

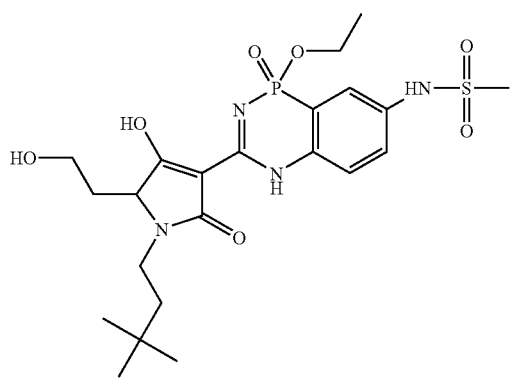
(IV-66)
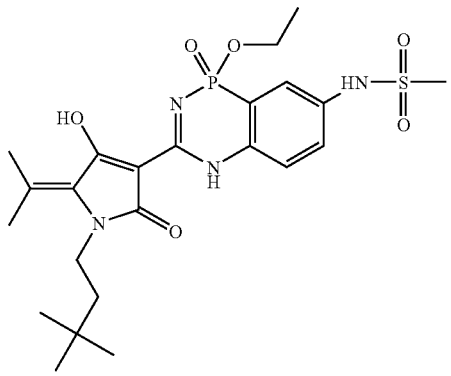
(IV-70)
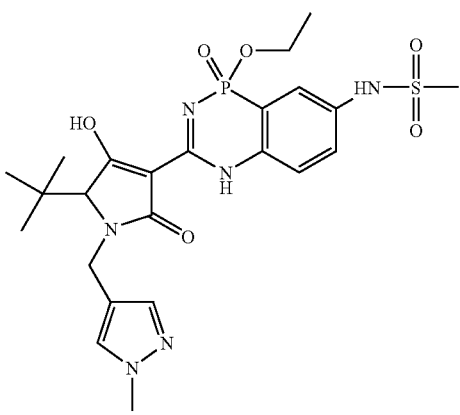
(IV-67)
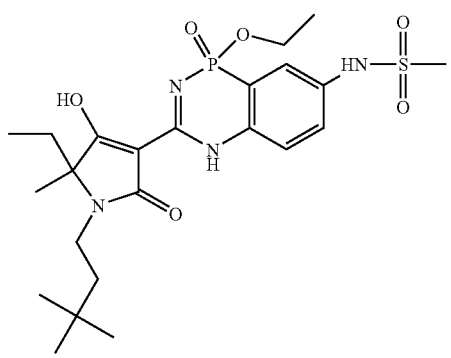
(IV-71)
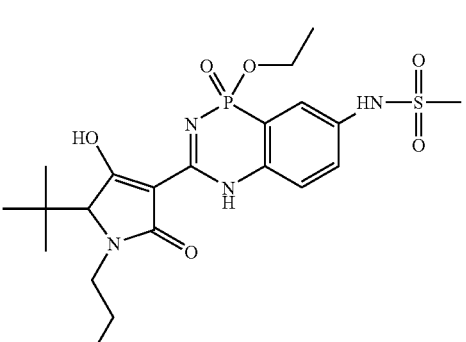
(IV-68)
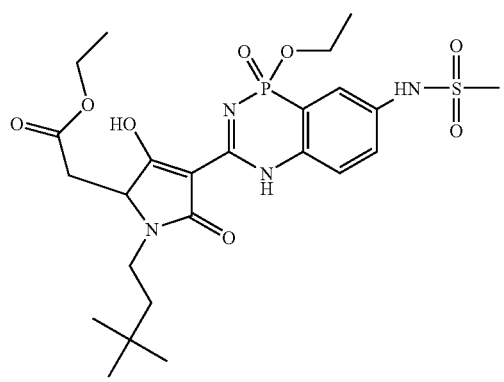
(IV-72)
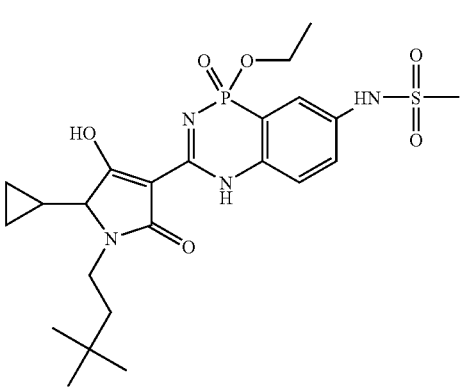
(IV-69)

(IV-74)
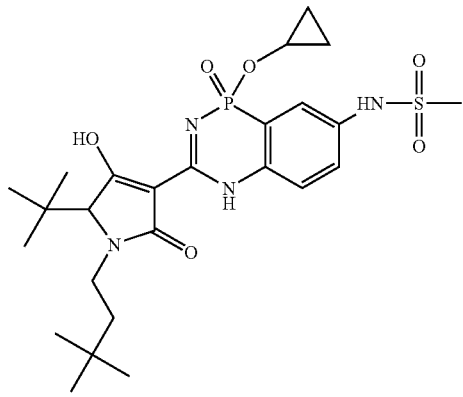
(IV-77)
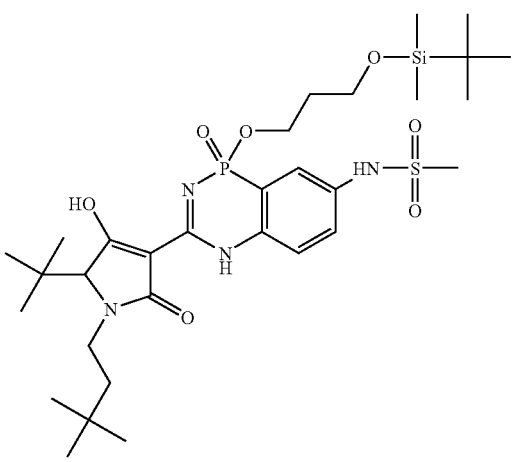
(IV-75)
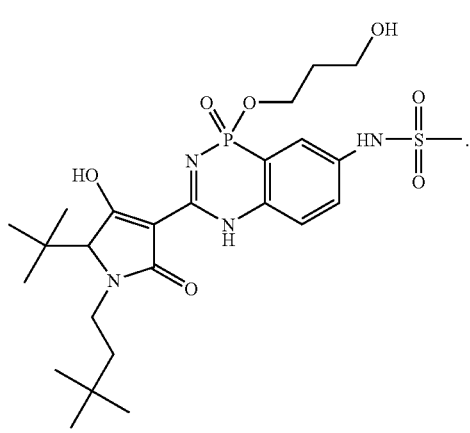
In certain embodiments, provided herein are the following compounds according to formulae IV-76 to IV-87:
(IV-76)
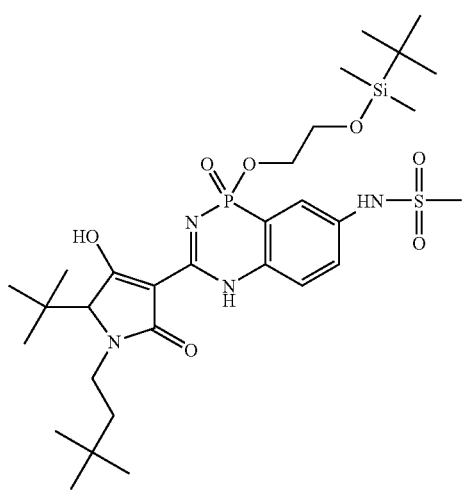
(IV-78)
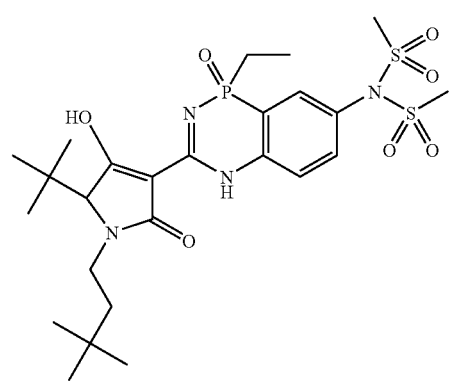
(IV-79)
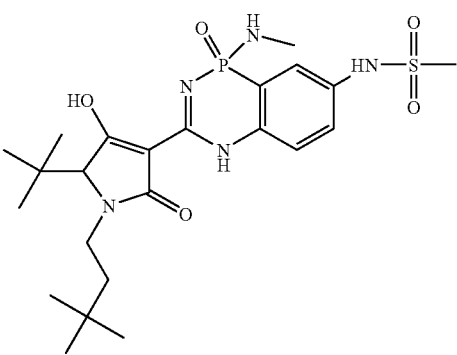
(IV-80)
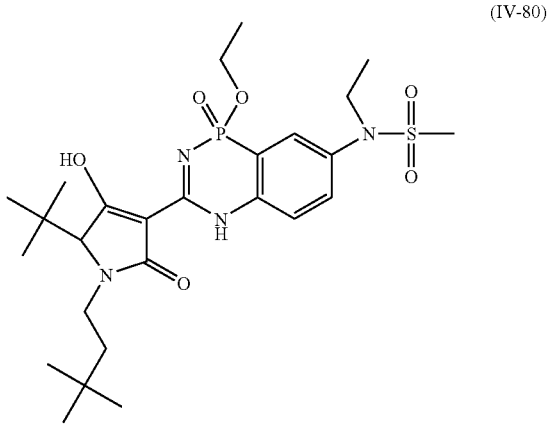

(IV-81)
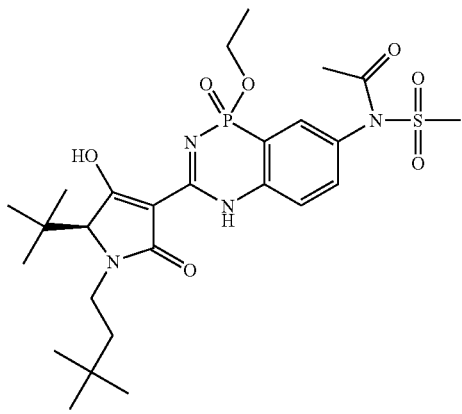
(IV-85)
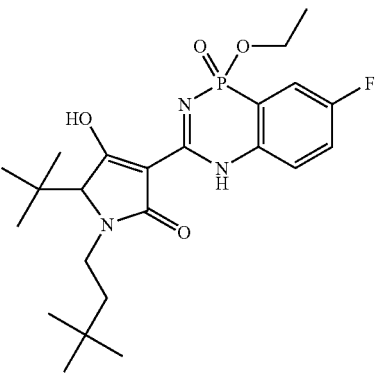
(IV-82)
(IV-86)
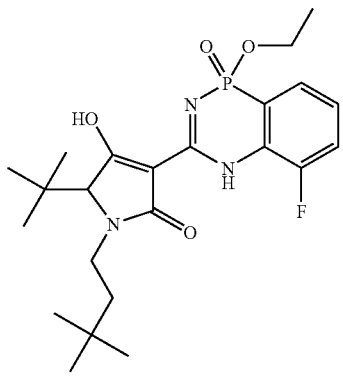
(IV-83)
(IV-87)
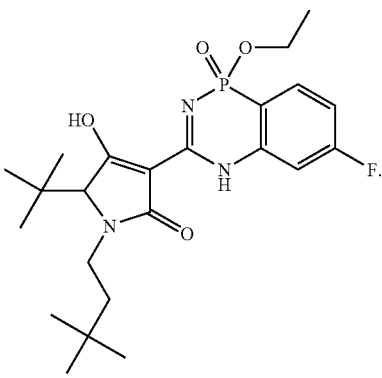
In certain embodiments, provided herein are the following compounds according to formulae IV-88 to IV-102:
(IV-84)
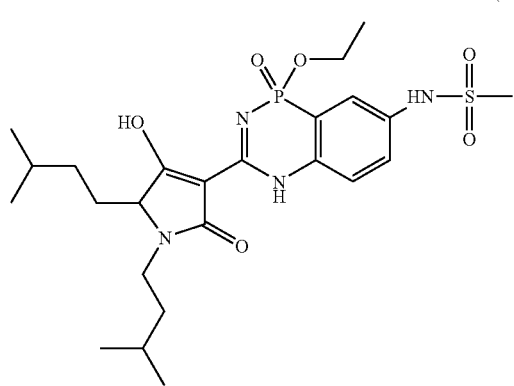
(IV-88)
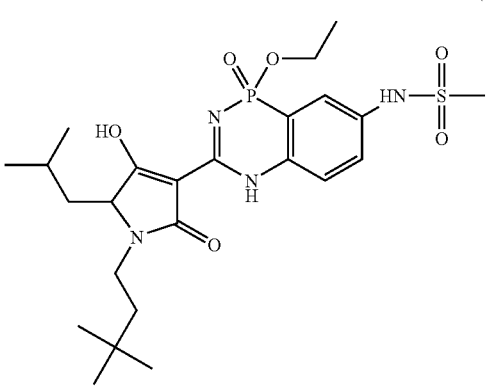

(IV-89)
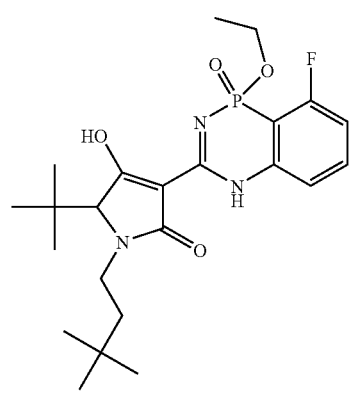
(IV-90)
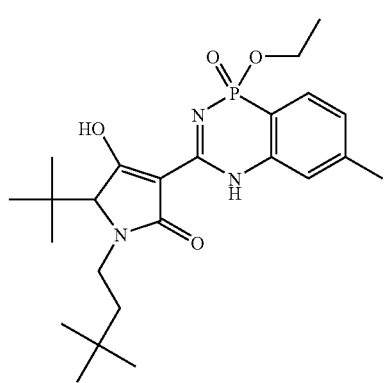
(IV-91)
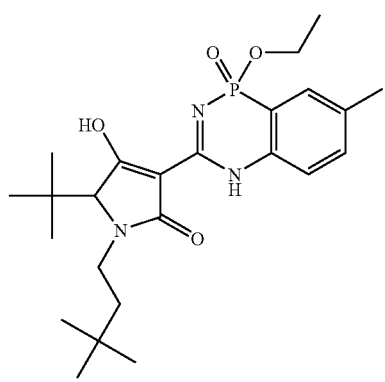
(IV-92)
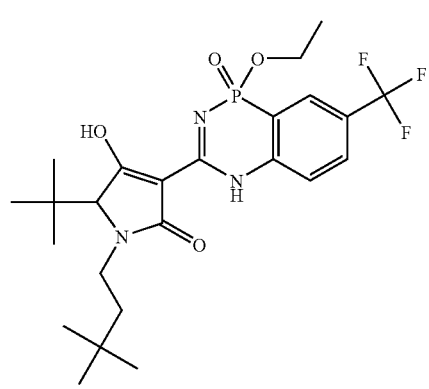
(IV-93)
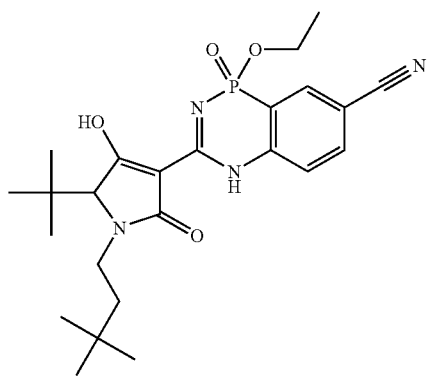
(IV-94)
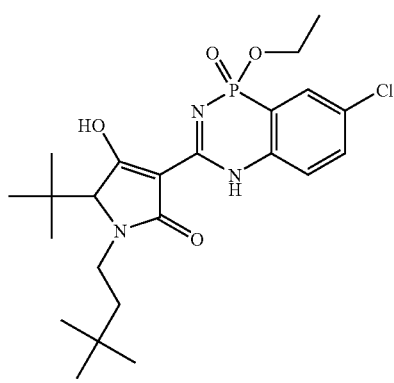
(IV-95)
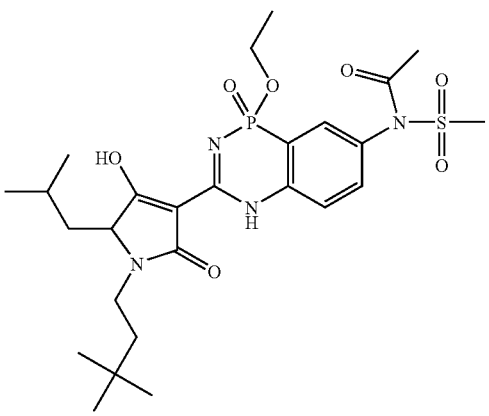
(IV-96)
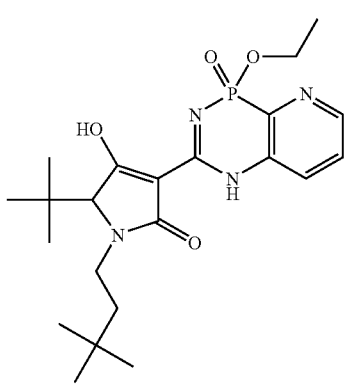

-continued
(IV-97)
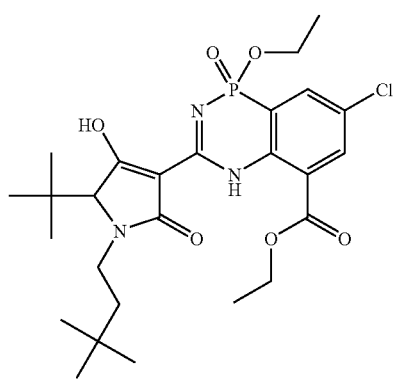
(IV-98)
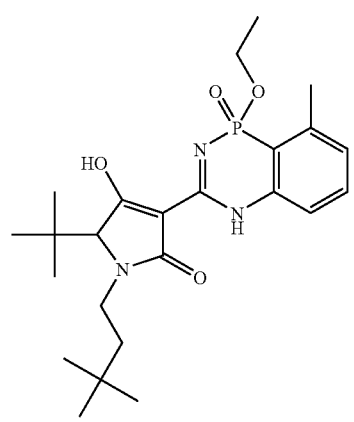
(IV-99)
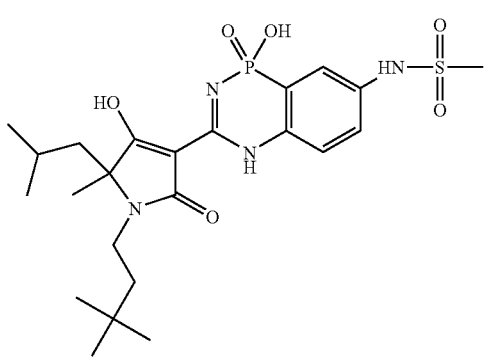
(IV-100)
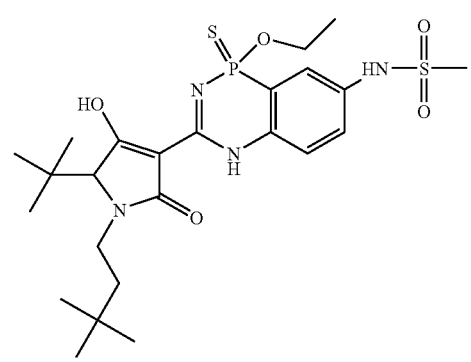
-continued
(IV-101)
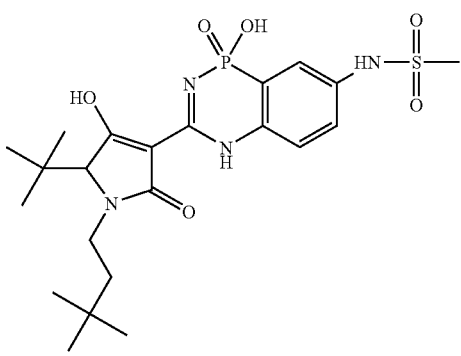
(IV-102)
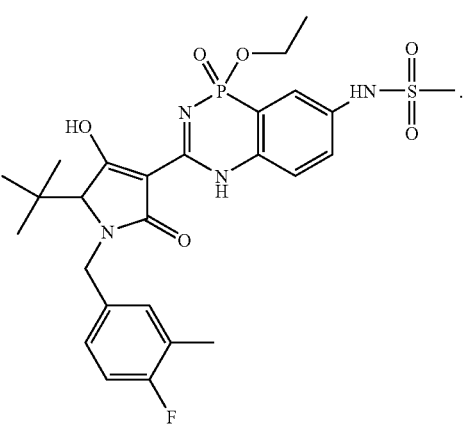
In certain embodiments, provided herein are the following compounds according to formulae IV-103 to IV-114:
(IV-103)
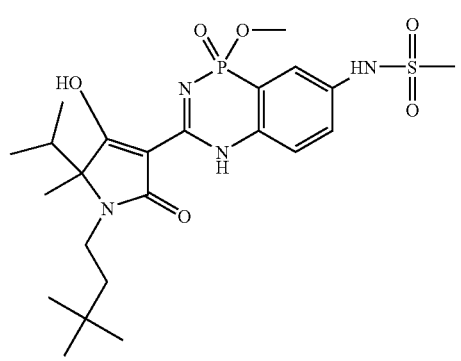
(IV-104)
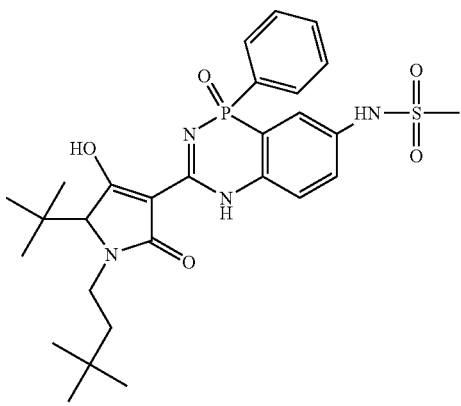

(IV-105)
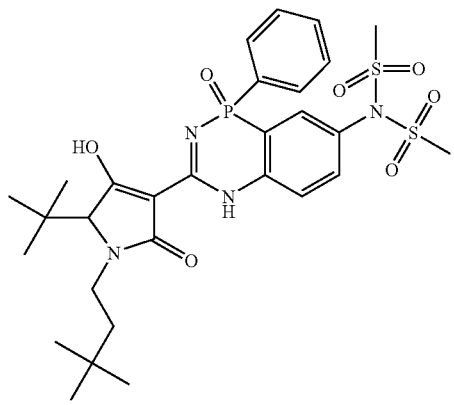
(IV-106)
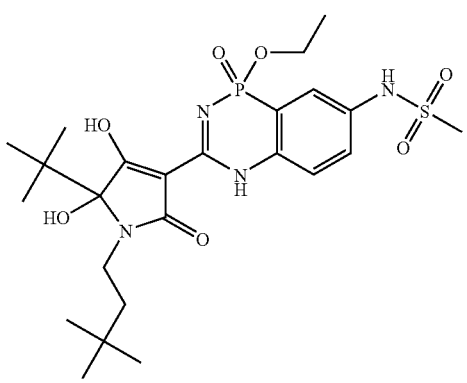
(IV-107)
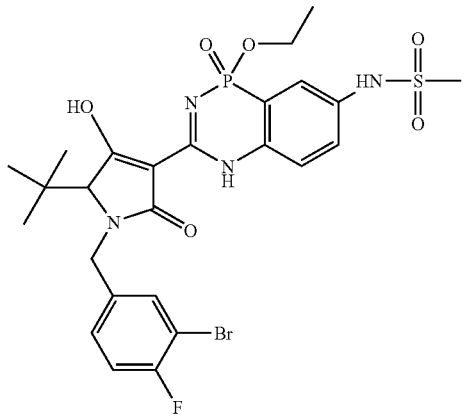
(IV-108)
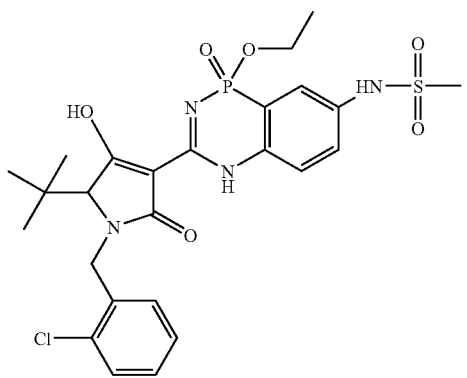
(IV-109)
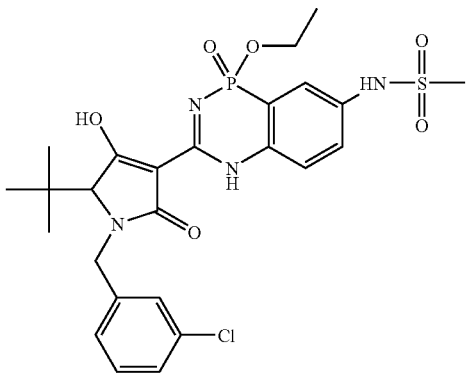
(IV-110)
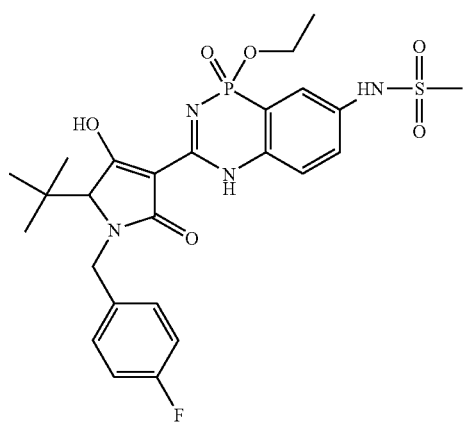
(IV-111)
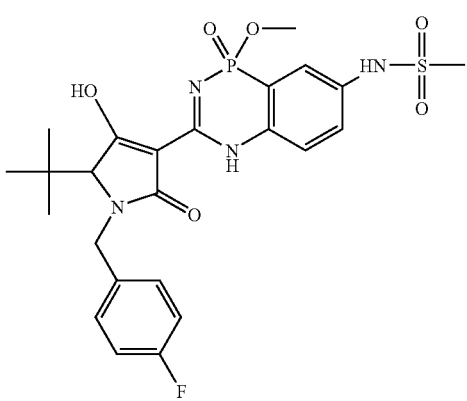
(IV-112)
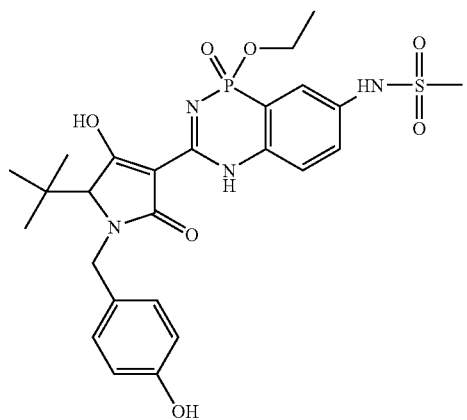

(IV-113)
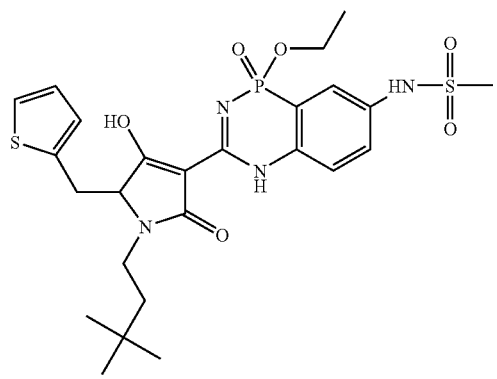
(IV-114)
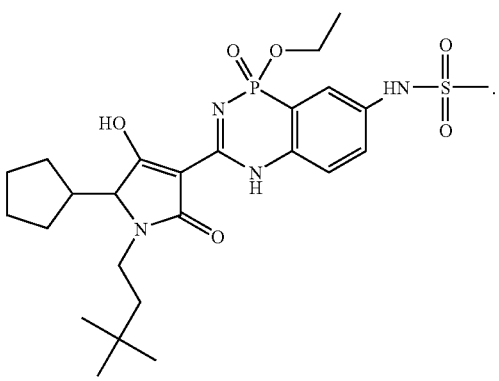
In certain embodiments, provided herein are the following compounds according to formulae IV-115 to IV-129:
(IV-115)
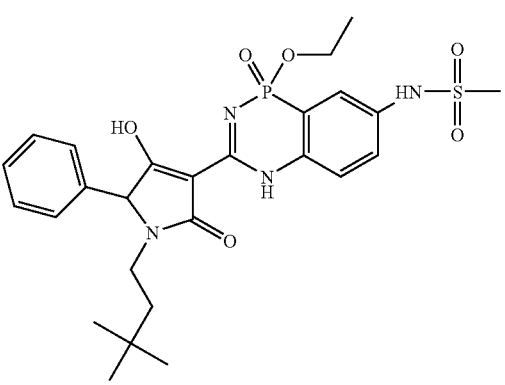
(IV-116)
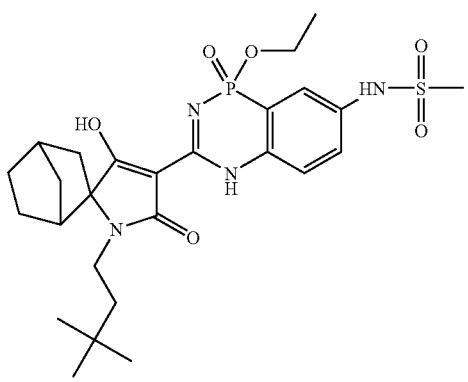
(IV-117)
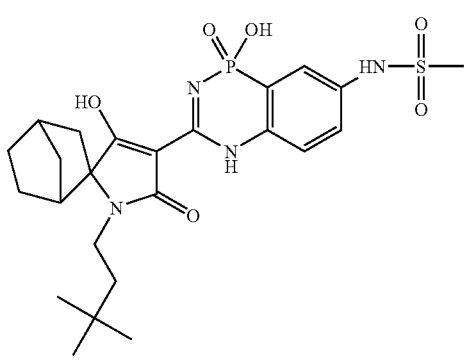
(IV-118)
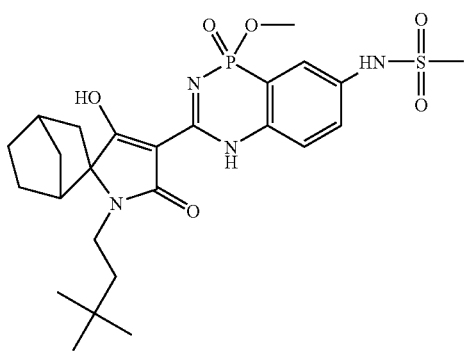
(IV-119)
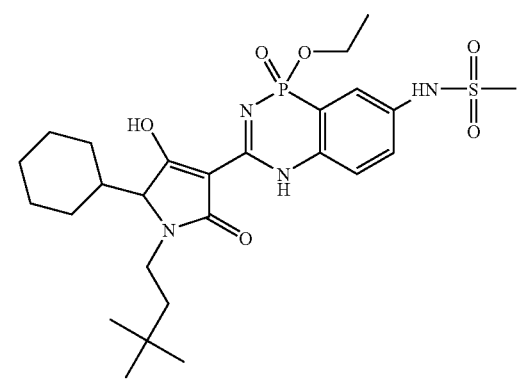

(IV-120)
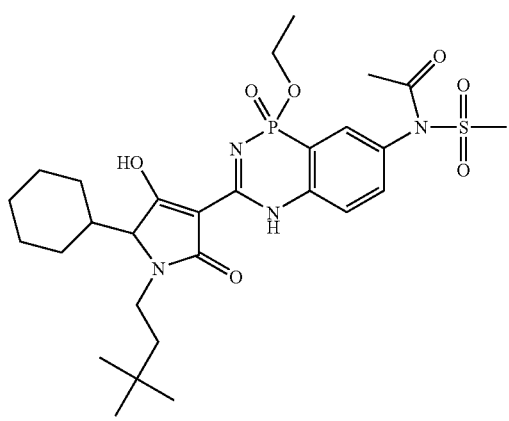
(IV-124)
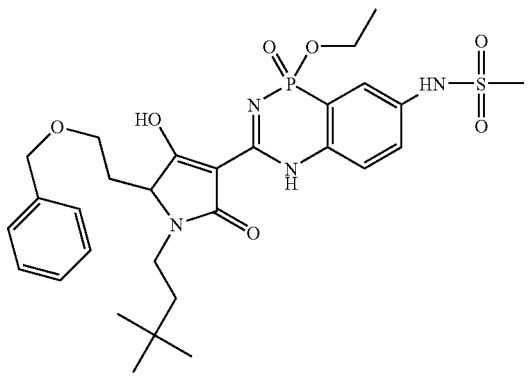
(IV-121)
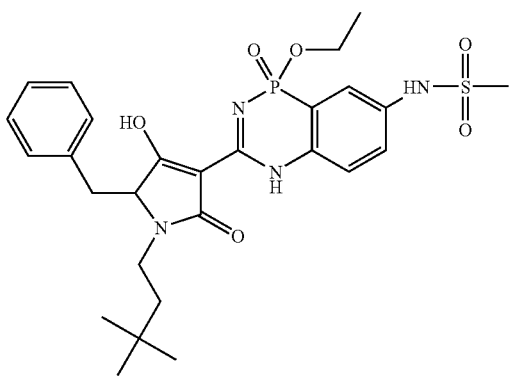
(IV-125)
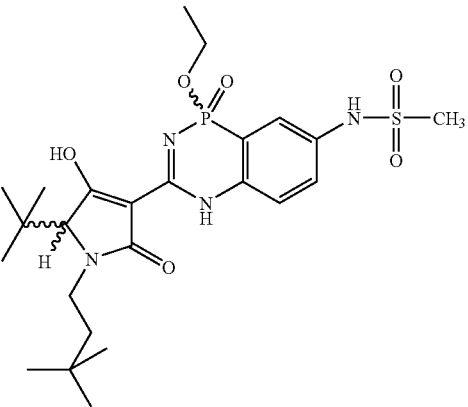
(IV-122)
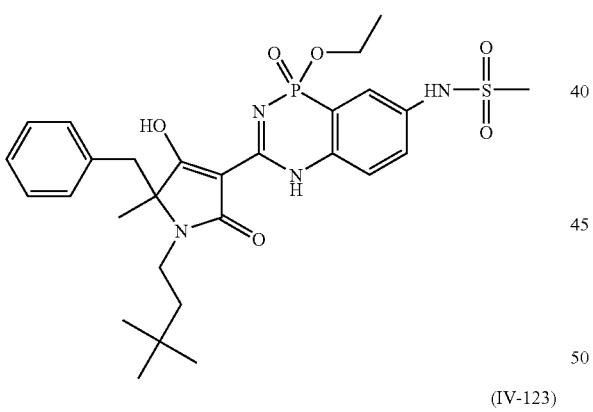
(IV-126)
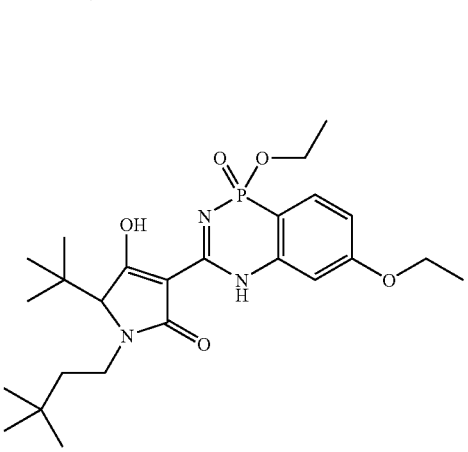
(IV-123)
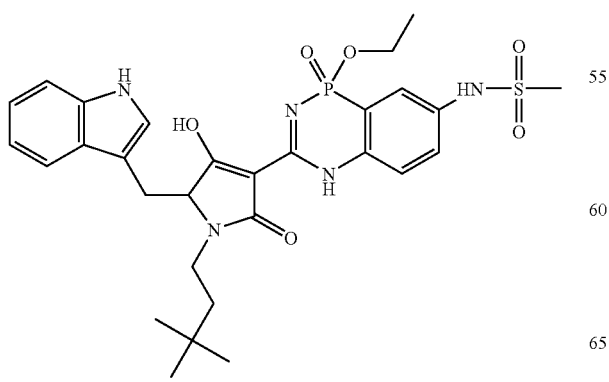
(IV-127)
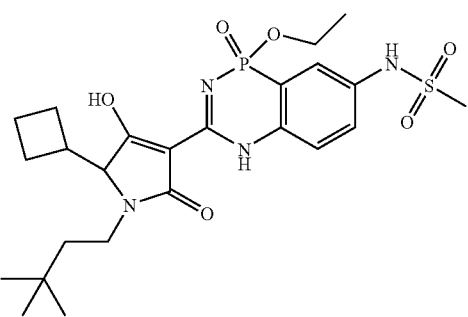

(IV-128)
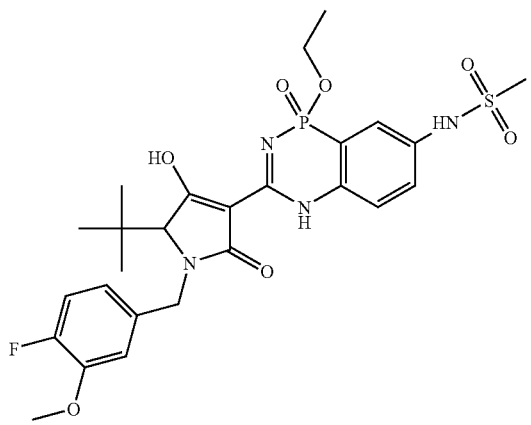
(IV-131)
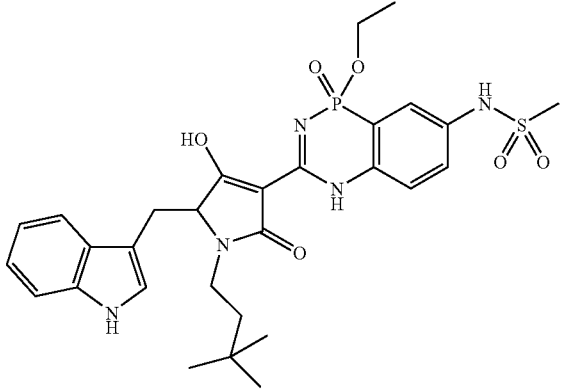
(IV-132)
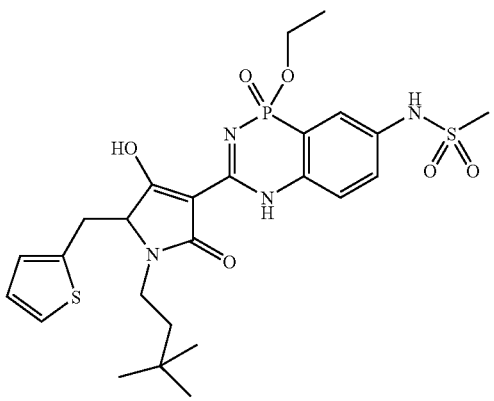
(IV-129)
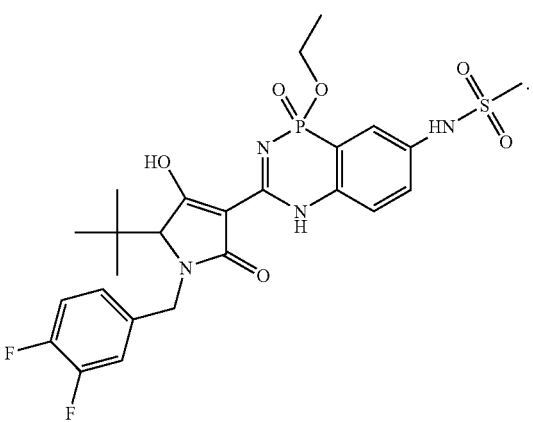
In certain embodiments, provided herein are the following compounds according to formulae IV-130 to IV-147:
(IV-130)
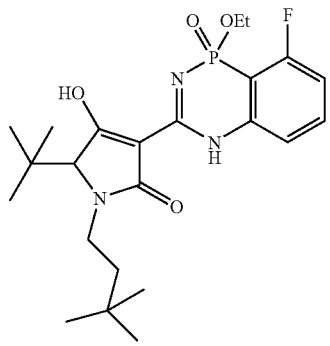
(IV-133)
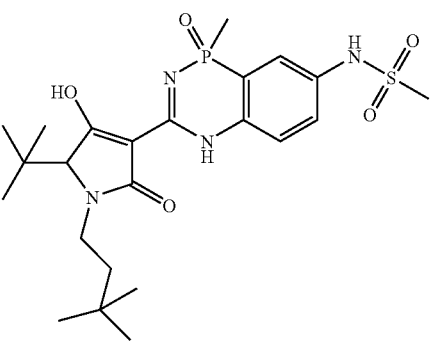
(IV-134)
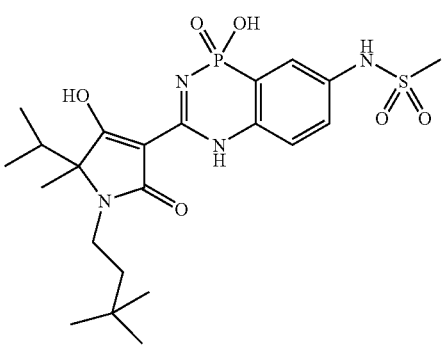

(IV-135)
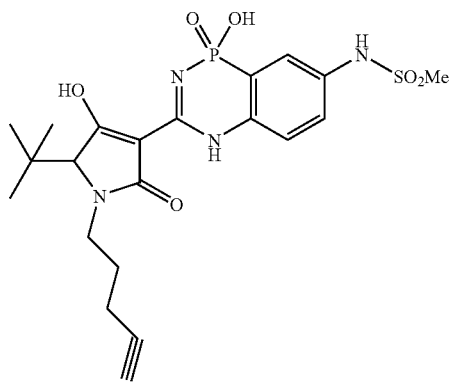
(IV-136)
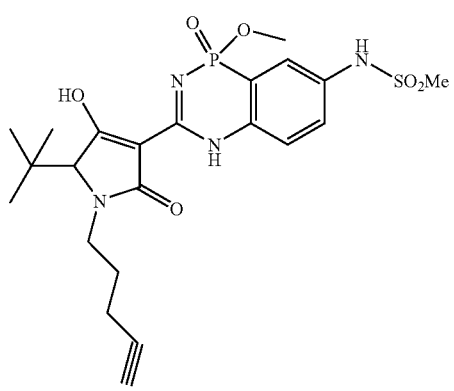
(IV-137)
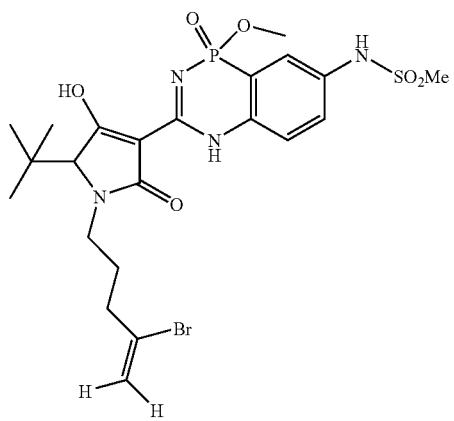
(IV-138)
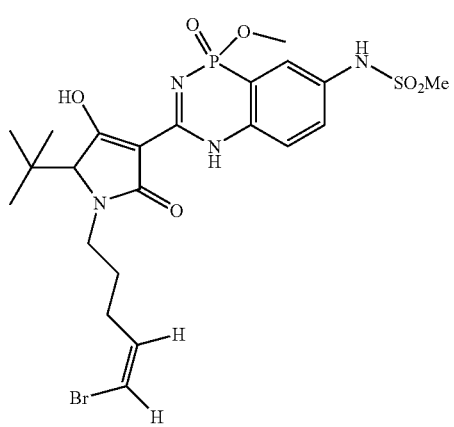
(IV-139)
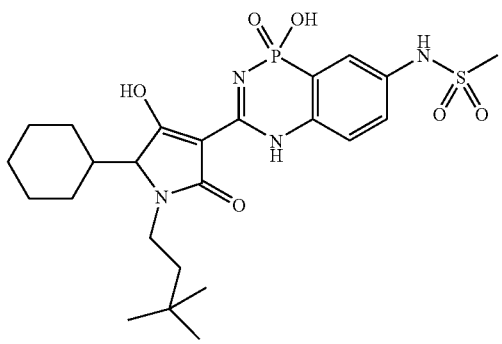
(IV-140)
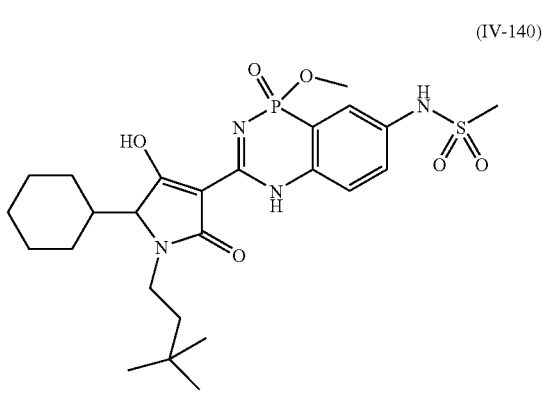
(IV-141)
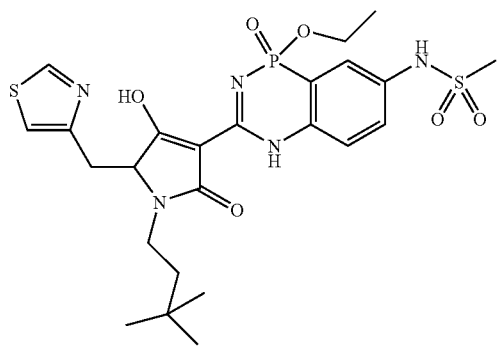
(IV-142)
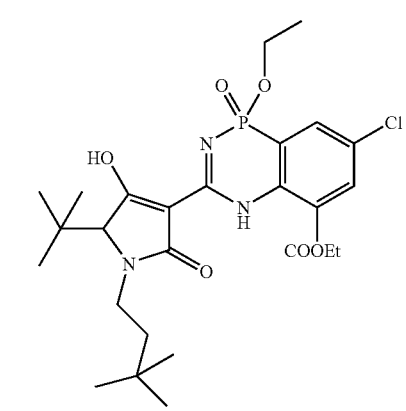

(IV-143)
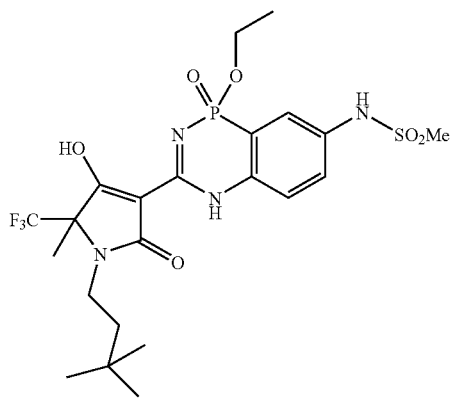
(IV-144)
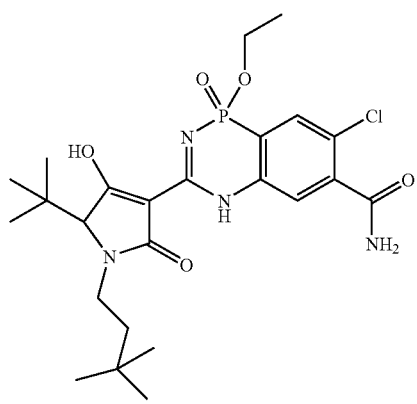
(IV-145)
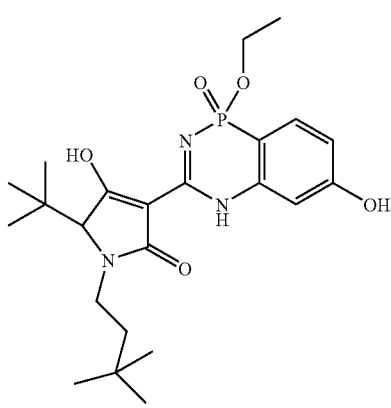
(IV-146)
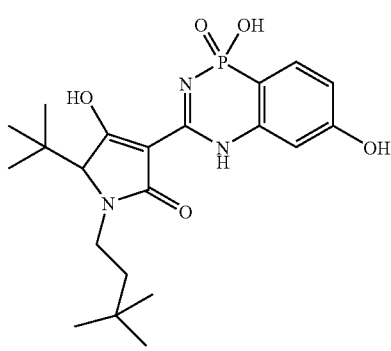
(IV-147)
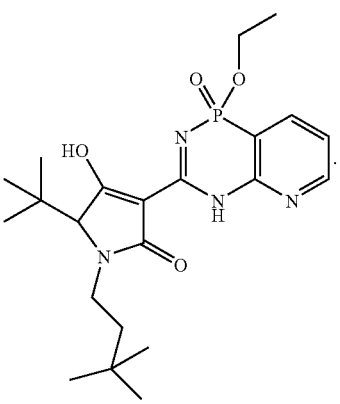
In certain embodiments, provided herein are the following compounds according to formulae IV-148 to IV-162:
(IV-148)
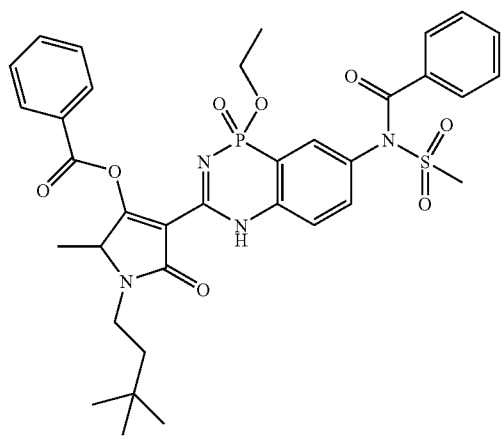
(IV-149)
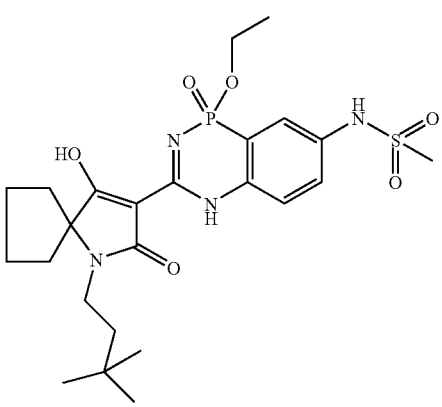

(IV-150)
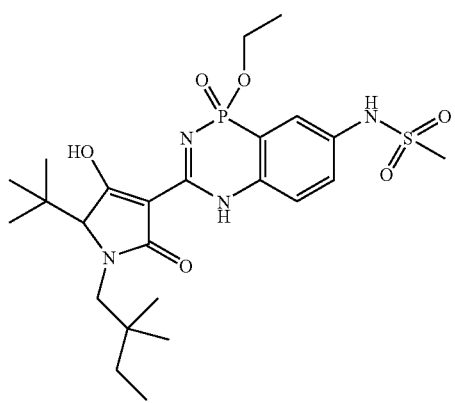
(IV-153)
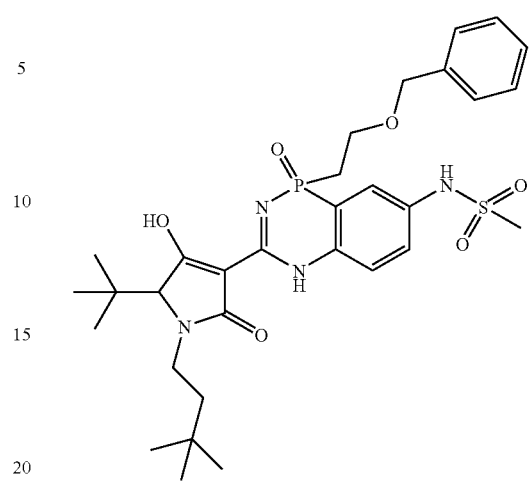
(IV-151)
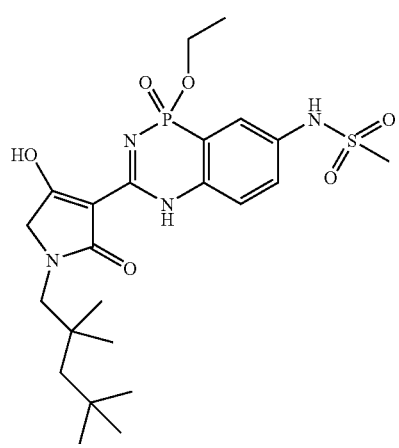
(IV-154)
(IV-155)
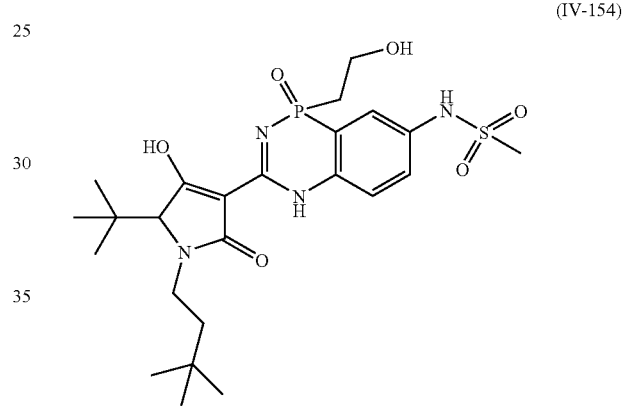
(IV-152)
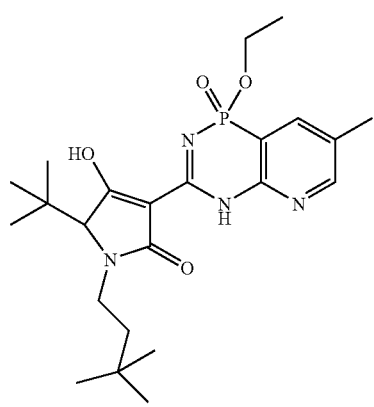
(IV-156)
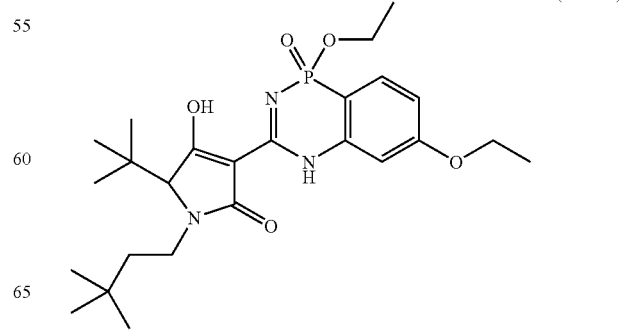

(IV-157)
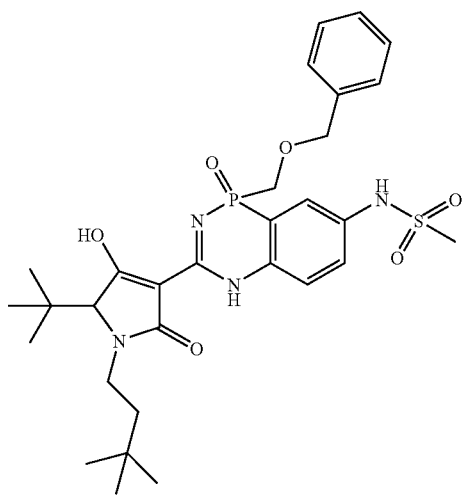
(IV-158)
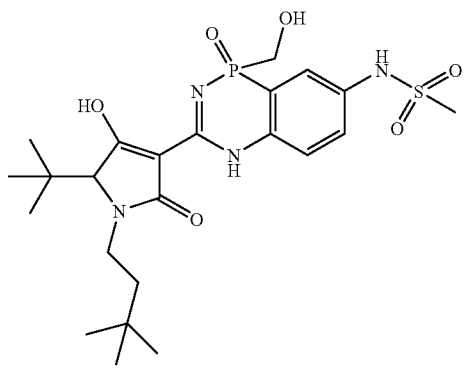
(IV-159)
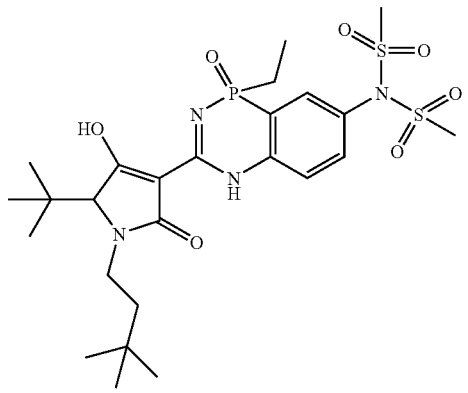
(IV-160)
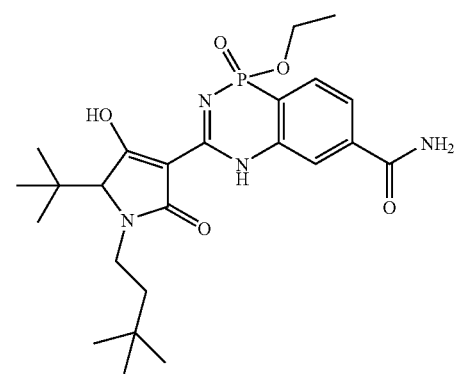
(IV-161)
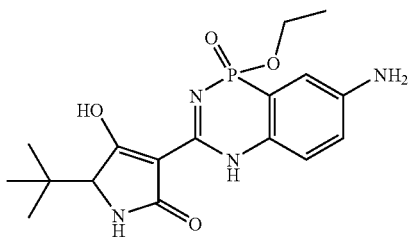
(IV-162)
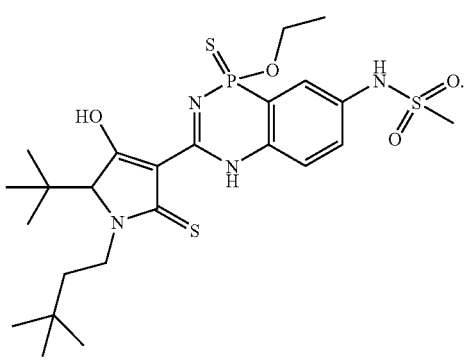
In certain embodiments, provided herein are the following compounds according to formulae IV-163 to IV-166:
(IV-163)
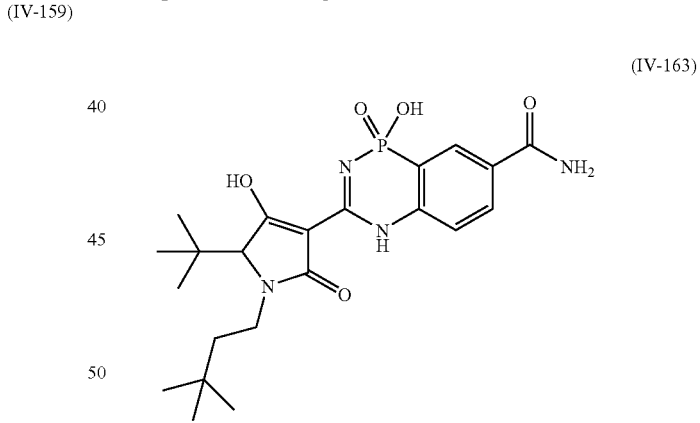
(IV-164)
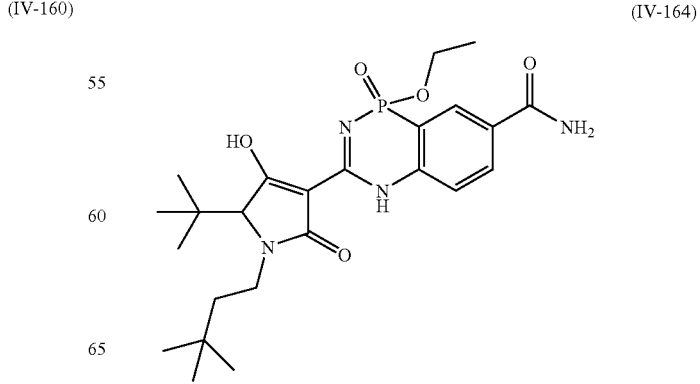

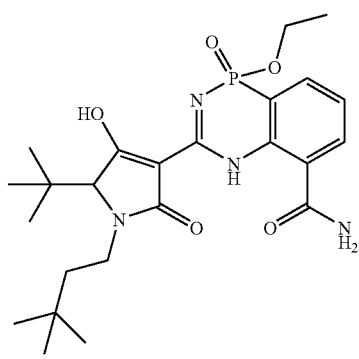
(IV-165)

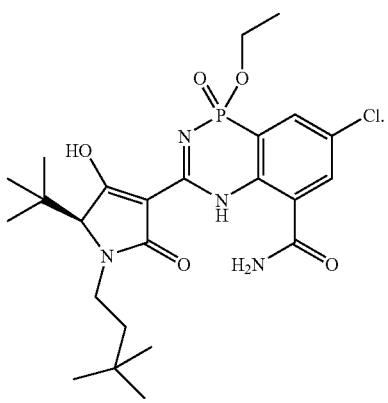
(IV-166)

The compounds provided herein are intended to encompass all possible stereoisomers, unless a particular stereochemistry is specified. Where the compound provided herein contains an alkenyl or alkenylene group, the compound may exist as one or mixture of geometric cis/trans (or Z/E) isomers. Where structural isomers are interconvertible via a low energy barrier, the compound may exist as a single tautomer or a mixture of tautomers. This can take the form of proton tautomerism in the compound that contains, for example, an imino, keto, or oxime group; or so-called valence tautomerism in the compound that contain an aromatic moiety. It follows that a single compound may exhibit more than one type of isomerism.

The compounds provided herein may be enantiomerically pure, such as a single enantiomer or a single diastereomer, or be stereoisomeric mixtures, such as a mixture of an enantiomeric pair, a racemic mixture, or a diastereomeric mixture. As such, one of skill in the art will recognize that administration of a compound in its (R) form is equivalent, for compounds that undergo epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When the compound provided herein contains an acidic or basic moiety, it may also be provided as a pharmaceutically acceptable salt (See, Berge et al., *J. Pharm. Sci.* 1977, 66, 1-19; and "Handbook of Pharmaceutical Salts, Properties, and Use," Stahl and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound provided herein may also be provided as a prodrug, which is a functional derivative of the compound, for example, of Formula IV, IV', I'', II'', or IVa and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol,* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

Methods of Synthesis

The compound provided herein can be prepared, isolated, or obtained by any method known to one of skill in the art. For an example, a compound of Formula I can be prepared as shown in Scheme 1.

A compound of Formula IV can be prepared as shown in Scheme 1.

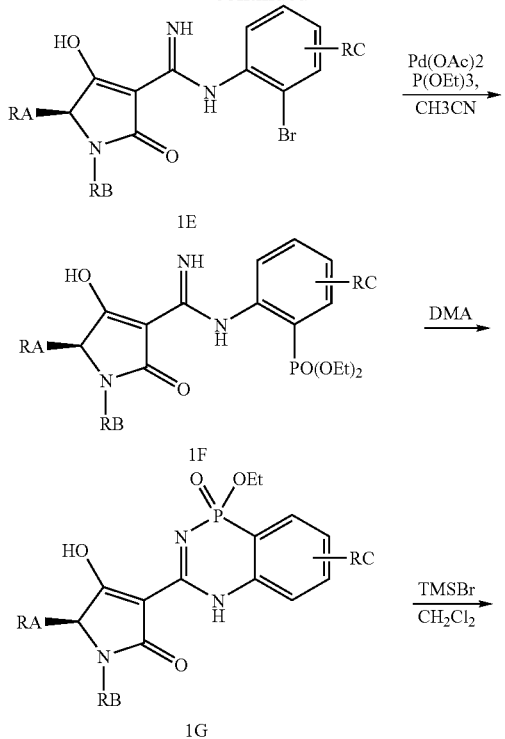

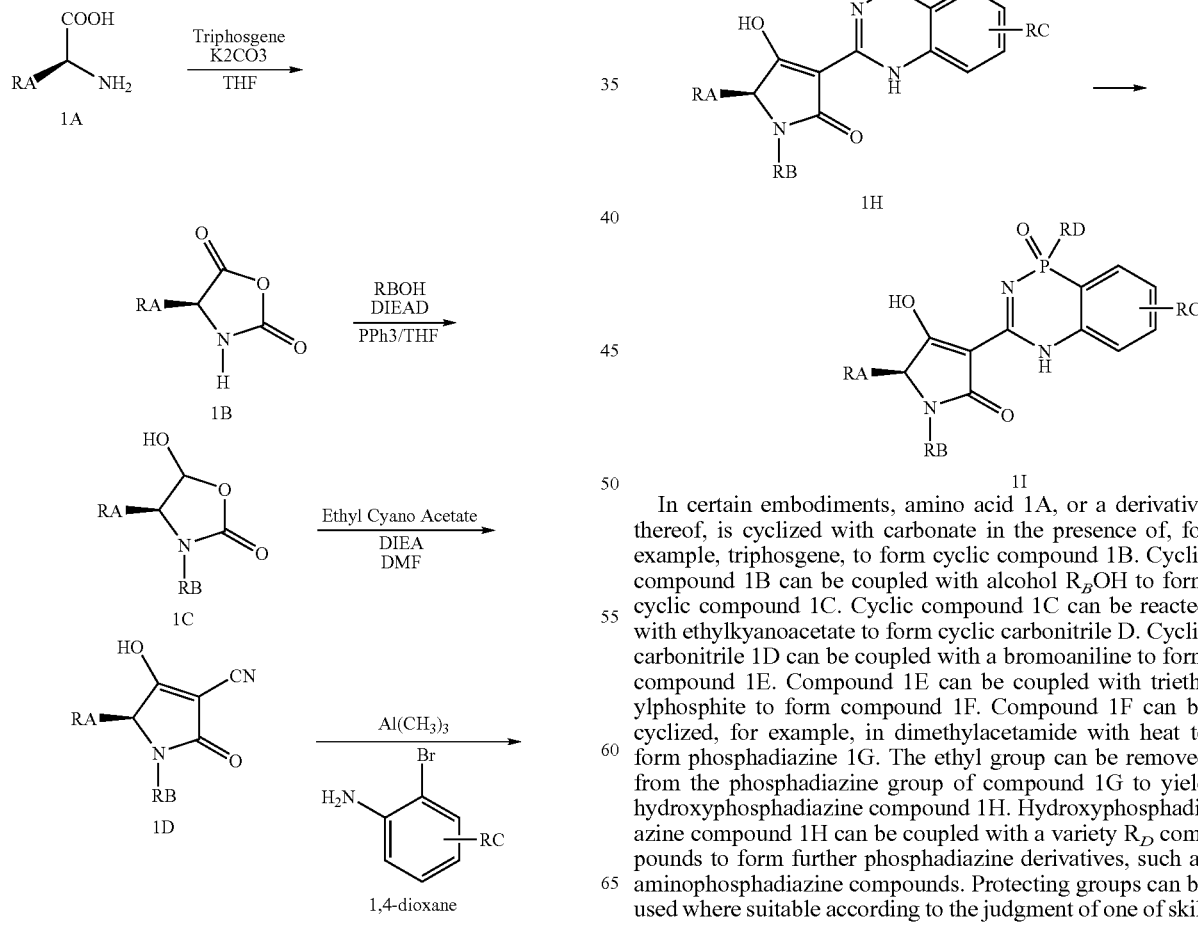

In certain embodiments, amino acid 1A, or a derivative thereof, is cyclized with carbonate in the presence of, for example, triphosgene, to form cyclic compound 1B. Cyclic compound 1B can be coupled with alcohol $R_BOH$ to form cyclic compound 1C. Cyclic compound 1C can be reacted with ethylkyanoacetate to form cyclic carbonitrile D. Cyclic carbonitrile 1D can be coupled with a bromoaniline to form compound 1E. Compound 1E can be coupled with triethylphosphite to form compound 1F. Compound 1F can be cyclized, for example, in dimethylacetamide with heat to form phosphadiazine 1G. The ethyl group can be removed from the phosphadiazine group of compound 1G to yield hydroxyphosphadiazine compound 1H. Hydroxyphosphadiazine compound 1H can be coupled with a variety $R_D$ compounds to form further phosphadiazine derivatives, such as aminophosphadiazine compounds. Protecting groups can be used where suitable according to the judgment of one of skill in the art.

A compound of Formula IV can be prepared as shown in Scheme 2.
Scheme 2
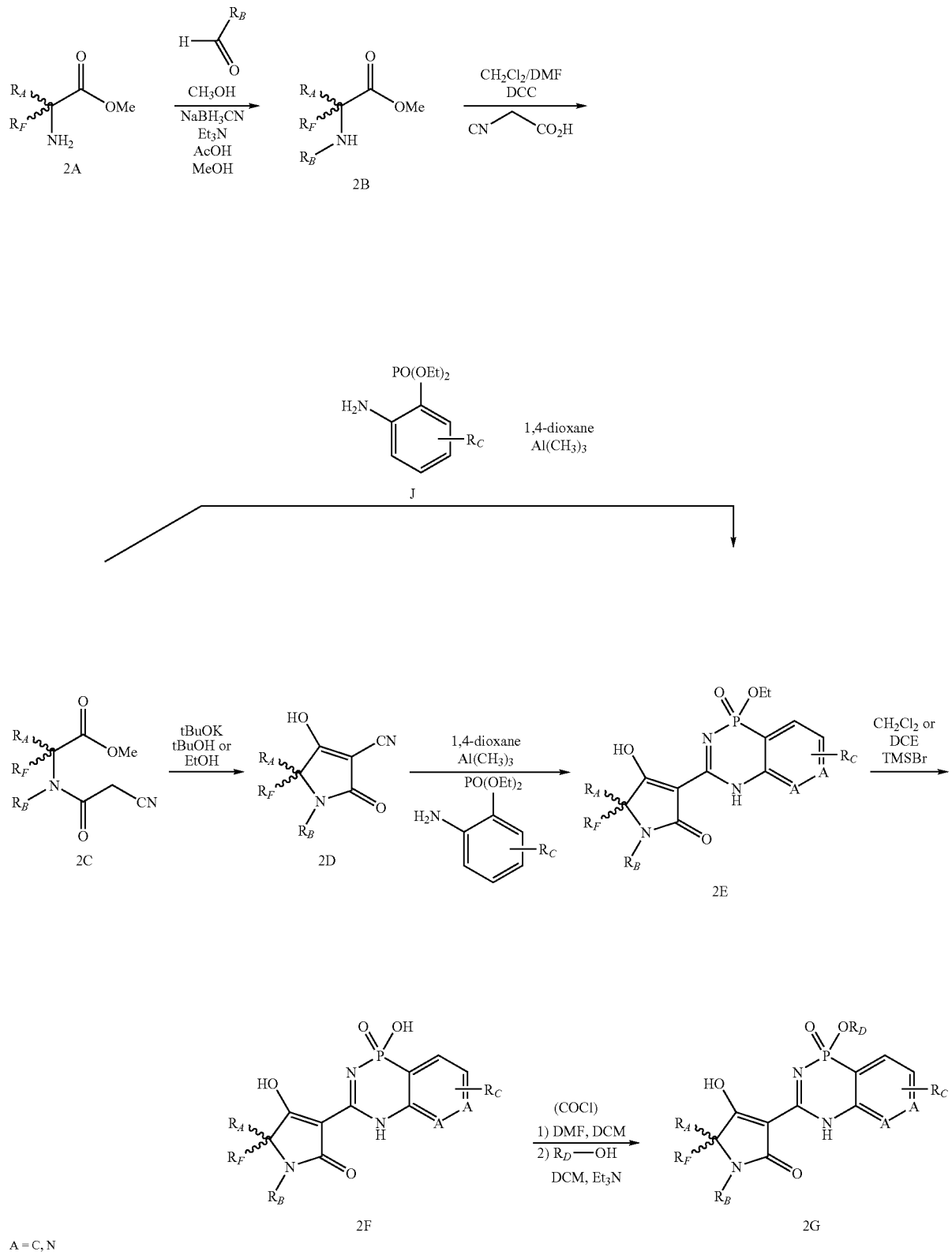
A = C, N In certain embodiments, compound 2A, or a derivative thereof, can react with an aldehyde in the presence of, for example, methanol, sodium cyanohydridoborate, triethylamine, and acetic acid, to form compound 2B. Compound 2B can couple with cyanoacetic acid in the presence of, for example, dichloromethane, dimethylformamide (DMF) and dicyclohexylcarbodiimide (DCC), to form compound 2C. Compound 2C can be cyclized by potassium tert-butoxide in the presence of tert-butanol or ethanol to form cyclic carbonitrile 2D. Cyclic carbonitrile 2D can couple with phosphoaniline compound, i.e., diethyl (1-aminophenyl)phosphonates, in the presence, for example, dioxane and trimethylaluminum, to form phosphadiazine 2E. The ethyl group of the phosphadiazine group of phosphadiazine 2E can be removed to yield hydroxyphosphadiazine 2F. Hydroxyphosphadiazine 2F can couple with a variety $R_D$ compounds to form further phosphadiazine derivatives 2G, such as aminophosphadiazine compounds. In certain embodiments, intermediate compound 2E can be converted from intermediate compound 2C directly by reacting with compound J in the presence of, for example, 1,2-dioxane and trimethyl aluminum. Protecting groups can be used where suitable according to the judgment of one of skill in the art.

A compound of Formula IV can be prepared as shown in Scheme 3.

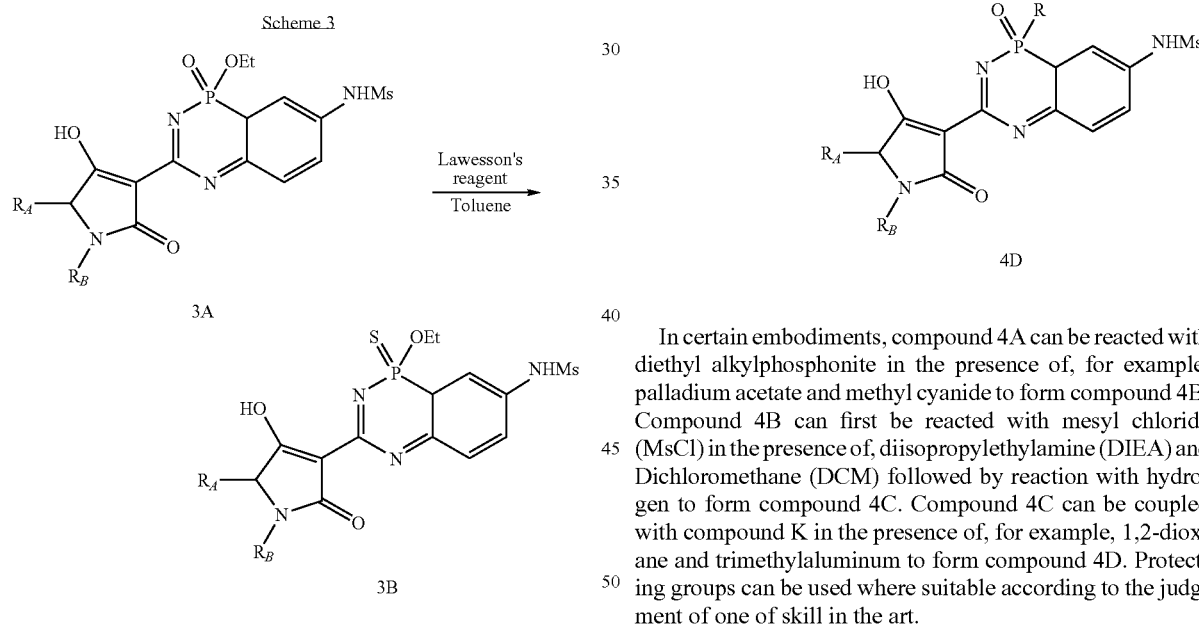

In certain embodiments, the oxygen in the phosphadiazine group of compound 3A can be replaced by sulfur by reacting with Lawesson's reagent and toluene to form compound 3B.

A compound of Formula IV can be prepared as shown in Schemes 4A and 4B.

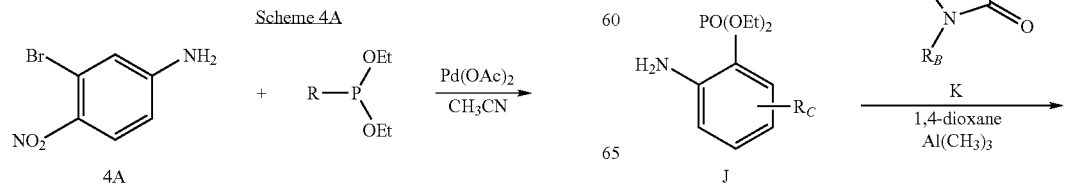

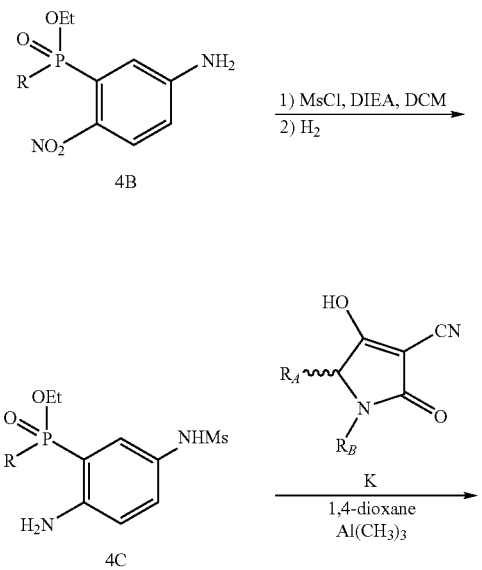

In certain embodiments, compound 4A can be reacted with diethyl alkylphosphonite in the presence of, for example, palladium acetate and methyl cyanide to form compound 4B. Compound 4B can first be reacted with mesyl chloride (MsCl) in the presence of, diisopropylethylamine (DIEA) and Dichloromethane (DCM) followed by reaction with hydrogen to form compound 4C. Compound 4C can be coupled with compound K in the presence of, for example, 1,2-dioxane and trimethylaluminum to form compound 4D. Protecting groups can be used where suitable according to the judgment of one of skill in the art.

-continued

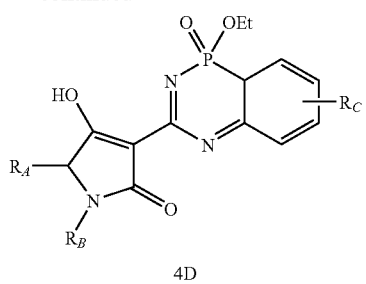

4D

In certain embodiments, Compound J can be coupled with compound K in the presence of, for example, 1,2-dioxane and trimethylaluminum to form compound 4D.

A compound of Formula IV can be prepared as shown in Scheme 5.

Scheme 5

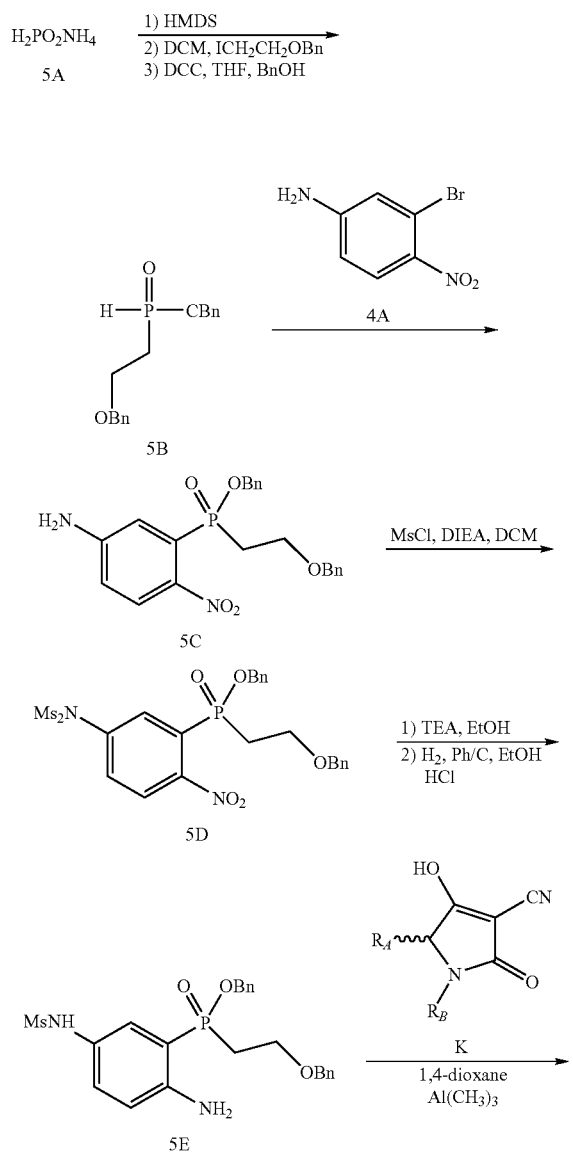

-continued

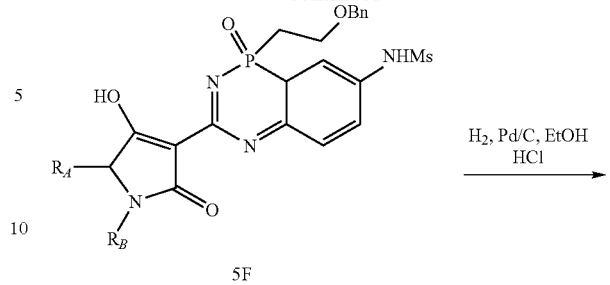

5F

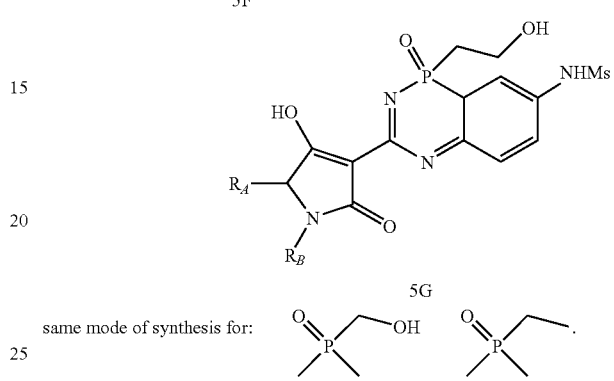

5G same mode of synthesis for:

In certain embodiments, ammonium hypophosphite 5A can first react hexamethyldisilazane (HMDS), then with ((2-iodoethoxy)methyl)benzene (ICH$_2$CH$_2$OBn) in the presence with, for example, dichloromethane (DCM), followed with reaction with benzyl alcohol (BnOH) in the presence, for example, N,N'-dicyclohexyl-carbodiimide (DCC) and tetrahydrofuran (THF), to form compound 5B. Compound 5B can be coupled with compound 4A to form compound 5C. Compound 5C can be reacted with mesyl chloride (MsCl) in the presence with, for example, diisopropylethylamine (DIEA) and dichloromethane (DCM), to form compound 5D. Compound 5D can first be reacted with ethanol in the presence of, for example, triethylamine (TEA), followed with hydrogenation reaction in the presence of, for example, hydrogen, ethanol, hydrochloride, and palladium catalyst, to form compound 5G. Protecting groups can be used where suitable according to the judgment of one of skill in the art.

Pharmaceutical Compositions

Provided herein are pharmaceutical compositions comprising a compound provided herein as an active ingredient, including a single enantiomer, a mixture of an enantiomeric pair, an individual diastereomer, or a mixture of diastereomers thereof, or a pharmaceutically acceptable salt, solvate, or prodrug thereof, in a pharmaceutically acceptable vehicle, carrier, diluent, or excipient, or a mixture thereof; in combination with one or more pharmaceutically acceptable excipients or carriers. In certain embodiments, the pharmaceutical composition comprises at least one release controlling excipient or carrier. In certain embodiments, the pharmaceutical composition comprises at least one nonrelease controlling excipient or carrier. In certain embodiments, the pharmaceutical composition comprises at least one release controlling and at least one nonrelease controlling excipients or carriers.

The compound provided herein may be administered alone, or in combination with one or more other compounds provided herein, one or more other active ingredients. The pharmaceutical compositions that comprise a compound provided herein may be formulated in various dosage forms for oral, parenteral, and topical administration. The pharmaceutical compositions may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Deliver Technology*, Rathbone et al., Eds., Drugs and the Pharmaceutical Science, Marcel Dekker, Inc.: New York, N.Y., 2003; Vol. 126).

In one embodiment, the pharmaceutical compositions are provided in a dosage form for oral administration, which comprise a compound provided herein, including a single enantiomer, a mixture of an enantiomeric pair, an individual diastereomer, or a mixture of diastereomers thereof; or a pharmaceutically acceptable salt, solvate, or prodrug thereof; and one or more pharmaceutically acceptable excipients or carriers.

In another embodiment, the pharmaceutical compositions are provided in a dosage form for parenteral administration, which comprise a compound provided herein, including a single enantiomer, a mixture of an enantiomeric pair, an individual diastereomer, or a mixture of diastereomers thereof; or a pharmaceutically acceptable salt, solvate, or prodrug thereof; and one or more pharmaceutically acceptable excipients or carriers.

In yet another embodiment, the pharmaceutical compositions are provided in a dosage form for topical administration, which comprise a compound provided herein, including a single enantiomer, a mixture of an enantiomeric pair, an individual diastereomer, or a mixture of diastereomers thereof; or a pharmaceutically acceptable salt, solvate, or prodrug thereof; and one or more pharmaceutically acceptable excipients or carriers.

The pharmaceutical compositions provided herein may be provided in unit-dosage forms or multiple-dosage forms. Unit-dosage forms, as used herein, refer to physically discrete units suitable for administration to human and animal subjects and packaged individually as is known in the art. Each unit-dose contains a predetermined quantity of the active ingredient(s) sufficient to produce the desired therapeutic effect, in association with the required pharmaceutical carriers or excipients. Examples of unit-dosage forms include ampoules, syringes, and individually packaged tablets and capsules. Unit-dosage forms may be administered in fractions or multiples thereof. A multiple-dosage form is a plurality of identical unit-dosage forms packaged in a single container to be administered in segregated unit-dosage form. Examples of multiple-dosage forms include vials, bottles of tablets or capsules, or bottles of pints or gallons.

The pharmaceutical compositions provided herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein may be provided in solid, semisolid, or liquid dosage forms for oral administration. As used herein, oral administration also include buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean-oil; zinc stearate; ethyl oleate; ethyl laureate; agar; starch; lycopodium; silica or silica gels, such as AERO- SIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation.

The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration may be also provided in the forms of liposomes, micelles, microspheres, or nanosystems. Micellar dosage forms can be prepared as described in U.S. Pat. No. 6,350,458.

The pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein may be formulated as immediate or modified release dosage forms, including delayed-, sustained, pulsed-, controlled, targeted-, and programmed-release forms.

The pharmaceutical compositions provided herein may be co-formulated with other active ingredients which do not impair the desired therapeutic action, or with substances that supplement the desired action, such as drotrecogin-α, and hydrocortisone.

B. Parenteral Administration

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcellulose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions provided herein may be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein may be formulated as immediate or modified release dosage forms, including delayed-, sustained, pulsed-, controlled, targeted-, and programmed-release forms.

The pharmaceutical compositions may be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein may be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein may be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation of the pharmaceutical compositions provided herein may also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions may also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein may be provided in the forms of ointments, creams, and gels. Suitable ointment vehicles include oleaginous or hydrocarbon vehicles, including such as lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, Remington: The Science and Practice of Pharmacy, supra). These vehicles are emollient but generally require addition of antioxidants and preservatives.

Suitable cream base can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include crosslinked acrylic acid polymers, such as carbomers, carboxypolyalkylenes, CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein may be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in Remington: The Science and Practice of Pharmacy, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to about 3 g.

The pharmaceutical compositions provided herein may be administered ophthalmically in the forms of solutions, suspensions, ointments, emulsions, gel-forming solutions, powders for solutions, gels, ocular inserts, and implants.

The pharmaceutical compositions provided herein may be administered intranasally or by inhalation to the respiratory tract. The pharmaceutical compositions may be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions may also be provided as a dry powder for insufflation, alone or in combination with an inert carrier such as lactose or phospholipids; and nasal drops. For intranasal use, the powder may comprise a bioadhesive agent, including chitosan or cyclodextrin.

Solutions or suspensions for use in a pressurized container, pump, spray, atomizer, or nebulizer may be formulated to contain ethanol, aqueous ethanol, or a suitable alternative agent for dispersing, solubilizing, or extending release of the active ingredient provided herein, a propellant as solvent; and/or a surfactant, such as sorbitan trioleate, oleic acid, or an oligolactic acid.

The pharmaceutical compositions provided herein may be micronized to a size suitable for delivery by inhalation, such as about 50 micrometers or less, or about 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

Capsules, blisters and cartridges for use in an inhaler or insufflator may be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include dextran, glucose, maltose, sorbitol, xylitol, fructose, sucrose, and trehalose. The pharmaceutical compositions provided herein for inhaled/intranasal administration may further comprise a suitable flavor, such as menthol and levomenthol, or sweeteners, such as saccharin or saccharin sodium.

The pharmaceutical compositions provided herein for topical administration may be formulated to be immediate release or modified release, including delayed-, sustained-, pulsed-, controlled-, targeted, and programmed release.

D. Modified Release

The pharmaceutical compositions provided herein may be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions provided herein in a modified release dosage form may be fabricated using a matrix controlled release device known to those skilled in the art (see, Takada et al in "Encyclopedia of Controlled Drug Delivery," Vol. 2, Mathiowitz Ed., Wiley, 1999).

In one embodiment, the pharmaceutical compositions provided herein in a modified release dosage form is formulated using an erodible matrix device, which is water-swellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(–)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In further embodiments, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device included, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethylene terephthalate, natural rubber, silicone rubbers, polydimethylsiloxanes, silicone carbonate copolymers, and; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form may be prepared by methods known to those skilled in the art, including direct compression, dry or wet granulation followed by compression, melt-granulation followed by compression.

2. Osmotic Controlled Release Devices

The pharmaceutical compositions provided herein in a modified release dosage form may be fabricated using an osmotic controlled release device, including one-chamber system, two-chamber system, asymmetric membrane technology (AMT), and extruding core system (ECS). In general, such devices have at least two components: (a) the core which contains the active ingredient(s); and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents water-swellable hydrophilic polymers, which are also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates may be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core may also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane may also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane may be formed post-coating by mechanical or laser drilling. Delivery port(s) may also be formed in situ by erosion of a plug of water-soluble material or by rupture of a thinner portion of the membrane over an indentation in the core. In addition, delivery ports may be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form may further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical compositions provided herein in a modified release dosage form may be fabricated a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates may be made by the processes know to those skilled in the art, including wet- and dry-granulation, extrusion/spheronization, roller-compaction, melt-congealing, and by spray-coating seed cores. See, for example, *Multiparticulate Oral*

*Drug Delivery*; Marcel Dekker: 1994; and *Pharmaceutical Pelletization Technology*; Marcel Dekker: 1989.

Other excipients or carriers as described herein may be blended with the pharmaceutical compositions to aid in processing and forming the multiparticulates. The resulting particles may themselves constitute the multiparticulate device or may be coated by various film-forming materials, such as enteric polymers, water-swellable, and water-soluble polymers. The multiparticulates can be further processed as a capsule or a tablet.

4. Targeted Delivery

The pharmaceutical compositions provided herein may also be formulated to be targeted to a particular tissue, receptor, or other area of the body of the subject to be treated, including liposome-, resealed erythrocyte-, and antibody-based delivery systems. Examples include, but are not limited to, U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

Methods of Use

Provided herein are methods for treating or preventing a hepatitis C viral infection in a subject, which comprises administering to a subject a therapeutically effective amount of a compound provided herein, including a single enantiomer, a mixture of an enantiomeric pair, an individual diastereomer, or a mixture of diastereomers thereof; or a pharmaceutically acceptable salt, solvate, or prodrug thereof. In one embodiment, the subject is a mammal. In another embodiment, the subject is a human.

Additionally, provided herein is a method for inhibiting replication of a virus in a host, which comprises contacting the host with a therapeutically effective amount of the compound of Formula IV, IV', I", II", or IVa, including a single enantiomer, a mixture of an enantiomeric pair, an individual diastereomer, or a mixture of diastereomers thereof; or a pharmaceutically acceptable salt, solvate, or prodrug thereof. In one embodiment, the host is a cell. In another embodiment, the host is a human cell. In yet another embodiment, the host is a mammal. In still another embodiment, the host is human.

In certain embodiments, administration of a therapeutically effective amount of a compound provided herein, including a single enantiomer, a mixture of an enantiomeric pair, an individual diastereomer, or a mixture of diastereomers thereof; or a pharmaceutically acceptable salt, solvate, or prodrug thereof, results in a 10%, 20%, 30%, 40%, 50%, 60%, 70%, 80%, 90%, 95%, 99% or more reduction in the replication of the virus relative to a subject without administration of the compound, as determined at 1 day, 2 days, 3 days, 4 days, 5 days, 10 days, 15 days, or 30 days after the administration by a method known in the art, e.g., determination of viral titer.

In certain embodiments, administration of a therapeutically effective amount of a compound provided herein, including a single enantiomer, a mixture of an enantiomeric pair, an individual diastereomer, or a mixture of diastereomers thereof; or a pharmaceutically acceptable salt, solvate, or prodrug thereof, results in a 1, 2, 3, 4, 5, 10, 15, 20, 25, 50, 75, 100-fold or more reduction in the replication of the virus relative to a subject without administration of the compound, as determined at 1 day, 2 days, 3 days, 4 days, 5 days, 10 days, 15 days, or 30 days after the administration by a method known in the art.

In certain embodiments, administration of a therapeutically effective amount of a compound provided herein, including a single enantiomer, a mixture of an enantiomeric pair, an individual diastereomer, or a mixture of diastereomers thereof; or a pharmaceutically acceptable salt, solvate, or prodrug thereof, results in a 10%, 20%, 30%, 40%, 50%, 60%, 70%, 80%, 90%, 95%, 99% or more reduction in the viral titer relative to a subject without administration of the compound, as determined at 1 day, 2 days, 3 days, 4 days, 5 days, 10 days, 15 days, or 30 days after the administration by a method known in the art.

In certain embodiments, administration of a therapeutically effective amount of a compound provided herein, including a single enantiomer, a mixture of an enantiomeric pair, an individual diastereomer, or a mixture of diastereomers thereof; or a pharmaceutically acceptable salt, solvate, or prodrug thereof, results in a 1, 2, 3, 4, 5, 10, 15, 20, 25, 50, 75, 100 or more fold reduction in the viral titer relative to a subject without administration of the compound, as determined at 1 day, 2 days, 3 days, 4 days, 5 days, 10 days, 15 days, or 30 days after the administration by a method known in the art.

Further provided herein is a method for inhibiting the replication of an HCV virus, which comprises contacting the virus with a therapeutically effective amount of a compound provided herein, including a single enantiomer, a mixture of an enantiomeric pair, an individual diastereomer, or a mixture of diastereomers thereof; or a pharmaceutically acceptable salt, solvate, or prodrug thereof.

In certain embodiments, the contacting of the virus with a therapeutically effective amount of a compound provided herein, including a single enantiomer, a mixture of an enantiomeric pair, an individual diastereomer, or a mixture of diastereomers thereof; or a pharmaceutically acceptable salt, solvate, or prodrug thereof, results in a 10%, 20%, 30%, 40%, 50%, 60%, 70%, 80%, 90%, 95%, 99% or more reduction in the virus titer relative to the virus without such contact, as determined at 1 day, 2 days, 3 days, 4 days, 5 days, 10 days, 15 days, or 30 days after the initial contact, by a method known in the art.

In certain embodiments, the contacting of the virus with a therapeutically effective amount of a compound provided herein, including a single enantiomer, a mixture of an enantiomeric pair, an individual diastereomer, or a mixture of diastereomers thereof; or a pharmaceutically acceptable salt, solvate, or prodrug thereof, results in a 1, 2, 3, 4, 5, 10, 15, 20, 25, 50, 75, 100-fold or more reduction in the virus titer relative to the virus without such contact, as determined at 1 day, 2 days, 3 days, 4 days, 5 days, 10 days, 15 days, or 30 days after the initial contact, by a method known in the art.

In certain embodiments, the contacting of the virus with a therapeutically effective amount of a compound provided herein, including a single enantiomer, a mixture of an enantiomeric pair, an individual diastereomer, or a mixture of diastereomers thereof; or a pharmaceutically acceptable salt, solvate, or prodrug thereof, results in a 10%, 20%, 30%, 40%, 50%, 60%, 70%, 80%, 90%, 95%, 99% or more reduction in the viral titer relative to the virus without such contact, as determined at 1 day, 2 days, 3 days, 4 days, 5 days, 10 days, 15 days, or 30 days after the initial contact by a method known in the art.

In certain embodiments, the contacting of the virus with a therapeutically effective amount of a compound provided herein, including a single enantiomer, a mixture of an enantiomeric pair, an individual diastereomer, or a mixture of diastereomers thereof; or a pharmaceutically acceptable salt, solvate, or prodrug thereof, results in a 1, 2, 3, 4, 5, 10, 15, 20, 25, 50, 75, 100 or more fold reduction in the viral titer relative to the virus without such contact, as determined at 1 day, 2 days, 3 days, 4 days, 5 days, 10 days, 15 days, or 30 days after the initial contact, by a method known in the art.

Also provided herein is a method for treating, preventing, or ameliorating one or more symptoms of a liver disease or disorder associated with an HCV infection, comprising administering to a subject a therapeutically effective amount of the compound provided herein, including a single enantiomer, a mixture of an enantiomeric pair, an individual diastereomer, or a mixture of diastereomers thereof, or a pharmaceutically acceptable salt, solvate, or prodrug thereof. Non-limiting examples of diseases associated with HCV infection include chronic hepatitis, cirrhosis, hepatocarcinoma, or extra hepatic manifestation.

Provided herein is a method for inhibiting the activity of a polymerase, which comprises contacting the polymerase with an effective amount of a compound provided herein, including a single enantiomer, a mixture of an enantiomeric pair, an individual diastereomer, or a mixture of diastereomers thereof; or a pharmaceutically acceptable salt, solvate, or prodrug thereof. In one embodiment, the polymerase is hepatitis C NS5B polymerase.

Depending on the condition, disorder, or disease, to be treated and the subject's condition, a compound provided herein may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical (e.g., transdermal or local) routes of administration, and may be formulated, alone or together, in suitable dosage unit with pharmaceutically acceptable carriers, adjuvants and vehicles appropriate for each route of administration.

The dose may be in the form of one, two, three, four, five, six, or more sub-doses that are administered at appropriate intervals per day. The dose or sub-doses can be administered in the form of dosage units containing from about 0.1 to about 1000 milligram, from about 0.1 to about 500 milligrams, or from 0.5 about to about 100 milligram active ingredient(s) per dosage unit, and if the condition of the patient requires, the dose can, by way of alternative, be administered as a continuous infusion.

In certain embodiments, an appropriate dosage level is about 0.01 to about 100 mg per kg patient body weight per day (mg/kg per day), about 0.01 to about 50 mg/kg per day, about 0.01 to about 25 mg/kg per day, or about 0.05 to about 10 mg/kg per day, which may be administered in single or multiple doses. A suitable dosage level may be about 0.01 to about 100 mg/kg per day, about 0.05 to about 50 mg/kg per day, or about 0.1 to about 10 mg/kg per day. Within this range the dosage may be about 0.01 to about 0.1, about 0.1 to about 1.0, about 1.0 to about 10, or about 10 to about 50 mg/kg per day.

Combination Therapy

The compounds provided herein may also be combined or used in combination with other therapeutic agents useful in the treatment and/or prevention of an HCV infection.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with a disease or disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

As used herein, the term "synergistic" includes a combination of a compound provided herein and another therapy (e.g., a prophylactic or therapeutic agent) which has been or is currently being used to treat, prevent, or manage a disease or disorder, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a disorder. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention or treatment of a disorder). In addition, a synergistic effect can result in improved efficacy of agents in the prevention or treatment of a disorder. Finally, a synergistic effect of a combination of therapies (e.g., a combination of prophylactic or therapeutic agents) may avoid or reduce adverse or unwanted side effects associated with the use of either therapy alone.

The compound provided herein can be administered in combination or alternation with another therapeutic agent, such as an anti-HCV agent. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

It has been recognized that drug-resistant variants of HCV can emerge after prolonged treatment with an antiviral agent. Drug resistance most typically occurs due to the mutation of a gene that encodes for an enzyme used in viral replication. The efficacy of a drug against the viral infection can be prolonged, augmented, or restored by administering the compound in combination or alternation with a second, and perhaps third, antiviral compound that induces a different mutation from that caused by the principle drug. Alternatively, the pharmacokinetics, biodistribution or other parameters of the drug can be altered by such combination or alternation therapy. In general, combination therapy is typically preferred over alternation therapy because it induces multiple simultaneous stresses on the virus.

In certain embodiments, the compound provided herein is combined with one or more agents selected from the group consisting of an interferon, ribavirin, amantadine, an interleukin, a NS3 protease inhibitor, a cysteine protease inhibitor, a phenanthrenequinone, a thiazolidine, a benzanilide, a helicase inhibitor, a polymerase inhibitor, a nucleotide analogue, a nucleoside analogue, a gliotoxin, a cerulenin, an antisense phosphorothioate oligodeoxynucleotide, an inhibitor of IRES-dependent translation, and a ribozyme.

In certain embodiments, the compound provided herein is combined with a HCV protease inhibitor, including, but not limited to, Medivir HCV protease inhibitor (Medivir/Tobotec); ITMN-191 (InterMune), SCH 503034 (Schering), VX950 (Vertex); substrate-based NS3 protease inhibitors as disclosed in WO 98/22496; Attwood et al., *Antiviral Chemistry and Chemotherapy* 1999, 10, 259-273; DE 19914474; WO 98/17679; WO 99/07734; non-substrate-based NS3 protease inhibitors, such as 2,4,6-trihydroxy-3-nitro-benzamide derivatives (Sudo et al., *Biochem. Biophys. Res. Commun.* 1997, 238, 643-647), RD3-4082, RD3-4078, SCH 68631, and a phenanthrenequinone (Chu et al., *Tetrahedron Letters* 1996, 37, 7229-7232); SCH 351633 (Chu et al., *Bioorganic and Medicinal Chemistry Letters* 1999, 9, 1949-1952); Eglin c, a potent polymerase inhibitor (Qasim et al., *Biochemistry* 1997, 36, 1598-1607).

Other suitable protease inhibitors for the treatment of HCV include those disclosed in, for example, U.S. Pat. No. 6,004, 933, which discloses a class of cysteine protease inhibitors of HCV endopeptidase 2.

Additional hepatitis C virus NS3 protease inhibitors include those disclosed in, for example, Llinàs-Brunet et al., *Bioorg. Med. Chem. Lett.* 1998, 8, 1713-1718; Steinkühler et al., *Biochemistry* 1998, 37, 8899-8905; U.S. Pat. Nos. 5,538, 865; 5,990,276; 6,143,715; 6,265,380; 6,323,180; 6,329,379; 6,410,531; 6,420,380; 6,534,523; 6,642,204; 6,653,295; 6,727,366; 6,838,475; 6,846,802; 6,867,185; 6,869,964; 6,872,805; 6,878,722; 6,908,901; 6,911,428; 6,995,174; 7,012,066; 7,041,698; 7,091,184; 7,169,760; 7,176,208; 7,208,600; U.S. Pat. App. Pub. Nos.: 2002/0016294, 2002/0016442; 2002/0037998; 2002/0032175; 2004/0229777; 2005/0090450; 2005/0153877; 2005/176648; 2006/0046956; 2007/0021330; 2007/0021351; 2007/0049536; 2007/0054842; 2007/0060510; 2007/0060565; 2007/0072809; 2007/0078081; 2007/0078122; 2007/0093414; 2007/0093430; 2007/0099825; 2007/0099929; 2007/0105781; WO 98/17679; WO 98/22496; WO 99/07734; WO 00/059929; WO 00/09543; WO 02/060926; WO 02/08187; WO 02/008251; WO 02/008256; WO 02/08198; WO 02/48116; WO 02/48157; WO 02/48172; WO 03/053349; WO 03/064416; WO 03/064456; WO 03/099274; WO 03/099316; WO 2004/032827; WO 2004/043339; WO 2005/037214; WO 2005/037860; WO 2006/000085; WO 2006/119061; WO 2006/122188; WO 2007/001406; WO 2007/014925; WO 2007/014926; and WO 2007/056120.

Other protease inhibitors include thiazolidine derivatives, such as RD-1-6250, RD4 6205, and RD4 6193, which show relevant inhibition in a reverse-phase HPLC assay with an NS3/4A fusion protein and NS5A/5B substrate (Sudo et al., *Antiviral Research* 1996, 32, 9-18); thiazolidines and benzanilides identified in Kakiuchi et al., *FEBS Lett.* 1998, 421, 217-220; Takeshita et al., *Analytical Biochemistry* 1997, 247, 242-246.

Suitable helicase inhibitors include, but are not limited to, those disclosed in U.S. Pat. No. 5,633,358; and WO 97/36554.

Suitable nucleotide polymerase inhibitors include, but are not limited to, gliotoxin (Ferrari et al., *Journal of Virology* 1999, 73, 1649-1654), and the natural product cerulenin (Lohmann et al., *Virology* 1998, 249, 108-118).

Suitable interfering RNA (iRNA) based antivirals include, but are not limited to, short interfering RNA (siRNA) based antivirals, such as Sirna-034 and those described in WO/03/070750, WO 2005/012525, and U.S. Pat. Pub. No. 2004/0209831.

Suitable antisense phosphorothioate oligodeoxynucleotides (S-ODN) complementary to sequence stretches in the 5' non-coding region (NCR) of HCV virus include, but are not limited to those described in Alt et al., *Hepatology* 1995, 22, 707-717, and nucleotides 326-348 comprising the 3' end of the NCR and nucleotides 371-388 located in the core coding region of HCV RNA (Alt et al., *Archives of Virology* 1997, 142, 589-599; Galderisi et al., *Journal of Cellular Physiology* 1999, 181, 251-257);

Suitable inhibitors of IRES-dependent translation include, but are not limited to, those described in Japanese Pat. Pub. Nos.: JP 08268890 and JP 10101591.

Suitable ribozymes include those disclosed in, for example, U.S. Pat. Nos. 6,043,077; 5,869,253 and 5,610,054.

Suitable nucleoside analogs include, but are not limited to, the compounds described in U.S. Pat. Nos. 6,660,721; 6,777, 395; 6,784,166; 6,846,810; 6,927,291; 7,094,770; 7,105,499; 7,125,855; and 7,202,224; U.S. Pat. Pub. Nos. 2004/0121980; 2005/0009737; 2005/0038240; and 2006/0040890; WO 99/43691; WO 01/32153; WO 01/60315; WO 01/79246; WO 01/90121, WO 01/92282, WO 02/18404; WO 02/32920, WO 02/48165, WO 02/057425; WO 02/057287; WO 2004/002422, WO 2004/002999, and WO 2004/003000.

Other miscellaneous compounds that can be used as second agents include, for example, 1-amino-alkylcyclohexanes (U.S. Pat. No. 6,034,134), alkyl lipids (U.S. Pat. No. 5,922, 757), vitamin E and other antioxidants (U.S. Pat. No. 5,922, 757), squalene, amantadine, bile acids (U.S. Pat. No. 5,846, 964), N-(phosphonacetyl)-L-aspartic acid (U.S. Pat. No. 5,830,905), benzenedicarboxamides (U.S. Pat. No. 5,633, 388), polyadenylic acid derivatives (U.S. Pat. No. 5,496,546), 2',3'-dideoxyinosine (U.S. Pat. No. 5,026,687), benzimidazoles (U.S. Pat. No. 5,891,874), plant extracts (U.S. Pat. Nos. 5,725,859; 5,837,257; and 6,056,961), and piperidines (U.S. Pat. No. 5,830,905).

In certain embodiments, one or more compounds provided herein are administered in combination or alternation with an anti-hepatitis C virus interferon, including, but not limited to, INTRON® A (interferon alfa-2b) and PEGASYS® (Peginterferon alfa-2a); ROFERON® A (recombinant interferon alfa-2a), INFERGEN® (interferon alfacon-1), and PEG-INTRON® (pegylated interferon alfa-2b). In one embodiment, the anti-hepatitis C virus interferon is INFERGEN®, IL-29 (PEG-Interferon lambda), R7025 (Maxy-alpha), BELEROFON®, oral interferon alpha, BLX-883 (LOCTERON®), omega interferon, MULTIFERON®, medusa interferon, ALBUFERON®, or REBIF®.

In certain embodiments, one or more compounds provided herein are administered in combination or alternation with an anti-hepatitis C virus polymerase inhibitor, such as ribavirin, viramidine, NM 283 (valopicitabine), PSI-6130, R1626, HCV-796, or R7128.

In certain embodiments, the one or more compounds provided herein are administered in combination with ribavirin and an anti-hepatitis C virus interferon, such as INTRON® A (interferon alfa-2b), PEGASYS® (Peginterferon alfa-2a), ROFERON® A (recombinant interferon alfa-2a), INFERGEN® (interferon alfacon-1), and PEG-INTRON® (pegylated interferon alfa-2b), In certain embodiments, one or more compounds provided herein are administered in combination or alternation with an anti-hepatitis C virus protease inhibitor, such as ITMN-191, SCH 503034, VX950 (telaprevir), or Medivir HCV protease inhibitor.

In certain embodiments, one or more compounds provided herein are administered in combination or alternation with an anti-hepatitis C virus vaccine, including, but not limited to, TG4040, PEVIPRO™, CGI-5005, HCV/MF59, GV1001, IC41, and INNO0101 (E1).

In certain embodiments, one or more compounds provided herein are administered in combination or alternation with an anti-hepatitis C virus monoclonal antibody, such as AB68 or XTL-6865 (formerly HepX-C); or an anti-hepatitis C virus polyclonal antibody, such as cicavir.

In certain embodiments, one or more compounds provided herein are administered in combination or alternation with an anti-hepatitis C virus immunomodulator, such as ZADAXIN® (thymalfasin), NOV-205, or oglufanide.

In certain embodiments, one or more compounds provided herein are administered in combination or alternation with NEXAVAR®, doxorubicin, PI-88, amantadine, JBK-122, VGX-410C, MX-3253 (celgosivir), SUVUS® (BIVN-401 or virostat), PF-03491390 (formerly IDN-6556), G126270, UT-231B, DEBIO-025, EMZ702, ACH-0137171, MitoQ, ANA975, AVI-4065, bavituximab (tarvacin), ALINIA® (nitrazoxanide) or PYN17.

In certain embodiments, the compounds provided herein can be combined with one or more steroidal drugs known in the art, including, but not limited to the group including, aldosterone, beclometasone, betamethasone, deoxycorticosterone acetate, fludrocortisone, hydrocortisone (cortisol), prednisolone, prednisone, methylprednisolone, dexamethasone, and triamcinolone.

In certain embodiments, the compounds provided herein can be combined with one or more antibacterial agents known in the art, including, but not limited to the group including amikacin, amoxicillin, ampicillin, arsphenamine, azithromycin, aztreonam, azlocillin, bacitracin, carbenicillin, cefaclor, cefadroxil, cefamandole, cefazolin, cephalexin, cefdinir, cefditorin, cefepime, cefixime, cefoperazone, cefotaxime, cefoxitin, cefpodoxime, cefprozil, cefiazidime, ceftibuten, ceftizoxime, ceftriaxone, cefuroxime, chloramphenicol, cilastin, ciprofloxacin, clarithromycin, clindamycin, cloxacillin, colistin, dalfopristin, demeclocycline, dicloxacillin, dirithromycin, doxycycline, erythromycin, enrofloxacir, ertepenem, ethambutol, flucloxacillin, fosfomycin, furazolidone, gatifloxacin, geldanamycin, gentamicin, herbimycin, imipenem, isoniazid, kanamycin, levofloxacin, linezolid, lomefloxacin, loracarbef, mafenide, moxifloxacin, meropenem, metronidazole, mezlocillin, minocycline, mupirocin, nafcillin, neomycin, netilmicin, nitrofurantoin, norfloxacin, ofloxacin, oxytetracycline, penicillin, piperacillin, platensimycin, polymyxin B, prontocil, pyrazinamide, quinupristine, rifampin, roxithromycin, spectinomycin, streptomycin, sulfacetamide, sulfamethizole, sulfamethoxazole, teicoplanin, telithromycin, tetracycline, ticarcillin, tobramycin, trimethoprim, troleandomycin, trovafloxacin, and vancomycin.

In certain embodiments, the compounds provided herein can be combined with one or more antifungal agents known in the art, including, but not limited to the group including amorolfine, amphotericin B, anidulafangin, bifonazole, butenafine, butoconazole, caspofungin, ciclopirox, clotrimazole, econazole, fenticonazole, filipin, fluconazole, isoconazole, itraconazole, ketoconazole, micafungin, miconazole, naftifine, natamycin, nystatin, oxyconazole, ravuconazole, posaconazole, rimocidin, sertaconazole, sulconazole, terbinafine, terconazolc, tioconazole, and voriconazole.

In certain embodiments, the compounds provided herein can be combined with one or more anticoagulants known in the art, including, but not limited to the group including acenocoumarol, argatroban, bivalirudin, lepirudin, fondaparinux, heparin, phenindione, warfarin, and ximelagatran.

In certain embodiments, the compounds provided herein can be combined with one or more thrombolytics known in the art, including, but not limited to the group including anistreplase, reteplase, t-PA (alteplase activase), streptokinase, tenecteplase, and urokinase.

In certain embodiments, the compounds provided herein can be combined with one or more non-steroidal anti-inflammatory agents known in the art, including, but not limited to, aceclofenac, acemetacin, amoxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, ibuprofen, indometacin, ketoprofen, ketorolac, lornoxicam, loxoprofen, lumiracoxib, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid, and tolmetin.

In certain embodiments, the compounds provided herein can be combined with one or more antiplatelet agents known in the art, including, but not limited to, abciximab, cilostazol, clopidogrel, dipyridamole, ticlopidine, and tirofibin.

The compounds provided herein can also be administered in combination with other classes of compounds, including, but not limited to, endothelin converting enzyme (ECE) inhibitors, such as phosphoramidon; thromboxane receptor antagonists, such as ifetroban; potassium channel openers; thrombin inhibitors, such as hirudin; growth factor inhibitors, such as modulators of PDGF activity; platelet activating factor (PAF) antagonists; anti-platelet agents, such as GPIIb/IIIa blockers (e.g., abciximab, eptifibatide, and tirofiban), P2Y (AC) antagonists (e.g., clopidogrel, ticlopidine and CS-747), and aspirin; anticoagulants, such as warfarin; low molecular weight heparins, such as enoxaparin; Factor VIIa Inhibitors and Factor Xa Inhibitors; renin inhibitors; neutral endopeptidase (NEP) inhibitors; vasopeptidase inhibitors (dual NEP-ACE inhibitors), such as omapatrilat and gemopatrilat; HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, atavastatin, or visastatin); squalene synthetase inhibitors; fibrates; bile acid sequestrants, such as questran; niacin; anti-atherosclerotic agents, such as ACAT inhibitors; MTP Inhibitors; calcium channel blockers, such as amlodipine besylate; potassium channel activators; alpha-adrenergic agents; beta-adrenergic agents, such as carvedilol and metoprolol; antiarrhythmic agents; diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, ticrynafen, chlorthalidone, furosenide, muzolimine, bumetanide, triamterene, amiloride, and spironolactone; thrombolytic agents, such as tissue plasminogen activator (tPA), recombinant tPA, streptokinase, urokinase, prourokinase, and anisoylated plasminogen streptokinase activator complex (APSAC); anti-diabetic agents, such as biguanides (e.g., metformin), glucosidase inhibitors (e.g., acarbose), insulins, meglitinides (e.g., repaglinide), sulfonylureas (e.g., glimepiride, glyburide, and glipizide), thiozolidinediones (e.g., troglitazone, rosiglitazone, and pioglitazone), and PPAR-gamma agonists; mineralocorticoid receptor antagonists, such as spironolactone and eplerenone; growth hormone secretagogues; aP2 inhibitors; phosphodiesterase inhibitors, such as PDE III inhibitors (e.g., cilostazol) and PDE V inhibitors (e.g., sildenafil, tadalafil, and vardenafil); protein tyrosine kinase inhibitors; antiinflammatories; antiproliferatives, such as methotrexate, FK506 (tacrolimus), mycophenolate mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); antimetabolites, such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids (e.g., cortisone), estrogens/antiestrogens, androgens/antiandrogens, progestins, and luteinizing hormone-releasing hormone antagonists, and octreotide acetate; microtubule-disruptor agents, such as ecteinascidins; microtubule-stabilizing agents, such as paclitaxel, docetaxel, and epothilones A-F; plant-derived products, such as vinca alkaloids, epipodophyllotoxins, and taxanes; and topoisomerase inhibitors; prenyl-protein transferase inhibitors; and cyclosporins; steroids, such as prednisone and dexamethasone; cytotoxic drugs, such as azathioprine and cyclophosphamide; TNF-alpha inhibitors, such as tenidap; anti-TNF antibodies or soluble TNF receptor, such as etanercept, rapamycin, and leflunimide; and cyclooxygenase-2 (COX-2) inhibitors, such as celecoxib and rofecoxib; and miscellaneous agents such as, hydroxyurea, procarbazine, mitotane, hexamethylmelamine, gold compounds, platinum coordination complexes, such as cisplatin, satraplatin, and carboplatin.

In certain embodiments, the pharmaceutical compositions provided herein further comprise a second antiviral agent as described herein. In one embodiment, the second antiviral is selected from the group consisting of an interferon, ribavirin, an interleukin, an NS3 protease inhibitor, a cysteine protease inhibitor, a phenanthrenequinone, a thiazolidine, a benzanilide, a helicase inhibitor, a polymerase inhibitor, a nucleotide analogue, a nucleoside analogue, a gliotoxin, a cerulenin, an antisense phosphorothioate oligodeoxynucleotide, an inhibitor of IRES-dependent translation, and a ribozyme. In another embodiment, the second antiviral agent is an interferon. In yet another embodiment, the t interferon is selected from the group consisting of pegylated interferon alpha 2a, interferon alphcon-1, natural interferon, ALBUFERON®, interferon beta-1a, omega interferon, interferon alpha, interferon gamma, interferon tau, interferon delta, and interferon gamma-1b.

The compounds provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

Provided herein also are kits which, when used by the medical practitioner, can simplify the administration of appropriate amounts of active ingredients to a subject. In certain embodiments, the kit provided herein includes a container and a dosage form of a compound provided herein, including a single enantiomer, a mixture of an enantiomeric pair, an individual diastereomer, or a mixture of diastereomers thereof, or a pharmaceutically acceptable salt, solvate, or prodrug thereof.

In certain embodiments, the kit includes a container comprising a dosage form of the compound provided herein, including a single enantiomer, a mixture of an enantiomeric pair, an individual diastereomer, or a mixture of diastereomers thereof; or a pharmaceutically acceptable salt, solvate, or prodrug thereof, in a container comprising one or more other therapeutic agent(s) described herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL (microliters); mM (millimolar); µM (micromolar); Hz (Hertz); MHz (megahertz); mmol (millimoles); hr (hours); min (minutes); TLC (thin layer chromatography); HPLC (high performance liquid chromatography); SCX (strong cation exchange); MS (mass spectrometry); ESI (electrospray ionization); $R_t$ (retention time); $SiO_2$ (silica); THF (tetrahydrofuran); $CD_3OD$ (deuterated methanol); $CDCl_3$ (deuterated chloroform); DCE (dichloroethane); DCM (dichloromethane); DMF (dimethylformamide); DMSO (dimethylsulfoxide); EtOAc (ethyl acetate); $CHCl_3$ (chloroform); DMF (N,N-dimethylformamide); DMA (N,N-dimethyacetamide); MeOH (methanol); EtOH (ethanol); HCl (hydrochloric acid); LiOH (lithium hydroxide); NaOH (sodium hydroxide); KOH (potassium hydroxide); $Cs_2CO_3$ (cesium carbonate); DIPEA (N,N-diisopropylethylamine); TEA (triethylamine); DBU (1,8-diazabicyclo[5.4.0]undec-7-ene; CDI (carbonyldiimidazole); TBTU (O-(benzotriazol-1-yl)-N,N,N',N'-tetramethyluronium tetrafluoroborate); Ac (acetyl); Me (methyl); Et (ethyl); tBu (tert-butyl); Boc (tert-butoxylcarbony); Bn (benzyl); and Ts (tosylate).

For all of the following examples, standard work-up and purification methods known to those skilled in the art can be utilized. Unless otherwise indicated, all temperatures are expressed in ° C. (degrees Centigrade). All reactions conducted at room temperature unless otherwise noted. Synthetic methodologies illustrated in Schemes 4 to 6 are intended to exemplify the applicable chemistry through the use of specific examples and are not indicative of the scope of the disclosure.

Intermediate 24

(2-amino-5-nitro-phenyl)-phosphonic acid diethyl ester

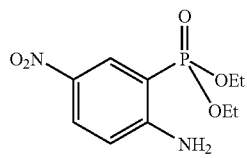

2-iodo-4-nitro aniline (7.57 mmol), triethyl phosphite (15.1 mmol) and palladium acetate (1.51 mmol) were mixed together in acetonitrile (36 ml), in a microwave tube. The vessel was sealed and placed in a microwave to react at 160° C., for 30 min. After cooling to room temperature, acetonitrile was removed. The residue obtained was diluted in ethyl acetate, washed with hydrochloric solution (1N) and phosphate buffer solution (pH 7). The solvent was removed and the crude material was purified by silica gel chromatography to yield intermediate 24, which was a brown solid. Intermediate 24 was characterized by the following spectroscopic data: $^1$H NMR (DMSO-d$_6$, 400 MHz) δ (ppm) 1.21 (t, J=7.1 Hz, 6H), 3.92 (m, 4H), 5.13 (s, NH$_2$), 6.50 (t, J=7.8 Hz, 1H), 6.61 (m, 2H); $^{31}$P NMR (DMSO-d$_6$, 162 MHz) δ (ppm) 21.68 (s, 1P); and MS (ESI, EI$^+$) m/z=275 (MH$^+$).

Intermediate 25

(2,5-diaminophenyl)-phosphonic acid diethyl ester

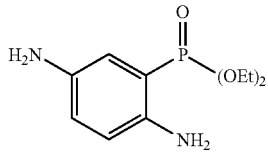

Intermediate 24 (3.65 mmol) was dissolved in methanol (5 ml) Pd/C was added under nitrogen. After several cycles vacuum/nitrogen, hydrogen was introduced at atmospheric pressure. The reaction mixture was stirred at room temperature, under hydrogen, overnight. The reaction mixture was then filtered through celite and concentrated to yield intermediate 25, which was a brown solid. Intermediate 25 was characterized by the following spectroscopic data: $^1$H NMR (DMSO-d$_6$, 400 MHz) δ (ppm) 1.20 (t, J=7.05 Hz, 6H), 3.87-4.00 (m, 4H), 4.45 (s, NH$_2$), 5.15 (s, NH$_2$), 6.50 (t, J=8 Hz, 1H), 6.58-6.60 (m, 2H); $^1$H NMR (DMSO-d$_6$, 162 MHz) δ (ppm) 21.46 (s, 1P); and MS (ESI, EI$^+$) m/z=245 (MH$^+$).

Intermediate 26

(2-amino-5-methanesulfonaminylphenyl)-phosphonic acid diethyl ester

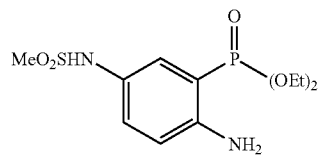

To a stirred solution of the intermediate 25 (3.52 mmol), triethylamine (4.22 mmol) in dichloromethane (7 ml) at 0° C. was added methane sulfonyl chloride (4.22 mmol) under nitrogen. The reaction mixture was stirred at room temperature, over night. The mixture was then quenched with phosphate buffer solution (pH 7). The organic layer was separated, concentrated and the crude material was purified by silica gel chromatography (dichloromethane/methanol) to yield intermediate 26, which was a beige solid. Intermediate 26 was characterized by the following spectroscopic data: $^1$H NMR (DMSO-d$_6$, 400 MHz) δ (ppm) 1.34 (t, J=7.07 Hz, 6H), 2.94 (s, 3H), 4.04-4.22 (m, 4H), 5.14 (s, NH$_2$), 6.57 (s, NH), 6.66 (t, J=7.26, 1H), 7.29 (d, J=8.79 Hz, 1H), 7.39 (d, J=14.9 Hz, 1H); $^{31}$P NMR (DMSO-d$_6$, 162 MHz) δ (ppm) 19.44 (s, 1P); and MS (ESI, EI$^+$) m/z=323 (MH$^+$).

Intermediate 73

(S)-2-(3,3-dimethyl-butylamino)-3,3-dimethyl-butyric acid methyl ester

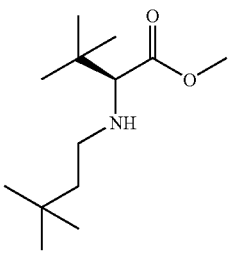

A solution of (S)-methyl 2-amino-3,3-dimethylbutanoate (6.89 mmol, Bionet) in anhydrous methanol (12 ml) was treated with 3,3-dimethylbutyraldehyde (6 mmol, Fluka), triethylamine (6.89 mmol) and sodium cyanoborohydride (6.89 mmol). After stirring at room temperature overnight, the reaction mixture was concentrated in vacuo, diluted with ethyl acetate, washed with brine, dried over sodium sulfate and concentrated under reduced pressure. The residue was purified by chromatography to give intermediate 73, which was a colorless oil. Intermediate 73 was characterized by the following spectroscopic data: $^1$H NMR (CDCl$_3$, 400 MHz) δ (ppm) 0.89 (s, 9H), 0.95 (s, 9H), 1.26-1.33 (m, 1H), 1.41-1.48

Intermediate 74

(S)-2-[(2-cyano-acetyl)-(3,3-dimethyl-butyl)amino]-3,3-dimethyl-butyric acid methyl ester

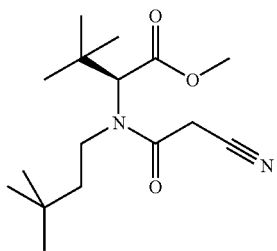

A solution of intermediate 73 (4.8 mmol) and cyanoacetic acid (4.8 mmol) in anhydrous methylene chloride (20 ml) and anhydrous dimethylformamide (3 ml) was treated with dicyclohexylcarbodiimide (5.28 mmol). After stirring at room temperature overnight, the reaction mixture was filtered over celite and concentrated in vacuo. The residue was purified on a silica gel column to give intermediate 74, which was a colorless oil. Intermediate 74 was characterized by the following spectroscopic data: $^1$H NMR (CDCl$_3$, 400 MHz) δ (ppm) 0.96 (s, 9H), 1.09 (s, 9H), 1.40 (td, J=5.03 Hz and J=13.05 Hz, 1H), 1.51 (td, J=4.65 Hz and J=13.05 Hz, 1H), 3.25-3.33 (m, 1H), 3.53 (s, 2H), 3.60-3.69 (m, 1H), 3.70 (s, 3H), 3.75 (s, 1H); and MS (ESI, EI$^+$) m/z=297 (MH$^+$).

Intermediate 75

(S)-2-(3-chloro-4-fluoro-benzylamino)-3,3-dimethyl-butyric acid methyl ester

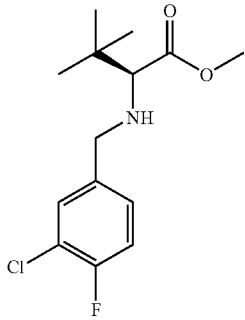

Intermediate 75 was synthesized from (3-chloro-4-fluorophenyl)benzaldehyde (Fluorochem) and L-tert-Leucine methyl ester hydrochloride (Fluka) as described for intermediate 73, which is colorless oil. Intermediate 75 was characterized by the following spectroscopic data: $^1$H NMR (DMSO-d$_6$, 400 MHz) δ (ppm) 0.89 (s, 9H), 2.76 (d, J=11.56 Hz, 1H), 3.46 (dd, J=4.35 Hz and J=14.33 Hz, 1H), 3.57 (s, 3H), 3.72 (dd, J=4.44 Hz and J=14.33 Hz, 1H), 7.26-7.35 (m, 2H), 7.49 (dd, J=1.82 Hz and J=7.41 Hz, 1H).

Intermediate 76

(S)-2-[(3-chloro-4-fluoro-benzyl)-2-cyano-acetyl)-amino]-3,3-dimethyl-butyric acid methyl ester

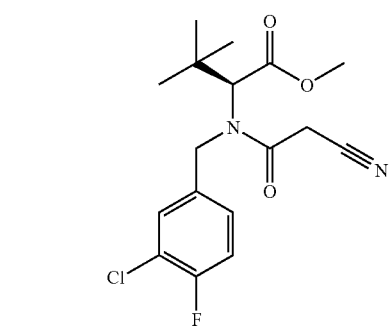

Intermediate 76 was synthesized from intermediate 75 and cyanoacetic acid as described for intermediate 74, which is yellowish syrup. Intermediate 76 was characterized by the following spectroscopic data: $^1$H NMR (CDCl$_3$, 400 MHz) δ (ppm) 1.11 (s, 9H), 3.23 (d, J=17.88 Hz, 1H), 3.34 (d, J=17.88 Hz, 1H), 3.62 (s, 3H), 4.60 (d, J=17.86 Hz, 1H), 5.20 (s, 1H), 5.17 (d, J=17.86 Hz, 1H), 7.02-7.05 (m, 1H), 7.15-7.21 (m, 2H); and $^{19}$F NMR (CDCl$_3$, 376 MHz) δ (ppm) −115.81 (s, 1F).

Intermediate 77

(S)-5-tert-butyl-1-(3,3-dimethyl-butyl)-4-hydroxy-2-oxo-1,5-dihydropyrrole-3-carbonitrile

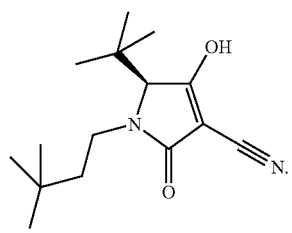

Intermediate 74 (4.79 mmol) was dissolved in THF (22 ml) and cooled to 0° C., potassium tert-butoxide (16.2 mmol) was carefully added during 30 min while keeping the temperature below 5° C., the reaction mixture was stirred at 0° C. for 20 nm in and then neutralized with 1N HCl to pH=2~3, extracted with ethyl acetate (50 ml). The organic phase was washed with brine for two times (each 25 ml); the combined aqueous phase was extracted with ethyl acetate (25 ml) for two times; the organic phase was combined and dried over anhydrous Na$_2$SO$_4$, filtered and concentrated to dryness, petroleum ether (20 ml) was added and heated to reflux for 1 h, cooled and filtered to get the intermediate 77 (82%, ee>98%), which was an off-white solid. Intermediate 77 was characterized by the following spectroscopic data: $^1$H NMR (DMSO-d$_6$, 400 MHz) δ (ppm) 0.86 (s, 9H), 0.97 (s, 9H), 1.18 (td, J=5.09 Hz and J=12.30 Hz, 1H), 1.53 (td, J=4.63 Hz and J=12.37 Hz, 1H), 2.95-3.02 (m, 1H), 3.61-3.69 (m, 1H), 3.68 (s, 1H). MS (ESI, EI$^+$) m/z=265 (MH$^+$).

Intermediate 78

(S)-1-(3-chloro-4-fluoro-benzyl)-5-tert-butyl-4-hydroxy-2-oxo-1,5-dihydropyrrole-3-carbonitrile

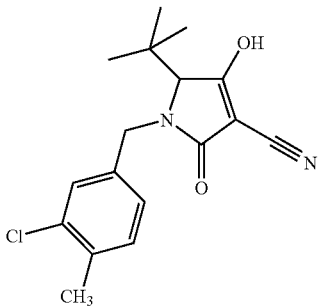

Intermediate 78 was synthesized from intermediate 76 as described for intermediate 77. Intermediate 78 was an orange syrup. Intermediate 78 was characterized by the following spectroscopic data: $^1$H NMR (CDCl$_3$, 400 MHz) δ (ppm) 1.04 (s, 9H), 3.55 (s, 1H), 4.32 (d, J=16.07 Hz, 1H), 5.03 (d, J=16.07 Hz, 1H), 7.03-7.10 (m, 2H), 7.22-7.24 (m, 1H); $^{19}$F NMR (CDCl$_3$, 376 MHz) δ (ppm) −116.93 (s, 1F); and MS (ESI, EI$^+$) m/z=323 (MH$^+$).

Intermediate 79

(S)-2-(2-cyclopropyl-ethylamino)-3,3-dimethyl-butyric acid methyl ester

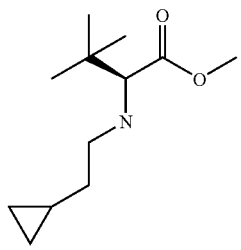

Intermediate 79 was synthesized from 3,3-dimethylbutyraldehyde (Fluka) and 2-cyclopropyl-ethylamine as described for intermediate 73. Intermediate 79 was characterized by the following spectroscopic data: $^1$H NMR (CDCl$_3$, 400 MHz) δ (ppm) 0.02-0.09 (m, 2H), 0.37-0.46 (m, 2H), 0.63-0.73 (m, 1H), 0.97 (s, 9H), 1.30-1.47 (m, 2H), 2.47-2.53 (m, 1H), 2.63-2.69 (m, 1H), 2.92 (s, 1H), 3.72 (s, 3H).

Intermediate 80

(S)-2-[(2-cyano-acetyl)-(2-cyclopropyl-ethylamino)]-3,3-dimethyl-butyric acid methyl ester

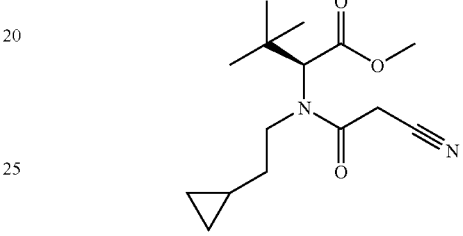

Intermediate 80 was synthesized from intermediate 79 and cyanoacetic acid as described for intermediate 74. Intermediate 80 was characterized by the following spectroscopic data: $^1$H NMR (CDCl$_3$, 400 MHz) δ (ppm) 0.06-0.19 (m, 2H), 0.51-0.55 (m, 2H), 0.62-0.71 (m, 1H), 1.09 (s, 9H), 1.44-1.53 (m, 2H), 3.33-3.41 (m, 1H), 3.58 (s, 2H), 3.69 (s, 3H), 3.68-3.73 (m, 1H), 3.74 (s, 1H).

Intermediate 81

5-tert-butyl-1-(2-cyclopropyl-ethyl)-4-hydroxy-2-oxo-1,5-dihydropyrrole-3-carbonitrile

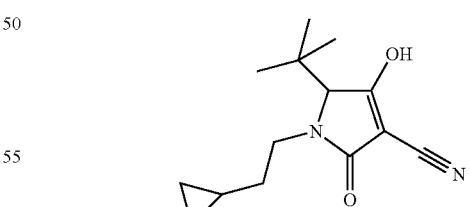

Intermediate 81 was synthesized from intermediate 80 as described for intermediate 77. Intermediate 81 was a white solid. Intermediate 81 was characterized by the following spectroscopic data: $^1$H NMR (DMSO-d$_6$, 400 MHz) δ (ppm) 0.02-0.09 (m, 2H), 0.33-0.40 (m, 2H), 0.47-0.59 (m, 1H), 0.98 (s, 9H), 1.25-1.36 (m, 1H), 1.42-1.53 (m, 1H), 3.02-3.12

(m, 1H), 3.68 (s, 1H), 3.68-3.77 (m, 1H), 6.17 (brs, 1H); and MS (ESI, EI⁺) m/z=249 (MH⁺).

Intermediate 82

2-(3,3-dimethyl-butylamino)-2,4-dimethyl-pentanoic acid methyl ester

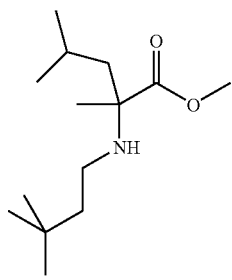

To a solution of DL-α-methylleucine methyl ester hydrochloride (11 mmol) and 3,3-dimethylbutyraldehyde (12.1 mmol, Aldrich) in anhydrous methanol (2 ml) were added triethylamine (11 mmol) and sodium cyanoborohydride (11 mmol) was added. After stirring, acetic acid was added (22 mmol) and the reaction mixture was stirred at room temperature for the week end. Then, a part of reaction mixture was evaporated in vacuo, diluted with ethyl acetate and washed twice with brine. The organic layer was dried over sodium sulfate and concentrated under reduced pressure. The residue was purified by chromatography to give intermediate 82, which was a colorless syrup. Intermediate 82 was characterized by the following spectroscopic data: $^1$H NMR (CDCl$_3$, 400 MHz) δ (ppm) 0.86 (d, J=6.40 Hz, 3H), 0.89 (s, 9H), 0.89 (d, J=6.16 Hz, 3H), 1.29-1.37 (m, 1H), 1.32 (s, 3H), 1.40-1.48 (m, 1H), 1.58-1.62 (m, 2H), 1.65-1.73 (m, 1H), 2.2 (s, 1H), 2.34 (td, J=5.10 Hz and J=10.66 Hz, 1H), 2.56 (td, J=5.10 Hz and J=10.60 Hz, 1H), 3.7 (s, 3H); and MS (ESI, EI⁺) m/z=244 (MH⁺).

Intermediate 83

2-[(2-cyano-acetyl)-(3,3-dimethyl-butyl)-amino]-2,4-dimethyl-pentanoic acid methyl ester

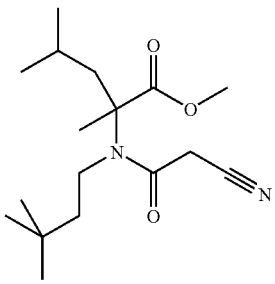

Intermediate 83 was synthesized from intermediate 82 and cyanoacetic acid as described for intermediate 74. Intermediate 83 was a white solid. Intermediate 83 was characterized by the following spectroscopic data: $^1$H NMR (CDCl$_3$, 400 MHz) δ (ppm) 0.92 (d, J=3.34 Hz, 3H), 0.94 (d, J=3.34 Hz, 3H), 0.99 (s, 9H), 1.45-1.54 (m, 1H), 1.52 (s, 3H), 1.60-1.71 (m, 2H), 1.76 (dd, J=4.63 Hz and J=13.90 Hz, 1H), 1.98 (dd, J=6.04 Hz and J=13.90 Hz, 1H), 3.27-3.41 (m, 2H), 3.43-3.54 (m, 2H), 3.69 (s, 3H).

Intermediate 84

5-isobutyl-1-(3,3-dimethyl-butyl)-4-hydroxy-5-methyl-2-oxo-1,5-dihydropyrrole-3-carbonitrile

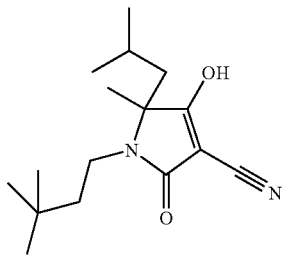

Intermediate 84 was synthesized from intermediate 83 as described for intermediate 77. Intermediate 84 was a pale yellow solid. Intermediate 84 was characterized by the following spectroscopic data: $^1$H NMR (CDCl$_3$, 400 MHz) δ (ppm) 0.84 (t, J=6.83 Hz, 6H), 0.94 (s, 9H), 1.35 (s, 3H), 1.39-1.51 (m, 2H), 1.58-1.63 (m, 1H), 1.68-1.80 (m, 2H), 3.01 (td, J=4.57 Hz and J=12.93 Hz, 1H), 3.41 (td, J=4.57 Hz and J=12.93 Hz, 1H), 6.76 (brs, 1H); and MS (ESI, EI⁺) m/z=279 (MH⁺).

Intermediate 85

2-(3,3-dimethyl-butylamino)-2-methyl-propionic acid methyl ester

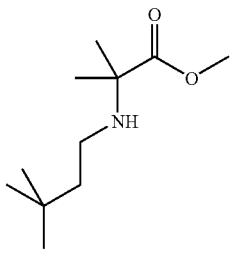

Intermediate 85 was synthesized from 2-amino-2-methyl-propionic acid methyl ester hydrochloride (6.5 mmol) and 3,3-dimethylbutyraldehyde (7.1 mmol, Fluka) as described for intermediate 82. Intermediate 85 was a colorless oil. Intermediate 85 was characterized by the following spectroscopic data: ¹H NMR (CDCl₃, 400 MHz) δ (ppm) 0.90 (s, 9H), 1.34 (s, 6H), 1.37-1.41 (m, 2H), 2.2 (s, 1H), 2.43-2.48 (m, 2H), 3.72 (s, 3H).

Intermediate 86

2-[(2-cyano-acetyl)-(3,3-dimethyl-butyl)-amino]-2-methyl-propionic acid methyl ester

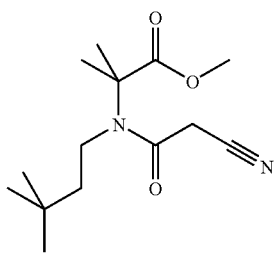

Intermediate 86 was synthesized from intermediate 85 and cyanoacetic acid as described for intermediate 74. Intermediate 86 was a colorless syrup. Intermediate 86 was characterized by the following spectroscopic data: ¹H NMR (CDCl₃, 400 MHz) δ (ppm) 0.99 (s, 9H), 1.51 (s, 6H), 1.54-1.58 (m, 2H), 3.33-3.38 (m, 2H), 3.50 (s, 2H), 3.7 (s, 3H).

Intermediate 87

1-(3,3-dimethyl-butyl)-4-hydroxy-5,5-dimethyl-2-oxo-1,5-dihydropyrrole-3-carbonitrile

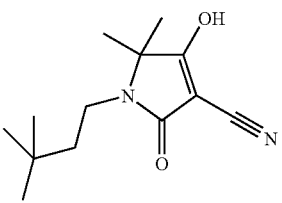

Intermediate 87 was synthesized from intermediate 86 as described for intermediate 77. Intermediate 87 a pale yellow solid. Intermediate 87 was characterized by the following spectroscopic data: ¹H NMR (CDCl₃, 400 MHz) δ (ppm) 0.95 (s, 9H), 1.29 (s, 6H), 1.52-1.56 (m, 2H), 3.26-3.31 (m, 2H), 8.47 (brs, 1H); and MS (ESI, EI⁺) m/z=237 (MH⁺).

Intermediate 88

(S)-2-isobutylamino-3,3-dimethyl-butyric acid methyl ester

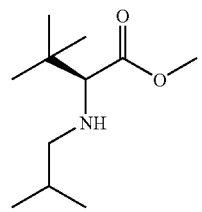

A solution of methyl-2-amino-3,3-dimethyl butanoate (4.82 mmol, Bionet) and isobutylaldehyde (4.82 mmol, Alfa Aesar) in anhydrous methanol (2 ml) and tetrahydrofuran (8 ml) was treated with acetic acid (9.64 mmol). After 1 hr of stirring at room temperature, sodium cyanoborohydride (7.7 mmol) was added. After stirring at room temperature four days, the reaction mixture was concentrated in vacuo, diluted with ethyl acetate and washed twice with NaHCO₃ saturated. The organic layer was dried over sodium sulfate and concentrated under reduced pressure. The residue was purified by chromatography to give intermediate 88, which was a yellow oil. Intermediate 88 was characterized by the following spectroscopic data: ¹H NMR (DMSO-d₆, 400 MHz) δ (ppm) 0.83 (t, J=7.05 Hz, 6H), 0.89 (s, 9H), 1.59 (sept, J=6.68 Hz, 1H), 2.05 (d, J=6.72 Hz, 0.5H), 2.08 (d, J=6.72 Hz, 0.5H), 2.26 (d, J=6.94 Hz, 0.5H), 2.29 (d, J=6.94 Hz, 0.5H), 2.78 (s, 1H), 3.62 (s, 3H).

Intermediate 89

2-[(2-cyano-acetyl)-isobutyl-amino]-3,3-dimethyl-butyric acid methyl ester

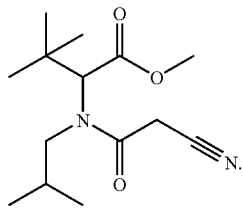

Intermediate 89 was synthesized from intermediate 88 and cyanoacetic acid as described for intermediate 74, which was an orange solid. Intermediate 89 was characterized by the following spectroscopic data: ¹H NMR (DMSO-d₆, 400 MHz) δ (ppm) 0.86 (d, J=6.61 Hz, 3H), 0.90 (d, J=6.61 Hz, 3H), 1.02 (s, 9H), 1.91-1.98 (In 1H), 3.02 (dd, J=5.38 Hz and J=15.14 Hz, 1H), 3.06 (dd, J=9.30 Hz and J=15.23 Hz, 1H), 3.53 (s, 3H), 3.71 (brs, 1H), 3.89 (d, J=18.63 Hz, 1H), 4.17 (d, J=18.79 Hz, 1H); and MS (ESI, EI⁺) m/z=291 (MNa⁺).

Intermediate 90

1-isobutyl-5-tert-butyl-4-hydroxy-2-oxo-1,5-dihydropyrrole-3-carbonitrile

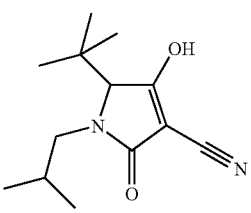

Intermediate 90 was synthesized from intermediate 89 as described for intermediate 77. Intermediate 90 was a beige solid. Intermediate 90 was characterized by the following spectroscopic data: $^1$H NMR (DMSO-d$_6$, 400 MHz) δ (ppm) 0.63 (d, J=6.59 Hz, 3H), 0.81 (d, J=6.59 Hz, 3H), 0.97 (s, 9H), 1.99-2.09 (m, 1H), 2.87 (dd, J=5.31 Hz and J=14.07 Hz, 1H), 3.60 (dd, J=10 Hz and J=14.01 Hz, 1H), 3.72 (s, 1H); and MS (ESI, EI$^+$) m/z=237 (MH$^+$).

Intermediate 91

(S)-2-(3-methyl-butylamino)-3,3-dimethyl-butyric acid methyl ester

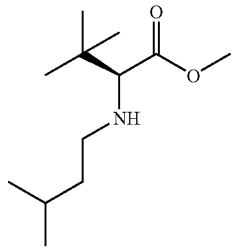

Intermediate 91 was synthesized from methyl-2-amino-3,3-dimethyl butanoate (4.82 mmol, Bionet) and isovaleraldehyde (4.82 mmol, Aldrich) as described for intermediate 88. Intermediate 91 was characterized by the following spectroscopic data: $^1$H NMR (DMSO-d$_6$, 400 MHz) δ (ppm) 0.82 (d, J=3.28 Hz, 3H), 0.84 (d, J=3.28 Hz, 3H), 0.87 (s, 9H), 1.23-1.28 (in 2H), 1.56-1.62 (m, 1H), 2.25-2.32 (m, 1H), 2.43-2.49 (m, 1H), 2.8 (s, 1H), 3.62 (s, 3H).

Intermediate 92

2-[(2-cyano-acetyl)-(3-methyl-butyl)-amino]-3,3-dimethyl-butyric acid methyl ester

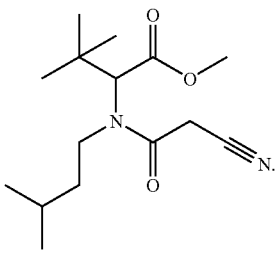

Intermediate 92 was synthesized from intermediate 91 and cyanoacetic acid as described for intermediate 74. Intermediate 92 was a yellow solid. Intermediate 92 was characterized by the following spectroscopic data: $^1$H NMR (DMSO-d$_6$, 400 MHz) δ (ppm) 0.85 (d, J=2.44 Hz, 3H), 0.87 (d, J=2.44 Hz, 3H), 0.99 (s, 9H), 1.18-1.28 (m, 1H), 1.44-1.60 (m, 2H), 3.14-3.20 (m, 1H), 3.39-3.47 (m, 1H), 3.56 (s, 3H), 4.04 (d, J=18.94 Hz, 1H), 4.15 (d, J=18.94 Hz, 1H), 4.19 (brs, 1H); and MS (ESI, EI$^+$) m/z=283 (MH$^+$).

Intermediate 93

5-tert-butyl-1-(3-methyl-butyl)-4-hydroxy-2-oxo-1,5-dihydropyrrole-3-carbonitrile

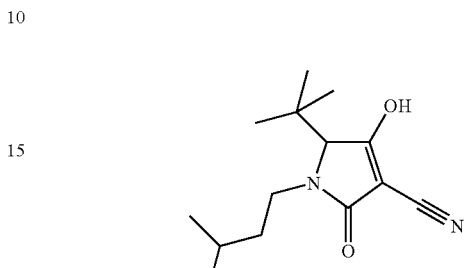

Intermediate 93 was synthesized from intermediate 92 as described for intermediate 77. Intermediate 93 was a beige solid. Intermediate 93 was characterized by the following spectroscopic data: $^1$H NMR (DMSO-d$_6$, 400 MHz) δ (ppm) 0.84 (d, J=6.43 Hz, 6H), 0.97 (s, 9H), 1.22-1.32 (m, 1H), 1.34-1.48 (m, 1H), 1.66-1.74 (m, 1H), 2.95-3.03 (m, 1H), 3.63-3.70 (m, 1H), 3.70 (s, 1H); and MS (ESI, EI$^+$) m/z=251 (MH$^+$).

Intermediate 94

2-(3,3-dimethyl-butylamino)-3-methyl-butyric acid methyl ester

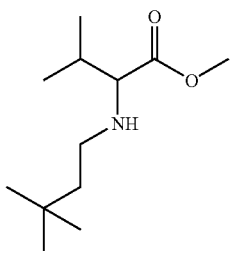

DL-valine methyl ester hydrochloride (5.96 mmol, Alfa Aesar), 3,3-dimethylbutyraldehyde (5.96 mmol, Fluka) and triethylamine (5.96 mmol) were crushed in mortar for 15 minutes. Sodium borohydride (5.96 mmol) and APTS (1.79 mmol) were added and the reaction mixture was crushed again 10 minutes. The reaction was neutralized with NaHCO$_3$ and extracted with dichloromethan. The organic layer was dried and concentrated in vacuo. The residue was purified by chromatography to give intermediate 94, which was a colorless oil. Intermediate 94 was characterized by the following spectroscopic data: $^1$H NMR (DMSO-d$_6$, 400 MHz) δ (ppm) 0.83 (d, J=6.76 Hz, 3H), 0.84 (s, 9H), 0.86 (d, J=6.76 Hz, 3H), 1.2-1.28 (m, 1H), 1.30-1.38 (m, 1H), 1.76 (octet, J=6.76 Hz, 1H), 2.29 (td, J=5.43 Hz and J=10.73 Hz, 1H), 2.48 (td, J=5.43 Hz and J=10.73 Hz, 1H), 2.88 (d, J=6.48 Hz, 1H), 3.62 (s, 3H).

Intermediate 95

2-[(2-cyano-acetyl)-(3,3-dimethyl-butyl)-amino]-3-methyl-butyric acid methyl ester

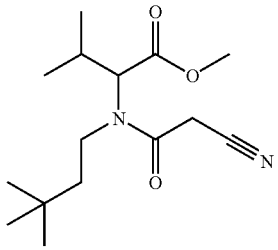

Intermediate 95 was synthesized from intermediate 94 and cyanoacetic acid as described for intermediate 74. Intermediate 95 was characterized by the following spectroscopic data: $^1$H NMR (DMSO-$d_6$, 400 MHz) δ (ppm) 0.78 (d, J=6.88 Hz, 3H), 0.87 (s, 9H), 0.94 (d, J=6.58 Hz, 3H); 1.24-1.32 (m, 1H), 1.41-1.54 (m, 1H), 2.20-2.30 (m, 1H), 3.20-3.24 (m, 2H), 3.6 (s, 3H), 4.11 (d, J=2.98 Hz, 2H), 4.23 (d, J=10.08 Hz, 1H); and MS (ESI, EI$^+$) m/z=283 (MH$^+$).

Intermediate 96

1-(3,3-dimethyl-butyl)-4-hydroxy-2-oxo-5-isopropyl-1,5-dihydropyrrole-3-carbonitrile

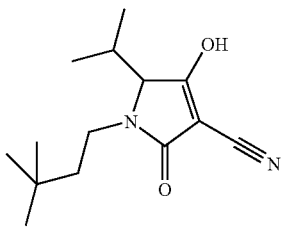

Intermediate 96 was synthesized from intermediate 95 as described for intermediate 77. Intermediate 96 was characterized by the following spectroscopic data: $^1$H NMR (DMSO-$d_6$, 400 MHz) δ (ppm) 0.83 (d, J=7.01 Hz, 3H), 0.87 (s, 9H), 0.95 (d, J=7.01 Hz, 3H), 1.18-1.27 (m, 1H), 1.41-1.49 (m, 1H), 2.17 (heptuplet dedoubled, J=2.64 Hz and J=7.01 Hz, 1H), 2.87-2.94 (m, 1H), 3.56-3.64 (m, 1H), 4.03 (d, J=2.64 Hz, 1H); and MS (ESI, EI$^+$) m/z=251 (MH$^+$).

Intermediate 97

2-[(furan-3-ylmethyl)-amino]-3,3-dimethyl-butyric acid methyl ester

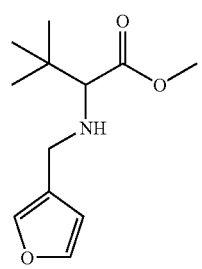

Intermediate 97 was synthesized from methyl-2-amino-3,3-dimethyl butanoate (4.82 mmol, Bionet) and 3-furaldehyde (4.82 mmol, Aldrich) as described for intermediate 88. Intermediate 97 was a yellow oil. Intermediate 97 was characterized by the following spectroscopic data: $^1$H NMR (DMSO-$d_6$, 400 MHz) δ (ppm) 0.87 (s, 9H), 2.13 (brs, 1H), 2.82 (s, 1H), 3.32 (d, J=13.69 Hz, 1H), 3.55 (d, J=13.69 Hz, 1H), 3.60 (s, 3H), 6.39 (s, 1H), 7.47 (s, 1H), 7.55 (s, 1H).

Intermediate 98

2-[(2-cyano-acetyl)-furan-3-ylmethyl-amino]-3,3-dimethyl-butyric acid methyl ester

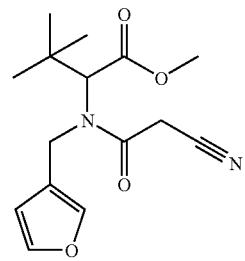

Intermediate 98 was synthesized from intermediate 23 and cyano acetic acid as described for intermediate 74. Intermediate 98 was a brown oil. Intermediate 98 was characterized by the following spectroscopic data: $^1$H NMR (DMSO-$d_6$, 400 MHz) δ (ppm) 1.02 (s, 9H), 3.48 (s, 3H), 3.95 (d, J=19 Hz, 1H), 4 (brs, 1H), 4.03 (d, J=19 Hz, 1H), 4.44 (d, J=17.26 Hz, 1H), 4.60 (d, J=17.26 Hz, 1H), 6.42 (s, 1H), 7.58 (s, 1H), 7.62-7.63 (m, 1H); and MS (ESI, EI$^+$) m/z=315 (MNa$^+$).

Intermediate 99

1-furan-3-ylmethyl-4-hydroxy-2-oxo-5-isopropyl-1,5-dihydropyrrole-3-carbonitrile

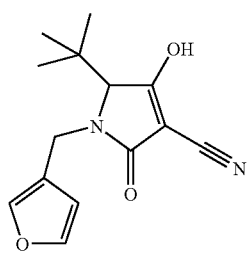

Intermediate 99 was synthesized from intermediate 98 as described for intermediate 77. Intermediate 99 was a brown solid. Intermediate 99 was characterized by the following spectroscopic data: $^1$H NMR (DMSO-$d_6$, 400 MHz) δ (ppm) 0.96 (s, 9H), 3.45 (s, 1H), 4.02 (d, J=15.53 Hz, 1H), 4.68 (d, J=15.53 Hz, 1H), 6.27 (s, 1H), 7.57 (s, 2H), 9.24 (brs, 1H); and MS (ESI, EI$^+$) m/z=261 (MH$^+$).

Intermediate 100

(3,3-dimethyl-butylamino)-phenyl-acetic acid ethyl ester

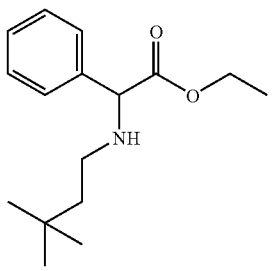

Intermediate 100 was synthesized from ethyl-2-amino-2-phenylacetate hydrochloride (4.64 mmol, Interchim) and 3,3-dimethylbutyraldehyde (4.64 mmol, Fluka) as described for intermediate 88. Intermediate 100 was a colorless oil. Intermediate 100 was characterized by the following spectroscopic data: $^1$H NMR (DMSO-d$_6$, 400 MHz) δ (ppm) 0.82 (s, 9H), 1.10 (t, J=7.14 Hz, 3H), 1.35 (t, J=8.11 Hz, 2H), 2.27 (brs, 1H), 2.37-2.49 (m, 2H), 3.99-4.13 (m, 2H), 4.33 (s, 1H), 7.24-7.38 (m, 5H); and MS (ESI, EI$^+$) m/z=286 (MNa$^+$).

Intermediate 101

[(2-cyano-acetyl)-(3,3-dimethyl-butyl)-amino]-phenyl-acetic acid methyl ester

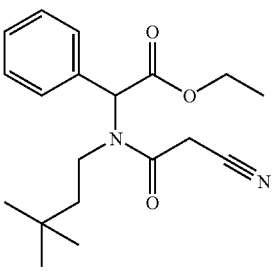

Intermediate 101 was synthesized from intermediate 100 and cyanoacetic acid as described for intermediate 74. Intermediate 101 was characterized by the following spectroscopic data: $^1$H NMR (DMSO-d$_6$, 400 MHz) δ (ppm) 0.64 (s, 9H), 0.92 (td, J=4.77 Hz and J=12.96 Hz, 1H), 1.15 (t, J=7.13 Hz, 3H), 1.32 (td, J=4.97 Hz and J=12.96 Hz, 1H), 3.02-3.10 (m, 1H), 3.13-3.21 (m, 1H), 4.09 (d, J=18.99 Hz, 1H), 4.10-4.16 (m, 2H), 4.26 (d, J=18.99 Hz, 1H), 5.66 (s, 1H), 7.32-7.34 (m, 2H), 7.38-7.42 (m, 3H); and MS (ESI, EI$^+$) m/z=353 (MNa$^+$).

Intermediate 102

1-(3,3-dimethyl-butyl)-4-hydroxy-2-oxo-5-phenyl-1,5-dihydropyrrole-3-carbonitrile

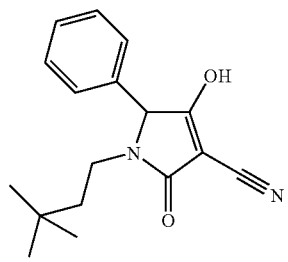

Intermediate 102 was synthesized from intermediate 101 as described for intermediate 77. Intermediate 102 was characterized by the following spectroscopic data: $^1$H NMR (DMSO-d$_6$, 400 MHz) δ (ppm) 0.74 (s, 9H), 1.06-1.16 (m, 1H), 1.29-1.38 (m, 1H), 2.49-2.55 (m, 1H), 3.46-3.53 (m, 1H), 5.13 (s, 1H), 7.21-7.23 (m, 2H), 7.36-7.41 (m, 3H), 9.62 (brs, 1H); and MS (ESI, EI$^+$) m/z=285 (MH$^+$).

Intermediate 103

2-(3,3-dimethyl-butylamino)-2-methyl-3-phenyl-propionic acid methyl ester

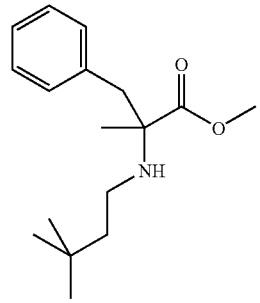

Intermediate 103 was synthesized from 2-amino-2-methyl-3-phenyl-propionic acid methyl ester and 3,3-dimethyl-butyraldehyde (Fluka) as described for intermediate 82. Intermediate 103 was a colorless oil. Intermediate 103 was characterized by the following spectroscopic data: $^1$H NMR (CDCl$_3$, 400 MHz) δ (ppm) 0.90 (s, 9H), 1.32 (s, 3H), 1.29-1.36 (m, 1H), 1.39-1.47 (m, 1H), 2.39-2.45 (m, 1H), 2.55-2.62 (m, 1H), 2.94 (s, 2H), 3.65 (s, 3H), 7.09-7.11 (m, 2H), 7.21-7.29 (m, 3H).

Intermediate 104

2-[(2-cyano-acetyl)-(3,3-dimethyl-butyl)-amino]-2-methyl-3-phenyl-propionic acid methyl ester

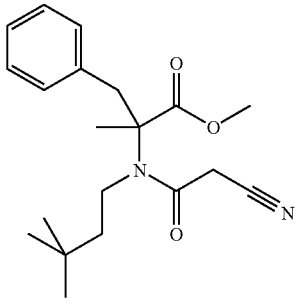

Intermediate 104 was synthesized from intermediate 103 as described for intermediate 74. Intermediate 104 was a yellowish syrup. Intermediate 104 was characterized by the following spectroscopic data: $^1$H NMR (CDCl$_3$, 400 MHz) δ (ppm) 0.78 (s, 9H), 1.02 (td, J=4.44 Hz and J=13.45 Hz, 1H), 1.30 (td, J=4.54 Hz and J=13.50 Hz, 1H), 1.49 (s, 3H), 2.53-2.62 (m, 1H), 2.81-2.89 (m, 1H), 2.97 (d, J=13.60 Hz, 1H), 3.48 (s, 2H), 3.74 (d, J=13.30 Hz, 1H), 3.75 (s, 3H), 7.09 (d, J=7.24 Hz, 2H), 7.27-7.33 (m, 3H).

Intermediate 105

5-benzyl-1-(3,3-dimethyl-butyl)-4-hydroxy-5-methyl-2-oxo-1,5-dihydropyrrole-3-carbonitrile

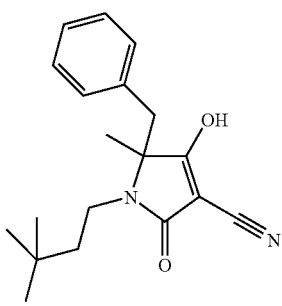

Intermediate 105 was synthesized from intermediate 104 as described for intermediate 77. Intermediate 105 was a pale yellow solid. Intermediate 105 was characterized by the following spectroscopic data: $^1$H NMR (CDCl$_3$, 400 MHz) δ (ppm) 0.94 (s, 9H), 1.25-1.36 (m, 1H), 1.46 (s, 3H), 1.79 (td, J=4.59 Hz and J=12.80 Hz, 1H), 2.93 (d, J=14.14 Hz, 1H), 2.99 (td, J=4.39 Hz and J=13.17 Hz, 1H), 3.06 (d, J=14.14 Hz, 1H), 3.56 (td, J=4.39 Hz and J=13.18 Hz, 1H), 4.07 (brs, 1H), 7.04-7.06 (m, 2H), 7.20-7.26 (m, 3H); and MS (ESI, EI$^+$) m/z=313 (ME).

Intermediate 106

4-hydroxy-N-methyl-butyramide

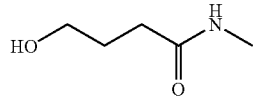

The γ-butyrolactone (0.013 mol, Aldrich) and methylamine 2M in methanol (0.066 mol) were stirred at 60° C. in a sealed MPS tube over 5 days. Then, the reaction mixture was evaporated to give intermediate 106, which was a colorless oil. Intermediate 106 was characterized by the following spectroscopic data: $^1$H NMR (DMSO-d$_6$, 400 MHz) δ (ppm) 1.6 (quintuplet, J=7.01 Hz, 2H), 2.07 (t, J=7.54 Hz, 2H), 2.53 (d, J=4.65 Hz, 3H), 3.34 (q, J=6.32 Hz, 2H), 4.44 (t, J=5.16 Hz, 1H), 7.67 (brs, 1H).

Intermediate 107

4-hydroxy-butyramide

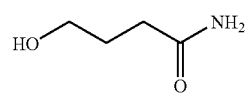

The γ-butyrolactone (0.013 mol, Aldrich) was put in methanol and the reaction mixture was saturated with ammonia gas. This mixture was stirred at 60° C. in a sealed MPS tube over 2 days. Then, the reaction mixture was evaporated and washed with hot ethyl acetate. This hot solution was filtered and cooled down to 0° C. The white solid was filtered and dried under vacuo to give intermediate 107, which was a white solid. Intermediate 107 was characterized by the following spectroscopic data: $^1$H NMR (DMSO-d$_6$, 400 MHz) δ (ppm) 1.60 (quintuplet, J=6.91 Hz, 2H), 2.06 (t, J=7.47 Hz, 2H), 3.35 (t, J=6.30 Hz, 2H), 4.43 (t, J=5.14 Hz, 1H), 6.68 (brs, 1H), 7.22 (brs, 1H).

Intermediate 108

2-amino-5-fluoro-phosphonic acid diethyl ester

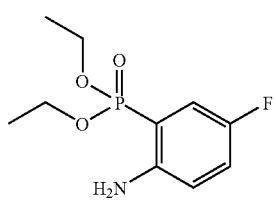

To a stirred solution of 2-bromo-4-fluoroaniline (0.53 mmol, Alfa Aesar) in acetonitrile (1.3 ml) was added triethylphosphite (0.74 mmol) and after nitrogen bubbling, palladium (II) acetate (0.05 mmol). The reaction mixture was stirred under microwave irradiations at 160° C. for 10 min. The solvent was evaporated and the crude material was purified by chromatography on silica gel to give intermediate 108, which was a beige solid. Intermediate 108 was characterized by the following spectroscopic data: $^1$H NMR (CDCl$_3$, 400 MHz) δ (ppm) 1.32-1.36 (t, J=7.00 Hz, 6H), 4.08-4.20 (m, 4H), 5.00 (brs, 2H), 6.59-6.64 (td, J=4.11 Hz and J=4.44 Hz, 1H), 6.98-7.03 (td, J=2.94 Hz and J=4.50 Hz, 1H), 7.11-7.18 (m, 1H).

Intermediate 109

2-amino-phosphonic acid diethyl ester

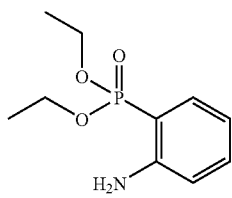

Intermediate 109 was synthesized from 2-iodoaniline (Aldrich) following the procedure as described for intermediate 108. Intermediate 109 was a beige solid. Intermediate 109 was characterized by the following spectroscopic data: $^1$H NMR (CDCl$_3$, 400 MHz) δ (ppm) 1.32-1.36 (t, J=7.00 Hz, 6H), 4.08-4.20 (t, J=6.93 Hz, 4H)), 5.18 (brs, 2H), 6.63-6.71 (m, 2H), 7.25-7.28 (t, J=7.55 Hz, 1H), 7.42-7.47 (dd, J=7.55 Hz, and J=6.29 Hz, 1H).

Intermediate 110

2-amino-6-fluoro-phosphonic acid diethyl ester

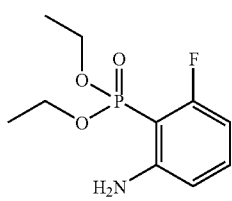

Intermediate 110 was synthesized from 2-bromo-3-fluoro-aniline (Fluorochem) following the procedure as described for intermediate 108. Intermediate 110 was a beige solid. Intermediate 110 was characterized by the following spectroscopic data: $^1$H NMR (CDCl$_3$, 400 MHz) δ (ppm) 1.30-1.35 (t, J=7.00 Hz, 6H), 4.00-4.10 (q, J=7.00 Hz, 2H), 4.09-4.18 (q, J=6.67 Hz, 2H), 5.30 (brs, 2H), 6.30-6.35 (m, 1H), 6.39-6.44 (m, 1H), 7.39-7.46 (m, 1H). $^{19}$F NMR (CDCl$_3$, 376 MHz) δ (ppm) −102.35 (s, 1F). $^{31}$P NMR (CDCl$_3$, 162 MHz) δ (ppm) 17.41 (m, 1P).

Intermediate 111

2-amino-4-fluoro-phosphonic acid diethyl ester

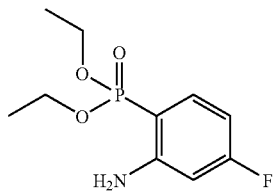

Intermediate 111 was synthesized from 2-bromo-5-fluoro-aniline (Alfa Aesar) following the procedure as described for intermediate 108. Intermediate 111 was a beige solid. Intermediate 111 was characterized by the following spectroscopic data: $^1$H NMR (CDCl$_3$, 400 MHz) δ (ppm) 1.31-1.36 (t, J=6.67 Hz, 6H), 4.00-4.09 (q, J=6.67 Hz, 2H), 4.09-4.18 (q, J=6.67 Hz, 2H), 5.33 (brs, 2H), 6.30-6.35 (m, 1H), 6.39-6.44 (t, J=8.23, 1H), 7.39-7.46 (m, 1H). $^{19}$F NMR (CDCl$_3$, 376 MHz) δ (ppm) −105.95 (s, 1F). $^{31}$P NMR (CDCl$_3$, 162 MHz) δ (ppm) 20.45 (m, 1P).

Intermediate 112

2-amino-3-fluoro-phosphonic acid diethyl ester

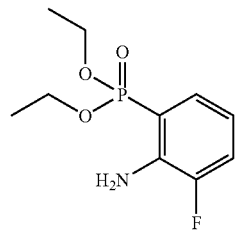

Intermediate 112 was synthesized from 2-bromo-6-fluoro-aniline (Alfa Aesar) following the procedure as described for intermediate 108. Intermediate 112 was a beige solid. Intermediate 112 was characterized by the following spectroscopic data: $^1$H NMR (CDCl$_3$, 400 MHz) δ (ppm) 1.31-1.36 (t, J=6.67 Hz, 6H), 4.00-4.09 (q, J=6.67 Hz, 2H), 4.09-4.18 (q, J=6.67 Hz, 2H), 5.27 (brs, 2H), 6.60-6.66 (m, 1H), 7.08-7.12 (m, 1H), 7.20-7.25 (m, 1H). $^{31}$P NMR (CDCl$_3$, 162 MHz) δ (ppm) 19.39 (s, 0.5P), 19.46 (s, 0.5P).

Intermediate 113

3-(tert-butyl-dimethyl-silanyloxy)propan-1-ol

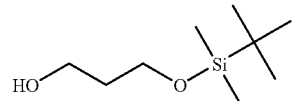

A solution of tert-butyldimethylsilylchloride (0.01 mol, Aldrich) was added dropwise to a stirred solution of 1,3-propanediol (0.1 mol, Aldrich) and pyridine (0.1 mol) in dichloromethane (13 ml) under nitrogen at 0° C. This reaction mixture was stirred at room temperature under nitrogen overnight. Then, the mixture was evaporated and extracted with petroleum ether. The combined petroleum ether layers were dried, evaporated and purified on silica gel to give intermediate 113, which was a colorless oil. Intermediate 113 was characterized by the following spectroscopic data: $^1$H NMR (DMSO-$d_6$, 400 MHz) δ (ppm) 0.01 (s, 6H), 0.84 (s, 9H), 1.58 (quintuplet, J=6.30 Hz, 2H), 3.41-3.46 (m, 2H), 3.63 (t, J=6.29 Hz, 2H), 4.31 (t, J=5.12 Hz, 1H).

Intermediate 114

2-(tert-butyl-dimethyl-silanyloxy)ethanol

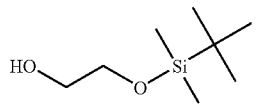

Intermediate 114 was synthesized from ethylene glycol (0.1 mol, Aldrich) and tert-butyldimethylsilylchloride (0.01 mol, Aldrich) as described for intermediate 113. Intermediate 114 was a colorless oil. Intermediate 114 was characterized by the following spectroscopic data: $^1$H NMR (DMSO-$d_6$, 400 MHz) δ (ppm) 0.02 (s, 6H), 0.85 (s, 9H), 3.40 (q, J=5.64 Hz, 2H), 3.56 (t, J=5.64 Hz, 2H), 4.49 (t, J=5.64 Hz, 1H).

Intermediate 115

(S)-3-tert-butoxy-2-(3,3-dimethylbutylamino)-propionic acid methyl ester

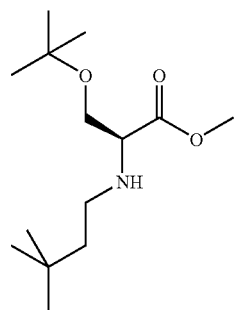

Intermediate 115 was synthesized from O-tBu-L-serine methyl ester hydrochloride (4.72 mmol, Iris Biotech) and 3,3-dimethylbutyraldehyde (4.63 mmol, Fluka) following the procedure as described for intermediate 88. Intermediate 115 was a colorless oil. Intermediate 115 was characterized by the following spectroscopic data: $^1$H NMR (DMSO-$d_6$, 400 MHz) δ (ppm) 0.84 (s, 9H), 1.06 (s, 9H), 1.28 (td, J=5.61 Hz and J=10.70 Hz, 2H), 1.72 (brs, 1H), 2.35-2.41 (m, 1H), 2.48-2.55 (m, 1H), 3.29 (brs, 1H), 3.39-3.47 (m, 2H), 3.61 (s, 3H).

Intermediate 116

(S)-3-tert-butoxy-2-[(2-cyano-acetyl)-(3,3-dimethyl-butylamino)-propionic acid methyl ester

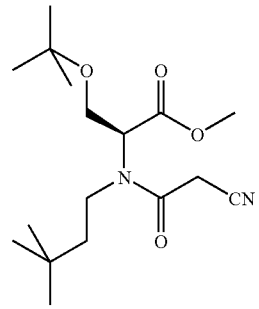

Intermediate 116 was synthesized from intermediate 115 and cyanoacetic acid following the procedure as described for intermediate 74. Intermediate 116 was a colorless oil. Intermediate 116 was characterized by the following spectroscopic data: $^1$H NMR (CDCl$_3$, 400 MHz) δ (ppm) 0.96 (s, 9H), 1.18 (s, 9H), 1.60-1.65 (m, 2H), 3.51 (d, J=3.51 Hz, 2H), 3.73 (s, 3H), 3.79 (3.85 (dd, J=3.71 Hz and J=10.06 Hz, 1H), 3.92 (t, J=9.18 Hz, 1H), 4.25 (dd, J=3.65 Hz and J=8.30 Hz, 1H). MS (ESI, EI$^+$) m/z=349 (MNa$^+$).

Intermediate 117

(S)-5-tert-butoxymethyl-1-(3,3-dimethyl-butyl)-4-hydroxy-2-oxo-2,5-dihydro-1H-pyrrole-3-carbonitrile

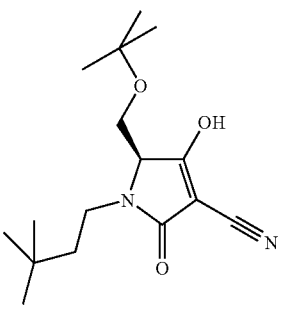

Intermediate 117 was synthesized from intermediate 115 following the procedure as described for intermediate 120. Intermediate 117 was a white solid. Intermediate 117 was characterized by the following spectroscopic data: $^1$H NMR (DMSO-$d_{63}$ 400 MHz) δ (ppm) 0.95 (s, 9H), 1.27 (s, 9H), 1.38 (td, J=5.50 Hz and J=12 Hz, 1H), 1.48 (td, J=4.75 Hz and J=12.24 Hz, 1H), 3.08-3.16 (m, 1H), 3.59 (t, J=8.25 Hz, 1H), 3.67-3.75 (m, 1H), 3.81-3.85 (m, 1H), 4.13 (t, J=6.90 Hz, 1H). MS (ESI, EI⁺) m/z=295 (MH⁺).

Intermediate 118

2-(3,3-dimethyl-butylamino)-3-phenyl-propionic acid methyl ester

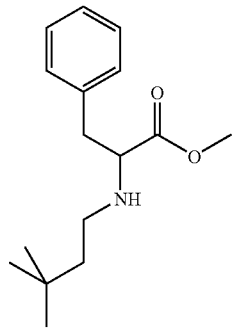

Intermediate 118 was synthesized from D-L-phenylalanine methyl ester hydrochloride (4.63 mmol, Alfa Aesar) and 3,3-dimethylbutyraldehyde (4.63 mmol, Fluka) following the procedure as described for intermediate 91. Intermediate 118 was a colourless oil. ¹H NMR (CDCl₃, 400 MHz) δ (ppm) 0.89 (s, 9H), 1.29-1.44 (m, 2H), 2.46 (td, J=5.35 Hz and J=10.96 Hz, 1H), 2.59 (td, J=5.35 Hz and J=10.85 Hz, 1H), 2.91-3.01 (m, 2H), 3.54 (t, J=6.99 Hz, 1H), 3.65 (s, 3H), 7.17-7.19 (m, 2H), 7.21-7.25 (m, 1H), 7.27-7.31 (m, 2H). MS (ESI, EI⁺) m/z=264 (MH⁺).

Intermediate 119

2-[cyanocarbonyl-(3,3-dimethyl-butyl)-amino]-3-phenyl-propionic acid methyl ester

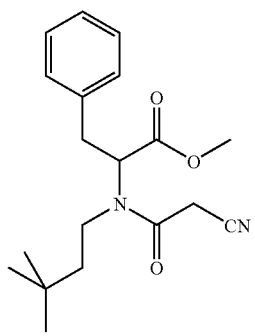

Intermediate 119 was synthesized from intermediate 118 and cyanoacetic acid following the procedure as described for intermediate 74. Intermediate 119 was a colourless oil. Intermediate 119 was characterized by the following spectroscopic data: ¹H NMR (CDCl₃, 400 MHz) δ (ppm) 0.79 (s, 9H), 1.11 (td, J=5.02 Hz and J=13.22 Hz, 1H), 1.20-1.28 (m, 1H), 2.59-2.68 (m, 1H), 2.97-3.06 (m, 1H), 3.37-3.40 (m, 1H), 3.41 (s, 2H), 3.77 (s, 3H), 4.06 (dd, J=5.13 Hz and J=10.27 Hz, 1H), 7.17-7.21 (m, 2H), 7.24-7.28 (m, 1H), 7.31-7.36 (m, 2H). MS (ESI, EI⁺) m/z=331 (MH⁺).

Intermediate 120

5-benzyl-1-(3,3-dimethyl-butyl)-4-hydroxy-2-oxo-2,5-dihydro-1H-pyrrole-3-carbonitrile

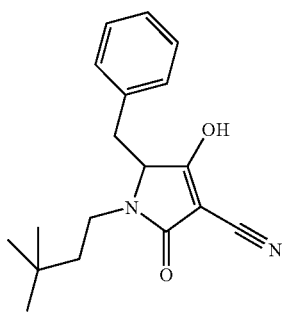

Intermediate 119 (1.5 mmol) and cesium carbonate (1.66 mmol) in ethanol (40 ml) was stirred at room temperature for 15 minutes. The mixture was acidified to pH=1 with HCl 1N and ethyl acetate was added before washing with brine. The organic layer was dried over sodium sulphate, filtered and concentrated under vacuo to give intermediate 120, which was a white solid. Intermediate 120 was characterized by the following spectroscopic data: ¹H NMR (DMSO-d₆, 400 MHz) δ (ppm) 0.80 (s, 9H), 1.74 (td, J=5.63 Hz and J=11.67 Hz, 1H), 1.31 (td, J=4.65 Hz and J=12.55 Hz, 1H), 2.75-2.83 (m, 1H), 2.92 (dd, J=5.33 Hz and J=14.42 Hz, 1H), 3.17 (dd, J=4.10 Hz and J=14.42 Hz, 1H), 3.53-3.61 (m, 1H), 4.37 (t, J=4.68 Hz, 1H), 7.12-7.14 (m, 2H), 7.17-7.21 (m, 1H), 7.24-7.28 (m, 2H). MS (ESI, EI⁺) m/z=299 (MH⁺).

Intermediate 121

Tryptophan Methyl Ester Hydrochloride

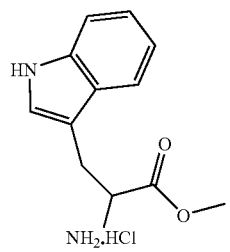

To a stirred solution of acetyl chloride (17.1 mmol, Fluka) in MeOH (25 ml) at 0° C., was added D,L-Tryptophan (4.89 mmol, Alfa Aesar). The mixture was let to warm up to room temperature and stirred at 50° C. for 6 hours. Solvent was concentrated under reduced pressure and the solid obtained was dried in vacuo to yield intermediate 121, which was a pink-white solid. Intermediate 121 was characterized by the following spectroscopic data: ¹H NMR (DMSO-d₆, 400 MHz) δ (ppm) 3.25-3.35 (m, 2H), 4.20 (s, 1H), 6.97-7.01 (t, J=7.19 Hz, 1H), 7.06-7.09 (t, J=7.19 Hz, 1H), 7.23 (s, 1H), 7.36 (d, J=7.36 Hz, 1H), 7.49 (d, J=7.36 Hz, 1H), 8.61 (s, H), 11.10 (s, 1H)

Intermediate 122

2-(3,3-dimethyl-butylamino)-3-(1H-indol-3-yl)-propionic acid methyl ester

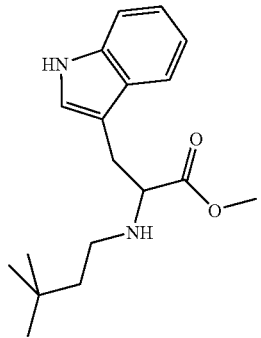

Intermediate 122 was synthesized from intermediate 121 (2.35 mmol) and 3,3-dimethylbutyraldehyde (2.35 mmol, Fluka) following the procedure as described for intermediate 88. Intermediate 122 was a colorless oil. Intermediate 122 was characterized by the following spectroscopic data: $^1$H NMR (CDCl$_3$, 400 MHz) δ (ppm) 0.86 (s, 9H), 1.32-1.40 (m, 2H), 2.44-2.52 (m; 1H), 2.57-2.65 (m, 1H), 3.15-3.18 (m, 2H), 3.64 (s, 3H), 3.64-3.67 (m, 1H), 7.07 (brs, 1H), 7.11-7.15 (m, 1H), 7.18-7.22 (m, 1H), 7.35-7.38 (m, 1H), 7.61-7.63 (m, 1H), 8.04 (brs, 1H). MS (ESI, EI$^+$) m/z=303 (MH$^+$).

Intermediate 123

2-[(cyanocarbonyl-(3,3-dimethyl-butylamino)]-3-(1H-indol-3-yl)-propionic acid methyl ester

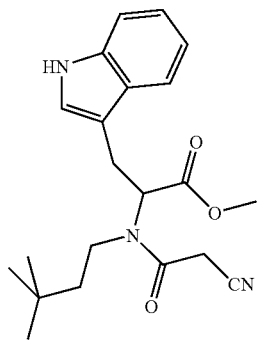

Intermediate 123 was synthesized from intermediate 122 and cyanoacetic acid following the procedure as described for intermediate 74. Intermediate 123 was a white solid. Intermediate 123 was characterized by the following spectroscopic data: $^1$H NMR (CDCl$_3$, 400 MHz) δ (ppm) 0.66 (s, 9H), 0.98 (td, J=5.02 Hz and J=13.25 Hz, 1H), 1.14 (td, J=4.60 Hz and J=13.25 Hz, 1H), 2.64-2.72 (m, 1H), 2.91-2.97 (m, 1H), 3.38 (s, 2H), 3.55 (d, J=7.72 Hz, 2H), 3.79 (s, 3H), 4.30 (t, J=7.72 Hz, 1H), 7.03-7.06 (m, 1H), 7.12-7.16 (m, 1H), 7.19-7.23 (m, 1H), 7.39 (d, J=8.04 Hz, 1H), 7.57 (d, J=7.89 Hz, 1H), 8.08 (brs, 1H). MS (ESI, EI$^+$) m/z=370 (MH$^+$).

Intermediate 124

1-(3,3-dimethyl-butyl)-4-hydroxy-5-(1H-indol-3-ylmethyl)-2-oxo-2,5-dihydro-1H-pyrrole-3-carbonitrile

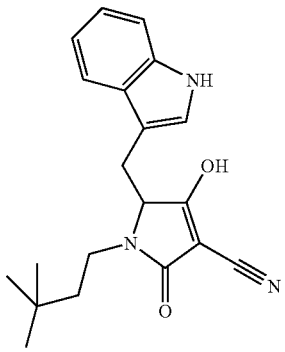

Intermediate 124 was synthesized from intermediate 123 following the procedure as described for intermediate 120. Intermediate 124 was a white blue solid. Intermediate 124 was characterized by the following spectroscopic data: $^1$H NMR (DMSO-d$_6$, 400 MHz) δ (ppm) 0.74 (s, 9H), 1.11-1.18 (m, 1H), 1.25-1.32 (m, 1H), 2.76-2.83 (m, 1H), 3.11 (dd, J=4.49 Hz and J=15.41 Hz, 1H), 3.27 (dd, J=3.26 Hz and J=15.41 Hz, 1H), 3.50-3.58 (m, 1H), 4.40-4.42 (m, 1H), 6.97 (t, J=7.64 Hz, 1H), 7.02 (brs, 1H), 7.04 (t, J=7.52 Hz, 1H), 7.31 (d, J=8.02 Hz, 1H), 7.53 (d, J=8.02 Hz, 1H), 10.88 (s, 1H). MS (ESI, EI$^+$) m/z=338 (MH$^+$).

Intermediate 125

2-(3,3-dimethyl-butylamino)-3-thiophen-3-yl-propionic acid methyl ester

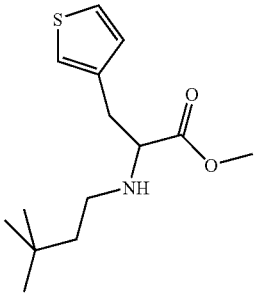

Intermediate 125 was synthesized from 2-amino-3-thiophen-2-yl-propionic acid methyl ester (2.70 mmol, synthesized from 3-(2-thienyl)-D-L-alanine following the procedure as described for intermediate 121) and 3,3-dimethylbutyraldehyde (2.35 mmol, Fluka) following the procedure as described for intermediate 88. Intermediate 125 was a colorless oil. Intermediate 125 was characterized by the following spectroscopic data: $^1$H NMR (CDCl$_3$, 400 MHz) δ (ppm) 0.91 (s, 9H), 1.32-1.47 (m, 2H), 2.51 (td, J=5.36 Hz and J=10.87 Hz, 1H), 2.63 (td, J=5.41 Hz and J=10.87 Hz, 1H), 3.15-3.25 (m, 2H), 3.54 (t, J=6.40 Hz, 1H), 3.71 (s, 3H), 6.83-6.84 (m, 1H), 6.92-6.94 (m, 1H), 7.16-7.17 (m, 1H). MS (ESI, EI⁺) m/z=270.1 (MH⁺).

Intermediate 126

2-[cyanocarbonyl-(3,3-dimethyl-butyl)-amino]-3-thiophen-2-yl-propionic acid methyl ester

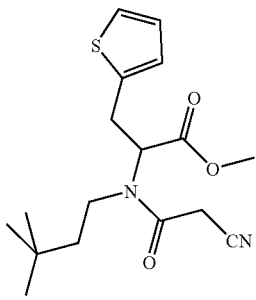

Intermediate 126 was synthesized from intermediate 125 and cyanoacetic acid following the procedure as described for intermediate 74. Intermediate 126 was a yellow oil. Intermediate 126 was characterized by the following spectroscopic data: ¹H NMR (CDCl₃, 400 MHz) δ (ppm) 0.84 (s, 9H), 1.22 (td, J=4.93 Hz and J=13.35 Hz, 1H), 1.37 (td, J=4.65 Hz and J=13.09 Hz, 1H), 2.74-2.82 (m, 1H), 3.09-3.17 (m, 1H), 3.46 (s, 2H), 3.60-3.62 (m, 2H), 3.78 (s, 3H), 4 (dd, J=6.14 Hz and J=9.05 Hz, 1H), 6.85 (d, J=3.28 Hz, 1H), 6.96 (dd, J=3.58 Hz and J=5.04 Hz, 1H), 7.19 (d, J=5.04 Hz, 1H). MS (ESI, EI⁺) m/z=337 (MH⁺).

Intermediate 127

1-(3,3-dimethyl-butyl)-4-hydroxy-2-oxo-5-thiophen-2-ylmethyl-2,5-dihydro-1H-pyrrole-3-carbonitrile

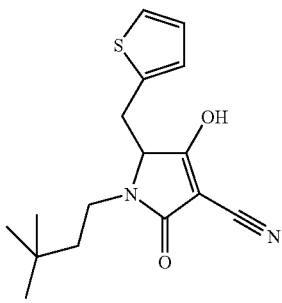

Intermediate 127 was synthesized from intermediate 126 following the procedure as described for intermediate 120. Intermediate 127 was a yellow oil. Intermediate 127 was characterized by the following spectroscopic data: ¹H NMR (DMSO-d₆, 400 MHz) δ (ppm) 0.86 (s, 9H), 1.26 (td, J=5.83 Hz and J=11.14 Hz, 1H), 1.40 (td, J=4.67 Hz and J=12.24 Hz, 1H), 2.83-2.90 (m, 1H), 3.25 (dd, J=4.10 Hz and J=15.61 Hz, 1H), 3.33 (dd, J=4.10 Hz and J=15.53 Hz, 1H), 3.58-3.66 (m, 1H), 4.28 (t, J=3.96 Hz, 1H), 6.80 (d, J=3.26 Hz, 1H), (dd, J=3.47 Hz and J=5.08 Hz, 1H), 7.33 (d, J=5.08 Hz, 1H). MS (ESI, EI⁺) m/z=305 (MH⁺).

Intermediate 128

(S)-3,3-dimethyl-2-[(1-methyl-pyrazol-4-ylmethyl)-amino]butyric acid methyl ester

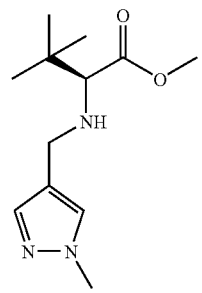

Intermediate 128 was synthesized from methyl-2-amino-3,3-dimethyl butanoate (6.89 mmol, Fluka) and 1-methyl-1H-pyrazole-4-carboxaldehyde (6.89 mmol, Aldrich) following the procedure as described for intermediate 88. Intermediate 128 was a colourless oil. Intermediate 128 was characterized by the following spectroscopic data: ¹H NMR (DMSO-d₆, 400 MHz) δ (ppm) 0.87 (s, 9H), 2.83 (d, J=11.42 Hz, 1H), 3.33-3.34 (m, 1H), 3.53 (d, J=13.45 Hz, 1H), 3.60 (s, 3H), 3.76 (s, 3H), 7.25 (s, 1H), 7.49 (s, 1H). MS ESI, EI⁺) m/z=240 (MH⁺).

Intermediate 129

(S)-2-[(2-cyano-acetyl)-(1-methyl-pyrazol-4-ylmethyl)-amino]-3,3-dimethyl-butyric acid methyl ester

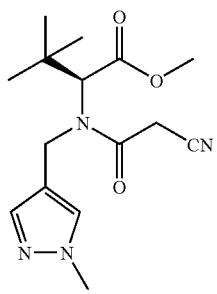

Intermediate 129 was synthesized from intermediate 128 and cyanoacetic acid following the procedure as described for intermediate 74. Intermediate 129 was a white oil. Intermediate 129 was characterized by the following spectroscopic data: ¹H NMR (CDCl₃, 400 MHz) δ (ppm) 1.11 (s, 9H), 3.40 (d, J=17.94 Hz, 1H), 3.49 (d, J=17.94 Hz, 1H), 3.66 (s, 3H), 3.71 (s, 1H), 3.90 (s, 3H), 4.51 (d, J=17.15 Hz, 1H), 4.90 (d, J=17.15 Hz, 1H), 7.29 (s, 1H), 7.34 (s, 1H). MS (ESI, EI⁺) m/z=307 (MH⁺).

Intermediate 130

(S)-5-tert-butyl-4-hydroxy-1-(1-methyl-pyrazol-4-ylmethyl-2-oxo-1,5-dihydropyrrole-3-carbonitrile

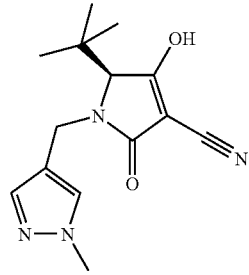

Intermediate 130 was synthesized from intermediate 129 following the procedure as described for intermediate 120. Intermediate 130 was a white solid. Intermediate 130 was characterized by the following spectroscopic data: ¹H NMR (DMSO-d₆, 400 MHz) δ (ppm) 0.95 (s, 9H), 3.3 (s, 1H), 3.76 (s, 3H), 3.81 (d, J=11.53 Hz, 1H), 3.91 (d, J=15.41 Hz, 1H), 4.72 (d, J=15.46 Hz, 1H), 7.24 (s, 1H), 7.53 (s, 1H). MS (ESI, EI⁺) m/z=275 (MH⁺).

Intermediate 131

Cyclohexyl-(3,3-dimethyl-butylamino)-acetic acid methyl ester

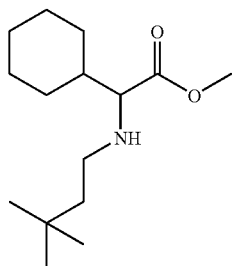

Intermediate 131 was synthesized from 1-methyl-1H-pyrazole-4-carboxaldehyde (6.89 mmol, synthesized from D-L-amino-cyclohexyl-acetic acid following the procedure as described for intermediate 121) and 3,3-dimethylbutyraldehyde (3.36 mmol, Aldrich) following the procedure as described for intermediate 88. Intermediate 131 was a colourless oil. Intermediate 131 was characterized by the following spectroscopic data: ¹H NMR (CDCl₃, 400 MHz) δ (ppm) 0.89 (s, 9H), 0.97-1.35 (m, 5H), 1.41-1.60 (m, 4H), 1.62-1.84 (m, 4H), 2.40 (td, J=5.25 Hz and J=10.96 Hz, 1H), 2.56 (td, J=5.05 Hz and J=10.96 Hz, 1H), 3.03 (d, J=6.04 Hz, 1H), 3.73 (s, 3H). MS (ESI, EI⁺) m/z=256 (MH⁺).

Intermediate 132

[Cyanocarbonyl-(3,3-dimethyl-butyl)-amino]-cyclohexyl-acetic acid methyl ester

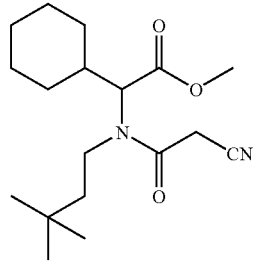

Intermediate 132 was synthesized from intermediate 131 and cyanoacetic acid following the procedure as described for intermediate 74. Intermediate 132 was a white solid. Intermediate 132 was characterized by the following spectroscopic data: ¹H NMR (CDCl₃, 400 MHz) δ (ppm) 3.71 (s, 3H), 3.76 (s, 2H), 4.52 (d, J=10.31 Hz, 1H).

Intermediate 133

Cyclohexyl-1-(3,3-dimethyl-butyl)-4-hydroxy-2-oxo-2,5-dihydro-1H-pyrrole-3-carbonitrile

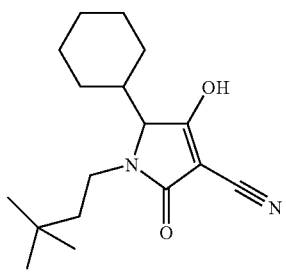

Intermediate 133 was synthesized from intermediate 132 following the procedure as described for intermediate 120. Intermediate 133 was a white solid. Intermediate 133 was characterized by the following spectroscopic data: ¹H NMR (DMSO-d₆, 400 MHz) δ (ppm) 0.88 (s, 9H), 0.94-1.26 (m, 5H), 1.35-1.51 (m, 4H), 1.60-1.79 (m, 4H), 2.86-2.93 (m, 1H), 3.56-3.63 (m, 1H), 3.86 (d, J=2.35 Hz, 1H). MS (ESI, EI⁺) m/z=291 (MH⁺).

Intermediate 134

(S)-3-benzyloxy-2-(3,3-dimethyl-butylamino)-butyric acid methyl ester

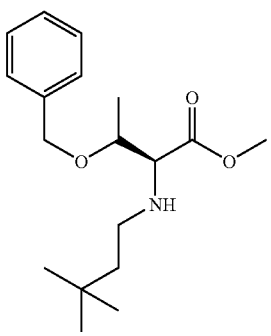

Intermediate 134 was synthesized from O-benzyl-L-threonine methyl ester (6.89 mmol, synthesized from O-benzyl-L-threonine following the procedure as described for intermediate 121) and 3,3-dimethylbutyraldehyde (6.89 mmol, Aldrich) following the procedure as described for intermediate 88. Intermediate 134 was a beige solid. Intermediate 134 was characterized by the following spectroscopic data: $^1$H NMR (CDCl$_3$, 400 MHz) δ (ppm) 0.89 (s, 9H), 1.26 (d, J=6.28 Hz, 3H), 1.34-1.48 (m, 2H), 2.44 (td, J=5.58 Hz and J=10.76 Hz, 1H), 2.66 (td, J=5.52 Hz and J=10.76 Hz, 1H), 3.30 (d, J=4.88 Hz, 1H), 3.71 (s, 3H), 3.80-3.86 (m, 1H), 4.47 (d, J=11.80 Hz, 1H), 4.60 (d, J=11.80 Hz, 1H), 7.27-7.36 (m, 5H). MS (ESI, EI$^+$) m/z=330 (MNa$^+$).

Intermediate 135

(S)-3-benzyloxy-2-[cyanocarbonyl-(3,3-dimethyl-butyl)-amino]-butyric acid methyl ester

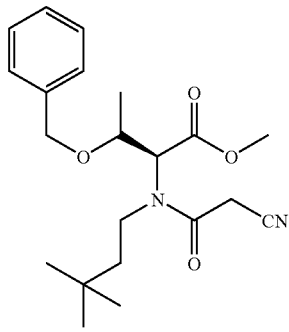

Intermediate 135 was synthesized from intermediate 134 and cyanoacetic acid following the procedure as described for intermediate 74. Intermediate 135 was a colourless oil. Intermediate 135 was characterized by the following spectroscopic data: $^1$H NMR (CDCl$_3$, 400 MHz) δ (ppm) 0.83 (s, 9H), 1.32 (d, J=6.28 Hz, 3H), 1.40-1.48 (m, 1H), 1.66-1.74 (m, 1H), 3.27-3.43 (m, 2H), 3.48 (d, J=3.32 Hz, 2H), 3.71 (s, 3H), 3.76 (s, 1H), 3.92-3.94 (m, 1H), 4.34-4.39 (m, 1H), 4.60-4.65 (m, 1H), 7.24-7.38 (m, 5H). MS (ESI, EI$^+$) m/z=396.99 (MNa$^+$).

Intermediate 136

(S)-5-(1-benzyloxy-ethyl)-1-(3,3-dimethyl-butyl)-4-hydroxy-2-oxo-2,5-dihydro-1H-pyrrole-3-carbonitrile

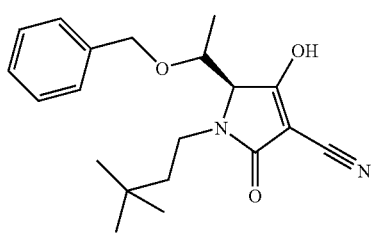

Intermediate 136 was synthesized from intermediate 135 following the procedure as described for intermediate 120. Intermediate 136 was a white solid. Intermediate 136 was characterized by the following spectroscopic data: $^1$H NMR (DMSO-d$_6$, 400 MHz) δ (ppm) 0.83 (s, 9H), 1.17 (d, J=6.51 Hz, 3H), 1.21-1.28 (m, 1H), 1.37-1.44 (m, 1H), 2.90-2.98 (1H), 3.55-3.64 (m, 1H), 3.85-3.91 (m, 1H), 4.14 (d, J=2.98 Hz, 1H), 4.46-4.58 (m, 2H), 7.27-7.35 (m, 5H).

Intermediate 137

2-(3,3-dimethyl-butylamino)-2,3-dimethyl-butyric acid methyl ester

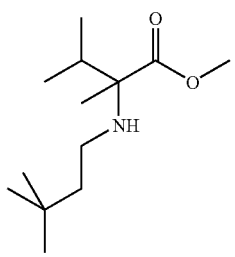

Intermediate 137 was synthesized from 2,2,3-trimethyl-butyric acid methyl ester (3.5 mmol, synthesized from 2,2,3-trimethyl-butyric acid following the procedure as described for intermediate 121) and 3,3-dimethylbutyraldehyde (3.5 mmol, Aldrich) following the procedure as described for intermediate 88. Intermediate 137 was a beige solid and was used just as it is in the next step.

Intermediate 138

2-[(2-cyano-acetyl)-(3,3-dimethyl-butyl)-amino]-2,3-dimethyl-butyric acid methyl ester

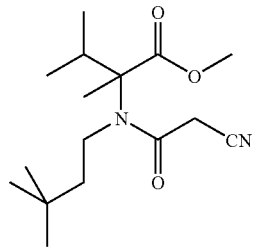

Intermediate 138 was synthesized from intermediate 137 and cyanoacetic acid following the procedure as described for intermediate 74. Intermediate 138 was a white solid. Intermediate 138 was characterized by the following spectroscopic data: $^1$H NMR (CDCl$_3$, 400 MHz) δ (ppm) 0.87 (d, J=6.82 Hz, 3H), 0.99 (s, 9H), 1.07 (d, J=6.82 Hz, 3H), 1.42 (s, 3H), 1.44-1.53 (m, 1H), 1.69-1.77 (m, 1H), 2.70 (heptuplet, J=6.82 Hz, 1H), 3.28-3.34 (m, 2H), 3.45 (d, J=17.66 Hz, 1H), 3.54 (d, J=17.66 Hz, 1H), 3.69 (s, 3H).

Intermediate 139

1-(3,3-dimethyl-butyl)-4-hydroxy-5-methyl-2-oxo-1,5-dihydropyrrole-3-carbonitrile

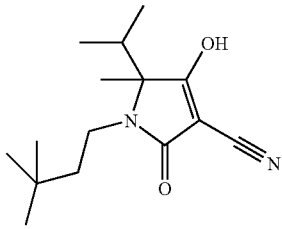

Intermediate 139 was synthesized from intermediate 138 following the procedure as described for intermediate 77. Intermediate 139 was a pale yellow solid. Intermediate 139 was characterized by the following spectroscopic data: $^1$H NMR (DMSO-$d_6$, 400 MHz) δ (ppm) 0.74 (d, J=6.83 Hz, 3H), 0.89 (s, 9H), (d, J=6.83 He, 3H), 1.28 (s, 3H), 1.42-1.46 (m, 2H), 1.97 (heptuplet, J=6.82 Hz, 1H), 3-3.07 (m, 1H), 3.12-3.20 (m, 1H). MS (ESI, EI$^+$) m/z=265 (MH$^+$).

Intermediate 140

(2-amino-5-trifluoro-phenyl)-phosphonic acid diethyl ester

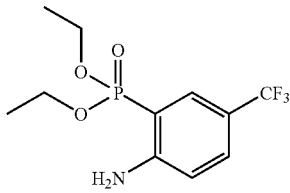

Intermediate 140 was synthesized from 4-amino-3-iodo-benzotrifluoride (Alfa Aesar) following the procedure as described for intermediate 108. Intermediate 140 was a beige solid. Intermediate 140 was characterized by the following spectroscopic data: $^1$H NMR (DMSO-$d_6$, 400 MHz) δ (ppm) 1.19-1.23 (td, J=7.04 Hz and J=2.04 Hz, 6H), 3.94-4.05 (m, 4H), 6.56 (s, 2H), 6.84-6.87 (m, 1H), 7.48 (s, 1H), 7.52 (m, 1H). $^{31}$P NMR (DMSO-$d_6$, 162 MHz) δ (ppm) 18.65 (s, 1P). $^{19}$F NMR (DMSO-$d_6$, 376 MHz) δ (ppm) −59.70 (s, 3F)

Intermediate 141

(5-amino-2-nitro-phenyl)-methyl-phosphinic acid ethyl ester

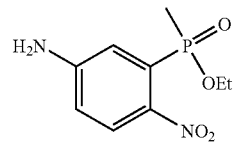

3-bromo-4-nitroaniline (2.1 mmol, Apollo), diethyl methylphosphonate (2.56 mmol, Aldrich), palladium acetate (0.21 mmol, Aldrich) and HCl (2N, 4.2 mmol) were mixed in a microwave vessel in acetonitrile (5 ml). The mixture was stirred at 160° C. for 30 min. Acetonitrile was evaporated. The residue was solubilised in EtOAc, washed with aq HCl 1N. The aqueous phase (pH 8 with NaHCO$_3$) was washed with EtOAc. Organics were washed with NaHCO$_3$, dried over Na$_2$SO$_4$, filtered and concentrated under reduced pressure. The crude material was purified by chromatography on silica gel to give intermediate 141, which was a brown oil. Intermediate 141 was characterized by the following spectroscopic data: $^1$H NMR (DMSO-$d_6$, 400 MHz) δ (ppm) 1.18-1.21 (t, J=7.12 Hz, 3H), 1.78-1.82 (d, J=15.47 Hz, 3H), 3.78-3.99 (m, 2H), 6.71 (d, J=8.89 Hz, 1H), 6.87 (s, 2H), 7.19-7.23 (d, J=14.31 Hz, 1H), 7.92-7.95 (m, 1H). $^{31}$P NMR (DMSO-$d_6$, 162 MHz) δ (ppm) 39.19 (s, 1P).

Intermediate 142

(5-dimethanesulfonamyl-2-nitro-phenyl)-methyl-phosphinic acid ethyl ester

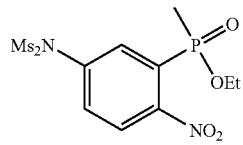

To a stirred solution of intermediate 141 (1.28 mmol) in DCM (11 ml) at 0° C. was added methanesulfonyl chloride (2.95 mmol, Fluka) and diisopropylethylamine (3.1 mmol, Aldrich). The reaction mixture was stirred at 0° C. for 15 min and at room temperature for 16 hours. HCl (1N, 10 ml) was added. Organics were dried over Na$_2$CO$_3$, filtered and concentrated under reduced pressure. The crude material was purified by chromatography on silica gel to give intermediate 142, which was a yellow foam. Intermediate 142 was characterized by the following spectroscopic data: $^1$H NMR (CDCl$_3$, 400 MHz) δ (ppm) 1.28-1.33 (t, J=7.20 Hz, 3H), 2.00 (d, J=15.90 Hz, 3H), 3.45 (s, 6H), 3.90-3.96 (m, 1H), 4.09-4.16 (m, 1H), 7.67-7.70 (d, J=8.68 Hz, 1H), 7.96-8.00 (m, 1H), 8.16-8.19 (d, J=12.53 Hz, 1H). $^{31}$P NMR (CDCl$_3$, 162 MHz) δ (ppm) 36.73 (s, 1P).

Intermediate 143

(2-amino-5-dimethanesulfonamyl-phenyl)-methyl-phosphinic acid ethyl ester

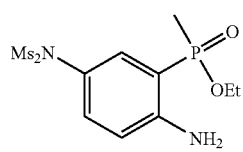

Intermediate 142 was hydrogenated in ethanol using the H-Cube® device (Thales nanotechnology). Intermediate 143

Intermediate 144

(2-amino-5-chloro-phenyl)-phosphonic acid diethyl ester

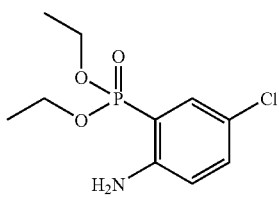

Intermediate 144 was synthesized from 4-chloro-3-iodoaniline (Apollo) following the procedure as described for intermediate 108. Intermediate 144 was a beige solid. Intermediate 144 was characterized by the following spectroscopic data: $^1$H NMR (DMSO-$d_6$, 400 MHz) δ (ppm) 1.25-1.28 (t, J=7.10 Hz, 6H), 3.95-4.12 (m, 4H), 5.11 (brs, 2H), 6.50-6.54 (t, J=8.01 Hz, 1H), 7.11-7.14 (dd, J=2.72 Hz and J=8.23 Hz, 1H), 7.29-7.34 (dd, J=2.70 Hz and J=14.95 Hz, 1H). $^{31}$P NMR (DMSO-$d_6$, 162 MHz) δ (ppm) 18.65 (s, 1P).

Intermediate 145

(2-amino-5-chloro-phenyl)-phosphonic acid diethyl ester

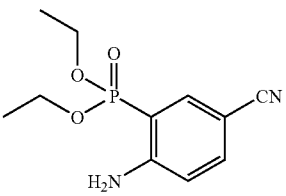

Intermediate 145 was synthesized from 4-amino-3-iodobenzonitrile (Aldrich) following the procedure as described for intermediate 108. Intermediate 145 was a yellow solid. Intermediate 145 was characterized by the following spectroscopic data: $^1$H NMR (CDCl$_3$, 400 MHz) δ (ppm) 1.33-1.38 (t, J=7.41 Hz, 6H), 4.13-4.21 (m, 4H), 5.82 (brs, 2H), 6.63-6.66 (m, 1H), 7.46 (d, J=8.48 Hz, 1H), 7.72 (d, J=14.95 Hz, 1H). $^{31}$P NMR (CDCl$_3$ 162 MHz) δ (ppm) 17.67 (s, 1P).

Intermediate 146

(3-nitro-pyridin-2-yl)-phosphonic acid diethyl ester

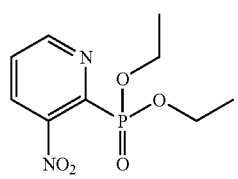

Intermediate 146 was synthesized from 2-bromo-3-nitropyridine (Aldrich) following the procedure as described for intermediate 108. Intermediate 146 was a beige solid and was used just as it is in the next step.

Intermediate 147

(3-amino-pyridin-2-yl)-phosphonic acid diethyl ester

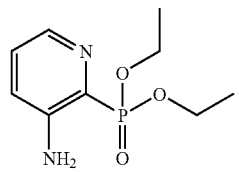

Intermediate 147 was synthesized from intermediate 146 following the procedure as described for intermediate 143. Intermediate 147 was a brown oil. Intermediate 147 was characterized by the following spectroscopic data: $^1$H NMR (CDCl$_3$, 400 MHz) δ (ppm) 1.32-1.36 (t, J=7.22 Hz, 6H), 4.11-4.25 (m, 4H), 5.37 (brs, 2H), 6.95-6.99 (m, 1H), 7.13-7.17 (m, 1H), 8.12 (d, J=4.24 Hz, 1H). $^{31}$P NMR (CDCl$_3$, 162 MHz) δ (ppm) 13.83 (s, 1P).

Intermediate 148

(S)-3,3-dimethyl-2-[(1H-pyrazol-4-ylmethyl)-amino] butyric acid methyl ester

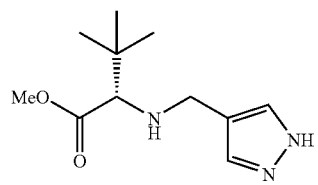

Intermediate 148 was synthesized from (S)-methyl-2-amino-3,3-dimethyl butanoate (6.86 mmol, Bionet) and 1H-pyrazole-4-carboxaldehyde (6.86 mmol, Biofone) following the procedure as described for intermediate 88. Intermediate 148 was a colourless oil. Intermediate 148 was characterized by the following spectroscopic data: MS (ESI, EI$^+$) m/z=226 (MH$^+$).

Intermediate 149

(S-2-[(2-cyano-acetyl)-(1H-pyrazol-4-ylmethyl)-amino]-3,3-dimethyl-butyric acid methyl ester

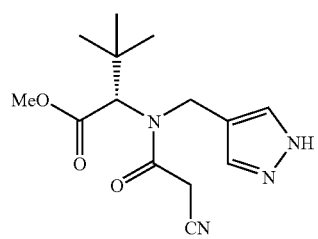

Intermediate 149 was synthesized from intermediate 148 following the procedure as described for intermediate 74. Intermediate 149 was a colourless oil. Intermediate 149 was characterized by the following spectroscopic data: MS (ESI, EI$^+$) m/z=293 (MH$^+$).

Intermediate 150

(S)-5-tert-butyl-4-hydroxy-2-oxo-1-(1H-pyrazol-4-ylmethyl)-2,5-dihydro-1H-pyrrole-3-carbonitrile

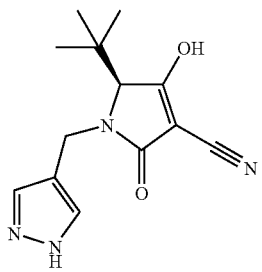

Intermediate 150 was synthesized from intermediate 149 following the procedure as described for intermediate 77. Intermediate 150 was a white solid. Intermediate 150 was characterized by the following spectroscopic data: $^1$H NMR (DMSO-d$_6$, 400 MHz) δ (ppm) 0.96 (s, 9H), 3.29 (m, 1H), 3.63 (s, 2H), 4.06 (s, 1H), 7.67 (s, 1H), 7.73 (s, 1H). MS (ESI, EI$^+$) m/z=261 (MH$^+$).

Intermediate 151

(S)-3,3-dimethyl-2-[(3-chloro-benzyl)-amino]butyric acid methyl ester

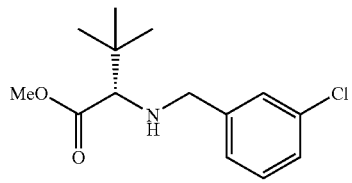

Intermediate 151 was synthesized from methyl-2-amino-3,3-dimethyl butanoate (6.86 mmol, Bionet) and 3-chloro-benzaldehyde (6.86 mmol, Alfa Aesar) following the procedure as described for intermediate 88. Intermediate 151 was a colourless oil. Intermediate 151 was characterized by the following spectroscopic data: MS (ESI, EI$^+$) m/z=270 (MH$^+$).

Intermediate 152

(S)-2-[2-cyano-acetyl)-(3-chloro-benzyl)-amino]-3,3-dimethyl-butyric acid methyl ester

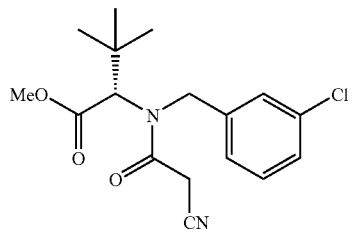

Intermediate 152 was synthesized from intermediate 151 following the procedure as described for intermediate 74. Intermediate 151 was a colourless oil. Intermediate 152 was characterized by the following spectroscopic data: MS (ESI, EI$^+$) m/z=337 (MH$^+$).

Intermediate 153

(S)-5-tert-butyl-4-hydroxy-2-oxo-1-(3-chloro-benzaldehyde)-2,5-dihydro-1H-pyrrole-3-carbonitrile

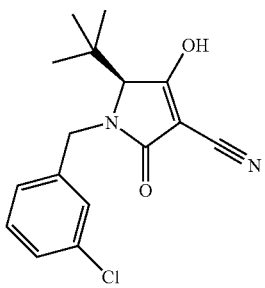

Intermediate 153 was synthesized from intermediate 152 following the procedure as described for intermediate 77. Intermediate 153 was a white solid. Intermediate 153 was characterized by the following spectroscopic data: $^1$H NMR (DMSO-d$_6$, 400 MHz) δ (ppm) 0.91 (s, 9H), 1.90 (s, 1H), 4.27 (d, J=16.14 Hz, 1H), 4.75 (d, J=16.14 Hz, 1H), 5.25 (brs, 1H), 7.09 (d, J=7.54 Hz, 1H), 7.19 (s, 1H), 7.26-7.36 (m, 2H). MS (ESI, EI$^+$) m/z=305 (MH$^+$).

Intermediate 154

(S)-Amino-cyclopentyl-acetic acid methyl ester hydrochloride

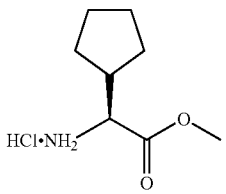

Intermediate 154 was synthesized from L-cyclopentylglycine (AK Scientific) following the procedure as described for intermediate 121. Intermediate 154 was a white solid. Intermediate 154 was characterized by the following spectroscopic data: $^1$H NMR (CDCl$_3$, 400 MHz) δ (ppm) 1.22-1.74 (m, 8H), 2.17-2.23 (m, 1H), 3.73 (s, 3H), 3.84 (m, 1H).

Intermediate 155

(S)-Cyclopentyl-(3,3-dimethyl-butylamino)-acetic acid methyl ester

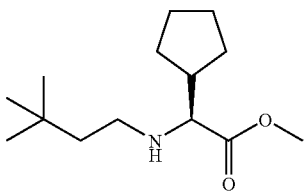

Intermediate 155 was synthesized from intermediate 154 and 3,3-dimethylbutyraldehyde (Fluka) following the procedure as described for intermediate 88. Intermediate 155 was a colourless oil. Intermediate 155 was characterized by the following spectroscopic data: $^1$H NMR (CDCl$_3$, 400 MHz) δ (ppm) 0.88 (s, 9H), 1.27-1.65 (m, 9H), 1.74-1.82 (m, 1H), 1.99-2.05 (s, J=8.11 Hz, 1H), 2.39-2.46 (td, J=11.07 Hz, J=5.24 Hz, 1H), 2.53-2.59 (td, J=11.07 Hz, J=5.24 Hz, 1H), 3.05 (d, J=8.07 Hz, 1H), 3.72 (s, 3H).

Intermediate 156

(S)-(2-cyano-acetyl)-(3,3-dimethyl-butylamino)-cyclopentyl-acetic acid methyl ester

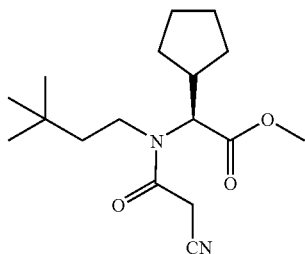

Intermediate 156 was synthesized from intermediate 155 following the procedure as described for intermediate 74. Intermediate 156 was a colourless oil. Intermediate 156 was characterized by the following spectroscopic data: $^1$H NMR (CDCl$_3$, 400 MHz) δ (ppm) 0.91 (s, 9H), 1.10-1.82 (m, 9H), 1.89-2.04 (m, 1H), 2.50-2.60 (s, J=7.59 Hz, 1H), 3.29-3.46 (m, 2H), 3.50 (s, 1H), 3.63 (s, 1H), 3.75 (s, 3H), 4.50 (d, J=10.67 Hz, 1H). MS (ESI, EI$^+$) m/z=309 (MH$^+$).

Intermediate 157

(S)-2-(3-bromo-4-fluoro-benzylamino)-3,3-dimethyl-butyric acid methyl ester

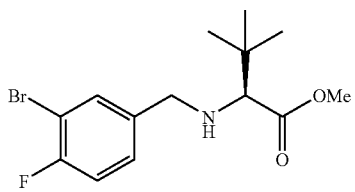

Intermediate 157 was synthesized from (S)-methyl-amino-3,3-dimethylbutanoate (Bionet) and 3-bromo-4-fluoro-benzaldehyde (Aldrich) following the procedure as described for intermediate 88. Intermediate 157 was a colourless oil. Intermediate 157 was characterized by the following spectroscopic data: $^1$H NMR (CDCl$_3$, 400 MHz) δ (ppm) 0.96 (s, 9H), 2.01 (s, 2H), 2.87 (s, 1H), 3.46 (d, J=13.75 Hz, 1H), 3.72-3.78 (m, 4H), 7.03-7.08 (t, J=8.33 Hz, 1H), 7.22-7.26 (m, 1H), 7.54 (d, J=6.67 Hz, 1H).

Intermediate 158

(S)-(2-cyano-acetyl)-(3-bromo-4-fluoro-benzylamino)-3,3-dimethyl-butyric acid methyl ester

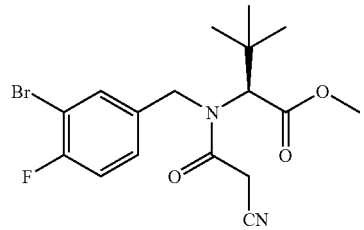

Intermediate 158 was synthesized from intermediate 157 following the procedure as described for intermediate 74. Intermediate 158 was a colourless oil. Intermediate 158 was characterized by the following spectroscopic data: $^1$H NMR (CDCl$_3$, 400 MHz) δ (ppm) 0.95 (s, 9H), 0.96 (m, 1H), 3.21-3.36 (m, 2H), 3.62 (s, 3H), 4.60 (d, J=18.41 Hz, 1H), 5.17 (d, J=18.41 Hz, 1H), 7.08 (m, 1H), 7.12-7.16 (t, J=8.07 Hz, 1H), 7.35 (d, J=5.77 Hz, 1H). MS (ESI, EI$^+$) m/z=400 (MH$^+$).

Intermediate 159

(S)-2-(4-fluoro-3-methyl-benzylamino)-3,3-dimethyl-butyric acid methyl ester

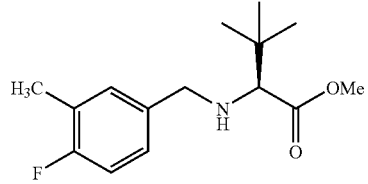

Intermediate 159 was synthesized from (S)-methyl-amino-3,3-dimethylbutanoate (Bionet) and 4-fluoro-3-methylbenzaldehyde (ABCR) following the procedure as described for intermediate 88. Intermediate 159 was a colourless oil. Intermediate 159 was characterized by the following spectroscopic data: MS (ESI, EI$^+$) m/z=268 (MH$^+$).

Intermediate 160

(2-amino-4-methyl-phenyl)-phosphonic acid diethyl ester

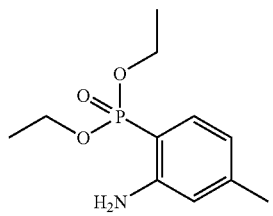

2-bromo-5-methyl aniline (1.08 mol, Aldrich) was dissolved in acetonitrile (2 ml). P(OEt)3 (1.62 mol) and Pd(OAc)2 (0.1 mol) were added carefully. The reaction mixture was stirred for 25 min at 160° C. under microwave irradiations. The mixture was evaporated and purified by silica gel chromatography to yield intermediate 160, which was a colourless syrup. Intermediate 160 was characterized by the following spectroscopic data: $^1$H NMR (CDCl$_3$, 400 MHz) δ (ppm) 1.32 (t, J=7.20 Hz, 6H), 2.27 (s, 3H), 3.99-4.17 (m, 4H), 5.22 (brs, 2H), 6.50 (d, J=6.33 Hz, 1H), 6.55 (d, J=7.57 Hz, 1H), 7.31-7.41 (dd, J=6.33 Hz, J=7.70 Hz, 1H). $^{31}$P NMR (CDCl$_3$, 162 MHz) δ (ppm) 21.73 (s, 1P)

Intermediate 161

(2-amino-5-methyl-phenyl)-phosphonic acid diethyl ester

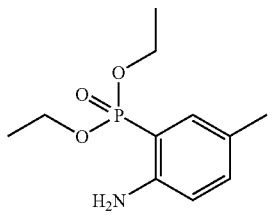

Intermediate 161 was synthesized from 2-bromo-4-methyl aniline (Aldrich) following the procedure as described for intermediate 160. Intermediate 161 was a pale yellow oil. Intermediate 161 was characterized by the following spectroscopic data: $^1$H NMR (CDCl$_3$, 400 MHz) δ (ppm) 1.32-1.37 (t, J=7.06 Hz, 6H), 2.24 (s, 3H), 4.01-4.20 (m, 4H), 6.61-6.65 (t, J=7.50 Hz, 1H), 7.11 (d, J=8.41 Hz, 1H), 7.26-7.29 (d, J=14.84 Hz, 1H).

Intermediate 162

2-amino-bicyclo[2.2.1]heptane-2-carboxylic acid methyl ester hydrochloride

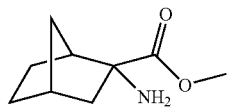

To a stirred solution of 2-amino-2-norbornane carboxylic acid (8.41 mmol, Biofine) in MeOH (11 ml) was added acetyl chloride at 0° C. The mixture was stirred at 50° C. for 2 days. Solvent was evaporated. The crude material was triturated in diethyl ether to yield intermediate 162, which was a beige powder. Intermediate 162 was characterized by the following spectroscopic data: $^1$H NMR (DMSO-d$_6$, 400 MHz) δ (ppm) 1.27-1.34 (t, J=13.04 Hz, 2H), 1.49 (s, 3H), 1.63-1.80 (t, J=11.41 Hz, 2H), 2.27-2.29 (m, 2H), 2.46 (s, 1H), 2.05 (m, 3H), 8.72 (brs, 2H).

Intermediate 163

2-(3,3-dimethyl-butylamino)-bicyclo[2.2.1]heptane-2-carboxylic acid methyl

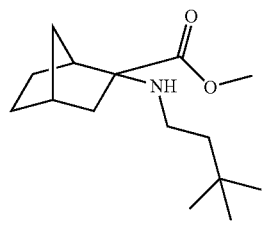

Intermediate 163 was synthesized from intermediate 162 following the procedure as described for intermediate 73. Intermediate 163 was a white powder. Intermediate 163 was characterized by the following spectroscopic data: $^1$H NMR (DMSO-d$_6$, 400 MHz) δ (ppm) 0.89 (s, 9H), 0.92-0.96 (m, 1H), 1.10-1.13 (m, 1H), 1.23-1.26 (m, 4H), 1.39-1.41 (m, 1H), 1.64 (s, 1H), 1.78-1.79 (m, 1H), 1.98-2.03 (m, 1H), 2.03-2.10 (m, 1H), 2.15-2.19 (m, 2H), 2.45 (m, 1H), 3.60 (m, 3H), Intermediate 164

2-[(2-cyano-acetyl)-(3,3-dimethyl-butyl)-amino]-bicyclo[2.2.1]heptane-2-carboxylic acid methyl ester

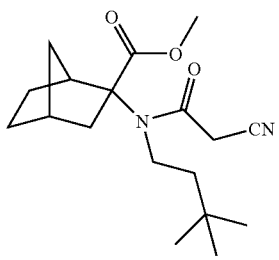

Intermediate 164 was synthesized from intermediate 163 following the procedure as described for intermediate 74. Intermediate 164 was a white powder. Intermediate 164 was characterized by the following spectroscopic data: $^1$H NMR (DMSO-d$_6$, 400 MHz) δ (ppm) 0.89 (s, 9H), 1.22-1.26 (m, 2H), 1.39-1.53 (m, 2H), 1.39-1.53 (m, 3H), 1.60-1.68 (m, 2H), 1.81 (s, 2H), 2.05-2.07 (m, 1H), 2.29 (s, 1H), 3.36-3.44 (m, 2H), 3.25 (brs, 1H), 3.68 (s, 3H).

Intermediate 165

(1-(3,3-dimethyl-butyl)-5-[bicylo[2.2.1]heptane]-4-hydroxy-5-methyl-2-oxo-2,5-dihydro-1H-pyrrole-3-carbonitrile

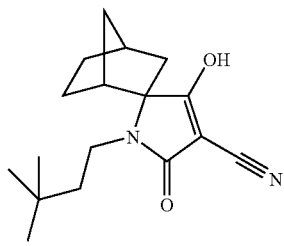

Intermediate 165 was synthesized from intermediate 164 following the procedure as described for intermediate 77. Intermediate 165 was a beige solid. Intermediate 165 was characterized by the following spectroscopic data: MS (ESI, EI$^+$) m/z=289 (MH$^+$).

Intermediate 166

(S)-3,3-dimethyl-2-pent-4-ynylamino-butyric acid methyl ester

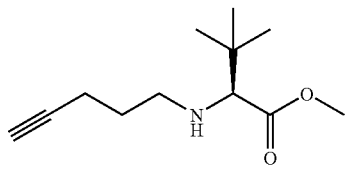

Intermediate 166 was synthesized from 4-pentynal (12.1 mmol, Fluka) and (S)-methyl-2-amino-3,3-dimethylbutanoate (12.1 mmol, bionet) following the procedure as described for intermediate 88. Intermediate 166 was a colourless oil. Intermediate 166 was characterized by the following spectroscopic data: MS (ESI, EI$^+$) m/z=212 (MH$^+$).

Intermediate 167

(S)-2-[2-cyano-acetyl)-pent-4-ynyl-amino]-3,3-dimethyl-butyric acid methyl ester

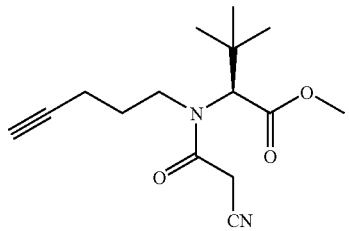

Intermediate 167 was synthesized from intermediate 166 following the procedure as described for intermediate 74. Intermediate 167 was a Yellow oil. Intermediate 167 was characterized by the following spectroscopic data: $^1$H NMR (CDCl$_3$, 400 MHz) δ (ppm) 1.09 (s, 9H), 1.13 (s, 2H), 1.75-1.83 (m, 2H), 2.08 (t, J=2.59 Hz, 1H), 2.17-2.35 (m, 3H), 3.41-3.49 (m, 1H), 3.69 (s, 3H), 3.72-3.81 (m, 1H) MS (ESI, EI$^+$) m/z=279 (MH$^+$).

Intermediate 168

(S)-Amino-cyclopropyl-acetic acid methyl ester

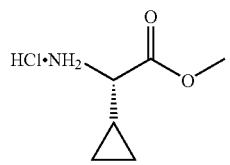

Intermediate 168 was synthesized from (L)-cyclopropyl glycine (Parkway) following the procedure as described for intermediate 121. Intermediate 168 was a white solid. Intermediate 168 was characterized by the following spectroscopic data: $^1$H NMR (DMSO-d$_6$, 400 MHz) δ (ppm) 0.30-0.38 (, 4H), 0.82-0.87 (m, 1H), 3.08-3.12 (m, 1H), 3.48 (s, 3H), 4.67 (brs, 1H).

Intermediate 169

(S)-Cyclopropyl-(3,3-dimethyl-butylamino)-acetic acid methyl ester

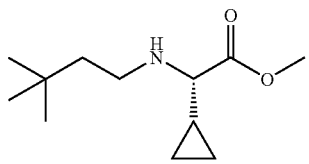

Intermediate 169 was synthesized from intermediate 168 following the procedure as described for intermediate 88. Intermediate 169 was a colourless oil. Intermediate 169 was characterized by the following spectroscopic data: MS (ESI, EI$^+$) m/z=214 (MH$^+$).

Intermediate 170

(S)-2-[(2-cyano-acetyl)-cyclopropyl-amino]-(3,3-dimethyl-butyric acetic acid methyl ester

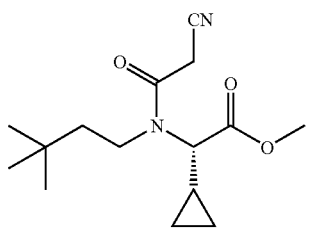

Intermediate 170 was synthesized from intermediate 169 following the procedure as described for intermediate 74. Intermediate 170 was a colourless oil. Intermediate 170 was characterized by the following spectroscopic data: MS (ESI, EI⁺) m/z=281 (MH⁺).

Intermediate 171

(S)-2-amino-3-hydroxy-3-methyl butyric acid methyl ester hydrochloride

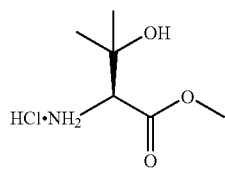

Intermediate 171 was synthesized from (2S)-2-amino-3-hydroxy-3-methylbutanoic acid (Acros) following the procedure as described for intermediate 121. Intermediate 171 was a white solid. Intermediate 171 was characterized by the following spectroscopic data: MS (ESI, EI⁺) m/z=184 (MH⁺).

Intermediate 172

(S)-2-(3,3-dimethyl-butylamino)-3-hydroxy-3-methyl butyric acid methyl ester

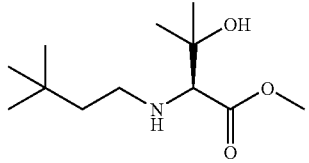

Intermediate 172 was synthesized from intermediate 171 and 3,3-dimethylbutyraldehyde (Fluka) following the procedure as described for intermediate 88. Intermediate 172 was a colourless oil. Intermediate 172 was characterized by the following spectroscopic data: MS (ESI, EI⁺) m/z=232 (MH⁺).

Intermediate 173

(S)-2-[(2-cyano-acetyl)-(3,3-dimethyl-butyl)-amino]-3-hydroxy-3-methyl butyric acid methyl ester

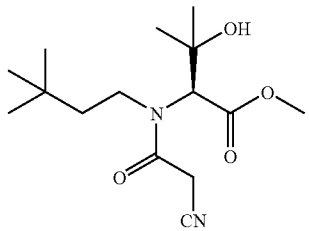

Intermediate 173 was synthesized from intermediate 172 following the procedure as described for intermediate 74. Intermediate 173 was a yellow oil. Intermediate 173 was characterized by the following spectroscopic data: MS (ESI, EI⁺) m/z=299 (MH⁺).

Intermediate 174

2-(3,3-dimethyl-butylamino)-propionic acid methyl ester

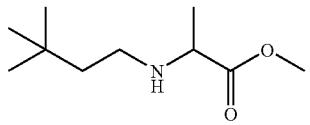

Intermediate 174 was synthesized from D-L-alanine methyl ester hydrochloride (Acros) and 3,3-dimethylbutyraldehyde (Fluka) following the procedure as described for intermediate 88. Intermediate 174 was a colourless oil. Intermediate 174 was characterized by the following spectroscopic data: MS (ESI, EI⁺) m/z=201 (MH⁺).

Intermediate 175

2-[(2-cyano-acethyl)-(3,3-dimethyl-butyl)-amino]-propionic acid methyl ester

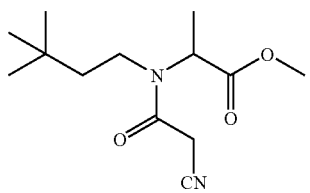

Intermediate 175 was synthesized from intermediate 174 following the procedure as described for intermediate 74. Intermediate 175 was a colourless oil. Intermediate 175 was characterized by the following spectroscopic data: MS (ESI, EI⁺) m/z=269 (MH⁺).

Intermediate 176

Ethyl Phosphinic Acid Benzyl Ester

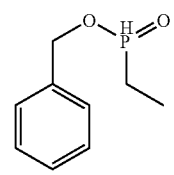

Intermediate 176 was synthesized from ammonium hypophosphite (Riedel) following the procedure as described in J. Med. Chem., 2006, 426. Intermediate 176 was a yellowish oil. Intermediate 176 was characterized by the following spectroscopic data: ¹H NMR (CDCl₃, 400 MHz) δ (ppm) 1.15 (dt, J=7.67 Hz and J=22.1 Hz, 3H), 1.80 (dq, J=7.67 Hz and J=22.1 Hz, 2H), 5.01-5.08 (m, 1H), 5.12-5.17 (m, 1H), 6.42 (t, J=3.95 Hz, 0.5H), 7.34-7.39 (m, 5H), 7.74 (t, J=3.95 Hz, 0.5H). $^{31}$P NMR (CDCl$_3$, 162 MHz) δ (ppm) 41.03 (s, 1P)

Intermediate 177

(5-amino-2-nitro-phenyl)ethyl phosphonic acid benzyl ester

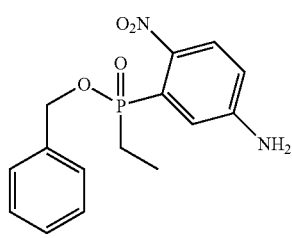

Intermediate 177 was synthesized from iodoethane following the procedure as described for intermediate 212. Intermediate 177 was a yellow oil. Intermediate 177 was characterized by the following spectroscopic data: $^1$H NMR (CDCl$_3$, 400 MHz) δ (ppm) 1.11-1.20 (m, 3H), 1.75-1.85 (m, 2H), 5.01-5.08 (m, 1H), 5.12-5.17 (m, 1H), 7.32-7.40 (m, 5H). $^{31}$P NMR (CDCl$_3$, 162 MHz) δ (ppm) 41.03 (s, 1P).

Intermediate 178

(S)-2-amino-3-thiazol-4-yl propionic acid methyl ester hydrochloride

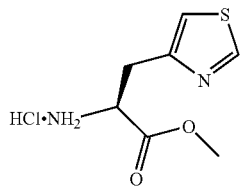

Intermediate 178 was synthesized from L-4-thiazolylalanine (Peptech) following the procedure as described for intermediate 121. Intermediate 178 was a yellow oil. Intermediate 178 was characterized by the following spectroscopic data: $^1$H NMR (CDCl$_3$, 400 MHz) δ (ppm) 3.35 (d, J=6.35 Hz, 2H), 3.65 (s, 3H), 4.31-4.36 (m, 1H), 7.56 (s, 1H), 9.10 (s, 1H).

Intermediate 179

(S)-2-(3,3-dimethyl-butylamino)-3-thiazol-4-yl-propionic acid methyl ester

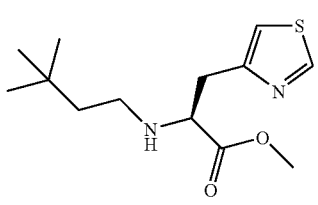

Intermediate 179 was synthesized from intermediate 178 following the procedure as described for intermediate 73. Intermediate 179 was a yellow oil. Intermediate 179 was characterized by the following spectroscopic data: MS (ESI, EI$^+$) m/z=271 (MH$^+$).

Intermediate 180

(S)-2-[(2-cyanoacetyl)-(3,3-dimethylbutyl)amino]-3-thiazol-4-yl-propionic acid methyl ester

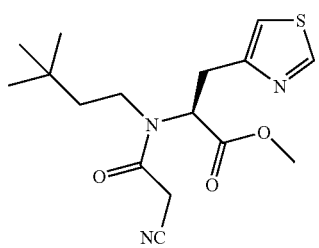

Intermediate 180 was synthesized from intermediate 179 as described for intermediate 74. Intermediate 180 was a yellow oil. Intermediate 180 was characterized by the following spectroscopic data: MS (ESI, EI$^+$) m/z=338 (MH$^+$).

Intermediate 181

(2-amino-6-methyl-phenyl)phosphonic acid diethyl ester

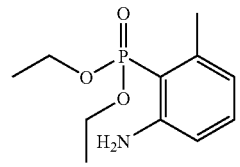

To a stirred solution of 2-bromo-3-methylaniline (1.07 mmol, Aldrich) in acetonitrile (3 ml) was added triethyl phosphite (1.6 mmol). The reaction mixture was degassed with nitrogen and palladium acetate (0.107 mmol) was then added. The mixture was degassed and let to stirred for 1 hour at 180° C. under microwave irradiations. The mixture was filtered, washed with water, concentrated under reduced pressure and purified by silica gel chromatography to yield intermediate 181, which was a yellow oil. Intermediate 181 was characterized by the following spectroscopic data: MS (ESI, EI$^+$) m/z=244 (MH$^+$).

Intermediate 182

2-amino-5-chloro-3-(diethoxy phosphoryl)benzoic acid methyl ester

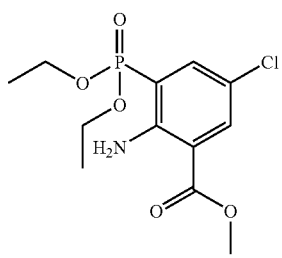

Intermediate 182 was synthesized from methyl-2-amino-5-chloro-3-iodobenzoate (Alfa Aesar) following the procedure as described for intermediate 181. Intermediate 182 was an orange oil. Intermediate 182 was characterized by the following spectroscopic data: ¹H NMR (CDCl₃, 400 MHz) δ (ppm) 1.34 (t, J=6.90 Hz, 6H), 3.87 (s, 3H), 4.03-4.21 (m, 4H), 7.41 (brs, 2H), 7.60 (dd, J=2.59 Hz and J=15.50 Hz, 1H), 8.00 (d, J=2.59 Hz, 1H). P NMR (CDCl₃, 162 MHz) δ (ppm) 17.79 (s, 1P).

Intermediate 183

2-(3,3-dimethylbutylamino)-2-methyl-butyric acid methyl ester

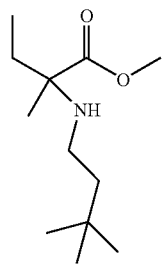

Intermediate 183 was synthesized from 2-amino-2-methylbutyric acid (Acros) following the procedure as described for intermediate 88. Intermediate 183 was a yellow oil. Intermediate 183 was characterized by the following spectroscopic data: ¹H NMR (DMSO-d₆, 400 MHz) δ (ppm) 0.74 (t, J=7.33 Hz, 3H), 0.84 (s, 9H), 0.88 (s, 3H), 1.24-1.27 (m, 3H), 1.40-1.54 (m, 3H), 2.32-2.37 (m, 1H), 3.59 (s, 3H).

Intermediate 184

2-[(2-cyano-acetyl)-(3,3-dimethyl-butyl)-amino]-2-methyl butyric acid methyl ester

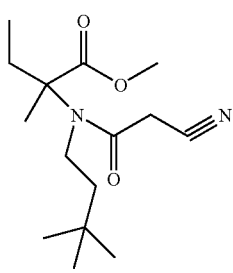

Intermediate 184 was synthesized from intermediate 183 following the procedure as described for intermediate 74. Intermediate 184 was a white gummy powder. Intermediate 184 was characterized by the following spectroscopic data: ¹H NMR (DMSO-d₆, 400 MHz) δ (ppm) 0.75 (t, J=7.82 Hz, 3H), 0.89 (s, 9H), 1.33 (s, 3H), 1.49 (t, J=8.47 Hz, 2H), 1.64-1.70 (m, 1H), 1.96-2.01 (m, 1H), 3.20-3.29 (m, 2H), 3.53 (s, 3H), 3.98-4.22 (m, 2H).

Intermediate 185

1-(3,3-dimethylbutyl)-5-ethyl-4-hydroxy-5-methyl-2-oxo-2,5-dihydro-1H-pyrrole-3-carbonitrile

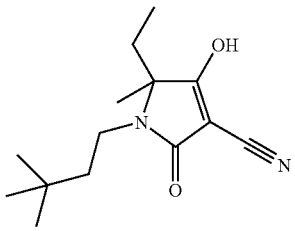

Intermediate 185 was synthesized from intermediate 184 following the procedure as described for intermediate 77. Intermediate 185 was a yellow solid. Intermediate 185 was characterized by the following spectroscopic data: MS (ESI, EI⁺) m/z=251 (MH⁺).

Intermediate 186

2-(3,3-dimethylbutylamino)-2-trifluoromethyl-butyric acid methyl ester

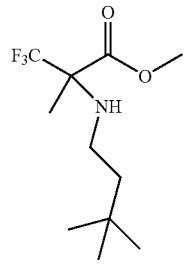

Intermediate 186 was synthesized from methyl-2-amino-3,3,3-trifluoro-2-methyl-propionate (Fluorochem) following the procedure as described for intermediate 88. Intermediate 186 was a yellow oil. Intermediate 186 was characterized by the following spectroscopic data: MS (ESI, EI⁺) m/z=172 (MH⁺).

Intermediate 187

2-[(2-cyano-acetyl)-(3,3-dimethyl-butyl)-amino]-2-trifluoromethyl butyric acid methyl ester

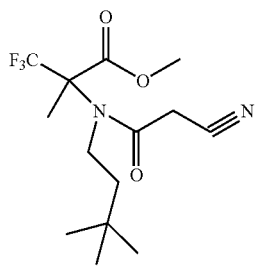

Intermediate 187 was synthesized from intermediate 186 following the procedure as described for intermediate 74. Intermediate 187 was a yellow oil. Intermediate 187 was characterized by the following spectroscopic data: MS (ESI, EI$^+$) m/z=269 (MH$^+$).

Intermediate 188

1-(3,3-dimethylbutyl)-4-hydroxy-5-methyl-2-oxo-5-trifluoromethyl-2,5-dihydro-1H-pyrrole-3-carbonitrile

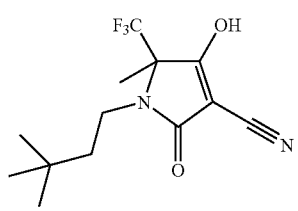

Intermediate 188 was synthesized from intermediate 187 following the procedure as described for intermediate 77. Intermediate 188 was a yellow solid. Intermediate 188 was characterized by the following spectroscopic data: MS (ESI, EI$^+$) m/z=291 (MH$^+$).

Intermediate 189

(S)-5-tert-butyl-1-(3,3-dimethyl-butyl-4-methoxy-2-oxo-1,5-dihydropyrrole-3-carbonitrile

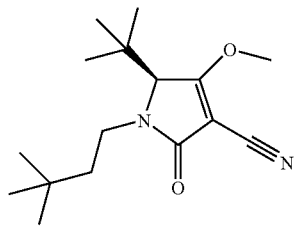

To a stirred solution of intermediate 77 (1.89 mmol) in acetone (8 ml) with potassium carbonate (2.45 mmol), under nitrogen, was added methyl iodide (2.45 mmol). The reaction mixture was stirred at 56° C. for 1 hour. The mixture was then filtered though celite, washed with diethyl ether. The filtrate was concentrated under reduced pressure and purified by silica gel chromatography to yield intermediate 189, which was a beige solid. Intermediate 189 was characterized by the following spectroscopic data: $^1$H NMR (CDCl$_3$, 400 MHz) δ (ppm) 0.92 (s, 9H), 1.04 (s, 9H), 1.36 (td, J=5.28 Hz and J=12.31 Hz, 1H), 1.47 (td, J=4.75 Hz and J=4.75 Hz, 1H), 3.07-3.15 (m, 1H), 3.68 (s, 1H), 3.88-3.96 (m, 1H), 4.32 (s, 3H).

Intermediate 190

4-fluoro-5-tert-butyl-1-(3,3-dimethyl-butyl)-4-methoxy-2-oxo-1,5-dihydropyrrole-3-carbonitrile

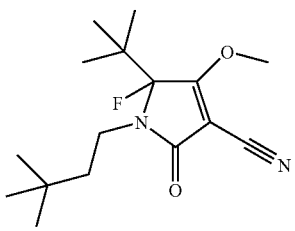

To a stirred solution of intermediate 189 (3.23 mmol) in THF, at −90° C. was added LiHMDS (4.19 mmol). The mixture was stirred at −80° C. for 50 min, N-fluorobenzenesulfonimide (3.87 mmol, Aldrich) was then added under nitrogen. The reaction was stirred for 2 hour (−80 to 10° C.). Solvent was evaporated, the residue was purified by silica gel chromatography to yield intermediate 190, which was a yellow solid. Intermediate 190 was characterized by the following spectroscopic data: MS (ESI, EI$^+$) m/z=298 (MH$^+$).

Intermediate 191

4-hydroxy-5-tert-butyl-1-(3,3-dimethyl-butyl-4-methoxy-2-oxo-1,5-dihydropyrrole-3-carbonitrile

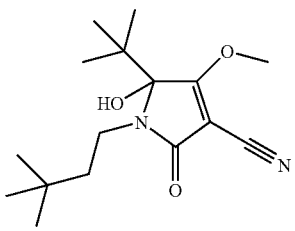

To a stirred solution of intermediate 190 (1.45 mmol) in dioxane (2 ml) was added NaOH 1N (5.22 mmol). The reaction mixture was stirred 2 hours at room temperature. Intermediate 191 was a beige solid. Intermediate 191 was characterized by the following spectroscopic data: MS (ESI, EI$^+$) m/z=281 (MH$^+$).

Intermediate 192

3-ethoxy-5-iodoaniline

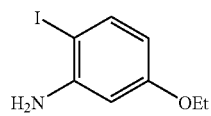

Intermediate 192 was synthesized following the procedure as described in JACS, 2007, 5288. Intermediate 192 was a red oil. Intermediate 192 was characterized by the following spectroscopic data: $^1$H NMR (CDCl$_3$, 400 MHz) δ (ppm) 1.12-1.19 (m, 3H), 3.69-3.82 (m, 2H), 5.87-5.92 (m, 1H), 6.06-6.11 (m, 1H), 7.19-7.26 (m, 1H).

Intermediate 193

2-amino-4-ethoxy-phosphonic acid diethyl ester

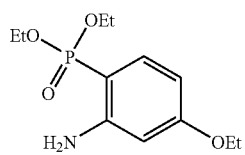

Intermediate 193 was synthesized from intermediate 192 following the procedure as described for intermediate 181. Intermediate 193 was characterized by the following spectroscopic data: MS (ESI, EI$^+$) m/z=275 (MH$^+$).

Intermediate 194

2-amino-5-chloro-3-iodo-benzamide

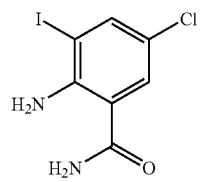

To a stirred solution of methyl-2-amino-5-chloro-3-iodo-benzoate (3.21 mmol, Acros) in methanol (13 ml), NH$_3$ $_{gas}$ was bubbled at 0° C. for 20 min. The reaction mixture was then stirred at 110° C. for 3 hours (110 bars). Solvent was then evaporated. The crude material was purified by silica gel chromatography to yield intermediate 194, which was an off-white powder. Intermediate 194 was characterized by the following spectroscopic data: $^1$H NMR (DMSO-d$_6$, 400 MHz) δ (ppm) 6.66 (s, 2H), 7.42 (brs, 1H), 7.65 (d, J=2.46 Hz, 1H), 7.76 (d, J=2.46 Hz, 1H), 8.00 (brs, 1H).

Intermediate 195

(2-amino-3-carbamoyl-5-chloro-phenyl)-phosphonic acid diethyl ester

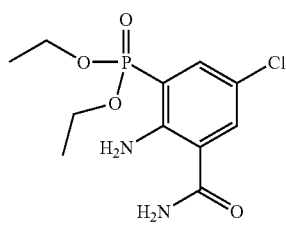

Intermediate 195 was synthesized from intermediate 194 following the procedure as described for intermediate 181. Intermediate 195 was a gummy powder. Intermediate 195 was characterized by the following spectroscopic data: MS (ESI, EI$^+$) m/z=307 (MH$^+$).

Intermediate 196

2-(3-bromo-pyridin-2-yl)-isoindole-1,3-dione

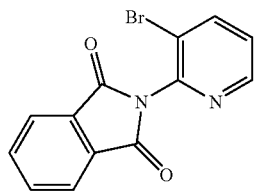

Intermediate 196 was synthesized from 2-amino-3-bromopyridine (Aldrich), phtalic anhydride (Fluka) and acetic acid following the procedure as described in Eur. J. Med. Chem., 2001, 36, 639. Intermediate 196 was a brown solid. Intermediate 196 was characterized by the following spectroscopic data: MS (ESI, EI$^+$) m/z=304 (MH$^+$).

Intermediate 197

[2-(1,3-dioxo-1,3-dihydroisoindole-2-yl)-pyridin-3-yl]-phosphonic acid diethyl ester

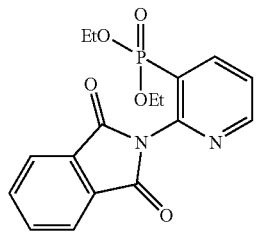

Intermediate 197 was synthesized from intermediate 196 following the procedure as described for intermediate 24. Intermediate 197 was a beige solid. Intermediate 197 was characterized by the following spectroscopic data: MS (ESI, EI$^+$) m/z=361 (MH$^+$).

Intermediate 198

(2-amino-pyridin-3-yl)-phosphonic acid diethyl ester

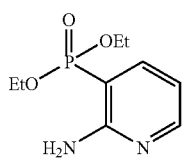

Intermediate 198 was synthesized from intermediate 197 following the procedure as described in JACS, 2005, 127(29), 10337. Intermediate 198 was a yellow solid. Intermediate 198 was characterized by the following spectroscopic data: MS (ESI, EI+) m/z=231 (MH+).

Intermediate 199

1-(3,3-dimethylbutylamino)-cyclopentane carboxylic acid methyl ester

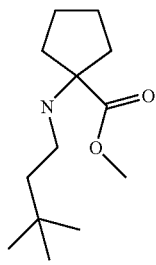

Intermediate 199 was synthesized from methyl-1-amino-1-cyclopentane carboxylate hydrochloride (ABCR) and 3,3-dimethylbutyraldehyde (Aldrich) following the procedure as described for intermediate 88. Intermediate 199 was a colourless oil. Intermediate 199 was characterized by the following spectroscopic data: $^1$H NMR (CDCl$_3$, 400 MHz) δ (ppm) 0.88 (s, 9H), 1.38 (m, 2H), 1.65-1.71 (m, 6H), 1.70-1.78 (a 2H), 2.38-2.42 (m, 2H), 3.71 (s, 3H).

Intermediate 200

1-[2-cyanoacetyl-(3,3-dimethylbutyl)-amino]-cyclopentane carboxylic acid methyl ester

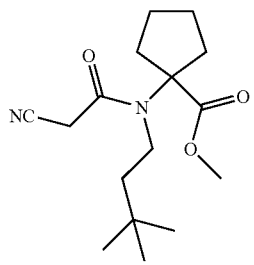

Intermediate 200 was synthesized from intermediate 199 and cyanoacetic acid (Aldrich) following the procedure as described for intermediate 74. Intermediate 200 was a white solid. Intermediate 200 was characterized by the following spectroscopic data: $^1$H NMR (CDCl$_3$, 400 MHz) δ (ppm) 0.88 (s, 9H), 1.55-1.59 (m, 2H), 1.70-1.87 (m, 6H), 2.39-2.42 (m, 2H), 3.30-3.35 (m, 2H), 3.48 (s, 2H), 3.68 (s, 3H).

Intermediate 201

(S)-2-(2,2-dimethyl-butylamino)-3,3-dimethyl-butyric acid methyl ester

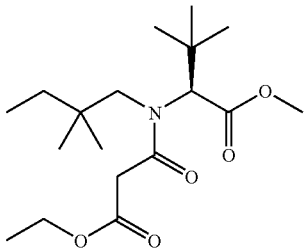

Intermediate 201 was synthesized from (L-)methyl-2-amino-3,3-dimethylbutanoate (Bionet) and 2,2-dimethyl-butanal (Chemsampco) following the procedure as described for intermediate 88. Intermediate 201 was a colourless oil. Intermediate 201 was characterized by the following spectroscopic data: $^1$H NMR (CDCl$_3$, 400 MHz) δ (ppm) 0.74 (t, J=7.74 Hz, 3H), 0.78 (s, 6H), 0.89 (s, 9H), 1.15-1.24 (m, 2H), 1.35 (td, J=4.20 Hz and J=11.50 Hz, 1H), 1.96 (t, J=11.16 Hz, 1H), 2.23-2.27 (dd, J=4.30 Hz and J=11.40 Hz, 1H), 2.76 (d, J=11.70 Hz, 1H), 3.62 (s, 3H).

Intermediate 202

(S)-2-[(2,2-dimethylbutyl)-(2-ethoxycarbonylacetyl)-amino]-3,3-dimethyl-butyric acid methyl ester Intermediate 201 (6 mmol) and ethyl malonyl chloride (6.6 mmol, Alfa Aesar) were mixed in dry THF (30 ml). TEA (6.6 mmol) was then added and the mixture was stirred at room temperature for 16 hours. Solvent was evaporated, EtOAc was added. The mixture was washed with aq HCl 1N, NaHCO$_3$ solution and brine. Organics were separated, dried over Na$_2$SO$_4$, filtered, concentrated under reduced pressure and purified by silica gel chromatography to give intermediate 202, which was a colourless oil. Intermediate 202 was characterized by the following spectroscopic data. $^1$H NMR (CDCl$_3$, 400 MHz) δ (ppm) 0.88 (t, J=7.42 Hz, 3H), 0.97 (s, 3H), 1.05 (s, 3H), 1.15 (s, 9H), 1.27 (t, J=7.42 Hz, 3H), 1.25-1.32 (m, 1H), 1.40-1.47 (m, 1H), 3.13 (d, J=15.67 Hz, 1H), 3.28 (d, J=15.67 Hz, 1H), 3.36 (brs, 1H), 3.42 (d, J=15.67 Hz, 1H), 3.69 (m, 4H), 4.16-4.21 (q, J=7.20 Hz, 2H), Intermediate 203

(S)-5-tert-butyl-1-(2,2-dimethylbutyl)-4-hydroxy-2-oxo-2,5-dihydro-pyrrole-3-carboxylic acid ethyl ester

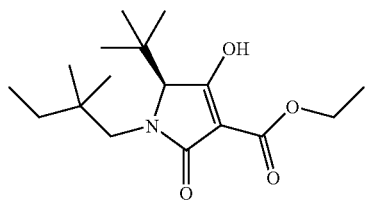

To a stirred solution of intermediate 202 (2.55 mmol) in EtOH (64 ml) was added cesium carbonate (2.81 mmol). The reaction mixture was stirred for 15 min at room temperature. Aq HCl 2N was added until pH 1, EtOAc was added and the mixture was washed with brine. Organics were separated, dried over $Na_2SO_4$, filtered and concentrated under reduced pressure to yield intermediate 203, which was a colourless oil. Intermediate 203 was characterized by the following spectroscopic data: MS (ESI, EI$^+$) m/z=312 (MH$^+$).

Intermediate 204

(S)-5-tert-butyl-1-(2,2-dimethylbutyl)-4-hydroxy-2-oxo-2,5-dihydro-pyrrole-3-carboxylic acid amide

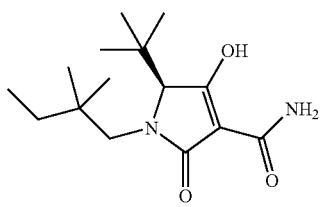

Intermediate 203 (0.8=mol) in solution in NH3/MeOH (7N) was stirred for 15 min at 150° C. under microwaves irradiations. The reaction mixture was concentrated under reduced pressure to yield intermediate 204, which was a pink solid. Intermediate 204 was characterized by the following spectroscopic data: MS (ESI, EI$^+$) m/z=283 (MH$^+$).

Intermediate 205

(S)-5-tert-butyl-4-chloro-1-(2,2-dimethylbutyl)-2-oxo-2,5-dihydro-pyrrole-3-carboxylic acid amide

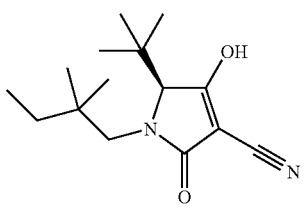

Intermediate 204 (1.8 mmol) in solution in phosphorus oxide trichloride (87.7 mmol) was stirred at 80° C., for 1 hour under microwave irradiations. The reaction mixture was then poured onto aq NaOH 2N (250 ml) and ice. AcOEt was added. Organics were separated, dried over $Na_2SO_4$, filtered and concentrated under reduced pressure to yield intermediate 205, which was a colourless oil. Intermediate 205 was characterized by the following spectroscopic data: MS (ESI, EI$^+$) m/z=264 (MH$^+$).

Intermediate 206

(2,2,4,4-tetramethyl-pentylamino)-acetic acid ethyl ester

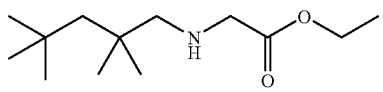

Intermediate 206 was synthesized from 1,1,3,3-tetramethylbutylamine (Aldrich) and ethylglyoxalate solution in toluene (50%) (Fluka) following the procedure as described for intermediate 88. Intermediate 206 was a colourless oil. Intermediate 206 was characterized by the following spectroscopic data: 111 NMR (CDCl$_3$, 400 MHz) δ (ppm) 1.02 (s, 9H), 1.12 (s, 6H), 3.14 (t, J=6.7 Hz, 3H), 1.40 (s, 2H), 1.53 (brs, 1H), 3.42 (s, 2H), 4.35 (q, J=6.7 Hz, 2H).

Intermediate 207

[(2-cyano-acetyl)-(2,2,4,4-tetramethyl-pentyl)-amino]-acetic acid ethyl ester

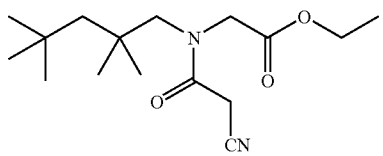

Intermediate 207 was synthesized from intermediate 206 following the procedure as described for intermediate 74. Intermediate 207 was a white solid. Intermediate 207 was characterized by the following spectroscopic data: MS (ESI, EI$^+$) m/z=283 (MH$^+$).

Intermediate 208

2-(3-bromo-5-methyl-pyridin-2-yl)-isoindole-1,3-dione

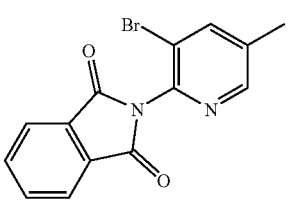

Intermediate 208 was synthesized from 2-amino-3-bromo-5-methyl-pyridine (Alfa Aesar), phtalic anhydride (Fluka) and acetic acid following the procedure as described in Eur. J. Med. Chem., 2001, 36, 639. Intermediate 208 was a beige solid. Intermediate 208 was characterized by the following spectroscopic data: MS (ESI, EI$^+$) m/z=318 (MH$^+$).

Intermediate 209

[2-(1,3-dioxo-1,3-dihydroisoindole-2-yl)-5-methyl-pyridin-3-yl]-phosphonic acid diethyl ester

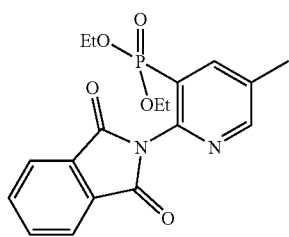

Intermediate 209 was synthesized from intermediate 208 following the procedure as described for intermediate 24. Intermediate 209 was a beige solid. Intermediate 209 was characterized by the following spectroscopic data: MS (ESI, EI$^+$) m/z=375 (MH$^+$).

Intermediate 210

(2-amino-5-methyl-pyridin-3-yl)-phosphonic acid diethyl ester

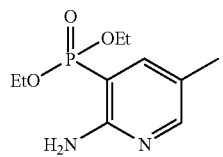

Intermediate 210 was synthesized from intermediate 209 following the procedure as described in JACS, 2005, 127(29), 10337. Intermediate 210 was a yellow solid. Intermediate 210 was characterized by the following spectroscopic data; MS (ESI, EI$^+$) m/z=245 (MH$^+$).

Intermediate 211

(2-iodo-ethoxy-methyl)-benzene

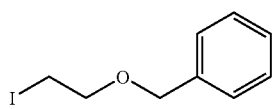

Benzyl-2-bromoethylether (46.49 mmol, Aldrich), NaI (46.5 mmol) in acetone (85 ml) were refluxed for 16 hours. The reaction mixture was filtered, evaporated, dissolved in MTBE (50 ml) washed with saturated sodium metabisulfite and water. Organics were separated, dried over Na$_2$SO$_4$, filtered, concentrated under reduced pressure and purified by silica gel chromatography to give intermediate 211, which was a colourless oil. Intermediate 211 was characterized by the following spectroscopic data: $^1$H NMR (CDCl$_3$, 400 MHz) δ (ppm) 3.26-3.29 (t, J=6.70 Hz, 2H), 3.71-3.75 (t, J=6.70 Hz, 2H), 4.57 (s, 2H), 7.29-7.35 (m, 5H).

Intermediate 212

(2-benzoyl-ethyl)-phosphinic acid benzyl ester

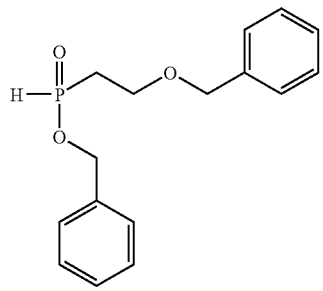

HMDS (38.15 mmol) and H$_2$PO$_2$NH$_4$ (38.15 mmol) were stirred under nitrogen at 110° C. for 24 hours. The reaction mixture was cooled down to 0° C., DCM (40 ml) was added followed by a solution of intermediate 211 (38.15 mmol) in DCM (10 ml). The mixture was stirred at room temperature for 16 hours, filtered and co-evaporated with dry BnOH (76.6 mmol) at room temperature under vacuum. The residue was diluted in dry THF (40 ml) and was stirred at 0° C. with BnOH (38.15 mmol) and DMAP (180 mg). A solution of DDC (49.6 mmol) in dry THF (10 ml) was added dropwise to the mixture at 0° C. and the white suspension obtained was stirred at room temperature for 1 hour. The reaction mixture was filtered. The solid obtained was washed with THF (10 ml) and purified by silica gel chromatography to yield intermediate 212, which was a colourless oil. Intermediate 212 was characterized by the following spectroscopic data: $^1$H NMR (CDCl$_3$, 400 MHz) δ (ppm) 2.12-2.17 (m, 2H), 3.78-3.81 (m, 2H), 4.48 (q, J=11.00 Hz, 2H), 5.04-5.13 (m, 2H), 7.30-7.36 (m, 10H). $^{31}$P NMR (CDCl$_3$, 162 MHz) δ (ppm) 35.35 (s, 1P).

Intermediate 213

(5-amino-2-nitrophenyl)-(2-benzyloxy-ethyl)-phosphinic acid benzyl ester

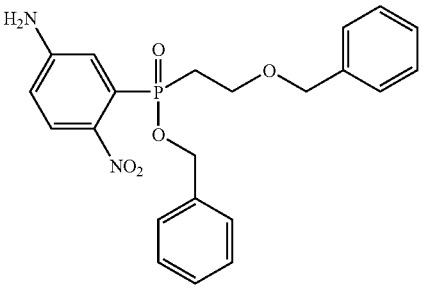

Intermediate 212 (3.44 mmol), 3-bromo-4-nitroaniline (3.44 mmol, Apollo), TEA (10.33 mmol), Pd(PPH$_3$)$_4$ (0.34 mmol in dry toluene (20 ml), DCM (1 ml) and methanol (10 ml) were stirred at 110° C. for 16 hours. The reaction mixture was concentrated under reduced pressure and by silica gel chromatography to yield intermediate 213, which was a brown oil. Intermediate 213 was characterized by the following spectroscopic data: MS (ESI, EI+) m/z=427 (MH+).

Intermediate 214

(5-dimesylamino-2-nitrophenyl)-(2-benzyloxy-ethyl)-phosphinic acid benzyl ester

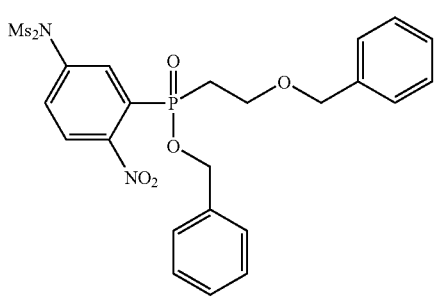

To a stirred solution of intermediate 213 (1.05 mmol) in DCM (10 ml) was added mesylchloride (3.16 mmol, Fluka). DIEA was then added at 0° C. The reaction mixture was stirred at room temperature for 4 hours, washed with water (10 ml), 2N HCl (10 ml), with saturated NaHCO₃ (10 ml), dried over Na₂SO₄, filtered and concentrated under reduced pressure to yield intermediate 214, which was used without further purification in the next step. Intermediate 214 was a brown oil. Intermediate 214 was characterized by the following spectroscopic data: MS (ESI, EI+) m/z=583 (MH+).

Intermediate 215

(5-mesylamino-2-nitrophenyl)-(2-benzyloxy-ethyl)-phosphinic acid benzyl ester

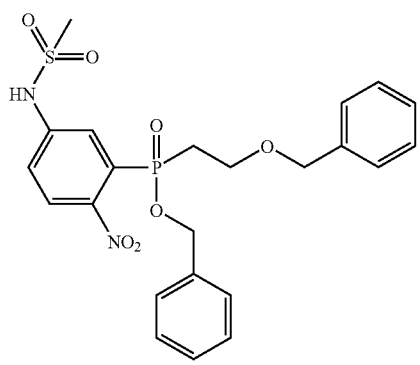

Intermediate 214 (1.05 mmol), TEA (10.55 mmol) in EtOH (10 ml) were stirred at 80° C. for 16 hours. The reaction mixture was evaporated, diluted in DCM (10 ml), washed with water (10 ml), with 2N HCl (10 ml), with saturated NaHCO₃ (10 ml), dried over Na₂SO₄, filtered and concentrated under reduced pressure to yield intermediate 215, which was used without further purification in the next step.

Intermediate 215 was a brown oil. Intermediate 215 was characterized by the following spectroscopic data: MS (ESI, EI+) m/z=505 (MH+).

Intermediate 216

(5-mesyl-5,2-diaminophenyl)-(2-benzyloxy-ethyl)-phosphinic acid benzyl ester

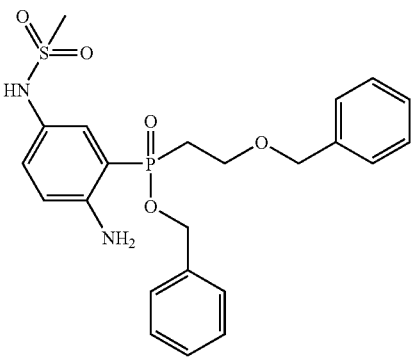

Intermediate 215 (0.365 mmol), in EtOH (20 ml) was stirred with 2N HCl (few drops) and Pd/C (0.036 mmol) under hydrogen atmosphere, for 16 hours. The reaction mixture was filtered though celite, concentrated under reduced pressure and used without further purifications in the next step. Intermediate 216 was a yellow oil. Intermediate 216 was characterized by the following spectroscopic data: MS (ESI, EI+) m/z=475 (MH+).

Intermediate 217

(5-amino-2-nitrophenyl)-2-ethyl-phosphinic acid benzyl ester

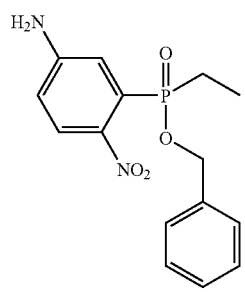

Intermediate 217 was synthesized from intermediate 177 following the procedure as described for intermediate 213. Intermediate 217 was a brown oil. Intermediate 217 was characterized by the following spectroscopic data: ¹H NMR (CDCl₃, 400 MHz) δ (ppm) 1.09-1.32 (m, 3H), 2.25-2.41 (m, 2H), 4.83-4.88 (m, 1H), 5.04-5.11 (m, 1H), 6.67-6.70 (dd, J=2.65 Hz and J=8.88 Hz, 1H), 7.29-7.35 (m, 5H), 7.53-7.57

(dd, J=2.65 Hz and J=8.88 Hz, 1H), 7.96-8.02 (dd, J=5.53 Hz and J=9.04 Hz, 1H). $^{31}$P NMR (CDCl$_3$, 162 MHz) δ (ppm) 46.34 (s, 1P).

Intermediate 218

(5-dimesylamino-2-nitrophenyl)-2-ethyl-phosphinic acid benzyl ester

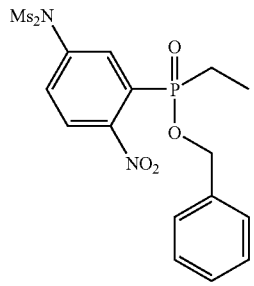

Intermediate 218 was synthesized from intermediate 217 following the procedure as described for intermediate 214. Intermediate 218 was a brown oil. Intermediate 218 was characterized by the following spectroscopic data: $^1$H NMR (CDCl$_3$, 400 MHz) δ (ppm) 1.12-1.21 (m, 3H), 2.25-2.35 (m, 2H), 3.39 (s, 6H), 4.90-4.95 (m, 1H), 5.08-5.29 (m, 1H), 6.67-6.70 (dd, J=2.65 Hz and J=8.88 Hz, 1H), 7.29-7.35 (m, 5H), 7.53-7.57 (dd, J=2.65 Hz and J=8.88 Hz, 1H), 7.96-8.02 (dd, J=5.53 Hz and J=9.04 Hz, 1H). $^{31}$P NMR (CDCl$_3$, 162 MHz) δ (ppm) 42.69 (s, 1P).

Intermediate 219

(5-mesylamino-2-nitrophenyl)-2-ethyl-phosphinic acid ethyl ester

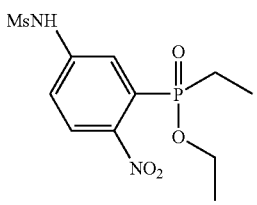

Intermediate 219 was synthesized from intermediate 218 following the procedure as described for intermediate 215. Intermediate 219 was a brown oil. Intermediate 219 was characterized by the following spectroscopic data: $^1$H NMR (CDCl$_3$, 400 MHz) δ (ppm) 1.14-1.24 (m, 3H), 2.40-2.55 (m, 2H), 3.06 (s, 3H), 5.00-5.05 (m, 1H), 5.12-5.18 (m, 1H), 7.23-7.29 (m, 5H), 7.82-7.85 (dd, J=2.50 Hz and J=8.83 Hz, 1H), 8.07-8.10 (dd, J=5.53 Hz and J=9.04 Hz, 1H), 8.34-8.38 (dd, J=2.50 Hz and J=14.04 Hz, 1H). $^{31}$P NMR (CDCl$_3$, 162 MHz) δ (ppm) 47.28 (s, 1P).

Intermediate 220

(5-mesylamino-2-aminophenyl)-2-ethyl-phosphinic acid ethyl ester

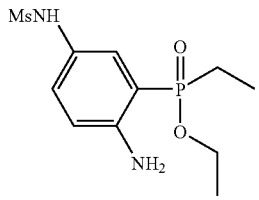

Intermediate 220 was synthesized from intermediate 219 following the procedure as described for intermediate 216. Intermediate 220 was a brown oil. Intermediate 220 was characterized by the following spectroscopic data: MS (ESI, EI$^+$) m/z=369 (MH$^+$).

Intermediate 221

(S)-(2-cyano-acetyl)-(4-fluoro-3-methylbenzy-lamino)-3,3-dimethyl-butyric acid methyl ester

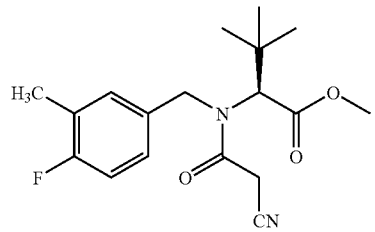

Intermediate 221 was synthesized from intermediate 159 following the procedure as described for intermediate 74. Intermediate 221 was a colourless oil. Intermediate 221 was characterized by the following spectroscopic data: $^1$H NMR (CDCl$_3$, 400 MHz) δ (ppm) 1.11 (s, 9H), 2.27 (brs, 3H), 3.21-3.25 (d, J=17.92 Hz, 1H), 3.33-3.38 (d, J=17.92 Hz, 1H), 3.58 (s, 3H), 4.56 (d, J=14.43 Hz, 1H), 5.12 (d, J=14.43 Hz, 1H), 5.23 (s, 1H), 6.90-7.02 (m, 3H). MS (ESI, EI$^+$) m/z=357 (MH+Na)$^+$.

Intermediate 222

Benzyloxy-methyl-phosphinic acid benzyl ester

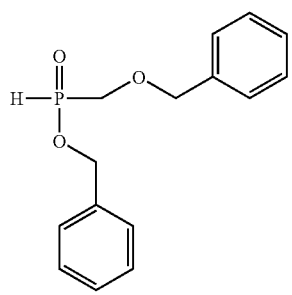

Intermediate 222 was synthesized from benzylchloromethyl ester (Fluka). following the procedure as described for intermediate 212. Intermediate 222 was a brown oil. Intermediate 222 was characterized by the following spectroscopic data: MS (ESI, EI$^+$) m/z=277 (MH$^+$).

Intermediate 223

(5-amino-2-nitrophenyl)-(2-benzyloxy-methyl-phosphinic acid benzyl ester

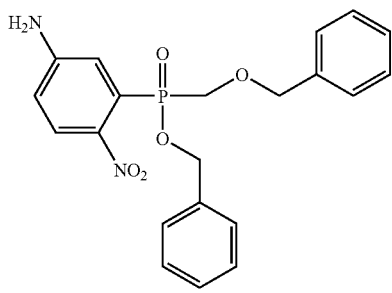

Intermediate 223 was synthesized from 3-bromo-4-nitroaniline (Apollo) following the procedure as described for intermediate 213. Intermediate 223 was a brown oil. Intermediate 223 was characterized by the following spectroscopic data: MS (ESI, EI$^+$) m/z=413 (MH$^+$).

Intermediate 224

(5-dimesylamino-2-nitrophenyl-(2-benzyloxy-methyl)-phosphinic acid benzyl ester

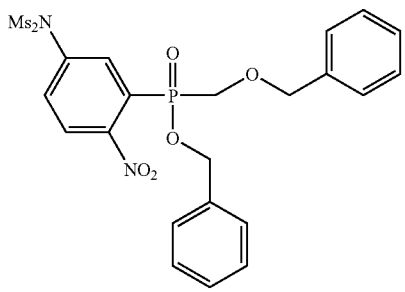

Intermediate 224 was synthesized from intermediate 223 following the procedure as described for intermediate 214. Intermediate 224 was a brown oil. Intermediate 224 was characterized by the following spectroscopic data: MS (ESI, EI$^+$) m/z=569 (MH$^+$).

Intermediate 225

(5-mesylamino-2-nitrophenyl)-(2-benzyloxy-methyl)-phosphinic acid benzyl ester

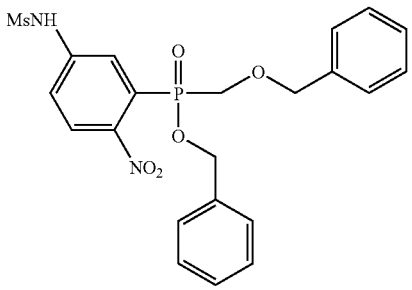

Intermediate 225 was synthesized from intermediate 224 following the procedure as described for intermediate 215. Intermediate 225 was a brown oil. Intermediate 225 was characterized by the following spectroscopic data: MS (ESI, EI$^+$) m/z=491 (MH$^+$).

Intermediate 226

(5-mesyl-2,5-diaminophenyl)-(2-benzyloxy-methyl)-phosphinic acid benzyl ester

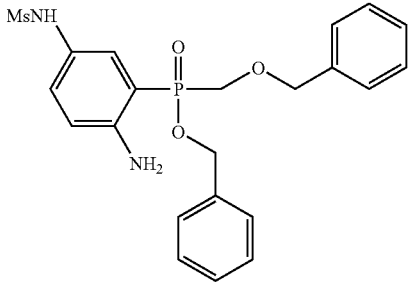

Intermediate 226 was synthesized from intermediate 225 following the procedure as described for intermediate 216. Intermediate 226 was a brown oil. Intermediate 226 was characterized by the following spectroscopic data: MS (ESI, EI$^+$) m/z=461 (MH$^+$).

Intermediate 227

(2-amino-5-dimesylamino-phenyl)-2-ethyl-phosphinic acid benzyl ester

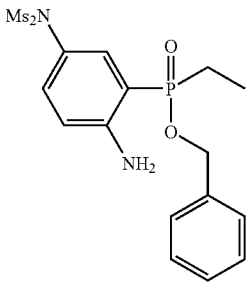

Intermediate 227 was synthesized from intermediate 5146 following the procedure as described for intermediate 217. Intermediate 227 was a yellow oil. Intermediate 227 was characterized by the following spectroscopic data: MS (ESI, EI+) m/z=447 (MH+).

Intermediate 228

3-amino-4-iodo-benzamide

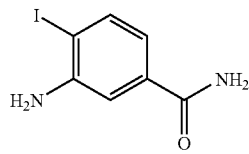

A solution of ammonia in methanol (7N, 10 ml), was added to 3-amino-4-iodo benzoic acid methyl ester (Alfa Aesar, 2.16 mmol). The mixture was degassed and let to stir for 20 minutes at 140° C. under microwave irradiations. The mixture was filtered, washed with water, concentrated under reduced pressure and purified by silica gel chromatography to yield Intermediate 228, which was a yellow oil. Intermediate 228 was characterized by the following spectroscopic data: MS (ESI, EI+) m/z=263 (MH+).

Intermediate 229

(2-amino-4-carbamoyl-phenyl)-phosphonic acid diethyl ester

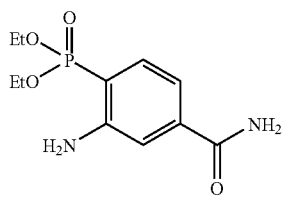

Intermediate 229 was synthesized from intermediate 228 following the procedure as described for intermediate 181. Intermediate 229 was a yellow oil. Intermediate 229 was characterized by the following spectroscopic data: MS (ESI, EI+) m/z=273 (MH+).

Intermediate 230

2-(cyano-acetylamino)-3,3-dimethyl-butyric acid methyl ester

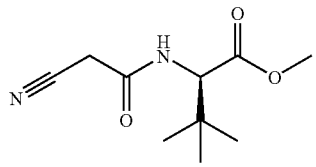

Intermediate 230 was synthesized from L-tert-leucine methyl ester (Topharman) following the procedure as described for intermediate 74 and was a white gum. Intermediate 230 was characterized by the following spectroscopic data: MS (ESI, EI+) m/z=211 (MH−).

Intermediate 231

2-[(2-cyano-acetyl)-(3,3-dimethyl-butyryl)-amino]-3,3-dimethylbutyric acid methyl ester

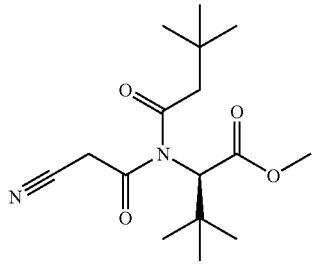

Intermediate 231 was synthesized from intermediate 230 and tert-butyl acetyl chloride (Acros) following the procedure as described in *Bioorg. Med. Chem.*, 2003, 11, 4315. Intermediate 231 was a yellow gum. Intermediate 231 was characterized by the following spectroscopic data: MS (ESI, EI+) m/z=309 (MH−).

Intermediate 232

4-amino-3-iodo-benzamide

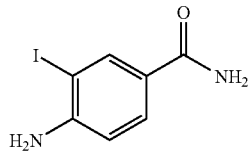

Intermediate 232 was synthesized from 4-aminobenzamide (Aldrich) following the procedure as described in *Tet. Lett*, 2002, 43, 5047 and was a yellow solid. Intermediate 232 was characterized by the following spectroscopic data: $^1$H NMR (DMSO-$d_6$, 400 MHz) δ (ppm) 5.70 (s, 2H), 6.69 (d, J=8.60 Hz, 1H), 6.97 (brs, 1H), 7.60 (dd, J=8.60 Hz and J=2.11 Hz, 1H), 7.64 (brs, 1H), 8.09 (d, J=2.11 Hz, 1H).

Intermediate 233

(2-amino-5-carbamoyl-phenyl)-phosphonic acid diethyl ester

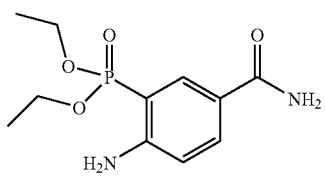

Intermediate 233 was synthesized from intermediate 232 following the procedure as described for intermediate 24 and was a beige solid. Intermediate 233 was characterized by the following spectroscopic data: $^1$H NMR (DMSO-$d_6$, 400 MHz) δ (ppm) 1.21 (t, J=7.05 Hz, 6H), 3.94-4.00 (m, 4H), 6.44 (s, 2H), 6.67-6.71 (m, 1H), 7.02 (brs, 1H), 7.70 (brs, 1H), 7.73-7.76 (dd, J=8.58 Hz and J=1.58 Hz, 1H), 7.86 (dd, J=15.18 Hz and J=2.11 Hz, 1H).

Intermediate 234

2-amino-5-chloro-3-iodo-benzamide

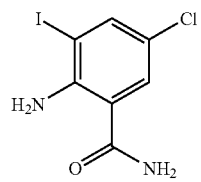

NH$_3$g was bubbled at 0° C. in a solution of methyl-2-amino-5-chloro-3-iodobenzoate (3.21 mmol, Alfa Aesar) in MeOH (13 ml) for 20 min. The reaction mixture was then stirred at 110° C. under microwave irradiations for 3 hours. Solvents were evaporated and the crude material was purified by silica gel chromatography to yield intermediate 234 and was an off-white powder. Intermediate 234 was characterized by the following spectroscopic data: $^1$H NMR (DMSO-$d_6$, 400 MHz) δ (ppm) 6.66 (s, 2H), 7.42 (brs, 1H), 7.65 (d, J=2.30 Hz, 1H), 7.76 (d, J=2.30 Hz, 1H), 8.00 (brs, 1H).

Intermediate 235

(2-amino-3-carbamoyl-5-chloro-phenyl)-phosphonic acid diethyl ester

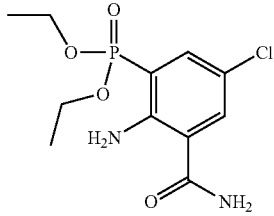

Intermediate 235 was synthesized from intermediate 234 following the procedure as described for intermediate 24 and was a beige solid. Intermediate 235 was characterized by the following spectroscopic data: $^1$H NMR (CDCl$_3$, 400 MHz) δ (ppm) 1.35 (t, J=7.05 Hz, 6H), 4.06-4.21 (m, 4H), 6.06 (s, 2H), 7.46 (d, J=2.46 Hz, 1H), 7.57 (dd, J=15.34 Hz and J=2.50 Hz, 1H).

Intermediate 236

(2-amino-3-carbamoyl-phenyl)-phosphonic acid diethyl ester

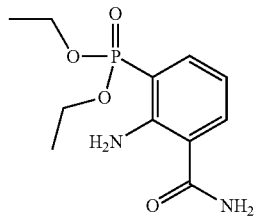

To a stirred solution of intermediate 235 (0.6 mmol) in anh DMF (4 ml) was added water (2 ml) and ammonium formate (1.8 mmol). Palladium on activated charcoal (10%) (20 mg) was added and the mixture was stirred at 80° C. for 24 hrs. The solution was filtered through celite, washed with EtOAC. Solvents were evaporated. The residue was dissolved in EtOAc, NaHCO$_3$ sat solution was added. Organics were separated, dried over Na$_2$SO$_3$, concentrated under reduced pressure and purified by silica gel chromatography to yield intermediate 236, which was a beige solid. Intermediate 236 was characterized by the following spectroscopic data: $^1$H NMR (CDCl$_3$, 400 MHz) δ (ppm) 1.33 (t, J=7.10 Hz, 6H), 4.04-4.16 (m, 4H), 5.74 (s, 2H), 6.59-6.64 (t, J=7.34 Hz, 1H), 7.30 (brs, 2H), 7.53 (d, J=2.46 Hz, 1H), 7.60-7.66 (dd, J=15.34 Hz and J=2.50 Hz, 1H).

Intermediate 237

(S)-2-(3,4-difluoro-benzylamino)-3,3-dimethyl-butyric acid methyl ester

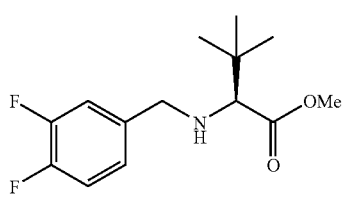

Intermediate 237 was synthesized from (S)-methyl-amino-3,3-dimethylbutanoate (Bionet) and 3,4-difluorobenzaldehyde (ABCR) following the procedure as described for intermediate 121 and was a colourless oil. Intermediate 237 was characterized by the following spectroscopic data: $^1$H NMR (CDCl$_3$, 400 MHz) δ (ppm) 0.95 (s, 9H), 1.88 (s, 1H), 2.86 (s, 1H), 3.44-3.47 (d, 1H), 3.72 (s, 3H), 3.74-3.78 (d, 1H), 7.00-7.07 (m, 2H), 7.08-7.11 (m, 1H).

Intermediate 238

(S)-(2-cyano-acetyl)-(3,4-fluoro-benzylamino)-3,3-dimethyl-butyric acid methyl ester

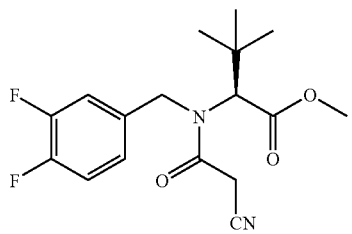

Intermediate 238 was synthesized from intermediate 237 following the procedure as described for intermediate 74 and was a colourless oil. Intermediate 238 was characterized by the following spectroscopic data: $^1$H NMR (CDCl$_3$, 400 MHz) δ (ppm) 1.11 (s, 9H), 2.27 (brs, 3H), 3.13-3.29 (q, 2H), 3.33-3.38 (d, J=17.92 Hz, 1H), 3.54 (s, 3H), 4.50 (d, J=14.43 Hz, 1H), 5.07 (s, 1H), 5.12 (d, J=14.43 Hz, 1H), 6.80-7.12 (m, 3H).

Intermediate 239

(S)-2-(3-methoxy,4-fluoro-benzylamino)-3,3-dimethyl-butyric acid methyl ester

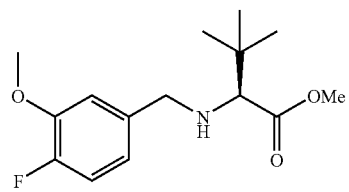

Intermediate 239 was synthesized from (S)-methyl-amino-3,3-dimethylbutanoate (Bionet) and 3-methoxy-4-fluorobenzaldehyde (ABCR) following the procedure as described for intermediate 121 and was a colourless oil. Intermediate 239 was characterized by the following spectroscopic data: $^1$H NMR (CDCl$_3$, 400 MHz) δ (ppm) 0.95 (s, 9H), 1.88 (s, 1H), 2.87 (s, 1H), 3.45-3.48 (d, 1H), 3.71 (s, 3H), 3.76-3.79 (d, 1H), 3.88 (s, 3H), 6.79-6.83 (m, 1H), 7.96-7.00 (m, 2H).

Intermediate 240

(S)-(2-cyano-acetyl)-(3-methoxy-4-fluoro-benzylamino)-3,3-dimethyl-butyric acid methyl ester

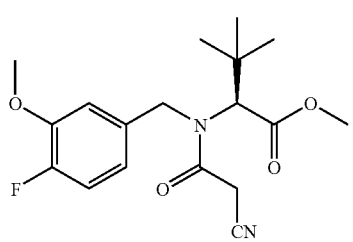

Intermediate 240 was synthesized from intermediate 239 following the procedure as described for intermediate 74 and was a colourless oil. Intermediate 240 was characterized by the following spectroscopic data: $^1$H NMR (CDCl$_3$, 400 MHz) δ (ppm) 1.11 (s, 9H), 2.27 (brs, 3H), 3.22-3.37 (q, 2H), 3.59 (s, 3H), 3.88 (s, 3H) 4.57-4.62 (d, J=14.43 Hz, 1H), 5.11-5.15 (d, J=14.43 Hz, 1H), 5.20 (s, 1H), 6.62-6.65 (m, 1H), 6.77-6.78 (d, 1H), 7.04-7.09 (m, 1H).

Intermediate 241

(S)-2-(benzylamino)-3,3-dimethyl-butyric acid methyl ester

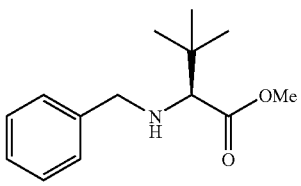

Intermediate 241 was synthesized from (S)-methyl-amino-3,3-dimethylbutanoate (Bionet) and benzaldehyde (ABCR) following the procedure as described for intermediate 121 and was a colourless oil. Intermediate 241 was characterized by the following spectroscopic data: $^1$H NMR (CDCl$_3$, 400 MHz) δ (ppm) 0.95 (s, 9H), 1.86 (s, 1H), 2.91 (s, 1H), 3.52-3.55 (d, 1H), 3.69 (s, 3H), 3.77-3.80 (d, 1H), 7.21-7.25 (m, 1H), 7.28-7.31 (m, 4H).

Intermediate 242

(S)-(2-cyano-acetyl)-(benzylamino)-3,3-dimethyl-butyric acid methyl ester

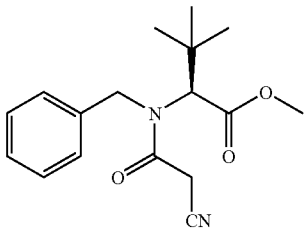

Intermediate 242 was synthesized from intermediate 241 following the procedure as described for intermediate 74 and was a colourless oil. Intermediate 242 was characterized by the following spectroscopic data: $^1$H NMR (CDCl$_3$, 400 MHz) δ (ppm) 1.11 (s, 9H), 3.20-3.40 (q, 2H), 3.54 (s, 3H), 4.60 (d, J=14.43 Hz, 1H), 5.15 (d, J=14.43 Hz, 1H), 5.25 (s, 1H), 7.11-7.13 (m, 2H), 7.27-7.35 (m, 3H).

Example 44

(S)-5-tert-butyl-1-(3,3-dimethyl-butyl)-3-(1-ethoxy-1-oxo-1,4-dihydro-7-methanesulfonamyl-1-benzo[1,2,4]phosphadiazin-3-yl)-4-hydroxy-1,5-dihydropyrrol-2-one

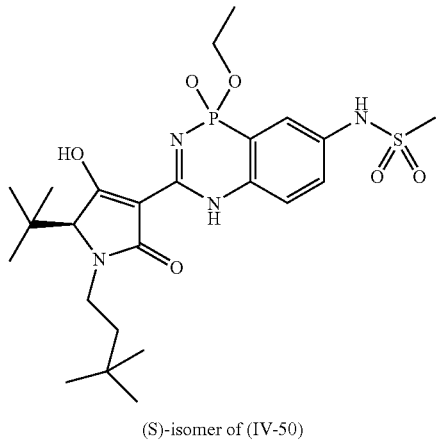

(S)-isomer of (IV-50)

To a solution of intermediate 77 (0.31 mmol) in dioxane (3 ml) was added intermediate 26 (0.465 mmol). This mixture was treated dropwise with trimethyl aluminium (1.55 mmol) and stirred at 80° C. for 4 hours. After, the reaction mixture was quenched with HCl 1N, diluted with TBDME or ethyl acetate, washed with water and brine, dried over sodium sulfate and concentrated in vacuo to give, after purification with preparative HPLC to give Example 44, which was a white solid. Example 44 was characterized by the following spectroscopic data: $^1$H NMR (CDCl$_3$, 400 MHz) δ (ppm) 0.95 (m, 9H), 1.01 (m, 9H), 1.32-1.36 (m, 3H), 1.54-1.64 (m, 1H), 1.84-1.89 (m, 1H), 3.04 (s, 3H), 3.15-3.22 (m, 1H), 3.49-3.52 (m, 1H), 3.92-4.00 (m, 1H), 4.10-4.24 (m) 2H), 7.15-7.22 (m, 1H), 7.64-7.72 (m, 2H), 8.15-8.21 (m, 1H), 11.53-11.57 (m, 0.5H), 11.69-11.77 (m, 0.5H); $^{31}$P NMR (DMSO-d$_6$, 162 MHz) δ (ppm) 0.83 (m, 1P); and MS (ESI, EI$^+$) m/z=541 (MH$^+$). Example 44 is equivalent to (S)-isomer of Compound IV-50.

The single enantiomers or diastereomers can be isolated in enriched form by preparative SFC separation (column: 250×30 mm CHIRALPAK® IA 5 μM; Mobil phase: 75/25 Carbon dioxide/Isopropanol+1% diethylamine; 120 ml/min; UV: 315 nm).

Example 45

(S)-5-tert-butyl-1-(3,3-dimethyl-butyl)-3-(1-hydroxy-1-oxo-1,4-dihydro-7-methanesulfonamyl-1-benzo[1,2,4]phosphadiazin-3-yl)-4-hydroxy-1,5-dihydropyrrol-2-one

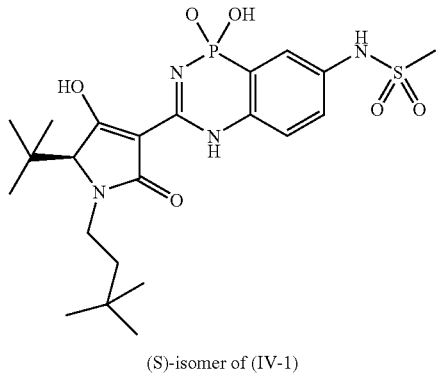

(S)-isomer of (IV-1)

Example 44 (0.05 mmol) was dissolved in 1,2-dichloroethane (2.5 ml) under nitrogen and tetramethylsilylbromide (0.5 mmol). The mixture was stirred at 60° C. for 2 hours and then, concentrated to dryness. The residue was quenched with methanol before new concentration under vacuo. The residue was purified by chromatography (RP18) and lyophilisation to give Example 45, which was a white solid. Example 45 was characterized by the following spectroscopic data: $^1$H NMR (DMSO-d$_6$, 400 MHz) δ (ppm) 0.88 (s, 9H), 1.01 (s, 9H), 1.21-1.28 (m, 1H), 1.54-1.68 (m, 1H), 2.98 (s, 3H), 3.01-3.11 (m, 1H), 3.47 (s, 1H), 3.73-3.86 (m, 1H), 7.32-7.38 (m, 2H), 7.39-7.46 (m, 1H), 9.89 (s, 1H), 10.11-10.35 (m, 1H), 11.11 (brs, 1H), 11.29 (s, 1H); $^{31}$P NMR (DMSO-d$_6$, 162 MHz) δ (ppm) −8.97 (s, 1P); and MS (ESI, EI$^+$) m/z=513 (MH$^+$). Example 45 is equivalent to (S)-isomer of Compound IV-1.

Example 46

(S)-5-tert-butyl-1-(3,3-dimethyl-butyl)-3-(1-methoxy-1-oxo-1,4-dihydro-7-methanesulfonamyl-1-benzo[1,2,4]phosphadiazin-3-yl)-4-hydroxy-1,5-dihydropyrrol-2-one

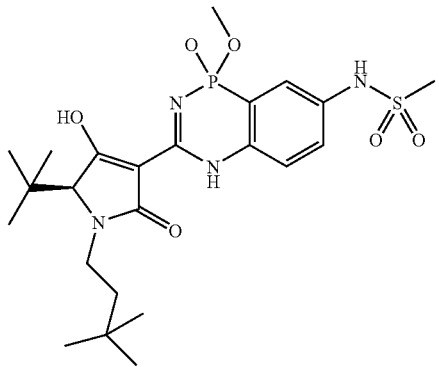

(S)-isomer of (IV-11)

Example 46 was synthesized from example 45. To a stirred solution of example 45 (45 mg, 0.082 mmol) in dichloromethane (4 ml) was added trimethylsilyl bromide (87 μl, 0.65 mmol) under nitrogen. The reaction mixture was stirred and heated to reflux for 2 hours. Trimethylsilyl bromide (1 eq) was added every 5 hours until the expected product was formed. The reaction mixture was then quenched with water. A white solid was filtered, washed with water and dried to give example 46, which was a white solid. Example 46 was characterized by the following spectroscopic data: $^1$H NMR (DMSO-d$_6$, 400 MHz) δ (ppm) 0.89 (m, 9H), 1.02 (m, 9H), 1.27 (td, J=5 Hz and J=11.77 Hz, 1H), 1.59-1.71 (m, 1H), 3.04 (s, 3H), 3.63 (d, J=12.49 Hz, 3H), 3.74-3.84 (m, 2H), 7.47-7.65 (m, 3H), 10.08 (brs, 1H), 11.37-11.50 (m, 1H); $^{31}$P NMR (DMSO-d$_6$, 162 MHz) δ (ppm) 1.66 (s, 1P), 1.78 (s, 1P); and MS (ESI, EI$^+$) m/z=526 (MH$^+$). Example 46 is equivalent to (S)-isomer of Compound IV-11.

Example 47

(S)-5-tert-butyl-1-(3-chloro-4-fluoro-benzyl)-3-(1-ethoxy-1-oxo-1,4-dihydro-7-methanesulfonamyl-1-benzo[1,2,4]phosphadiazin-3-yl)-4-hydroxy-1,5-dihydropyrrol-2-one

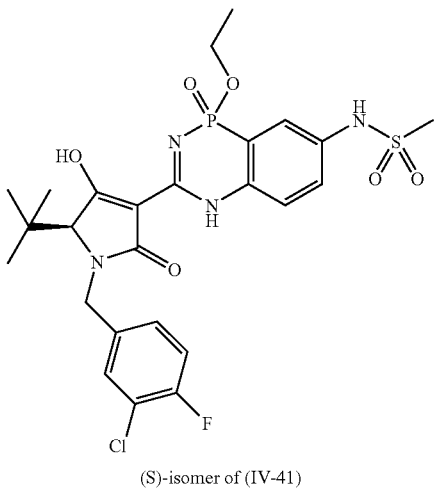

(S)-isomer of (IV-41)

Example 47 was synthesized from intermediate 78 as described for example 44 and was a white solid. Example 47 was characterized by the following spectroscopic data: $^1$H NMR (CDCl$_3$, 400 MHz) δ (ppm) 1.08-1.10 (m, 9H), 1.36-1.42 (m, 3H), 3.06 (s, 3H), 3.32-3.39 (m, 1H), 4.17-4.33 (m, 3H), 5.15-5.30 (m, 1H), 7.04-7.14 (m, 2H), 7.17-7.27 (m, 2H), 7.52-7.58 (m, 1H), 7.63-7.71 (m, 2H), 11.46-11.52 (m, 0.5H), 11.80 (brs, 0.5H); $^{31}$P NMR (CDCl$_3$, 162 MHz) δ (ppm) 0.36 (s, 1P), 0.38 (s, 1P), 0.46 (s, 1P), 0.53 (s, 1P); $^{19}$F NMR (CDCl$_3$, 376 MHz) δ (ppm) (−116.87)-(−116.99) (m, 1F); and MS (ESI, EI$^+$) m/z=599 (MH$^+$). Example 47 is equivalent to (S)-isomer of Compound IV-41.

Example 48

(S)-5-tert-butyl-1-(3-chloro-4-fluoro-benzyl)-3-(1-hydroxy-1-oxo-1,4-dihydro-7-methanesulfonyl-1-benzo[1,2,4]phosphadiazin-3-yl)-4-hydroxy-1,5-dihydropyrrol-2-one

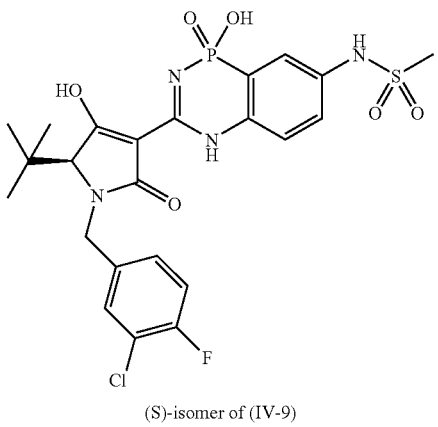

(S)-isomer of (IV-9)

Example 48 was synthesized from example 47 as described for example 45 and was a white solid. Example 48 was characterized by the following spectroscopic data: $^1$H NMR (DMSO-d$_6$, 400 MHz) δ (ppm) 0.96 (s, 9H), 2.99 (s, 3H), 3.38 (brs, 1H), 4.40 (d, J=16.18 Hz, 1H), 4.81 (d, J=16.18 Hz, 1H), 7.17-7.22 (m, 1H), 7.33-7.48 (m, 5H), 9.94 (s, 1H), 10.11 (brs, 0.5H), 10.46 (brs, 0.5H), 11.04 (brs, 0.5H), 11.36 (brs, 0.5H); $^{31}$P NMR (DMSO-d$_6$, 162 MHz) δ (ppm) −8.28 (s, 1P); $^{19}$F NMR (DMSO-d$_6$, 376 MHz) δ (ppm) (−118.97)-(−119.13) (m, 1F); and MS (ESI, EI$^+$) m/z=571 (MH$^+$). Example 48 is equivalent to (S)-isomer of Compound IV-9.

Example 49

(S)-5-tert-butyl-1-(3-chloro-4-fluoro-benzyl)-3-(1-methoxy-1-oxo-1,4-dihydro-7-methanesulfonamyl-1-benzo[1,2,4]phosphadiazin-3-yl)-4-hydroxy-1,5-dihydropyrrol-2-one

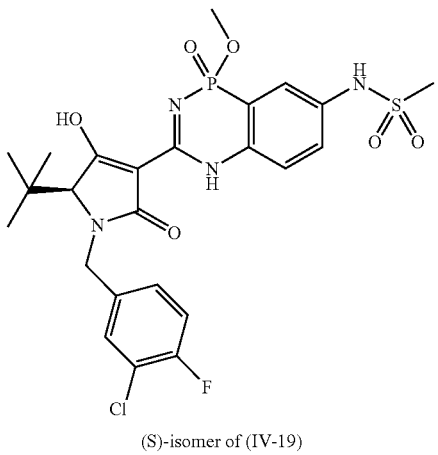

(S)-isomer of (IV-19)

Example 49 was synthesized from example 48. To a stirred solution of example 48 (45 mg, 0.082 mmol) in dichloromethane (4 ml) was added trimethylsilyl bromide (87 µl, 0.65 mmol) under nitrogen. The reaction mixture was stirred and heated to reflux for 2 hours. Trimethylsilyl bromide (1 eq) was added every 5 hours until the expected product was formed. The reaction mixture was then quenched with water. A white solid was filtered, washed with water and dried to give example 49, which was a white solid. Example 49 was characterized by the following spectroscopic data: $^1$H NMR (DMSO-d$_6$, 400 MHz) δ (ppm) 0.95 (s, 9H), 3.03 (s, 3H), 3.64 (brs, 3H), 4.37-4.52 (m, 1H), 4.73-4.84 (m, 1H), 7.15-7.70 (m, 6H), 10.10 (brs, 1H), 11.36 (brs, 0.5H), 11.57 (brs, 0.5H); $^{31}$P NMR (DMSO-d$_6$, 162 MHz) δ (ppm) 1.52-1.89 (m, 1P);

¹⁹F NMR (DMSO-d₆, 376 MHz) δ (ppm) (−118.96)-(−119.09) (m, 1F); and MS (ESI, EI⁺) m/z=585 (MH⁺). Example 49 is equivalent to (S)-isomer of Compound IV-19.

Example 50

(S)-5-tert-butyl-1-(2-cyclopropyl-ethyl)-3-(1-ethoxy-1-oxo-1,4-dihydro-7-methanesulfonamyl-1-benzo[1,2,4]phosphadiazin-3-yl)-4-hydroxy-1,5-dihydropyrrol-2-one

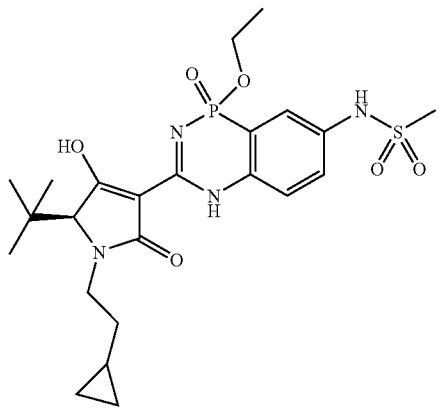

(S)-isomer of (IV-42)

Example 50 was synthesized from intermediate 81 as described for example 44 and was a white powder. Example 50 was characterized by the following spectroscopic data: ¹H NMR (DMSO-d₆, 400 MHz) δ (ppm) −0.01-0.01 (m, 2H), 0.33-0.39 (m, 2H), 0.52-0.60 (m, 1H), 1.02 (s, 9H), 1.17-1.25 (m, 3H), 1.32-1.44 (m, 1H), 1.51-1.63 (m, 1H), 3.03 (s, 3H), 3.80-3.91 (m, 2H), 3.98-4.10 (m, 2H), 7.47-7.65 (m, 3H), 10.08 (brs, 1H), 11.04 (brs, 0.5H); ³¹P NMR (DMSO-d₆, 162 MHz) δ (ppm) (−0.008)-0.14 (m, 1P); and MS (EST, EI⁺) m/z=525 (MH⁺). Example 50 is equivalent to (S)-isomer of Compound IV-42.

Example 51

(S)-5-tert-butyl-1-(2-cyclopropyl-ethyl)-3-(1-hydroxy-1-oxo-1,4-dihydro-7-methanesulfonamyl-1-benzo[1,2,4]phosphadiazin-3-yl)-4-hydroxy-1,5-dihydropyrrol-2-one

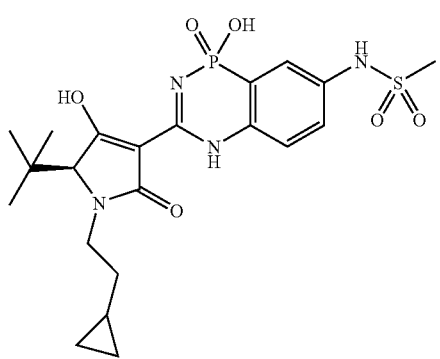

(S)-isomer of (IV-59)

Example 51 was synthesized from example 50 as described for example 45 but in this case, the mixture was quenched with a solution of sodium hydroxide (3 ml). After purification by chromatography, the product was dissolved in methanol and the resin Dowex H⁺ was added and the mixture stirred at room temperature for 4 hours. After stirring, the mixture was filtered and the filtrate concentrated under vacuo. The residue obtained was diluted with water and acetonitrile before lyophilization, which was a white powder. Example 51 was characterized by the following spectroscopic data: ¹H NMR (DMSO-d₆, 400 MHz) δ (ppm) −0.03-0.03 (m, 2H), 0.34-0.39 (m, 2H), 0.51-0.60 (m, 1H), 1.01 (s, 9H), 1.31-1.42 (m, 1H), 1.49-1.62 (m, 1H), 2.99 (s, 3H), 3.80-3.92 (m, 2H), 7.39-7.44 (m, 2H), 7.44-7.47 (0.5H), 7.47-7.50 (m, 0.5H), 9.97 (brs, 1H), 11.13-11.37 (m, 1H); ³¹P NMR (DMSO-d₆, 162 MHz) δ (ppm) −6.87 (s, 1P), −1.18 (s, 1P). Example 51 is equivalent to (S)-isomer of Compound IV-59.

Example 52

(S)-5-tert-butyl-1-(2-cyclopropyl-ethyl-3-(1-methoxy-1-oxo-1,4-dihydro-7-methanesulfonamyl-1-benzo[1,2,4]phosphadiazin-3-yl)-4-hydroxy-1,5-dihydropyrrol-2-one

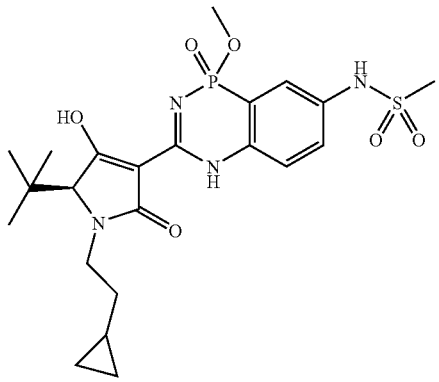

(S)-isomer of (IV-58)

Example 52 was synthesized from example 51. To a stirred solution of example 51 (45 mg, 0.082 mmol) in dichloromethane (4 ml) was added trimethylsilyl bromide (87 µl, 0.65 mmol) under nitrogen. The reaction mixture was stirred and heated to reflux for 2 hours. Trimethylsilyl bromide (1 eq) was added every 5 hours until the expected product was formed. The reaction mixture was then quenched with water. A white solid was filtered, washed with water and dried to give example 52, which was a white solid. Example 52 was characterized by the following spectroscopic data: ¹H NMR (DMSO-d₆, 400 MHz) δ (ppm) −0.03-0.03 (m, 2H), 0.33-0.41 (m, 2H), 0.51-0.63 (m, 1H), 1.02 (s, 9H), 1.32-1.45 (m, 1H), 1.50-1.67 (m, 1H), 3.04 (s, 3H), 3.64 (m, 3H), 3.80-3.93 (m, 2H), 7.47-7.60 (m, 3H), 10.08 (brs, 1H), 11.44 (brs, 1H); ³¹P NMR (DMSO-d₆, 162 MHz) δ (ppm) 1.70-1.80 (m, 1P); and MS (ESI, EI⁺) m/z=511 (MH⁺). Example 52 is equivalent to Compound (S)-isomer of IV-58.

Example 53

(S)-5-tert-butyl-1-isobutyl-3-(1-ethoxy-1-oxo-1,4-dihydro-7-methanesulfonamyl-1-benzo[1,2,4]phosphadiazin-3-yl)-4-hydroxy-1,5-dihydropyrrol-2-one

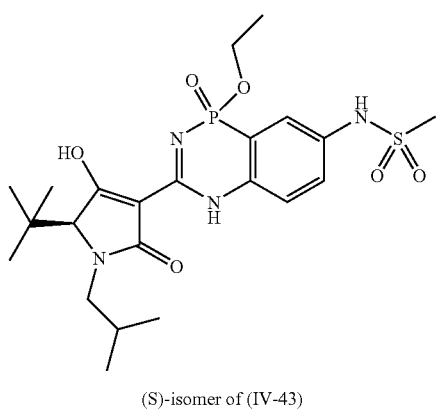

(S)-isomer of (IV-43)

Example 53 was synthesized from intermediate 90 as described for example 44 and was a white solid. Example 53 was characterized by the following spectroscopic data: $^1$H NMR (CDCl$_3$, 400 MHz) δ (ppm) 0.77-0.81 (nm 3H), 0.90-0.96 (m, 3H), 1.07-1.11 (m, 9H), 1.34-1.39 (m, 3H), 2.97-3.04 (m, 1H), 3.05 (s, 3H), 3.52-3.56 (m, 1H), 3.70-3.82 (m, 1H), 3.87-3.95 (m, 1H), 4.15-4.26 (m, 2H), 7.13-7.22 (m, 1H), 7.61-7.68 (m, 2H), 11.59-11.63 (, 0.5H), 11.70-11.75 (m, 0.5H); $^{31}$P NMR (CDCl$_3$, 162 MHz) δ (ppm) 0.43 (s, 1P), 0.49 (s, 1P), 0.72 (s, 1H), 0.78 (s, 1P); and MS (ESI, EI$^+$) m/z=513 (MH$^+$). Example 53 is equivalent to (S)-isomer of Compound IV-43.

Example 54

(S)-5-tert-butyl-1-(3-methylbutyl)-3-(1-ethoxy-1-oxo-1,4-dihydro-7-methanesulfonamyl-1-benzo[1,2,4]phosphadiazin-3-yl)-4-hydroxy-1,5-dihydropyrrol-2-one

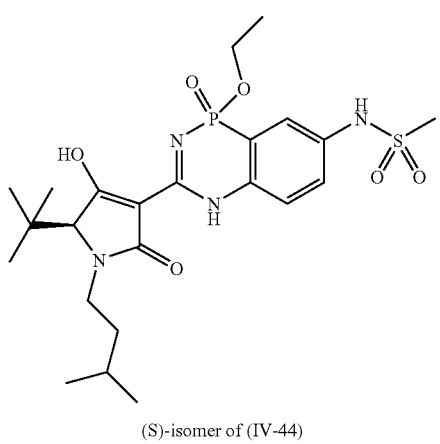

(S)-isomer of (IV-44)

Example 54 was synthesized from intermediate 93 as described for example 44 and was a white solid. Example 54 was characterized by the following spectroscopic data: $^1$H NMR (CDCl$_3$, 400 MHz) δ (ppm) 0.91-0.97 (m, 6H), 1.08-1.13 (m, 9H), 1.36 (td, J=2.67 Hz and J=7.04 Hz, 3H), 1.40-1.60 (m, 3H), 3.05 (s, 3H), 3.14-3.23 (m, 1H), 3.49-3.53 (m, 1H), 3.93-4.03 (m, 1H), 4.13-4.24 (m, 2H), 7.15-7.21 (m, 1H), 7.62-7.69 (m, 2H), 7.8 (brs, 1H), 11.54-11.59 (m, 0.5H), 11.69-11.74 (m, 0.5H); $^{31}$P NMR (CDCl$_3$, 162 MHz) δ (ppm) 0.56 (s, 1P), 0.82 (s, 1P), 0.86 (s, 1P); and MS (ESI, EI$^+$) m/z=527 (MH$^+$). Example 54 is equivalent to (S)-isomer of Compound IV-44.

Example 55

(S)-5-isobutyl-1-(3,3-dimethylbutyl)-3-(1-ethoxy-1-oxo-1,4-dihydro-7-methanesulfonamyl-1-benzo[1,2,4]phosphadiazin-3-yl)-4-hydroxy-1,5-dihydropyrrol-2-one

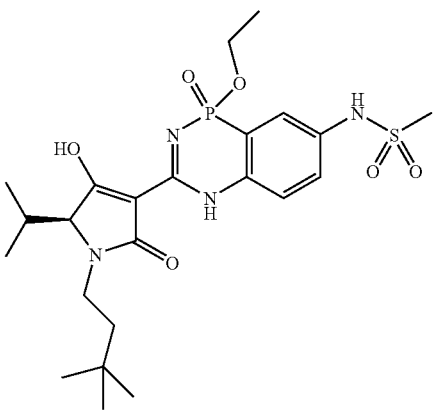

(S)-isomer of (IV-45)

Example 55 was synthesized from intermediate 96 as described for example 44 and was a white solid. Example 55 was characterized by the following spectroscopic data: $^1$H NMR (CDCl$_3$, 400 MHz) δ (ppm) 0.90-0.95 (m, 3H), 0.98 (s, 9H), 1.17-1.20 (m, 3H), 1.32-1.37 (m, 3H), 1.38-1.44 (m, 1H), 1.48-1.57 (m, 1H), 2.20-2.30 (m, 1H), 2.98-3.05 (m, 1H), 3.04 (s, 3H), 3.72-3.77 (m, 1H), 3.83-3.91 (m, 1H), 4.11-4.24 (m, 2H), 7.13-7.20 (m, 1H), 7.63-7.70 (m, 2H), 7.89 (brs, 1H), 11.48-11.64 (m, 1H); $^{31}$P NMR (CDCl$_3$, 162 MHz) δ (ppm) 0.50 (s, 1P), 0.85 (s, 1P); and MS (ESI, EI$^+$) m/z=527 (MH$^+$). Example 55 is equivalent to (S)-isomer of Compound IV-45.

Example 56

(S)-5-tert-butyl-1-furan-3-ylmethyl-3-(1-ethoxy-1-oxo-1,4-dihydro-7-methanesulfonamyl-1-benzo[1,2,4]phosphadiazin-3-yl)-4-hydroxy-1,5-dihydropyrrol-2-one

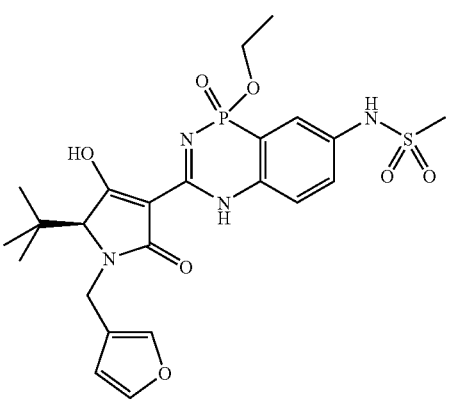

(S) isomer of (IV-46)

Example 56 was synthesized from intermediate 99 as described for example 44 and was a white solid. Example 56 was characterized by the following spectroscopic data: $^1$H NMR (CDCl$_3$, 400 MHz) δ (ppm) 1.09-1.10 (m, 9H), 1.34-1.40 (m, 3H), 3.05 (s, 3H), 3.38-3.42 (m, 1H), 3.71 (s, 2H), 4.14-4.25 (m 2H), 5.07-5.18 (m, 1H), 6.25-6.28 (m, 1H), 7.15-7.23 (m, 1H), 7.35-7.38 (m, 2H), 7.67-7.71 (m, 2H), 11.53-11.54 (m, 0.5H), 11.77 (brs, 0.5H); $^{31}$P NMR (CDCl$_3$, 162 MHz) δ (ppm) 0.57 (s, 1P), 0.69 (s, 1P), 0.76 (s, 1P); and MS (ESI, EI$^+$) m/z=537 (MH$^+$). Example 56 is equivalent to (S) isomer of Compound IV-46.

Example 57

5-isobutyl-1-(3,3-dimethylbutyl)-5-methyl-3-(1-ethoxy-1-oxo-1,4-dihydro-7-methanesulfonamyl-1-benzo[1,2,4]phosphadiazin-3-yl)-4-hydroxy-1,5-dihydropyrrol-2-one (IV-47)

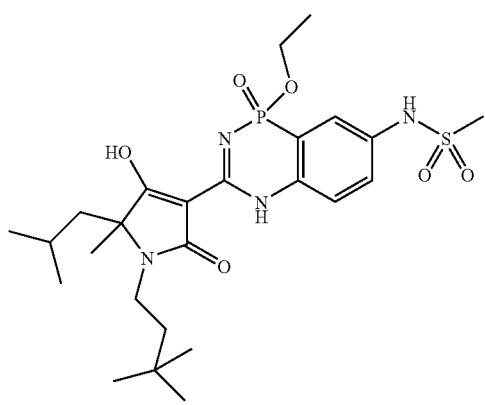

Example 57 was synthesized from intermediate 84 as described for example 44 and was a white solid. Example 57 was characterized by the following spectroscopic data: $^1$H NMR (CDCl$_3$, 400 MHz) δ (ppm) 0.78-0.81 (m, 3H), 0.84-0.88 (m, 3H), 0.99-1 (m, 9H), 1.29-1.32 (m, 3H), 1.33-1.37 (m, 3H), 1.40-1.50 (m, 2H), 1.54-1.62 (m, 1H), 1.71-1.82 (m, 2H), 2.94-3 (m, 1H), 3.04-3.05 (m, 3H), 3.46-3.57 (m, 1H), 4.11-4.24 (m, 2H), 7.14-7.19 (m, 1H), 7.64-7.69 (m, 2H), 11.46-11.48 (m, 0.55H), 11.59 (d, J=16.48 Hz, 0.5H); $^{31}$P NMR (CDCl$_3$, 162 MHz) δ (ppm) 0.49 (s, 1P), 0.53 (s, 1P), 0.89 (s, 1P), 0.95 (s, 1P); and MS (ESI, EI$^+$) m/z=554.89 (MH$^+$). Example 57 is equivalent to Compound IV-47.

Example 58

5-dimethyl-1-(3,3-dimethylbutyl)-3-(1-ethoxy-1-oxo-1,4-dihydro-7-methanesulfonamyl-1-benzo[1,2,4]phosphadiazin-3-yl)-4-hydroxy-1,5-dihydropyrrol-2-one (IV-48)

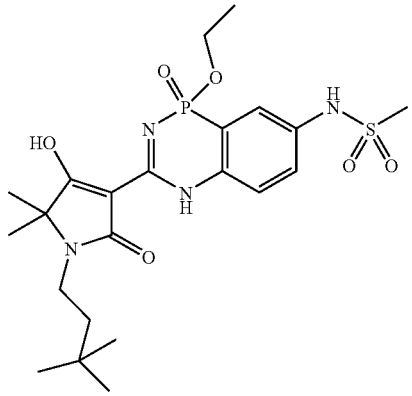

Example 58 was synthesized from intermediate 87 as described for example 44 and was a white solid. Example 58 was characterized by the following spectroscopic data: $^1$H NMR (CDCl$_3$, 400 MHz) δ (ppm) 0.99-1 (m, 9H), 1.32-1.35 (m, 9H), 1.56-1.61 (m, 2H), 3.04-3.05 (m, 3H), 3.29-3.34 (m, 2H), 4.11-4.22 (m, 2H), 7.13-7.19 (m, 1H), 7.65-7.70 (m, 2H), 8.07 (s, 0.5H), 8.13 (s, 0.5H), 11.42 (s, 0.5H), 11.63 (s, 0.5H); $^{31}$P NMR (CDCl$_3$, 162 MHz) δ (ppm) 0.50 (s, 1P), 0.91 (s, 1P); and MS (ESI, EI$^+$) m/z=512.88 (MH$^+$). Example 58 is equivalent to Compound IV-48.

Example 59

5-benzyl-1-(3,3-dimethylbutyl)-5-methyl-3-(1-ethoxy-1-oxo-1,4-dihydro-7-methanesulfonyl-1-benzo[1,2,4]phosphadiazin-3-yl)-4-hydroxy-1,5-dihydropyrrol-2-one (IV-49)

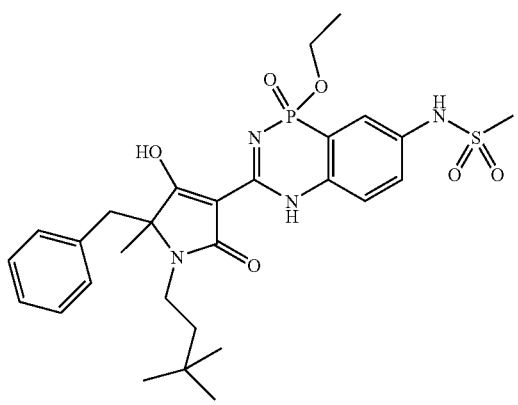

Example 59 was synthesized from intermediate 105 as described for example 44 and was a white solid. Example 59 was characterized by the following spectroscopic data: $^1$H NMR (CDCl$_3$, 400 MHz) δ (ppm) 0.99-1.02 (m, 9H), 1.30-1.35 (m, 3H), 1.33-1.43 (m, 1H), 1.47 (s, 3H), 1.78-1.85 (m, 1H), 2.91 (d, J=14.09 Hz, 1H), 3-3.02 (m, 3H), 3.08 (d, J=14.09 Hz, 1H), 3.62-3.76 (m, 2H), 3.88-4.17 (m, 2H), 7.02-7.08 (m, 2.5H), 7.11-7.20 (m, 3.5H), 7.59-7.72 (m, 2H), 8.09-8.26 (m, 1H), 11.25-11.34 (m, 1H); and MS (ESI, EI$^+$) m/z=588.85 (MH$^+$). Example 59 is equivalent to Compound IV-49.

Example 60

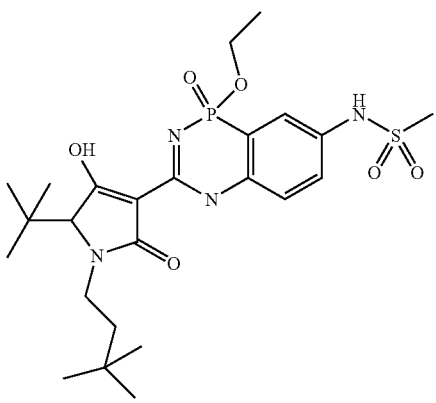

(Example 60A; IV-50)

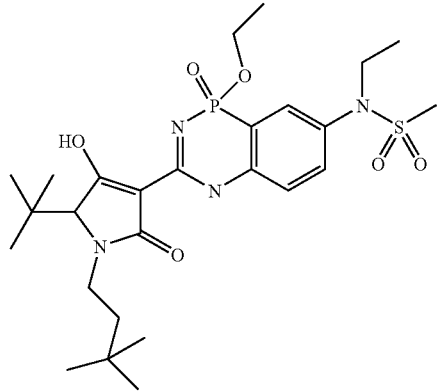

(Example 60B; IV-51)

Example 60 was synthesized from intermediate 77 as described for example 44. Two compounds were isolated (Examples 60A and 60B).

Example 60A: 5-tert-butyl-1-(3,3-dimethyl-butyl)-3-(1-ethoxy-1-oxo-1,4-dihydro-7-methanesulfonamyl-1-benzo[1,2,4]phosphadiazin-3-yl)-4-hydroxy-1,5-dihydropyrrol-2-one, which was a white solid. Example 60A was characterized by the following spectroscopic data: $^1$H NMR (CDCl$_3$, 400 MHz) δ (ppm) 0.96 (s, 9H), 1.1 (s, 9H), 1.34-1.37 (m, 3H), 1.36-1.43 (m, 1H), 1.55-1.63 (m, 1H), 3.05 (s, 3H), 3.16-3.23 (m, 1H), 3.5-3.52 (m, 1H), 3.93-4.01 (m, 1H), 4.12-4.24 (m, 2H), 7.16-7.21 (m, 1H), 7.64-7.68 (m, 2H), 7.82-7.89 (m, 1H), 11.55 (s, 0.5H), 11.7-11.73 (m, 0.5H); $^{31}$P NMR (CDCl$_3$, 400 MHz) δ (ppm) 0.52 (s, 1P), 0.55 (s, 1P), 0.83 (s, 1P), 0.86 (s, 1P); and MS (ESI, EI$^+$) m/z=541 (MH$^+$). Example 60A is equivalent to Compound IV-50.

Example 60B: 5-tert-butyl-1-(3,3-dimethyl-butyl)-3-(1-ethoxy-1-oxo-1,4-dihydro-7-(N-ethyl)methanesulfonamyl)-1-benzo[1,2,4]phosphadiazin-3-yl)-4-hydroxy-1,5-dihydropyrrol-2-one, which was a white solid. Example 60B was characterized by the following spectroscopic data: $^1$H NMR (DMSO-d$_6$, 400 MHz) δ (ppm) 0.89 (s, 9H), 0.97-1 (m, 3H), 1.02 (s, 9H), 1.18-1.21 (m, 3H), 1.24-1.31 (m, 1H), 1.59-1.71 (m, 1H), 2.99 (s, 3H), 3.09-3.16 (m, 1H), 3.56-3.62 (m, 1H), 3.68-3.74 (m, 2H), 3.77-3.82 (m, 1H), 4.01-4.13 (m, 2H), 7.63-7.79 (m, 3H), 11.48 (brs, 1H); $^{31}$P NMR (DMSO-d$_6$, 400 MHz) δ (ppm) −0.57 (s, 1P), −0.46 (s, 1P); and MS (ESI, EI$^+$) m/z=568.96 (MH$^+$). Example 60B is equivalent to Compound IV-51.

Example 61

(S)-5-tert-butyl-1-(3,3-dimethyl-butyl)-3-(1-hydroxy-1-oxo-1,4-dihydro-7-methanesulfonamyl-1-benzo[1,2,4]phosphadiazin-3-yl)-4-hydroxy-1,5-dihydropyrrol-2-one

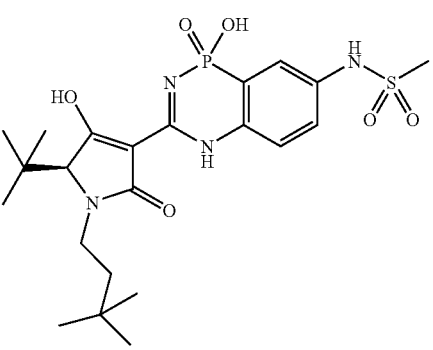

(S)-isomer of (IV-1)

Example 61 was synthesized from example 60A. Example 60A and tetramethylsilylbromide (10 eq) dissolved in 1,2-dichloroethane (10 ml), were stirred in sealed tube, at 60° C., for 2 hours. The reaction mixture was then evaporated, diluted in methanol (1 ml) and added to HCl 1N. (15 ml). The precipitate was filtered, washed with water and dried over P$_2$O$_5$ to give example 61, which was a white solid. Example 61 was characterized by the following spectroscopic data: $^1$H NMR (DMSO-d$_6$, 400 MHz) δ (ppm) 0.89 (s, 9H), 1.01 (s, 9H), 1.25 (td, J=5 Hz and J=12.09 Hz, 1H), 1.60-1.66 (m, 1H), 3 (s, 3H), 3.05-3.12 (m, 1H), 3.5 (s, 1H), 3.76-3.83 (m, 1H), 7.42-7.51 (m, 3H), 10 (s, 1H), 10.6 (brs, 1H), 11.29 (brs, 1H); $^{31}$P NMR (DMSO-d$_6$, 400 MHz) δ (ppm) −5.73 (s, 1P); and MS (ESI, EI$^+$) m/z=512.88 (MH$^+$). Example 61 is equivalent to (S)-isomer of Compound IV-1.

Example 62

(S)-5-tert-butyl-1-(3,3-dimethyl-butyl)-3-(1-cyclopropylmethoxy-1-oxo-1,4-dihydro-7-methanesulfonamyl-1-benzo[1,2,4]phosphadiazin-3-yl)-4-hydroxy-1,5-dihydropyrrol-2-one

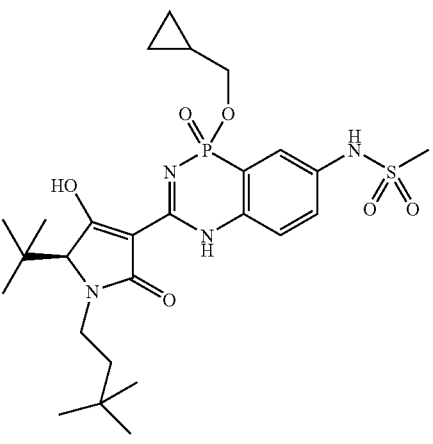

(S)-isomer of (IV-52)

To a stirred solution of example 61 (0.814 mmol) in dichloromethane (30 ml) and a few drops of dimethylformamide, oxalyl chloride (2.44 mmol) was added dropwise under nitrogen. The reaction mixture was stirred under nitrogen at room temperature for 2 hours and then, concentrated and diluted with dichloromethane to obtain a solution at 0.215M. This solution (1 ml) was added dropwise to a solution of cyclopropanemethanol (0.645 mmol) with triethylamine (0.645 mmol) in dichloromethane (1 ml) under nitrogen. This mixture was stirred at room temperature for 3 hours and concentrated. The residue was purified by chromatography in a first time and by preparative HPLC in a second time to give Example 62, which was a white solid. Example 62 was characterized by the following spectroscopic data: $^1$H NMR (CDCl$_3$, 400 MHz) δ (ppm) 0.34-0.38 (m, 2H), 0.65-0.69 (m, 2H), 0.95 (s, 9H), 1.1 (s, 9H), 1.17-1.25 (m, 1H), 1.36-1.43 (m, 1H), 1.55-1.62 (m, 1H), 3.04 (s, 3H), 3.14-3.23 (m, 1H), 3.49-3.51 (m, 1H), 3.93-4.03 (m, 3H), 7.15-7.20 (m, 1H), 7.64-7.68 (m, 2H), 7.80-7.82 (m, 1H), 11.55 (s, 0.5H), 11.74 (s, 0.5H); $^{31}$P NMR (CDCl$_3$, 400 MHz) δ (ppm) 0.68 (s, 1P), 0.73 (s, 1P), 1.01 (s, 1P), 1.03 (s, 1P); and MS (ESI, EI$^+$) m/z=566.94 (MH$^+$). Example 62 is equivalent to (S)-isomer of Compound IV-52.

Example 63

(S)-5-tert-butyl-1-(3,3-dimethyl-butyl-3-(1-propoxy-1-oxo-1,4-dihydro-7-methanesulfonamyl-1-benzo[1,2,4]phosphadiazin-3-yl)-4-hydroxy-1,5-dihydropyrrol-2-one

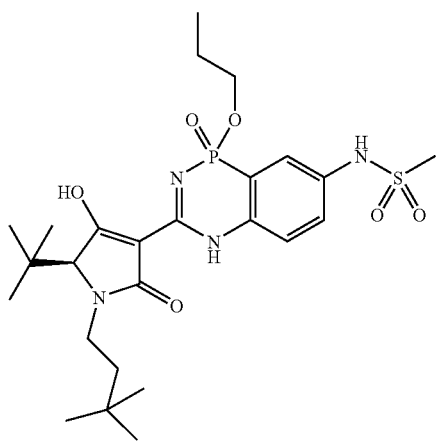

(S)-isomer of (IV-53)

Example 63 was synthesized from example 61 and n-propanol as described for example 62 and was a yellow solid. Example 63 was characterized by the following spectroscopic data: $^1$H NMR (CDCl$_3$, 400 MHz) δ (ppm) 0.89-0.94 (m, 3H), 0.95 (s, 9H), 1.1 (s, 9H), 1.36-1.43 (m, 1H), 1.54-1.63 (m, 1H), 1.67-1.74 (m, 2H), 3.04 (s, 3H), 3.16-3.24 (m, 1H), 3.50-3.53 (m, 1H), 3.93-4.01 (m, 1H), 4.04-4.12 (m, 2H), 7.15-7.21 (m, 1H), 7.65-7.76 (m, 3H), 11.55 (s, 0.5H), 11.70-11.74 (m, 0.511); $^{31}$P NMR (CDCl$_3$, 400 MHz) δ (ppm) 0.56 (s, 1H), 0.61 (s, 1H), 0.89 (s, 1H); and MS (ESI, EI$^+$) m/z=554.94 (MH$^+$). Example 63 is equivalent to (S)-isomer of Compound IV-53.

Example 64

(S)-5-tert-butyl-1-(3,3-dimethyl-butyl)-3-(1-isopropoxy-1-oxo-1,4-dihydro-7-methanesulfonamyl-1-benzo[1,2,4]phosphadiazin-3-yl)-4-hydroxy-1,5-dihydropyrrol-2-one

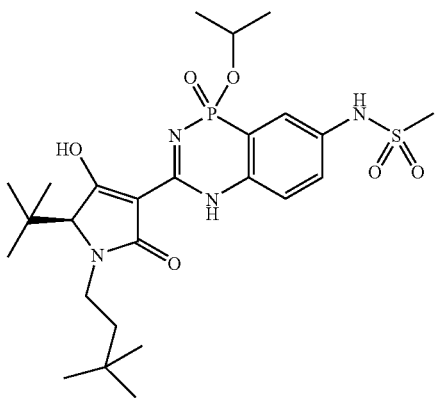

(S)-isomer of (IV-54)

Example 64 was synthesized from example 61 and 2-propanol as described for example 62 and was a yellow solid. Example 64 was characterized by the following spectroscopic data: $^1$H NMR (CDCl$_3$, 400 MHz) δ (ppm) 0.95 (s, 9H), 1.05 (s, 9H), 1.31-1.37 (m, 6H), 1.35-1.43 (m, 1H), 1.55-1.62 (m, 1H), 3.03 (s, 3H), 3.16-3.19 (m, 1H), 3.48-3.52 (m, 1H), 3.93-4 (m, 1H), 4.74-4.85 (m, 1H), 7.16-7.20 (m, 1H), 7.66-7.70 (m, 2H), 8.07-8.15 (m, 1H), 11.50 (s, 0.5H), 11.71 (s, 0.5H); $^{31}$P NMR (CDCl$_3$, 400 MHz) δ (ppm) −0.7 (s, 1P), −0.65 (s, 1P), −0.48 (s, 1P), −0.43 (s, 1P); and MS (ESI, EI$^+$) m/z=554.93 (MH$^+$). Example 64 is equivalent to (S)-isomer of Compound IV-54.

Example 65

(S)-5-tert-butyl-1-(3,3-dimethyl-butyl)-3-(1-N-methylbutyramidoxy-1-oxo-1,4-dihydro-7-methanesulfonamyl-1-benzo[1,2,4]phosphadiazin-3-yl)-4-hydroxy-1,5-dihydropyrrol-2-one

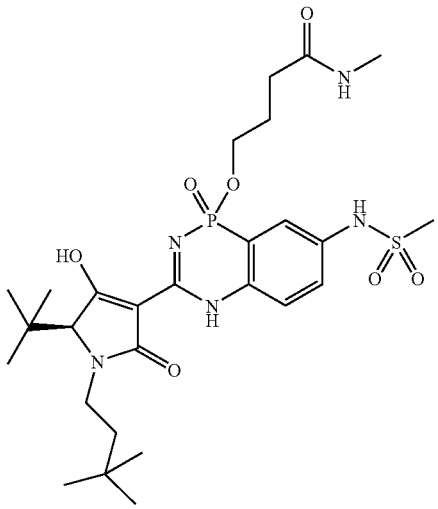

(S)-isomer of (IV-55)

Example 65 was synthesized from example 61 and intermediate 106 as described for example 62 and was a white solid. Example 65 was characterized by the following spectroscopic data: $^1$H NMR (CDCl$_3$, 400 MHz) δ (ppm) 0.96 (s, 9H), 1.10 (s, 9H), 1.36-1.44 (m, 1H), 1.55-1.63 (m, 1H), 2-2.07 (m, 2H), 2.26-2.31 (m, 2H), 2.76-2.79 (brs, 3H), 3.05 (s, 3H), 3.16-3.23 (m, 1H), 3.5-3.53 (m, 1H), 3.93-4 (m, 1H), 4.04-4.12 (m, 1H), 4.18-4.27 (m, 1H), 6.21-6.33 (m, 1H), 7.15-7.19 (m, 1H), 7.67-7.73 (m, 2H), 11.56-11.59 (m, 0.5H), 11.69-11.74 (m, 0.5H); $^{31}$P NMR (CDCl$_3$, 400 MHz) δ (ppm) 1.12 (s, 1P), 1.15 (s, 1P), 1.42 (s, 1P), 1.46 (s, 1P); and MS (ESI, EI$^+$) m/z=611.95 (MH$^+$). Example 65 is equivalent to (S)-isomer of Compound IV-55.

Example 66

(S)-5-tert-butyl-1-(3,3-dimethyl-butyl)-3-(1-butyramidoxy-1-oxo-1,4-dihydro-7-methanesulfonamyl-1-benzo[1,2,4]phosphadiazin-3-yl-4-hydroxy-1,5-dihydropyrrol-2-one

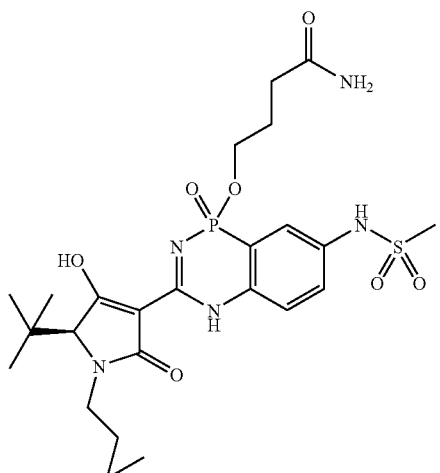

(S)-isomer of (IV-56)

Example 66 was synthesized from example 61 and intermediate 107 as described for example 62 and was a white solid. Example 66 was characterized by the following spectroscopic data: $^1$H NMR (CDCl$_3$, 400 MHz) δ (ppm) 0.95 (s, 9H), 1.10 (s, 9H), 1.35-1.43 (m, 1H), 1.54-1.62 (m, 1H), 2-2.08 (m, 2H), 2.33-2.38 (m, 2H), 3.05 (s, 3H), 3.15-3.22 (m, 1H), 3.49-3.52 (m, 1H), 3.91-4 (m, 1H), 4.07-4.17 (m, 1H), 4.19-4.29 (m, 1H), 5.79-5.88 (m, 1H), 6.13-6.31 (m, 1H), 7.13-7.20 (m, 1H), 7.65-7.69 (m, 2H), 11.58 (brs, 0.5H), 11.73 (brs, 0.5H); $^{31}$P NMR (CDCl$_3$, 400 MHz) δ (ppm) 1.2 (s, 1P), 1.52 (s, 1P); and MS (ESI, EI$^+$) m/z=597.93 (MH$^+$). Example 66 is equivalent to (S)-isomer of Compound IV-56.

Example 67

(S)-5-tert-butyl-1-(3,3-dimethyl-butyl)-3-(1-(2-methoxyethoxy)-1-oxo-1,4-dihydro-7-methanesulfonamyl-1-benzo[1,2,4]phosphadiazin-3-yl)-4-hydroxy-1,5-dihydropyrrol-2-one

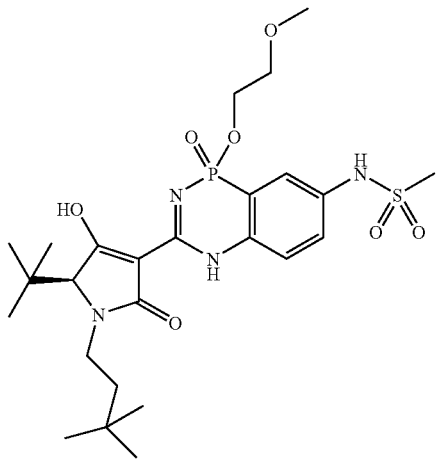

(S)-isomer of (IV-57)

Example 67 was synthesized from example 61 and 2-methoxyethanol as described for example 62 and was a beige solid. Example 67 was characterized by the following spectroscopic data: $^1$H NMR (CDCl$_3$, 400 MHz) δ (ppm) 0.96 (s, 9H), 1.10 (s, 9H), 1.36-1.44 (m, 1H), 1.54-1.62 (m, 1H), 3.04 (s, 3H), 3.14-3.23 (m, 1H), 3.42-3.49 (m, 4H), 3.55-3.70 (m, 2H), 3.92-4.02 (m, 1H), 4.20-4.33 (m, 1H), 4.42-4.54 (m, 1H), 7.14-7.20 (m, 2H), 7.59-7.68 (m, 2H), 11.63-11.66 (m, 0.5H), 11.80-11.83 (m, 0.5H); $^{31}$P NMR (CDCl$_3$, 400 MHz) δ (ppm) 1.11 (s, 1P), 1.27 (s, 1P), 1.49 (s, 1P); and MS (ESI, EI$^+$) m/z=570.91 (MH$^+$). Example 67 is equivalent to (S)-isomer of Compound IV-57.

Example 68

(S)-5-tert-butyl-1-(3,3-dimethyl-butyl)-3-(1-ethoxy-1-oxo-1,4-dihydro-7-fluoro-1-benzo[1,2,4]phosphadiazin-3-yl)-4-hydroxy-1,5-dihydropyrrol-2-one

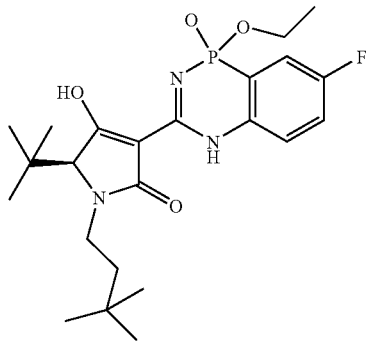

(S)-isomer of (IV-85)

Example 68 was synthesized from intermediate 77 and intermediate 108 following the procedure as described for example 44. The crude material was purified by preparative HPLC to yield example 68, which was a white lyophilised solid. Example 68 was characterized by the following spectroscopic data: $^1$H NMR (DMSO-d$_6$, 400 MHz) δ (ppm) 0.88 (s, 9H), 1.01 (s, 9H), 1.21-1.28 (m, 4H), 1.65 (brs, 1H), 3.11

(m, 1H), 3.55-3.56 (m, 2H), 3.78 (m, 1H), 4.07 (m, 1H), 7.67 (m, 3H), 11.44 (brs, 1H). $^{31}$P NMR (DMSO-d$_6$, 162 MHz) δ (ppm) –0.81 (s, 1P). $^{19}$F NMR (DMSO-d$_6$, 376 MHz) δ (ppm) –115.57 (d, J=36.46 Hz, 1F). MS (ESI, EI$^+$) m/z=466 (MH$^+$). Example 68 is equivalent to (S)-isomer of Compound IV-85.

Example 69

(S)-5-tert butyl-1-(3,3-dimethyl-butyl)-3-(1-ethoxy-1-oxo-1,4-dihydro-1-benzo[1,2,4]phosphadiazin-3-yl)-4-hydroxy-1,5-dihydropyrrol-2-one

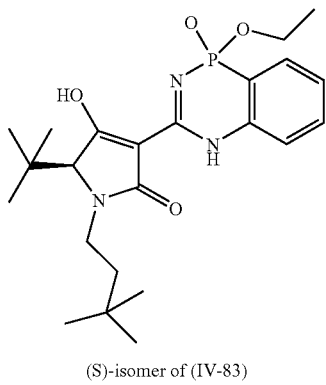

(S)-isomer of (IV-83)

Example 69 was synthesized from intermediate 77 and intermediate 109 following the procedure as described for example 44. The crude material was purified by preparative HPLC to yield example 69, which was a white lyophilised solid. Example 69 was characterized by the following spectroscopic data: $^1$H NMR (DMSO-d$_6$, 400 MHz) δ (ppm) 0.88 (s, 9H), 1.01 (s, 9H), 1.17-1.22 (t, J=7.07 Hz, 3H), 1.22-1.29 (td, J=12.31 Hz and J=5.03 Hz, 1H), 1.61-1.66 (m, 1H), 3.06-3.12 (m, 2H), 3.74-3.82 (td, J=12.87 Hz and J=4.48 Hz, 1H), 4.00 (brs, 2H), 7.36-7.75 (m, 4H), 11.52 (brs, 1H). $^{31}$P NMR (DMSO-d$_6$, 162 MHz) δ (ppm) 0.59 (s, 1P). MS (ESI, EI$^+$) m/z=448 (MH$^+$). Example 69 is equivalent to (S)-isomer of Compound IV-83.

Example 70

(S)-5-tert-butyl-1-(3,3-dimethyl-butyl)-3-(1-ethoxy-1-oxo-1,4-dihydro-8-fluoro-1-benzo[1,2,4]phosphadiazin-3-yl)-4-hydroxy-1,5-dihydropyrrol-2-one

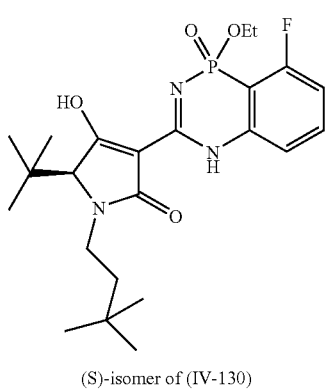

(S)-isomer of (IV-130)

Example 70 was synthesized from intermediate 77 and intermediate 110 following the procedure as described for example 44. The crude material was purified by preparative HPLC to yield example 70, which was a white lyophilised solid. Example 70 was characterized by the following spectroscopic data: $^1$H NMR (DMSO-d$_6$, 400 MHz) δ (ppm) 0.88 (s, 9H), 1.02 (s, 9H), 1.22-1.25 (m, 4H), 1.65 (m, 1H), 3.11-3.14 (m, 1H), 3.56 (s, 1H), 3.76-3.81 (m, 1H), 4.12 (brs, 2H), 7.19-7.38 (m, 2H), 7.73-7.75 (m, 1H), 11.54 (brs, 1H). $^{31}$P NMR (DMSO-d$_6$, 162 MHz) δ (ppm) 0.59 (s, 1P). $^{19}$F NMR (DMSO-d$_6$, 376 MHz) δ (ppm) –102.06 (s, 1F). MS (ESI, EI$^+$) m/z=466 (MH$^+$). Example 70 is equivalent to (S)-isomer of Compound IV-130.

Example 71

(S)-5-tert-butyl-1-(3,3-dimethyl-butyl)-3-(1-ethoxy-1-oxo-1,4-dihydro-6-fluoro-1-benzo[1,2,4]phosphadiazin-3-yl)-4-hydroxy-1,5-dihydropyrrol-2-one

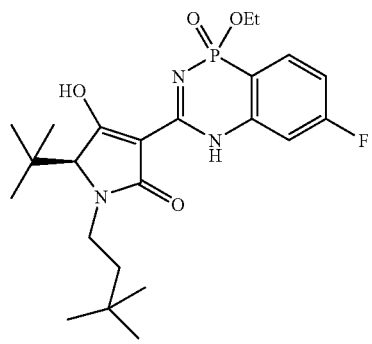

(S)-isomer of (IV-87)

Example 71 was synthesized from intermediate 77 and intermediate 111 following the procedure as described for example 44. The crude material was purified by preparative HPLC to yield example 71, which was a white lyophilised solid. Example 71 was characterized by the following spectroscopic data: $^1$H NMR (DMSO-d$_6$, 400 MHz) δ (ppm) 0.89 (s, 9H), 1.02 (s, 9H), 1.21-1.28 (m, 4H), 1.65 (m, 1H), 3.11-3.14 (m, 1H), 3.56 (s, 1H), 3.76-3.81 (m, 1H), 4.12 (brs, 2H), 7.19-7.38 (m, 2H), 7.73-7.75 (m, 1H), 11.42 (brs, 1H). $^{31}$P NMR (DMSO-d$_6$, 162 MHz) δ (ppm) 0.14 (s, 1P). $^{19}$F NMR (DMSO-d$_6$, 376 MHz) δ (ppm)-102.71 (s, 1F). MS (ESI, EI$^+$) m/z=466 (MH$^+$). Example 71 is equivalent to (S)-isomer of Compound IV-87.

Example 72

(S)-5-tert-butyl-1-(3,3-dimethyl-butyl)-3-(1-ethoxy-1-oxo-1,4-dihydro-5-fluoro-1-benzo[1,2,4]phosphadiazin-3-yl)-4-hydroxy-1,5-dihydropyrrol-2-one

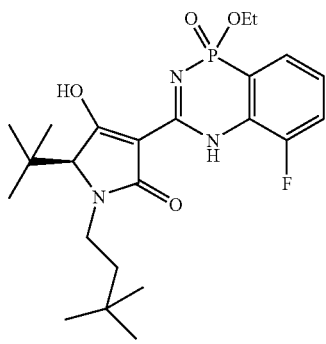

(S)-isomer of (IV-86)

Example 72 was synthesized from intermediate 77 and intermediate 112 following the procedure as described for example 44. The crude material was purified by preparative HPLC to yield example 72, which was a white lyophilised solid. Example 72 was characterized by the following spectroscopic data: $^{31}$P NMR (DMSO-d$_6$, 162 MHz) δ (ppm) −1.84 (s, 1P). $^{19}$F NMR (DMSO-d$_6$, 376 MHz) δ (ppm) −130.67 (s, 1F). MS (ESI, EI$^+$) m/z=466 (MH$^+$). Example 72 is equivalent to (S)-isomer of Compound IV-86.

Example 73

(S)-5-tert-butyl-1-(3,3-dimethyl-butyl)-3-(1-[(3-(tert-butyl-dimethyl-silanoxy)-propoxy]-7-methane-sulfonamyl-1-oxo-1,4-dihydro-1-benzo[1,2,4]phosphadiazin-3-yl)-4-hydroxy-1,5-dihydropyrrol-2-one

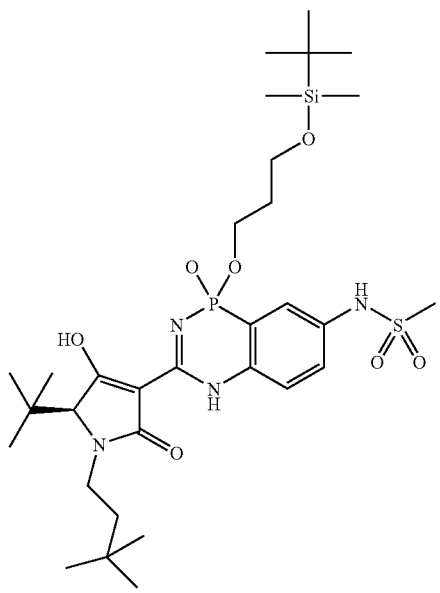

(S)-isomer of (IV-77)

Example 73 was synthesized from example 61 and intermediate 113 following the procedure as described for example 62. Example 73 was a yellow resin. Example 73 was characterized by the following spectroscopic data: $^1$H NMR (CDCl$_3$, 400 MHz) δ (ppm) 0 (s, 6H), 0.83 (s, 9H), 0.96 (m, 9H), 1.10-1.11 (m, 9H), 1.40 (td, J=4.86 Hz and J=12.38 Hz, 1H), 1.58 (td, J=4.86 Hz and J=12.38 Hz, 1H), 1.85-1.89 (m, 2H), 3.04 (s, 3H), 3.16-3.22 (m, 1H), 3.49-3.52 (m, 1H), 3.65 (t, J=5.78 Hz, 2H), 3.97 (td, J=5.41 Hz and J=12.87 Hz, 1H), 4.16-4.25 (m, 2H), 7.15-7.21 (m, 1H), 7.40 (d, J=6.68 Hz, 0.5H), 7.46 (d, J=3.62 Hz, 0.5H), 7.61-7.68 (m, 2H), 11.55 (d, J=5.88 Hz, 0.5H), 11.72 (d, J=10.81 Hz, 0.5H). $^{31}$P NMR (CDCl$_3$, 162 MHz) δ (ppm) 0.50 (d, J=13.01 Hz, 1P), 0.83 (d, J=9.84 Hz, 1P). MS (ESI, EI$^+$) m/z=685 (MH$^+$). Example 73 is equivalent to (S)-isomer of Compound IV-77.

Example 74

(S)-5-tert-butyl-1-(3,3-dimethyl-butyl)-3-(1-(3-hydroxy-propoxy)-7-methanesulfonamyl-1-oxo-1,4-dihydro-1-benzo[1,2,4]phosphadiazin-3-yl)-4-hydroxy-1,5-dihydropyrrol-2-one

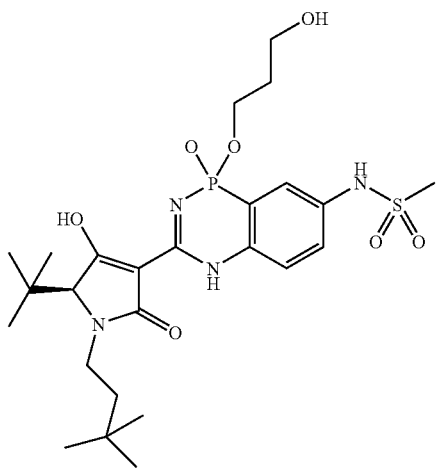

(S)-isomer of (IV-75)

Example 73 (0.0073 mmol) was stirred in anh THF (1 ml) with tetra-butylammonium fluoride (0.015 mol) at room temperature for 6 hours. Then, the mixture was purified by HPLC semi-preparative to give example 74, which was a white lyophilized solid. Example 74 was characterized by the following spectroscopic data: $^1$H NMR (CDCl$_3$, 400 MHz) δ (ppm) 0.95-0.96 (m, 9H), 1.09-1.11 (m, 9H), 1.35-1.44 (m, 1H), 1.55-1.63 (m, 1H), 1.88-1.93 (m, 2H), 3.05 (s, 3H), 3.15-3.24 (m, 1H), 3.50-3.52 (m, 1H), 3.70-3.75 (m, 2H), 3.93-4.01 (m, 1H), 4.27-4.36 (m, 2H), 7.16-7.21 (m, 1H), 7.66-7.70 (m, 2H), 8.1 (brs, 1H), 11.62 (brs, 0.5H), 11.77 (brs, 0.5H). $^{31}$P NMR (CDCl$_3$, 162 MHz) δ (ppm) 1.63 (s, 1P), 2.02 (s, 1P). MS (ESI, EI$^+$) m/z=571 (MH$^+$). Example 74 is equivalent to (S)-isomer of Compound IV-75.

Example 75

(S)-5-tert-butyl-1-(3,3-dimethyl-butyl)-3-(1-[(3-(tert-butyl-dimethyl-silanoxy)-ethoxy]-7-methane-sulfonamyl-1-oxo-1,4-dihydro-1-benzo[1,2,4]phosphadiazin-3-yl)-4-hydroxy-1,5-dihydropyrrol-2-one

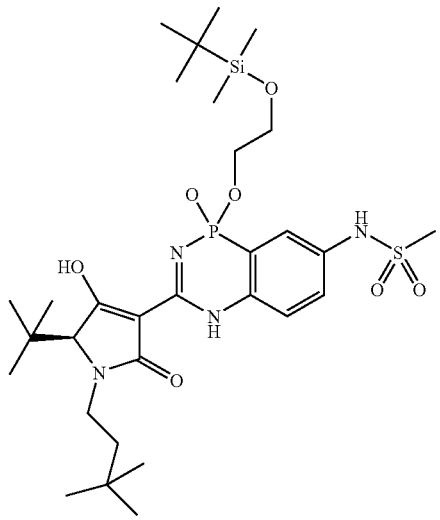

(S)-isomer of (IV-76)

Example 75 was synthesized from example 61 and intermediate 114 following the procedure as described for example 62. Example 75 was a white solid. Example 75 was characterized by the following spectroscopic data: $^1$H NMR (CDCl$_3$, 400 MHz) δ (ppm) 0-0.015 (m, 6H), 0.82-0.84 (m, 9H), 0.95-0.96 (m, 9H), 1.09-1.11 (m, 9H), 1.39 (td, J=4.83 Hz and J=12.38 Hz, 1H), 3.03 (s, 3H), 3.15-3.23 (m, 1H), 3.49-3.51 (m, 1H), 3.80-3.83 (m, 2H), 3.97 (td, J=4.83 Hz and J=12.38 Hz, 1H), 4.10-4.19 (m, 2H), 7.15-7.20 (m, 1H), 7.62-7.71 (m, 3H), 11.57 (d, J=6.23 Hz, 0.5H), 11.72 (d, J=8.34 Hz, 0.5H). $^{31}$P NMR (CDCl$_3$, 162 MHz) δ (ppm) 1.02 (d, J=11.71 Hz, 1P), 1.33 (d, J=11.71 Hz, 1P). MS (ESI, EI$^+$) m/z=671 (MH$^+$). Example 75 is equivalent to (S)-isomer of Compound IV-76.

Example 76

5-methylene-1-(3,3-dimethyl-butyl)-3-(1-ethoxy-7-methanesulfonamyl-1-oxo-1,4-dihydro-1-benzo[1,2,4]phosphadiazin-3-yl)-4-hydroxy-1,5-dihydropyrrol-2-one

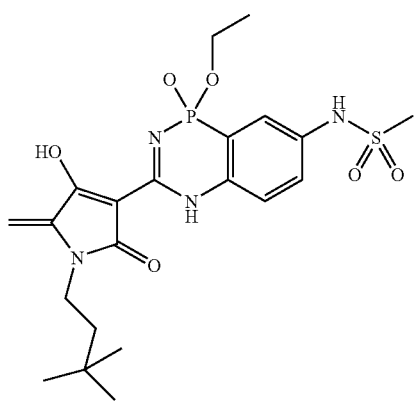

(IV-60)

Example 76 was synthesized from intermediate 117 following the procedure as described for example 44. Example 76 was a white solid. Example 76 was characterized by the following spectroscopic data: $^1$H NMR (DMSO-d$_6$+CDCl$_3$, 400 MHz) δ (ppm) 0.85-0.96 (m, 3H), 1 (s, 9H), 1.31-1.37 (m, 1H), 1.48-1.52 (m, 1H), 3.05 (s, 3H), 3.60-3.64 (m, 2H), 4.16-4.22 (m, 2H), 4.60 (brs, 1H), 5.28-5.31 (m, 1H), 7.15-7.23 (m, 1H), 7.68-7.72 (m, 2H), 8.15 (brs, 1H), 11.06 (s, 0.4H), 11.52 (brs, 0.4H). $^{31}$P NMR ((DMSO-d$_6$÷CDCl$_3$, 162 MHz) δ (ppm) 0.56 (s, 1P), 0.69 (s, 1P). MS (ESI, EI$^+$) m/z=497 (MH$^+$). Example 76 is equivalent to Compound IV-60.

Example 77

5-benzyl-1-(3,3-dimethyl-butyl)-3-(1-ethoxy-7-methanesulfonamyl-1-oxo-1,4-dihydro-1-benzo[1,2,4]phosphadiazin-3-yl)-4-hydroxy-1,5-dihydropyrrol-2-one

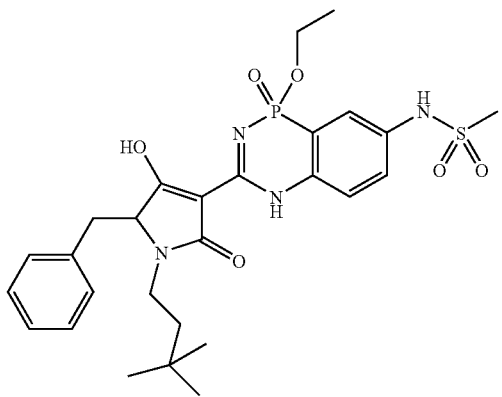

(IV-121)

Example 77 was synthesized from intermediate 120 following the procedure as described for example 44. Example 77 was a white solid. Example 77 was characterized by the following spectroscopic data: $^1$H NMR (CDCl$_3$, 400 MHz) δ (ppm) 0.85-0.87 (m, 9H), 1.29-1.37 (m, 5H), 2.82-2.91 (r, 1H), 2.99-3.09 (m, 1H), 3.04 (s, 3H), 3.19-3.27 (m, 1H), 3.82-3.91 (m, 1H), 4.09-4.20 (m, 3H), 7.10-7.37 (m, 8H), 7.60 (s, 1H), 7.64 (s, 1H), 11.39-11.44 (m, 1H). MS (ESI, EI⁺) m/z=575 (MH⁺). Example 77 is equivalent to Compound IV-121.

Example 78

5-(1H-indol-3-yl-methyl)-1-(3,3-dimethyl-butyl)-3-(1-ethoxy-7-methanesulfonamyl-1-oxo-1,4-dihydro-1-benzo[1,2,4]phosphadiazin-3-yl)-4-hydroxy-1,5-dihydropyrrol-2-one

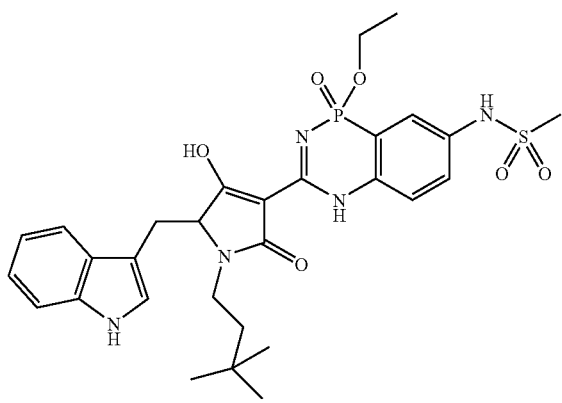

(IV-131)

Example 78 was synthesized from intermediate 123 following the procedure as described for example 44. Example 78 was a green solid. Example 78 was characterized by the following spectroscopic data: ¹H NMR (CDCl₃, 400 MHz) δ (ppm) 0.81-0.85 (m, 9H), 1.24-1.38 (m, 5H), 2.90-2.97 (m, 1H), 3.03 (s, 3H), 3.32-3.34 (m, 2H), 6.99-7.17 (m, 5H), 7.30-7.34 (m, 1H), 7.56-7.69 (m, 3H), 8.02 (brs, 1H), 8.11 (brs, 1H), 11.40 (s, 0.5H), 11.44 (s, 0.5H). MS ESI, EI⁺) m/z=614 (MH⁺). Example 78 is equivalent to Compound IV-131.

Example 79

5-(tiophen-2-yl-methyl)-1-(3,3-dimethyl-butyl)-3-(1-ethoxy-7-methanesulfonamyl-1-oxo-1,4-dihydro-1-benzo[1,2,4]phosphadiazin-3-yl)-4-hydroxy-1,5-dihydropyrrol-2-one

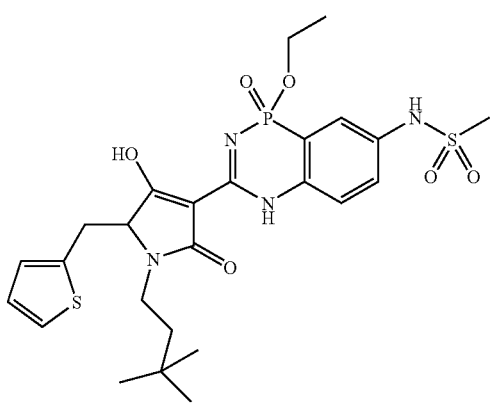

(IV-132)

Example 79 was synthesized from intermediate 127 following the procedure as described for example 44. Example 79 was a yellow solid. Example 79 was characterized by the following spectroscopic data: ¹H NMR (CDCl₃, 400 MHz) δ (ppm) 0.95 (s, 9H), 1.29-1.37 (m, 3H), 1.41-1.48 (m, 2H), 2.93-3.03 (m, 1H), 3.04 (s, 3H), 3.32-3.46 (m, 2H), 3.91-3.99 (m, 1H), 4.08-4.15 (m, 2H), 4.14-4.20 (m, 1H), 6.81-6.85 (m, 1H), 6.86-6.90 (m, 1H), 7.11-7.21 (m, 2H), 7.42 (brs, 0.3H), 7.51 (brs, 0.7H), 7.61-7.66 (m, 2H), 11.34-11.43 (m, 1H). MS (ESI, EI⁺) m/z=581 (MH⁺). Example 79 is equivalent to Compound IV-132.

Example 80

(S)-5-tert-butyl-1-(1-methyl-pyrazol-4-ylmethyl)-3-(1-ethoxy-7-methanesulfonamyl-1-oxo-1,4-dihydro-1-benzo[1,2,4]phosphadiazin-3-yl)-4-hydroxy-1,5-dihydropyrrol-2-one

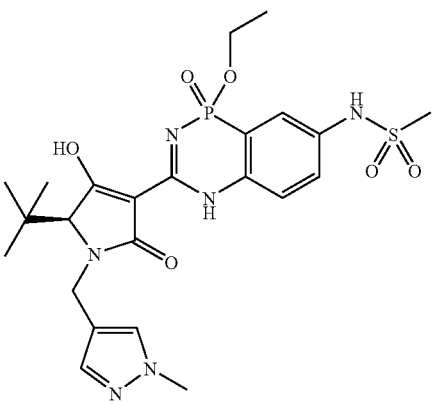

(S)-isomer of (IV-67)

Example 80 was synthesized from intermediate 130 following the procedure as described for example 44. Example 80 was a white solid. Example 80 was characterized by the following spectroscopic data: ¹H NMR (CDCl₃, 400 MHz) δ (ppm) 1.09-1.11 (m, 9H), 1.34-1.38 (m, 3H), 3.05 (s, 3H), 3.39-3.42 (m, 1H), 3.87 (d, J=3.23 Hz, 3H), 4.09-4.23 (m, 3H), 5.07-5.15 (m, 1H), 7.14-7.23 (m, 1H), 7.31 (d, J=3.81 Hz, 1H), 7.38 (d, J=5.88 Hz, 1H), 7.64-7.67 (m, 2H), 11.54 (d, J=8.32 Hz, 0.5H), 11.75 (brs, 0.5H). MS (ESI, EI⁻) m/z=549 (MH⁺). Example 80 is equivalent to (S)-isomer of Compound IV-67.

Example 81

(S)-5-cyclohexyl-1-(3,3-dimethyl-butyl)-3-(1-ethoxy-7-methanesulfonamyl-1-oxo-1,4-dihydro-1-benzo[1,2,4]phosphadiazin-3-yl)-4-hydroxy-1,5-dihydropyrrol-2-one

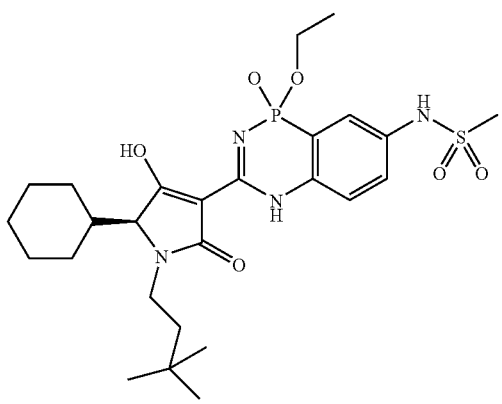

(S)-isomer of (IV-119)

Example 81 was synthesized from intermediate 133 following the procedure as described for example 44. Example 81 was a white solid. Example 81 was characterized by the following spectroscopic data: ¹H NMR (CDCl₃, 400 MHz) δ (ppm) 0.98-0.99 (m, 9H), 1.15-1.90 (m, 1H), 2.98-3.08 (m, 1H), 3.05 (s, 3H), 3.68-3.71 (m, 1H), 3.83-3.92 (m, 1H), 4.14-4.24 (m, 2H), 7.14-7.20 (m, 1H), 7.44-7.51 (m, 1H), 7.61-7.67 (m, 2H), 11.52-11.60 (m, 1H). MS (ESI, EI⁺) m/z=567 (MH⁺). Example 81 is equivalent to (S) isomer of Compound IV-119.

Example 82

5-ethylidene-1-(3,3-dimethyl-butyl)-3-(1-ethoxy-7-methanesulfonamyl-1-oxo-1,4-dihydro-1-benzo[1,2,4]phosphadiazin-3-yl)-4-hydroxy-1,5-dihydropyrrol-2-one (IV-65)

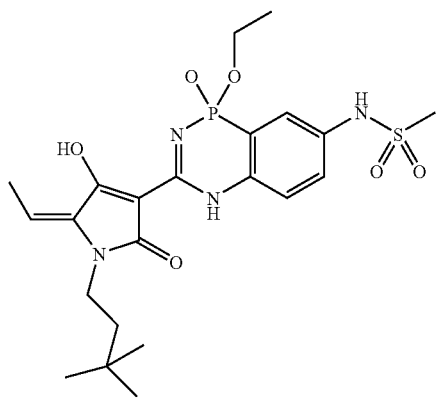

Example 82 was synthesized from intermediate 136 following the procedure as described for example 44. Example 82 was a white solid. Example 82 was characterized by the following spectroscopic data: ¹H NMR (CDCl₃, 400 MHz) δ (ppm) 1-1.01 (m, 9H), 1.36 (t, J=7.13 Hz, 3H), 1.44-1.48 (m, 2H), 2.29 (d, J=7.60 Hz, 3H), 3.06-3.07 (m, 3H), 3.57-3.61 (m, 2H), 4.15-4.24 (m, 2H), 5.37-5.44 (m, 1H), 7.14-7.22 (m, 2H), 7.63-7.66 (m, 2H), 11.18 (brs, 0.51H), 11.80 (brs, 1H). MS (ESI, EI⁺) m/z=511 (MH⁺). Example 82 is equivalent to Compound IV-65.

Example 83

5-isopropyl-5-methyl-1-(3,3-dimethyl-butyl)-3-(1-ethoxy-7-methanesulfonamyl-1-oxo-1,4-dihydro-1-benzo[1,2,4]phosphadiazin-3-yl)-4-hydroxy-1,5-dihydropyrrol-2-one (IV-82)

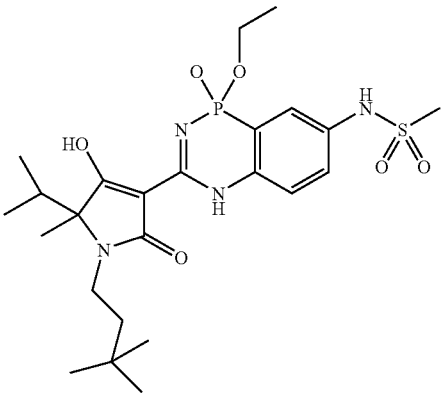

Example 83 was synthesized from intermediate 139 following the procedure as described for example 44. Example 83 was a white solid. Example 83 was characterized by the following spectroscopic data: ¹H NMR (CDCl₃, 400 MHz) δ (ppm) 0.84-0.90 (m, 3H), 0.99-1 (m, 9H), 1.10-1.14 (m, 3H), 1.33-1.38 (m, 6H), 1.55-1.69 (m, 2H), 1.97-2.05 (m, 1H), 3.04-3.05 (r, 3H), 3.15-3.23 (m, 1H), 3.33-3.44 (m, 1H), 4.14-4.22 (nm 2H), 7.13-7.19 (m, 1H), 7.49-7.59 (m, 1H), 7.64-7.67 (m, 2H), 11.56-11.58 (m, 1H). ³¹P NMR (CDCl₃, 162 MHz) δ (ppm) 0.36 (s, 1P), 0.38 (s, 1P), 0.78 (s, 1P). MS (ESI, EI⁺) m/z=541 (MH⁺). Example 83 is equivalent to Compound IV-82.

Example 84

5-isopropyl-5-methyl-1-(3,3-dimethyl-butyl)-3-(7-methanesulfonamyl-1-methoxy-1-oxo-1,4-dihydro-1-benzo[1,2,4]phosphadiazin-3-yl)-4-hydroxy-1,5-dihydropyrrol-2-one (IV-103)

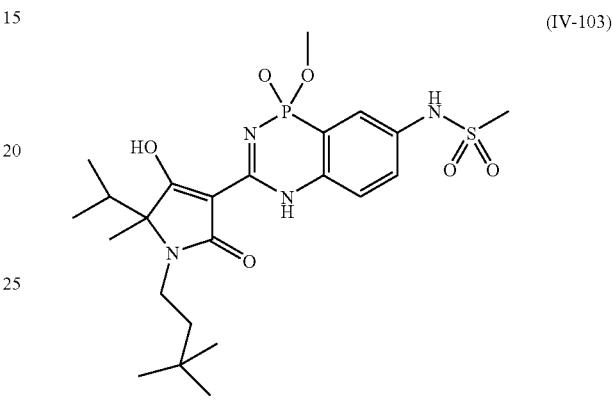

Example 84 was synthesized from example 83. To a stirred solution of example 83 (0.042 mmol) in dichloromethane (2 ml) and a few drops of dimethylformamide, oxalyl chloride (0.0063 mmol) was added dropwise, under nitrogen. The reaction mixture was stirred at room temperature, under nitrogen for 24 hours. Methanol was then added and the mixture was stirred for one hour. Solvents were concentrated under reduced pressure and the crude material was purified using preparative HPLC to yield example 84, which was a white solid. Example 84 was characterized by the following spectroscopic data. MS (ESI, EI⁺) m/z=527 (MH⁺). Example 84 is equivalent to Compound IV-103.

Example 85

5-isobutyl-1-(3,3-dimethylbutyl)-5-methyl-3-(1-hydroxy-7-methanesulfonamyl-1-oxo-1,4-dihydro-7-methanesulfonamyl-1-benzo[1,2,4]phosphadiazin-3-yl)-4-hydroxy-1,5-dihydropyrrol-2-one (IV-99)

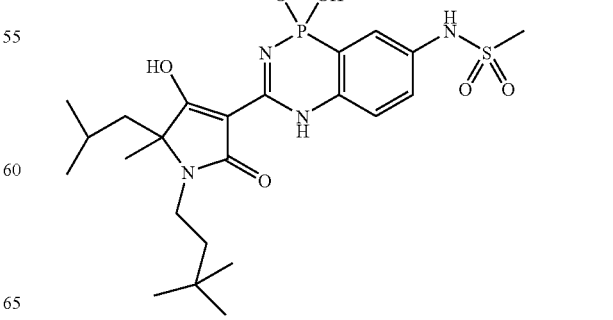

Example 85 was synthesized from example 57 following the procedure as described for example 45. Example 85 was a white solid. Example 85 was characterized by the following spectroscopic data: $^1$H NMR (CDCl$_3$, 400 MHz) δ (ppm) 0.71 (d, J=6.63 Hz, 3H), 0.78 (d, J=6.63 Hz, 3H), 0.85-0.88 (m, 2H), 0.92 (s, 9H), 1.14 (s, 3H), 1.32-1.39 (m, 1H), 1.52-1.59 (m, 2H), 2.93 (s, 3H), 3.33-3.39 (m, 1H), 4.11-4.14 (m, 1H), 7.09-7.14 (m, 1H), 7.22-7.25 (m, 1H), 7.31-7.35 (m, 1H), 7.65-7.72 (m, 1H), 10.97-11.03 (m, 1H). $^{31}$P NMR (CDCl$_3$, 162 MHz) δ (ppm) −13.80 (s, 1P), −13.95 (s, 1P). MS (ESI, EI$^+$) m/z=527 (MH$^+$). Example 85 is equivalent to Compound IV-99.

Example 86

(S)-5-tert-butyl-1-(3,3-dimethyl-butyl)-3-(1-ethoxy-1-oxo-1,4-dihydro-7-trifluoro-1-benzo[1,2,4]phosphadiazin-3-yl)-4-hydroxy-1,5-dihydropyrrol-2-one

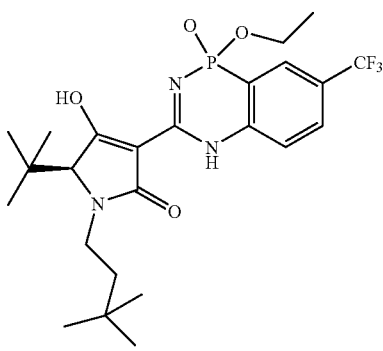

(S)-isomer of (IV-92)

Example 86 was synthesized from intermediate 140 and intermediate 77 following the procedure as described for example 44. Example 86 was a white lyophilized powder. Example 86 was characterized by the following spectroscopic data: $^1$H NMR (CDCl$_3$, 400 MHz) δ (ppm) 0.96 (s, 9H), 1.10 (s, 9H), 1.37-1.41 (m, 5H), 3.20 (m, 1H), 3.51 (s, 1H), 3.95-3.98 (m, 1H), 4.26 (m, 2H), 7.85 (m, 1H), 8.08 (d, J=15.02 Hz, 1H), 10.92 (brs, 1H), 11.72-11.84 (m, 1H). $^{31}$P NMR (CDCl$_3$, 162 MHz) δ (ppm) −0.78 (s, 1P) −0.73 (s, 1P), −0.43 (s, 1P), −0.35 (s, 1P) $^{19}$F NMR (CDCl$_3$, 376 MHz) δ (ppm) −62.53 (s, 3F). MS (ESI, EI$^+$) m/z=516 (MH$^+$). Example 86 is equivalent to (S)-isomer of Compound IV-92.

Example 87

(S)-5-tert-butyl-1-(3,3-dimethyl-butyl)-3-(7-methanesulfonamyl-1-methyl-1-oxo-1,4-dihydro-1-benzo[1,2,4]phosphadiazin-3-yl)-4-hydroxy-1,5-dihydropyrrol-2-one

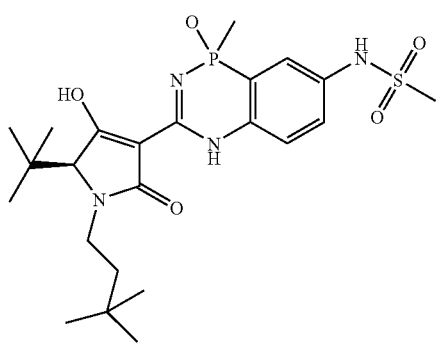

(S)-isomer of (IV-133)

Example 87 was synthesized from intermediate 143 and intermediate 77 following the procedure as described for example 44. Example 87 was a white solid. Example 87 was characterized by the following spectroscopic data: $^1$H NMR (DMSO-d$_6$, 400 MHz) δ (ppm) 0.88 (s, 9H), 1.02 (s, 9H), 1.22 (m, 1H), 1.63 (m, 1H), 2.05-2.10 (m, 3H), 3.01 (s, 1H), 3.04 (s, 3H), 3.50 (m, 1H), 3.78 (s, 1H), 7.45-7.58 (m, 3H), 9.97 (brs, 1H), 10.67 (brs, 1H), 11.65 ((m, 1H) $^{31}$P NMR (DMSO-d$_6$, 162 MHz) δ (ppm) 11.94 (s, 1P), 12.94 (s, 1P), 12.54 (s, 1P). MS (ESI, EI$^+$) m/z=511 (MH$^+$). Example 87 is equivalent to (S)-isomer of Compound IV-133.

Example 88

(S)-5-tert-butyl-1-(3,3-dimethyl-butyl)-3-(7-chloro-1-ethoxy-1-oxo-1,4-dihydro-1-benzo[1,2,4]phosphadiazin-3-yl)-4-hydroxy-1,5-dihydropyrrol-2-one

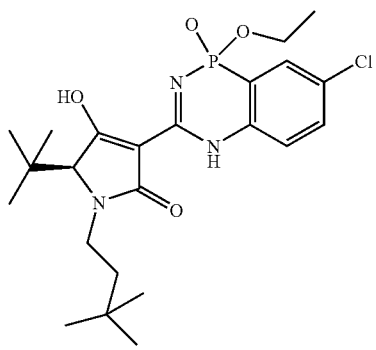

(S)-isomer of (IV-94)

Example 88 was synthesized from intermediate 144 and intermediate 77 following the procedure as described for example 44. Example 88 was a white lyophilized powder. Example 88 was characterized by the following spectroscopic data: $^1$H NMR (DMSO-d$_6$, 400 MHz) δ (ppm) 0.96 (s, 9H), 1.08 (s, 9H), 1.29 (t, J=7.00 Hz, 3H), 1.33-1.38 (m, 1H), 1.70-1.73 (m, 1H), 3.15-3.21 (m, 1H), 3.64-3.67 (m, 1H), 3.82-3.90 (m, 1H), 4.16 (m, 2H), 7.68 (brs, 1H), 7.84 (d, J=9.11 Hz, 1H), 7.90 (d, J=15.10 Hz, 1H), 11.54 (m, 1H). $^{31}$P NMR (DMSO-d$_6$, 162 MHz) δ (ppm) −1.18 (s, 1P). MS (ESI, EI$^+$) m/z=482 (MH$^+$). Example 88 is equivalent to (S)-isomer of Compound IV-94.

Example 89

(S)-5-tert-butyl-1-(3,3-dimethyl-butyl)-3-(7-cyano-1-ethoxy-1-oxo-1,4-dihydro-1-benzo[1,2,4]phosphadiazin-3-yl)-4-hydroxy-1,5-dihydropyrrol-2-one

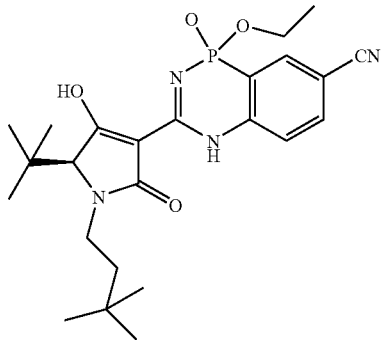

(S)-isomer of (IV-93)

Example 89 was synthesized from intermediate 145 and intermediate 77 following the procedure as described for example 44. Example 89 was a white lyophilized powder. Example 89 was characterized by the following spectroscopic data: $^1$H NMR (DMSO-$d_6$, 400 MHz) δ (ppm) 0.96 (s, 9H), 1.08 (s, 9H), 1.27-1.29 (t, J=7.00 Hz, 3H), 1.34-1.38 (m, 1H), 1.69-1.76 (m, 1H), 3.16-3.21 (t, J=12.41 Hz, 1H), 3.66 (s, 1H), 3.83-3.91 (t, J=12.41 Hz, 1H), 4.18 (brs, 2H), 7.77 (brs, 1H), 8.16 (d, J=9.00 Hz, 1H), 8.42 (d, J=14.80 Hz, 1H), 11.64-11.73 (m, 1H). $^{31}$P NMR (DMSO-$d_6$, 162 MHz) δ (ppm) −2.03 (s, 1P). MS (ESI, EI$^+$) m/z=473 (MH$^+$). Example 89 is equivalent to (S)-isomer of Compound IV-93.

Example 90

(S)-5-tert-butyl-1-(3,3-dimethyl-butyl)-3-(1-ethoxy-1-oxo-1,4-dihydro-1-benzo[1,2,4,8]phosphatriazin-3-yl)-4-hydroxy-1,5-dihydropyrrol-2-one

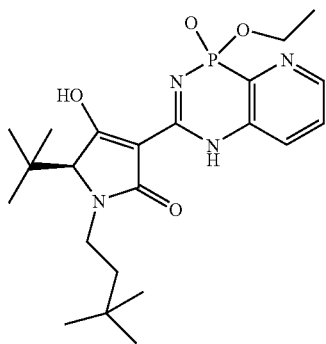

(S)-isomer of (IV-96)

Example 90 was synthesized from intermediate 147 and intermediate 77 following the procedure as described for example 44. Example 90 was a white lyophilized powder. Example 90 was characterized by the following spectroscopic data: $^1$H NMR (CDCl$_3$, 400 MHz) δ (ppm) 0.70 (s, 9H), 0.84 (s, 9H), 1.16-1.20 (m, 3H), 1.31 (m, 2H), 2.93 (m, 1H), 3.23-3.28 (m, 1H), 3.73 (m, 1H), 4.18-4.20 (m, 2H), 7.02 (d, J=9.00 Hz, 1H), 7.20-7.26 (m, 1H), 8.40 (s, 1H), 10.72 (brs, 1H), 11.33-11.51 (m, 1H). $^{31}$P NMR (CDCl$_3$, 162 MHz) δ (ppm) −5.82 (s, 1P), −5.75 (s, 1P), −5.55 (s, 1P). MS (ESI, EI$^+$) m/z=449 (MH$^+$). Example 90 is equivalent to (S)-isomer of Compound IV-96.

Example 91

(S)-5-tert-butyl-1-(1H-pyrazol-4-ylmethyl-3-(1-ethoxy-7-methanesulfonamyl-1-oxo-1,4-dihydro-1-benzo[1,2,4]phosphadiazin-3-yl)-4-hydroxy-1,5-dihydropyrrol-2-one

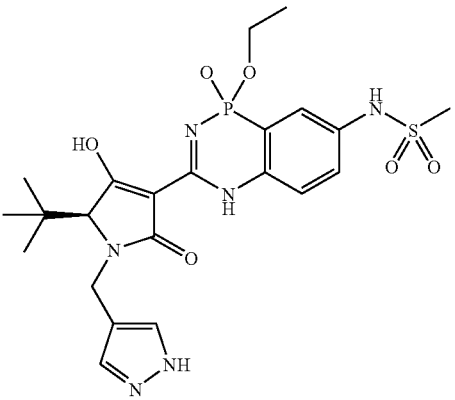

(S)-isomer of (IV-63)

Example 91 was synthesized from intermediate 26 and intermediate 150 following the procedure as described for example 44. Example 91 was a white solid. Example 91 was characterized by the following spectroscopic data: $^1$H NMR (CDCl$_3$, 400 MHz) δ (ppm) 1.09 (s, 9H), 1.36-1.41 (m, 3H), 3.06 (s, 3H), 3.39 (dd, J=4.40 Hz and J=8.80 Hz, 1H), 4.19-4.24 (m, 3H), 5.15-5.19 (m, 1H), 7.15-7.23 (m, 2H), 7.51-7.61 (m, 4H), 15.52-15.76 (m, 1H). MS (ESI, EI$^+$) m/z=537 (MH$^+$). Example 91 is equivalent to (S)-isomer of Compound IV-63.

Example 92

(S)-5-tert-butyl-1-(3-chloro-benzyl)-3-(1-ethoxy-7-methanesulfonamyl-1-oxo-1,4-dihydro-1-benzo[1,2,4]phosphadiazin-3-yl)-4-hydroxy-1,5-dihydropyrrol-2-one

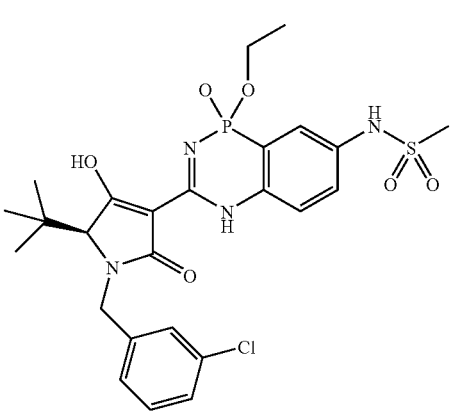

(S)-isomer of (IV-109)

Example 92 was synthesized from intermediate 26 and intermediate 153 following the procedure as described for example 44. Example 92 was a white solid. Example 92 was characterized by the following spectroscopic data: $^1$H NMR (CDCl$_3$, 400 MHz) δ (ppm) 1.08 (s, 9H), 1.36-1.41 (m, 3H), 3.06 (s, 3H), 3.34-3.39 (m, 1H), 4.18-4.32 (m, 3H), 5.23-5.35 (m, 1H), 7.03-7.08 (m, 1H), 7.17-7.25 (m, 4H), 7.36-7.44 (m, 1H), 7.63-7.67 (m, 2H), 11.51-11.80 (m, 1H). $^{31}$P NMR (CDCl$_3$, 162 MHz) δ (ppm) 0.35 (s, 1P), 0.47 (s, 1P), 0.53 (s, 1P). MS (ESI, EI⁺) m/z=581 (MH⁺). Example 92 is equivalent to (S)-isomer of Compound IV-109.

Example 93

(S)-5-cyclopentyl-1-(3,3-dimethylbutyl)-3-(1-ethoxy-7-methanesulfonamyl-1-oxo-1,4-dihydro-1-benzo[1,2,4]phosphadiazin-3-yl)-4-hydroxy-1,5-dihydropyrrol-2-one

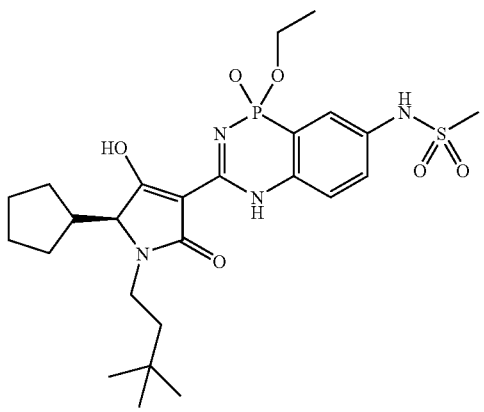

(S)-isomer of (IV-114)

Example 93 was synthesized from intermediate 26 and intermediate 156 following the procedure as described for example 44. Example 93 was a white solid. Example 93 was characterized by the following spectroscopic data: $^1$H NMR (CDCl$_3$, 400 MHz) δ (ppm) 0.96 (s, 9H), 1.28-1.42 (m, 5H), 1.50-1.76 (m, 7H), 1.85 (m, 1H), 2.36-2.45 (m, 1H), 3.03 (d, J=2.01 Hz, 4H), 3.85-3.95 (m, 2H), 4.12-4.21 (m, 2H), 7.13-7.25 (m, 1H), 7.50-7.66 (m, 3H), 11.53-11.58 (m, 1H). MS (ESI, EI⁺) m/z=553 (MH⁺). Example 93 is equivalent to (S)-isomer of Compound IV-114.

Example 94

(S)-5-tert-butyl-1-(3-bromo-4-fluorobenzyl)-3-(1-ethoxy-7-methanesulfonamyl-1-oxo-1,4-dihydro-1-benzo[1,2,4]phosphadiazin-3-yl)-4-hydroxy-1,5-dihydropyrrol-2-one

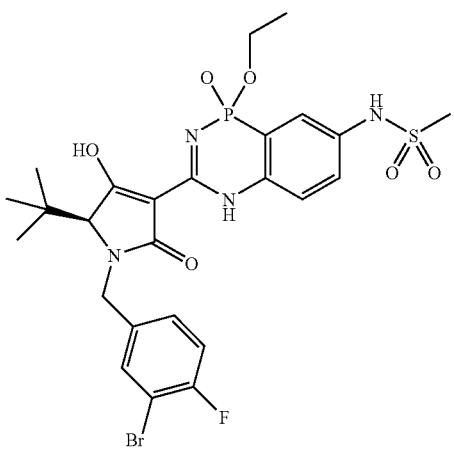

(S)-isomer of (IV-107)

Example 94 was synthesized from intermediate 26 and intermediate 158 following the procedure as described for example 44. Example 94 was a white solid. Example 94 was characterized by the following spectroscopic data: $^1$H NMR (CDCl$_3$, 400 MHz) δ (ppm) 1.09 (s, 9H), 1.36-1.42 (m, 3H), 3.06 (s, 3H), 3.34-3.39 (m, 1H), 4.19-4.32 (m, 3H), 5.16-5.29 (m, 1H), 7.06-7.21 (m, 3H), 7.29-7.41 (m, 2H), 7.63-7.66 (m, 2H), 11.48 (m, 1H), 11.80 (s, 1H). $^{31}$P NMR (CDCl$_3$, 162 MHz) δ (ppm) 0.40 (s, 1P). $^{19}$F NMR (CDCl$_3$, 376 MHz) δ (ppm) −108.50 (s, 1F). MS (ESI, EI⁺) m/z=644 (MH⁺). Example 94 is equivalent to (S)-isomer of Compound IV-107.

Example 95

(S)-5-tert-butyl-1-(4-fluoro-3-methylbenzyl)-3-(1-ethoxy-7-methanesulfonamyl-1-oxo-1,4-dihydro-1-benzo[1,2,4]phosphadiazin-3-yl)-4-hydroxy-1,5-dihydropyrrol-2-one

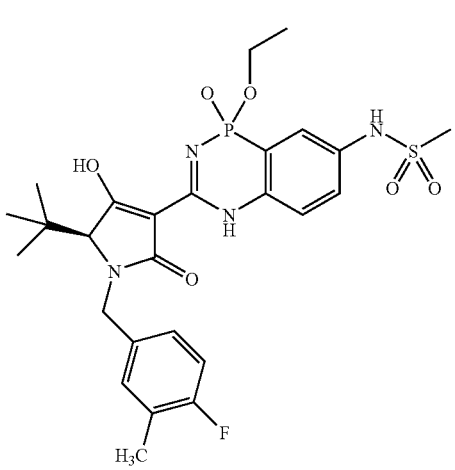

(S)-isomer of (IV-102)

Example 95 was synthesized from intermediate 26 and intermediate 221 following the procedure as described for example 44. Example 95 was a white solid. Example 95 was characterized by the following spectroscopic data: $^1$H NMR (CDCl$_3$, 400 MHz) δ (ppm) 1.07 (s, 9H), 1.34-1.40 (m, 3H), 2.24 (s, 3H), 3.05 (s, 3H), 3.35-3.38 (m, 1H), 4.12-4.25 (m, 3H), 5.24-5.33 (m, 1H), 6.93-6.99 (m, 3H), 7.16-7.23 (m, 1H), 7.65-7.69 (m, 2H), 7.81-7.89 (m, 1H), 11.54 (d, J=3.48 Hz, 0.5H), 11.77 (d, J=3.48 Hz, 0.5H). $^{31}$P NMR (CDCl$_3$, 162 MHz) δ (ppm) 0.81 (s, 1P). $^{19}$F NMR (CDCl$_3$, 376 MHz) δ (ppm) −119.18 (s, 1F). MS (ESI, EI⁺) m/z=579 (MH⁺). Example 95 is equivalent to (S)-isomer of Compound IV-102.

Example 96

(S)-5-tert-butyl-1-(3,3-dimethyl-butyl)-3-(1-ethoxy-1-oxo-1,4-dihydro-6-methyl-1-benzo[1,2,4]phosphadiazin-3-yl)-4-hydroxy-1,5-dihydropyrrol-2-one

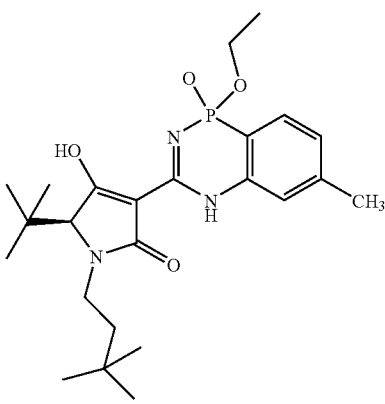

(S)-isomer of (IV-90)

Example 96 was synthesized from intermediate 77 and intermediate 160 following the procedure as described for example 44. Example 96 was a white solid. Example 96 was characterized by the following spectroscopic data: $^1$H NMR (CDCl$_3$, 400 MHz) δ (ppm) 0.96 (s, 9H), 1.09 (s, 9H), 1.32-1.36 (m, 2H), 1.55-1.61 (m, 3H), 2.42 (s, 3H), 3.10-3.22 (m, 1H), 3.47 (s, 1H), 3.93-4.01 (m, 1H), 4.10-4.20 (m, 2H), 6.97 (d, J=6.90 Hz, 1H), 7.13 (d, J=7.85 Hz, 1H), 7.67-7.73 (dd, J=7.85 Hz, J=6.92 Hz, 1H). $^{31}$P NMR (CDCl$_3$, 162 MHz) δ (ppm) 1.63-1.98 (m, 1P). MS (EST, EI$^+$) m/z=462 (MH$^+$). Example 96 is equivalent to (S)-isomer of Compound IV-90.

Example 97

(S)-5-tert-butyl-1-(3,3-dimethyl-butyl)-3-(1-ethoxy-1-oxo-1,4-dihydro-7-methyl-1-benzo[1,2,4]phosphadiazin-3-yl)-4-hydroxy-1,5-dihydropyrrol-2-one

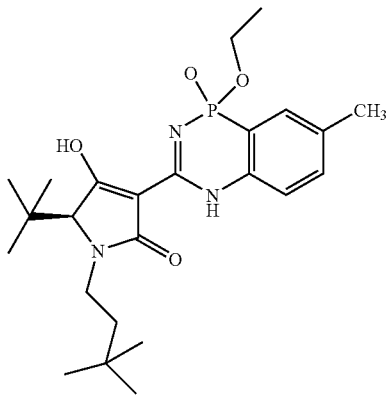

(S)-isomer of (IV-91)

Example 97 was synthesized from intermediate 77 and intermediate 161 following the procedure as described for example 44. Example 97 was a white solid. Example 97 was characterized by the following spectroscopic data: $^1$H NMR (CDCl$_3$, 400 MHz) δ (ppm) 0.96 (s, 9H), 1.09 (s, 9H), 1.32-1.36 (m, 2H), 1.55-1.61 (m, 3H), 2.40 (s, 3H), 3.12-3.22 (m, 1H), 3.47 (s, 1H), 3.93-4.01 (m, 1H), 4.10-4.20 (m, 2H), 7.03-7.08 (m, 1H), 7.42 (d, J=8.26 Hz, 1H), 7.62 (d, J=14.87 Hz, 1H). $^{31}$P NMR (CDCl$_3$, 162 MHz) δ (ppm) 1.38-1.71 (m, 1P). MS (ESI, EI$^+$) m/z=462 (MH$^+$), Example 97 is equivalent to (S)-isomer of Compound IV-91.

Example 98

5-isopropyl-5-methyl-1-(3,3-dimethyl-butyl)-3-(7-methanesulfonamyl-1-hydroxy-1-oxo-1,4-dihydro-1-benzo[1,2,4]phosphadiazin-3-yl)-4-hydroxy-1,5-dihydropyrrol-2-one

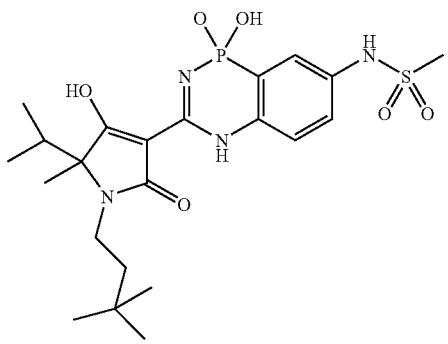

(IV-134)

Example 98 was synthesized from example 84 following the procedure as described for example 45. Example 98 was a white solid. Example 98 was characterized by the following spectroscopic data: MS (ESI, EI$^+$) m/z=513 (MH$^+$). Example 98 is equivalent to Compound IV-134.

Example 99

5-[bicyclo[2.2.1]heptane]-1-(3,3-dimethyl-butyl)-3-(7-methanesulfonamyl-1-ethoxy-1-oxo-1,4-dihydro-1-benzo[1,2,4]phosphadiazin-3-yl)-4-hydroxy-1,5-dihydropyrrol-2-one

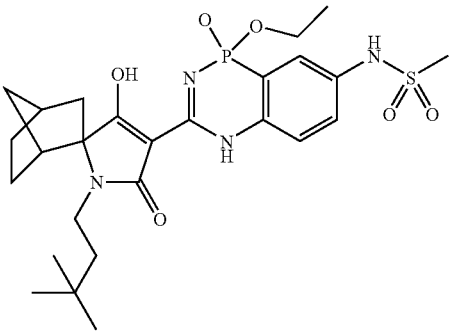

(IV-116)

Example 99 was synthesized from intermediate 165 and intermediate 26 following the procedure as described for example 44. Example 99 was a white solid. Example 99 was characterized by the following spectroscopic data: $^1$H NMR (CDCl$_3$, 400 MHz) δ (ppm) 0.99 (s, 9H), 1.23-1.25 (m, 1H), 1.32-1.35 (t, J=6.85 Hz, 3H), 1.39-1.42 (m, 2H), 1.50-1.57 (m, 2H), 1.74-1.85 (m, 3H), 2.00-2.03 (m, 1H), 2.29-2.31 (m, 1H), 2.41 (m, 1H), 2.47-2.49 (m, 1H), 3.04 (s, 3H), 3.16-3.21 (m, 1H), 3.54-3.59 (m, 1H), 4.13-4.17 (m, 2H), 7.14-7.16 (m, 1H), 7.65-7.69 (m, 2H). $^{31}$P NMR (CDCl$_3$, 162 MHz) δ (ppm) 0.63-1.02 (m, 1P). MS (ESI, EI$^+$) m/z=565 (MH$^+$). Example 99 is equivalent to Compound IV-116.

Example 100

5-[bicyclo[2.2.1]heptane]-1-(3,3-dimethyl-butyl)-3-(7-methanesulfonamyl-1-hydroxy-1-oxo-1,4-dihydro-1-benzo[1,2,4]phosphadiazin-3-yl)-4-hydroxy-1,5-dihydropyrrol-2-one

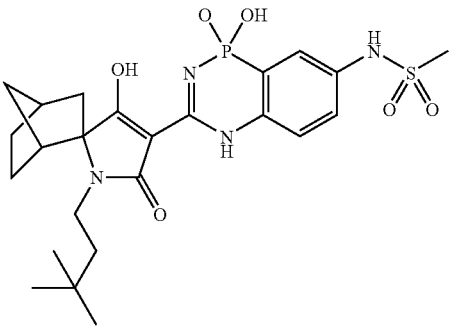

(IV-117)

Example 100 was synthesized from example 99 following the procedure as described for example 45. Example 100 was a beige solid. Example 100 was characterized by the following spectroscopic data: $^1$H NMR (CDCl$_3$, 400 MHz) δ (ppm) 0.95 (s, 9H), 1.20-2.45 (m, 12H), 3.02 (s, 3H), 3.15 (m, 1H), 3.58 (m, 1H), 7.11 (brs, 1H), 7.67-7.79 (m, 2W), 11.55 (s, 1H). $^{31}$P NMR (CDCl$_3$, 162 MHz) δ (ppm) 1.59-2.25 (m, 1P). MS (ESI, EI$^+$) m/z=537 (MH$^+$). Example 100 is equivalent to Compound IV-117.

Example 101
5-[bicyclo[2.2.1]heptane]-1-(3,3-dimethyl-butyl)-3-(7-methanesulfonamyl-1-methoxy-1-oxo-1,4-dihydro-1-benzo[1,2,4]phosphadiazin-3-yl)-4-hydroxy-1,5-dihydropyrrol-2-one

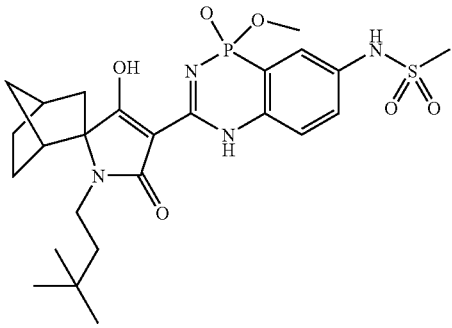

(IV-118)

Example 101 was synthesized from example 100. To a stirred solution of example 100 (0.042 mmol) in dichloromethane (2 ml) and a few drops of dimethylformamide, oxalyl chloride (0.0063 mmol) was added dropwise, under nitrogen. The reaction mixture was stirred at room temperature, under nitrogen for 24 hours. Methanol was then added and the mixture was stirred for one hour. Solvents were concentrated under reduced pressure and the crude material was purified using preparative HPLC to yield example 101, which was an off-white solid. Example 101 was characterized by the following spectroscopic data: $^1$H NMR (CDCl$_3$, 400 MHz) δ (ppm) 0.98 (s, 9H), 1.20-2.25 (m, 1H), 1.36-1.46 (m, 2H), 1.50-1.61 (m, 2H), 1.96-2.03 (m, 1H), 2.27-2.48 (m, 3H), 3.04 (s, 3H), 3.12-3.22 (m, 1H), 3.50-3.63 (m, 1H), 3.75-3.80 (m, 3H), 7.12-7.20 (m, 1H), 7.62-7.70 (m, 2H), 7.77 (brs, 1H), 11.50-11.59 (m, 1H). $^{31}$P NMR (CDCl$_3$, 162 MHz) δ (ppm) 1.20-2.66 (m, 1P). MS (ESI, EI$^+$) m/z=551 (MH$^+$). Example 101 is equivalent to Compound IV-118.

Example 102
(S)-5-tert-butyl-1-pent-4-ynyl-3-(1-ethoxy-7-methanesulfonamyl-1-oxo-1,4-dihydro-7-methyl-1-benzo[1,2,4]phosphadiazin-3-yl)-4-hydroxy-1,5-dihydropyrrol-2-one

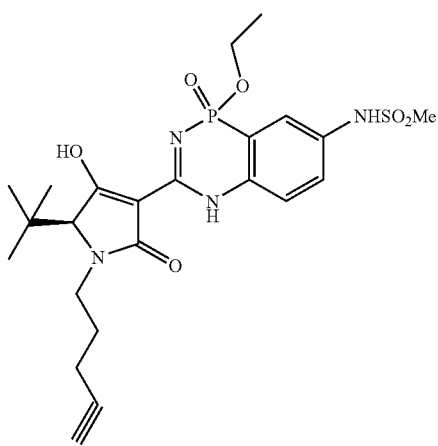

(S)-isomer of (IV-68)

Example 102 was synthesized from intermediate 26 and intermediate 167 following the procedure as described for example 44. Example 102 was a white solid. Example 102 was characterized by the following spectroscopic data: $^1$H NMR (CDCl$_3$, 400 MHz) δ (ppm) 1.09 (s, 9H), 1.33-1.37 (m, 3H), 1.73-1.83 (m, 1H), 1.91-1.96 (m, 2H), 2.17-2.22 (m, 2H), 3.04 (s, 3H), 3.30-3.39 (m, 1H), 3.52-3.55 (m, 1H), 3.95-4.03 (m, 1H), 4.13-4.21 (m, 2H), 7.14-7.20 (m, 1H), 7.63-7.67 (m, 2H), 7.76-7.81 (m, 1H), 11.52-11.72 (m, 1H). $^{31}$P NMR (CDCl$_3$, 162 MHz) δ (ppm) 0.60 (s, 1P). MS (ESI, EI$^+$) m/z=523 (MH$^+$). Example 102 is equivalent to (S)-isomer of Compound IV-68.

Example 103

(S)-5-cyclopropyl-1-(3,3-dimethyl-butyl)-3-(1-ethoxy-7-methanesulfonamyl-1-oxo-1,4-dihydro-7-methyl-1-benzo[1,2,4]phosphadiazin-3-yl)-4-hydroxy-1,5-dihydropyrrol-2-one

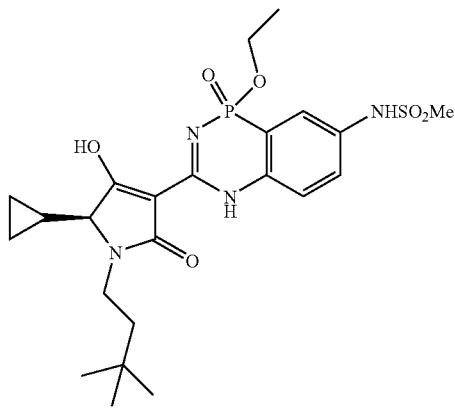

(S)-isomer of (IV-69)

Example 103 was synthesized from intermediate 26 and intermediate 170 following the procedure as described for example 44. Example 103 was a white solid. Example 103 was characterized by the following spectroscopic data: $^1$H NMR (CDCl$_3$, 400 MHz) δ (ppm) 0.43-0.47 (m, 1H), 0.68-0.83 (m, 4H), 0.98 (s, 9H), 1.33-1.36 (m, 3H), 1.48 (m, 2H), 3.03-3.06 (m, 1H), 3.04 (s, 3H), 3.31-3.39 (m, 1H), 3.72-3.80 (m, 1H), 4.16-4.22 (m, 2H), 7.05-7.18 (m, 2H), 7.59-7.63 (m, 1H), 11.54-11.58 (m, 1H). $^{31}$P NMR (CDCl$_3$, 162 MHz) δ

(ppm) 0.44 (s, 1P). MS (ESI, EI+) m/z=525 (MH+). Example 103 is equivalent to (S)-isomer of Compound IV-69.

Example 104

5-isopropylydene-1-(3,3-dimethyl-butyl)-3-(1-ethoxy-7-methanesulfonamyl-1-oxo-1,4-dihydro-7-methyl-1-benzo[1,2,4]phosphadiazin-3-yl)-4-hydroxy-1,5-dihydropyrrol-2-one

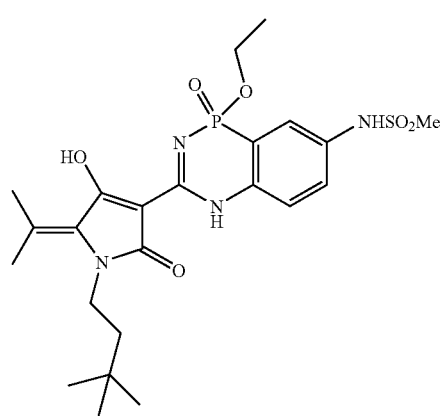

(IV-70)

Example 104 was synthesized from intermediate 26 and intermediate 173 following the procedure as described for example 44. Example 104 was a white solid. Example 104 was characterized by the following spectroscopic data: $^1$H NMR (CDCl$_3$, 400 MHz) δ (ppm) 0.89 (s, 9H), 1.32-1.36 (t, J=7.02 Hz and J=2.25 Hz, 3H), 1.47-1.52 (t, J=8.67 Hz, 2H), 2.09 (s, 3H), 2.38 (s, 3H), 3.04 (s, 3H), 3.81-3.87 (m, 2H), 4.13-4.20 (m, 2H), 7.12-7.21 (m, 2H), 7.59-7.63 (m, 2H), 11.29 (s, 1H), 12.08 (s, 1H). $^{31}$P NMR (CDCl$_3$, 162 MHz) δ (ppm) 0.30 (s, 1P). MS (ESI, EI+) m/z=525 (MH+). Example 104 is equivalent to Compound IV-70.

Example 105

1-(3,3-dimethyl-butyl)-3-(1-ethoxy-7-methanesulfonamyl-1-oxo-1,4-dihydro-7-methyl-1-benzo[1,2,4]phosphadiazin-3-yl)-4-hydroxy-5-methyl-1,5-dihydropyrrol-2-one

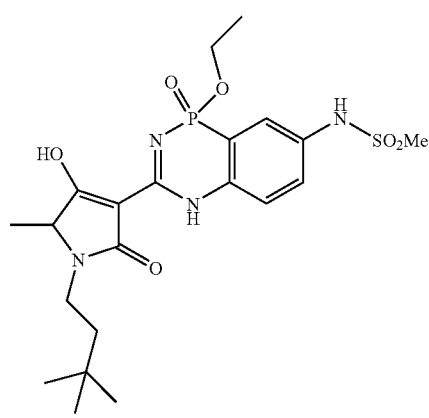

(IV-61)

Example 105 was synthesized from intermediate 26 and intermediate 175 following the procedure as described for example 44. Example 105 was a beige solid. Example 105 was characterized by the following spectroscopic data: $^1$H NMR (CDCl$_3$, 400 MHz) δ (ppm) 0.96 (s, 9H), 1.33-1.37 (m, 8H), 3.04 (s, 3H), 3.08-3.12 (m, 1H), 3.73-3.83 (m, 2H), 4.13-4.21 (m, 2H), 7.14-7.19 (m, 1H), 7.67-7.71 (m, 2H), 8.61 (brs, 1H), 11.41 (brs, 1H), 11.55 (m, 1H). $^{31}$P NMR (CDCl$_3$, 162 MHz) δ (ppm) 0.68-1.07 (s, 1P). MS (ESI, EI+) m/z=499 (MH+). Example 105 is equivalent to Compound IV-61.

Example 106

(S)-5-tert-butyl-1-pent-4-ynyl-3-(1-hydroxy-7-methanesulfonamyl-1-oxo-1,4-dihydro-7-methyl-1-benzo[1,2,4]phosphadiazin-3-yl)-4-hydroxy-1,5-dihydropyrrol-2-one

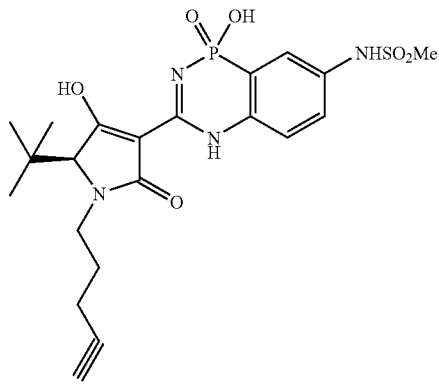

(S)-isomer of (IV-135)

Example 106 was synthesized from example 102 following the procedure as described for example 45. Example 106 was an orange solid. Example 106 was characterized by the following spectroscopic data: MS (ESI, EI+) m/z=495 (MH+). Example 106 is equivalent to (S)-isomer of Compound IV-135.

Example 107

To a stirred solution of example 106 (0.28 mmol) in dry MeOH (115 µl), at room temperature was added oxalyl chloride (0.425 mmol). The reaction mixture was stirred at room temperature for 2 hours, concentrated under reduced pressure and purified by preparative HPLC (A30B70) to yield 3 compounds:

Example 107a (S)-5-tert-butyl-1-pent-4-ynyl-3-(1-methoxy-7-methanesulfonamyl-1-oxo-1,4-dihydro-7-methyl-1-benzo[1,2,4]phosphadiazin-3-yl)-4-hydroxy-1,5-dihydropyrrol-2-one

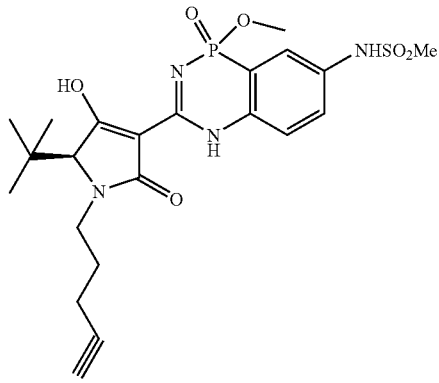

(S)-isomer of (IV-136)

Example 107a was a white solid. Example 107a was characterized by the following spectroscopic data: $^1$H NMR (CDCl$_3$, 400 MHz) δ (ppm) 1.08-1.10 (m, 9H), 1.73-1.80 (m, 1H), 1.92-1.97 (m, 2H), 2.18-2.22 (m, 2H), 3.05 (s, 1H), 3.29-3.38 (m, 1H), 3.52-3.55 (m, 1H), 3.79-3.84 (dd, J=12.38 Hz and J=6.04 Hz, 3H), 3.95-4.03 (m, 1H), 6.99-7.08 (m, 1H), 714-7.21 (m, 1H), 7.59-7.63 (m, 2H), 11.52-11.73 (m, 1H) $^{31}$P NMR (CDCl$_3$, 162 MHz) δ (ppm) 1.90 (s, 1P). MS (ESI, EI$^+$) m/z=499 (MH$^+$). Example 107a is equivalent to (S)-isomer of Compound IV-136.

Example 107b (S)-5-tert-butyl-1-(4-bromo-pent-4-enyl-3-(1-methoxy-7-methanesulfonamyl-1-oxo-1,4-dihydro-7-methyl-1-benzo[1,2,4]phosphadiazin-3-yl)-4-hydroxy-1,5-dihydropyrrol-2-one

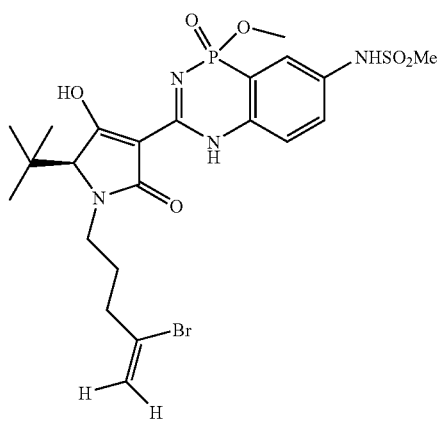

(S)-isomer of (IV-137)

Example 107b was a white solid. Example 107b was characterized by the following spectroscopic data: $^1$H NMR (CDCl$_3$, 400 MHz) δ (ppm) 1.08-1.10 (m, 9H), 1.81-1.85 (m, 1H), 2.26 (m, 2H), 3.05 (s, 1H), 3.18-3.24 (m, 1H), 3.50-3.55 (m, 1H), 3.80-3.84 (m, 3H), 3.89-4.03 (m, 1H), 5.42 (d, J=1.29 Hz, 1H), 5.61 (m, 1H), 6.99-7.04 (m, 1H), 7.15-7.22 (m, 1H), 7.59-7.64 (m, 2H), 11.53-11.74 (m, 1H). $^{31}$P NMR (CDCl$_3$, 162 MHz) δ (ppm) 1.90 (s, 1P). MS (ESI, EI$^+$) m/z=591 (MH$^+$). Example 107b is equivalent to (S)-isomer of Compound IV-137.

Example 107c (S)-5-tert-butyl-1-(5-bromo-pent-4-enyl-3-(1-methoxy-7-methanesulfonamyl-1-oxo-1,4-dihydro-7-methyl-1-benzo[1,2,4]phosphadiazin-3-yl)-4-hydroxy-1,5-dihydropyrrol-2-one

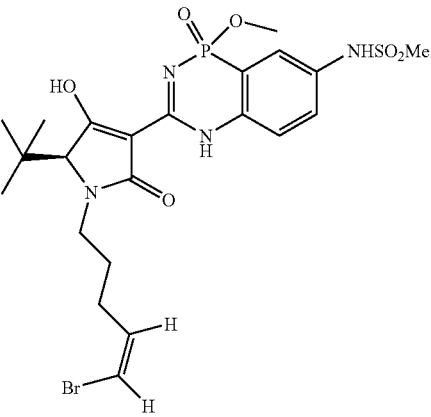

(S)-isomer of (IV-138)

Example 107c was a white solid. Example 107c was characterized by the following spectroscopic data: $^1$H NMR (CDCl$_3$, 400 MHz) δ (ppm) 1.08-1.10 (m, 9H), 2.36-2.52 (m, 2H), 3.05 (s, 1H), 3.17-3.25 (m, 1H), 3.44-3.55 (m, 1H), 3.79-3.85 (m, 3H), 3.91-4.09 (m, 1H), 5.54-5.61 (m, 1H), 7.04-7.06 (m, 1H), 7.16-7.22 (m, 1H), 7.59-7.63 (m, 2H), 11.53-11.75 (m, 1H). $^{31}$P NMR (CDCl$_3$, 162 MHz) δ (ppm) 1.90 (s, 1P). MS (ESI, EI$^+$) m/z=591 (MH$^+$). Example 107c is equivalent to (S)-isomer of Compound IV-138.

Example 108

5-cyclohexyl-1-(3,3-dimethyl-butyl-3-(1-hydroxy-7-methanesulfonamyl-1-oxo-1,4-dihydro-1-benzo[1,2,4]phosphadiazin-3-yl)-4-hydroxy-1,5-dihydropyrrol-2-one

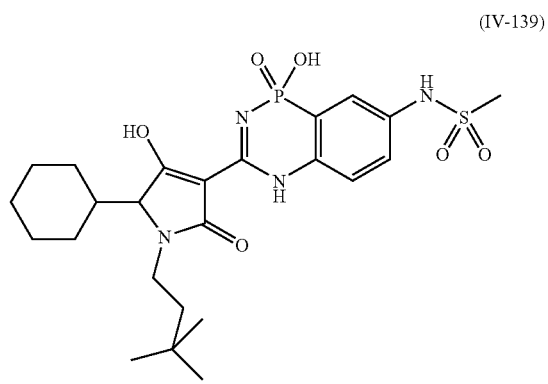

(IV-139)

Example 108 was synthesized from example 81 following the procedure as described for example 45. Example 108 was an orange solid. Example 108 was characterized by the following spectroscopic data: MS (ESI, EI$^+$) m/z=539 (MH$^+$). Example 108 is equivalent to Compound IV-139.

Example 109

5-cyclohexyl-1-(3,3-dimethyl-butyl)-3-(1-methoxy-7-methanesulfonamyl-1-oxo-1,4-dihydro-1-benzo[1,2,4]phosphadiazin-3-yl)-4-hydroxy-1,5-dihydropyrrol-2-one

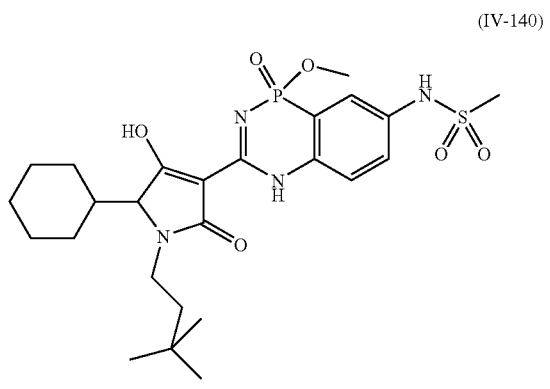

(IV-140)

Example 109 was synthesized from example 108 following the procedure as described for example 107. Example 109 was a yellow solid. Example 109 was characterized by the following spectroscopic data: $^1$H NMR (CDCl$_3$, 400 MHz) δ (ppm) 0.99 (s, 9H), 1.19-1.87 (m, 13H), 2.98-3.03 (m, 1H), 3.05 (s, 3H), 3.67-3.90 (m, 5H), 7.10-7.26 (m, 2H), 7.58-7.66 (m, 2H), 11.52-11.58 (m, 1H). $^{31}$P NMR (CDCl$_3$, 162 MHz) δ (ppm) 1.90 (s, 1P). MS (ESI, EI$^+$) m/z=553 (MH$^+$). Example 109 is equivalent to Compound IV-140.

Example 110

(S)-5-thiazol-4-yl-1-(3,3-dimethyl-butyl)-3-(1-ethoxy-7-methanesulfonamyl-1-oxo-1,4-dihydro-1-benzo[1,2,4]phosphadiazin-3-yl)-4-hydroxy-1,5-dihydropyrrol-2-one

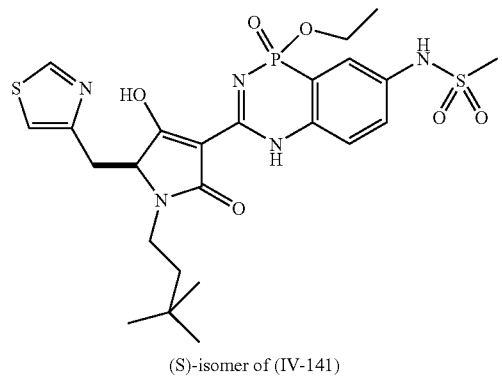

(S)-isomer of (IV-141)

Example 110 was synthesized from intermediate 180 and intermediate 26 following the procedure as described for example 44. Example 110 was a white solid. Example 110 was characterized by the following spectroscopic data: $^1$H NMR (CDCl$_3$, 400 MHz) δ (ppm) 0.88 (s, 9H), 1.25-1.43 (m, 5H), 2.81-2.90 (m, 1H), 3.04 (s, 3H), 3.22-3.31 (m, 1H), 3.36-3.47 (m, 1H), 3.76-3.86 (m, 1H), 4.14-4.20 (m, 2H), 4.30-4.32 (m, 1H), 6.99-7.14 (m, 2H), 7.32 (brs, 1H), 7.58-7.63 (m, 2H), 8.72-8.75 (m, 1H), 11.40-11.50 (m, 1H). $^{31}$P NMR (CDCl$_3$, 162 MHz) δ (ppm) 0.12 (s, 1P). MS (ESI, EI$^+$) m/z=582 (MH$^+$). Example 110 is equivalent to (S)-isomer of Compound IV-141.

Example 111

(S)-5-tert-butyl-1-(3,3-dimethyl-butyl)-3-(1-ethoxy-1-oxo-1,4-dihydro-8-methyl-1-benzo[1,2,4]phosphadiazin-3-yl)-4-hydroxy-1,5-dihydropyrrol-2-one

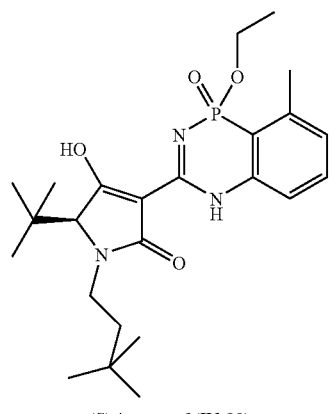

(S)-isomer of (IV-98)

Example 111 was synthesized from intermediate 77 and intermediate 181 following the procedure as described for example 44. The 2 diastereoisomers were separated but not identified.

Example 111a was an off-white solid. Example 111a was characterized by the following spectroscopic data: $^1$H NMR (CDCl$_3$, 400 MHz) δ (ppm) 0.94 (s, 9H), 1.08 (s, 9H), 1.34-1.38 (td, J=7.10 Hz and J=3.29 Hz, 3H), 1.39-1.42 (m, 1H), 1.59 (m, 1H), 2.68 (s, 3H), 3.13-3.21 (td, J=12.61 Hz and J=4.50 Hz, 1H), 3.47 (d, J=12.06 Hz, 1H), 3.92-3.99 (m, 1H), 4.05-4.19 (m, 2H), 6.95-6.98 (t, J=7.17 Hz, 1H), 7.06-7.10 (m, 1H), 7.44-7.49 (m, 1H), 10.7 (brs, 1H), 11.38-11.60 (m, 1H). $^{31}$P NMR (CDCl$_3$, 162 MHz) δ (ppm) 1.36 (s, 1P). MS (ESI, EI$^+$) m/z=462 (MH$^+$).

Example 111b: was an off-white solid. Example 111b was characterized by the following spectroscopic data: $^1$H NMR (CDCl$_3$, 400 MHz) δ (ppm) 0.94 (s, 9H), 1.08 (s, 9H), 1.34-1.38 (td, J=7.10 Hz and J=3.29 Hz, 3H), 1.39-1.43 (m, 1H), 1.56 (m, 1H), 2.68 (s, 3H), 3.11-3.21 (td, J=12.61 Hz and J=4.50 Hz, 1H), 3.46 (s, 1H), 3.92-4.01 (m, 1H), 4.05-4.13 (m, 2H), 6.97-6.98 (t, J=7.79 Hz, 1H), 7.07-7.10 (m, 1H), 7.45-7.49 (t, J=7.79 Hz, 1H), 10.8 (brs, 1H), 11.36-11.60 (m, 1H). ³¹P NMR (CDCl₃, 162 MHz) δ (ppm) 1.36 (s, 1P). MS (ESI, EI⁺) m/z=462 (MH⁺).

Example 112

(S)-5-tert-butyl-1-(3,3-dimethyl-butyl)-3-(1-ethoxy-1-oxo-1,4-dihydro-8-methyl-1-benzo[1,2,4]phosphadiazin-3-yl)-4-hydroxy-1,5-dihydropyrrol-2-one

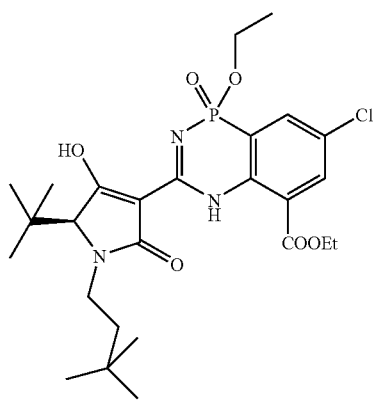

(S)-isomer of (IV-142)

Example 112 was synthesized from intermediate 77 and intermediate 182 following the procedure as described for example 44. Example 112 was an off-white solid. Example 112 was characterized by the following spectroscopic data: ¹H NMR (CDCl₃, 400 MHz) δ (ppm) 0.93 (d, J=10.23 Hz, 9H), 1.08 (d, J=3.66 Hz, 9H), 1.34-1.40 (m, 6H), 1.48-1.60 (m, 2H), 3.04-3.20 (m, 1H), 3.50 (d, J=12.87 Hz, 1H), 4.18-4.29 (m, 4H), 7.98-8.07 (m, 1H), 8.31 (t, J=4.59 Hz, 1H), 12.05 (m, 1H), 12.65 (m, 1H). ³¹P NMR (CDCl₃, 162 MHz) δ (ppm) 12.00 (s, 1P). MS (ESI, EI⁺) m/z=554 (MH⁺). Example 112 is equivalent to (S)-isomer of Compound IV-142.

Example 113

(S)-5-tert-butyl-1-(3,3-dimethyl-butyl)-3-(1-ethoxy-1-oxo-1,4-dihydro-7-(N-acetyl-methanesulfonamidyl)-1-benzo[1,2,4]phosphadiazin-3-yl)-4-hydroxy-1,5-dihydropyrrol-2-one

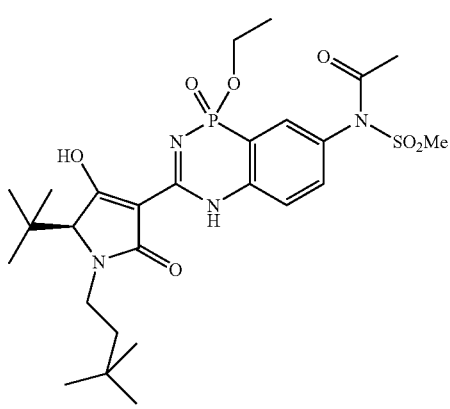

(S)-isomer of (IV-81)

Example 113 was synthesized from example 44. To a stirred suspension of example 44 (30 mmol) in anhydrous THF (1.7 ml) was added a few drop of TEA and acetylchloride (6 μl). The mixture was stirred at room temperature for 5 hours. Purification by preparative HPLC yield example 113, which was a white solid. Example 113 was characterized by the following spectroscopic data: ¹H NMR (DMSO-d₆, 400 MHz) δ (ppm) 0.89 (s, 9H), 1.02 (s, 9H), 1.20 (t, J=7.09 Hz, 3H), 1.25-1.31 (m, 1H), 1.67 (brs, 1H), 1.92 (s, 3H), 3.09-3.16 (m, 1H), 3.40 (m, 4H), 4.02-4.13 (m, 3H), 7.65-7.72 (m, 1H), 7.77-7.79 (m, 1H), 8.02 (d, J=15.19 Hz, 1H), 11.55 (m, 1H). ³¹P NMR (DMSO-d₆, 162 MHz) δ (ppm) −0.85 (s, 1P). MS (ESI, EI⁺) m/z=583 (MH⁺). Example 113 is equivalent to (S)-isomer of Compound IV-81.

Example 114

5-ethyl-5-methyl-1-(3,3-dimethyl-butyl)-3-(1-ethoxy-1-oxo-1,4-dihydro-7-methanesulfonamidyl-1-benzo[1,2,4]phosphadiazin-3-yl)-4-hydroxy-1,5-dihydropyrrol-2-one

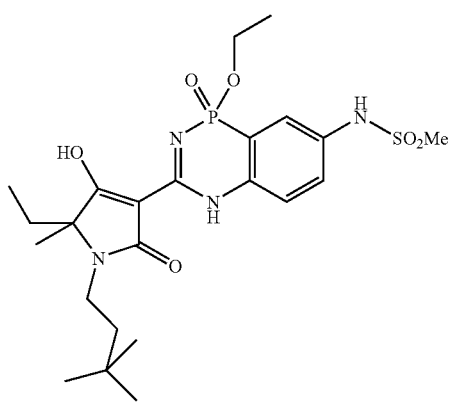

(IV-71)

Example 114 was synthesized from intermediate 185 following the procedure as described for example 44. Example 114 was a white solid. Example 114 was characterized by the following spectroscopic data: ¹H NMR (DMSO-d₆, 400 MHz) δ (ppm) 0.69-0.72 (m, 3H), 0.99 (s, 9H), 1.32-1.37 (m, 6H), 1.50-1.53 (m, 1H), 1.63-1.68 (m, 2H), 1.85-1.89 (m, 1H), 3.05 (s, 3H), 3.41-3.45 (m, 1H), 4.17-4.21 (m, 2H), 7.13-7.19 (m, 1H), 7.46-7.55 (m, 1H), 7.62-7.66 (m, 2H), 11.45 (brs, 1H), 11.59 (m, 1H). $^{31}$P NMR (DMSO-d$_6$, 162 MHz) δ (ppm) 0.34 (s, 1P). MS (ESI, EI$^+$) m/z=527 (MH$^+$). Example 114 is equivalent to Compound IV-71.

Example 115

4-hydroxy-5-methyl-5-trifluoromethyl-1-(3,3-dimethyl-butyl)-3-(1-ethoxy-1-oxo-1,4-dihydro-7-methanesulfonamidyl-1-benzo[1,2,4]phosphadiazin-3-yl)-1,5-dihydropyrrol-2-one

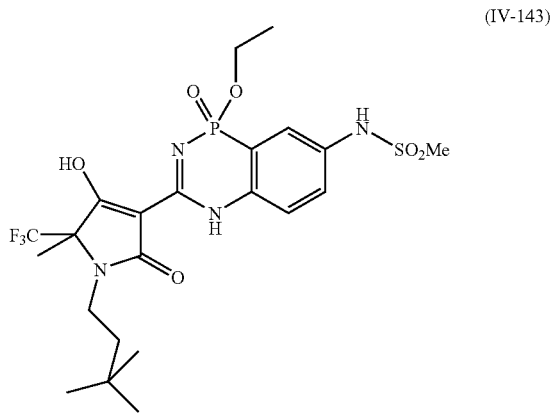

(IV-143)

Example 115 was synthesized from intermediate 188 following the procedure as described for example 44. Example 115 was a white solid. Example 115 was characterized by the following spectroscopic data: $^1$H NMR (DMSO-d$_6$, 400 MHz) δ (ppm) 0.96 (s, 9H), 1.09 (s, 9H), 1.36 (m, 3H), 1.60-1.70 (m, 1H), 1.79-1.85 (m, 1H), 2.93 (s, 1H), 3.06 (s, 3H), 3.29-3.38 (m, 1H), 3.44-3.53 (m, 1H), 4.03-4.19 (m, 2H), 5.12 (brs, 1H), 7.10-7.21 (m, 1H), 7.65-7.69 (m, 2H), 11.59 (m, 1H). $^{31}$P NMR (DMSO-d$_6$, 162 MHz) δ (ppm) 19.07 (s, 1P). MS (ESI, EI$^+$) m/z=557 (MH$^+$). Example 115 is equivalent to Compound IV-143.

Example 116

5-tert-butyl-4,5-dihydroxy-1-(3,3-dimethyl-butyl)-3-(1-ethoxy-1-oxo-1,4-dihydro-7-methanesulfonamidyl-1-benzo[1,2,4]phosphadiazin-3-yl)-1,5-dihydropyrrol-2-one

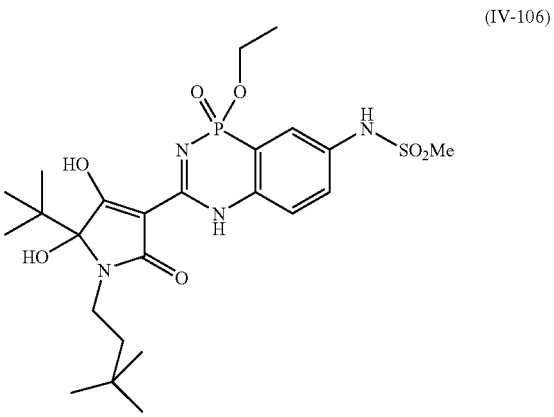

(IV-106)

Example 116 was synthesized from intermediate 191 following the procedure as described for example 44. Example 116 was a white solid. Example 116 was characterized by the following spectroscopic data: $^1$H NMR (DMSO-d$_6$, 400 MHz) δ (ppm) 0.97 (s, 9H), 1.36 (m, 3H), 1.60 (m, 4H), 3.06 (s, 3H), 3.35-3.45 (m, 2H), 4.17-4.24 (m, 2H), 7.17-7.21 (m, 1H), 7.65-7.69 (m, 2H), 7.99-8.03 (m, 1H), 11.59 (m, 1H). $^{31}$P NMR (DMSO-d$_6$, 162 MHz) δ (ppm) 0.35 (s, 1P). $^{19}$F NMR (DMSO-d$_6$, 376 MHz) δ (ppm) −75.04 (s, 1F). MS (ESI, EI$^+$) m/z=567 (MH$^+$). Example 116 is equivalent to Compound IV-106

Example 117

(S)-5-tert-butyl-1-(3,3-dimethyl-butyl)-3-(1-ethoxy-1-oxo-1,4-dihydro-6-ethoxy-1-benzo[1,2,4]phosphadiazin-3-yl)-4-hydroxy-1,5-dihydropyrrol-2-one

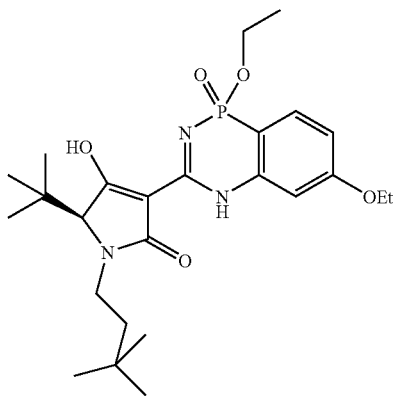

(S)-isomer of (IV-126)

Example 117 was synthesized from intermediate 193 and intermediate 77 following the procedure as described for example 44. Example 117 was a white solid. Example 117 was characterized by the following spectroscopic data: $^1$H NMR (DMSO-d$_6$, 400 MHz) δ (ppm) 0.94 (s, 9H), 1.30-1.34 (t, J=8.64 Hz, 3H), 1.35-1.38 (m, 1H), 1.40-1.46 (t, J=7.02 Hz, 3H), 1.54-1.61 (m, 2H), 3.15-3.18 (m, 1H), 3.92-3.99 (m, 1H), 4.04-4.16 (m, 4H), 6.56 (m, 1H), 6.84 (d, J=8.04 Hz, 1H), 7.65-7.71 (dd, J=15 Hz and J=8.04 Hz, 1H), 10.68-10.82 (m, 1H), 11.44-11.63 (m, 1H). $^{31}$P NMR (DMSO-d$_6$, 162 MHz) δ (ppm) 2.11-2.47 (s, 1P). MS (ESI, EI$^+$) m/z=492 (MH$^+$). Example 117 is equivalent to (S)-isomer of Compound IV-126.

Example 118

(S)-5-tert-butyl-1-(3,3-dimethyl-butyl)-3-(1-ethoxy-1-oxo-1,4-dihydro-7-chloro-5-carbamoyl-1-benzo[1,2,4]phosphadiazin-3-yl)-4-hydroxy-1,5-dihydropyrrol-2-one

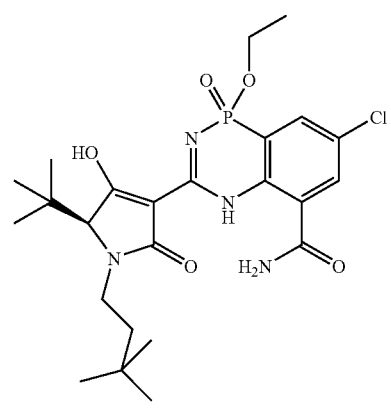

(S)-isomer of (IV-144)

Example 118 was synthesized from intermediate 195 and intermediate 77 following the procedure as described for example 44. The 2 diastereoisomers were separated but not identified.

Example 118a was an off-white solid. Example 118a was characterized by the following spectroscopic data: ¹H NMR (CDCl₃, 400 MHz) δ (ppm) 0.92 (m, 9H), 1.08 (s, 9H), 1.32-1.37 (m, 4H), 1.55-1.61 (m, 4H), 3.12-3.18 (m, 1H), 3.93-3.99 (m, 1H), 4.14-4.19 (m, 1H), 6.56-6.62 (brs, 1H), 7.83-7.88 (m, 1H), 11.63-12.05 (m, 1H), 13.16-13.29 (m, 1H). ³¹P NMR (CDCl₃, 162 MHz) δ (ppm) −1.53 (s, 1P). MS (ESI, EI⁺) m/z=525 (MH⁺).

Example 118b was an off-white solid. Example 118b was characterized by the following spectroscopic data: ¹H NMR (CDCl₃, 400 MHz) δ (ppm) 0.91 (s, 9H), 1.07 (s, 9H), 1.35-1.41 (m, 3H), 1.52-1.62 (m, 4H), 3.10-3.13 (m, 1H), 3.43-3.51 (m, 1H), 4.13-4.17 (m, 2H), 6.41 (m, 1H), 7.84-7.91 (m, 1H), 11.83 (brs, 1H), 13.26 (m, 1H). ³¹P NMR (CDCl₃, 162 MHz) δ (ppm) −1.50 (s, 1P). MS (ESI, EI⁺) m/z=525 (MH⁺).

Example 119

(S)-5-tert-butyl-1-(3,3-dimethyl-butyl)-3-(1-ethoxy-1-oxo-1,4-dihydro-6-hydroxy-1-benzo[1,2,4]phosphadiazin-3-yl)-4-hydroxy-1,5-dihydropyrrol-2-one

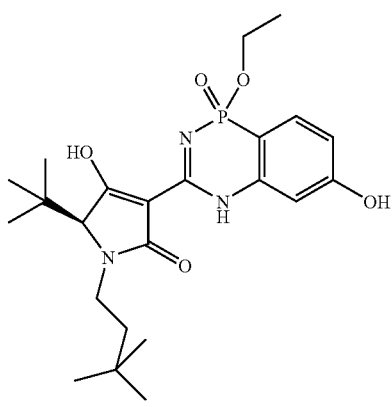

(S)-isomer of (IV-145)

To a cooled solution of intermediate 146 (0.06 mmol) in DCM (600 μl) was added boron tribromide (0.12 mmol). The reaction mixture was stirred at 0° C. for 1 hour. 2 more equivalents of borontribromide were added and the mixture was stirred at room temperature for 16 hours. A few drops of MeOH were added. The mixture was directly purified by silica gel chromatography. Example 119 was a beige powder. Example 119 was characterized by the following spectroscopic data: ¹H NMR (MeOH, 400 MHz) δ (ppm) 0.97 (s, 9H), 1.10 (s, 9H), 1.31 (t, J=7.10 Hz, 3H), 1.39 (m, 1H), 1.64 (m, 1H), 3.20 (m, 1H), 3.58 (s, 1H), 3.94 (m, 1H), 4.06 (m, 2H), 6.72 (d, J=5.91 Hz, 1H), 6.87 (d, J=8.18 Hz, 1H), 7.65 (dd, J=8.64 Hz and J=14.54 Hz, 1H). ³¹P NMR (MeOH, 162 MHz) δ (ppm) 3.95 (s, 1P). MS (ESI, EI⁺) m/z=464 (MH⁺).

Example 119 is equivalent to (S)-isomer of Compound IV-145.

Example 120

(S)-5-tert-butyl-1-(3,3-dimethyl-butyl)-3-(1-hydroxy-1-oxo-1,4-dihydro-6-hydroxy-1-benzo[1,2,4]phosphadiazin-3-yl)-4-hydroxy-1,5-dihydropyrrol-2-one

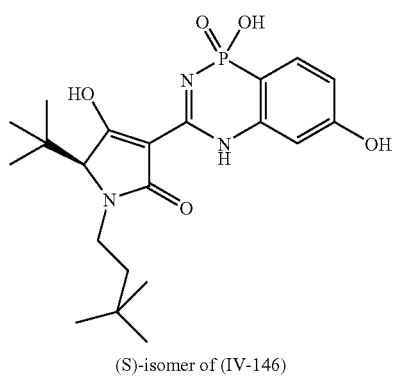

(S)-isomer of (IV-146)

Example 120 was obtained as a by-product from the synthesis of example 119. Example 120 was a beige powder. Example 120 was characterized by the following spectroscopic data: ¹H NMR (MeOH, 400 MHz) δ (ppm) 0.96 (s, 9H), 1.10 (s, 9H), 1.41 (m, 1H), 1.62 (m, 1H), 3.14-3.21 (m, 1H), 3.55 (s, 1H), 3.92-3.99 (m, 1H), 6.66 (m, 1H), 6.83 (m, 1H), 7.62-7.68 (m, 1H). ³¹P NMR (MeOH, 162 MHz) δ (ppm)-2.96 (s, 1P). MS (ESI, EI⁺) m/z=436 (MH⁺). Example 120 is equivalent to (S)-isomer of Compound IV-146.

Example 121

(S)-5-tert-butyl-1-(3,3-dimethyl-butyl)-3-(1-ethoxy-1-oxo-1,4-dihydro-2,4,5-triaza-phospha naphtalen-3-yl-4-hydroxy-1,5-dihydropyrrol-2-one

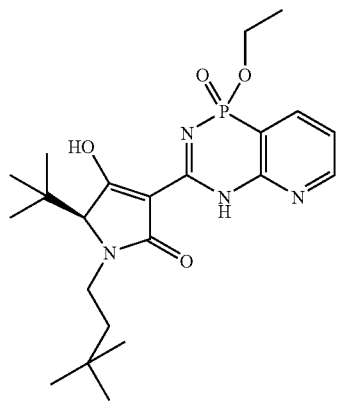

(S)-isomer of (IV-147)

Example 121 was synthesized from intermediate 198 and intermediate 77 following the procedure as described for example 44. Example 121 was a white solid. Example 121 was characterized by the following spectroscopic data: ¹H NMR (CDCl₃, 400 MHz) δ (ppm) 0.87 (s, 9H), 1.01 (s, 9H), 1.30 (m, 3H), 1.51 (m, 2H), 3.07-3.13 (m, 1H), 3.42 (s, 1H), 3.90-3.94 (m, 1H), 4.14-4.17 (m, 2H), 8.03-8.08 (m, 1H), 8.53 (m, 1H), 8.56 (m, 1H), 11.50 (brs, 1H), 11.65 (m, 1H).

$^{31}$P NMR (CDCl$_3$, 162 MHz) δ (ppm) 2.37 (s, 1P). MS (ESI, EI$^+$) m/z=449 (MH$^+$). Example 121 is equivalent to (S)-isomer of Compound IV-147.

Example 122
4-[7-(benzoyl-methanesulfonyl-amino)-1-ethoxy-1-oxo-1,4-dihydro-benzo[1,2,4]diazaphosphinin-3-yl]-1-(3,3-dimethyl-butyl)-2-methyl-5-oxo-2,5-dihydro-pyrrol-3-yl benzoic acid ester (IV-148)

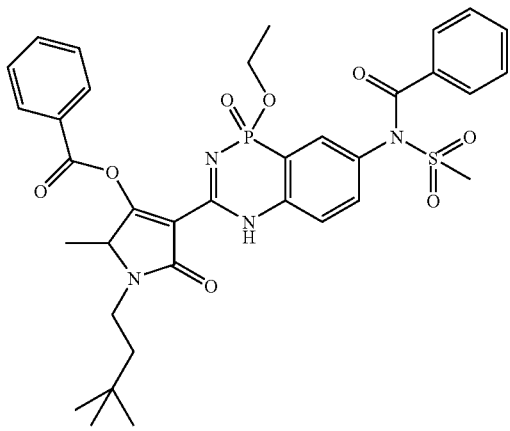

To a stirred solution of example 105 (0.06 mmol) in anh THF (400 μL) was added TEA (10 μl) and benzoyl chloride (8 μl). The reaction mixture was stirred at room temperature for 1 hour. The same amounts of TEA and benzoyl chloride were added and the mixture was stirred for 2 hours at room temperature. EtOAc and brine were then added, organics were separated, dried over Na$_2$CO$_3$, filtered and concentrated under reduced pressure. The crude material was purified by preparative HPLC to give example 122, which was an off-white solid. Example 122 was characterized by the following spectroscopic data: $^1$H NMR (CDCl$_3$, 400 MHz) δ (ppm) 0.80 (t, J=7.18 Hz, 3H), 0.90 (s, 9H), 1.57-1.65 (m, 2H), 2.14 (s, 3H), 2.75 (s, 3H), 3.23-3.29 (m, 1H), 3.42-3.49 (m, 1H), 3.74-3.85 (m, 2H), 6.30-6.34 (m, 1H), 7.58-7.75 (m, 8H), 8.27 (d, J=8.16 Hz, 4H), 8.89 (s, 1H), 8.97 (brs, 1H). $^{31}$P NMR (CDCl$_3$, 162 MHz) δ (ppm) 3.07 (s, 1P). MS (ESI, EI$^+$) m/z=707 (MH$^+$). Example 122 is equivalent to Compound IV-148.

Example 123
N-{3-[1-(3,3-dimethylbutyl)-4-hydroxy-2-oxo-1-aza-spiro[4,4]non-3-en-3-yl]-1-ethoxy-1-oxo-1,4-dihydro-benzo[1,2,4]diazaphosphinin-3-yl}-methanesulfonamide (IV-149)

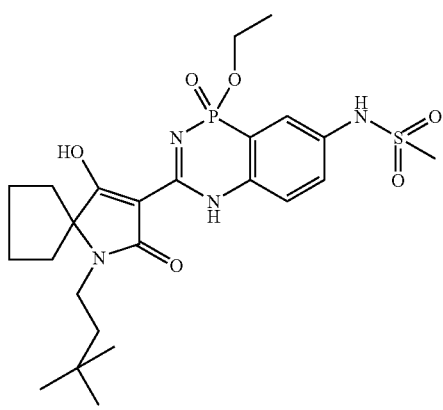

Example 123 was synthesized from intermediate 200 and intermediate 26 following the procedure as described for example 44. Example 123 was a white solid. Example 123 was characterized by the following spectroscopic data: $^1$H NMR (CDCl$_3$, 400 MHz) δ (ppm) 0.98 (s, 9H), 1.31-1.35 (td, J=2.60 Hz and J=7.03 Hz, 3H), 1.60-1.64 (m, 2H), 1.81-1.93 (m, 6H), 2.00-2.04 (m, 2H), 3.02 (d, J=2.60 Hz, 3H), 3.28 (m, 2H), 4.16 (m, 2H), 7.10-7.17 (m, 1H), 7.61-7.66 (m, 2H), 7.70 (brs, 1H), 11.54 (brs, 1H). $^{31}$P NMR (CDCl$_3$, 162 MHz) δ (ppm) 0.83 (s, 1P). MS (ESI, EI$^+$) m/z=539 (MH$^+$). Example 123 is equivalent to Compound IV-149.

Example 124
(S)—N-{3-[5-tert-butyl-1-(2,2-dimethyl-butyl)-4-hydroxy-2-oxo-2,5-dihydro-pyrrol-3-yl]-1-ethoxy-1-oxo-1,4-dihydro-benzo[1,2,4]phosphadiazin-7-yl}-methanesulfonamide

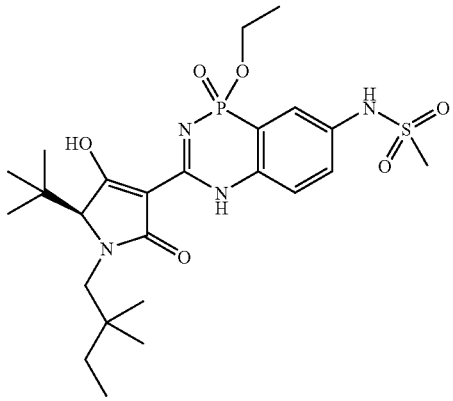

(S)-isomer of (IV-150)

Example 124 was synthesized from intermediate 205 and intermediate 26 following the procedure as described for example 44. Example 124 was a white solid. Example 124 was characterized by the following spectroscopic data: $^1$H NMR (CDCl$_3$, 400 MHz) δ (ppm) 0.88-0.95 (m, 9H), 1.11 (s, 9H), 1.27-1.33 (m, 2H), 1.36-1.42 (m, 3H), 3.09 (s, 3H), 3.81-3.84 (m, 1H), 4.08-4.24 (m, 3H), 7.22 (m, 2H), 7.63-7.66 (m, 2H), 11.69 (m, 1H). $^{31}$P NMR (CDCl$_3$, 162 MHz) δ (ppm) 0.57 (s, 1P). MS (ESI, EI$^+$) m/z=541 (MH$^+$). Example 124 is equivalent to (S)-isomer of Compound IV-150.

Example 125

N-{3-[1-(2,2,4,4-tetramethyl-pentyl)-4-hydroxy-2-oxo-2,5-dihydro-pyrrol-3-yl]-1-ethoxy-1-oxo-1,4-dihydro-benzo[1,2,4]phosphadiazin-7-yl}-methane-sulfonamide

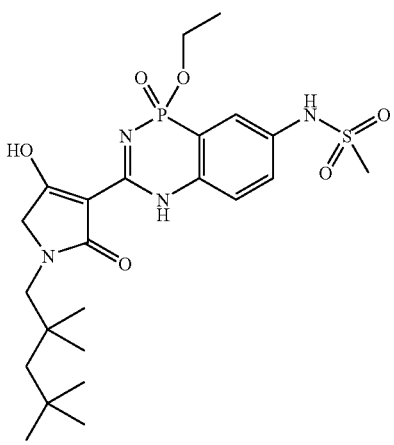

(IV-151)

Example 125 was synthesized from intermediate 207 and intermediate 26 following the procedure as described for example 44. Example 125 was a beige solid. Example 125 was characterized by the following spectroscopic data: $^1$H NMR (CDCl$_3$, 400 MHz) δ (ppm) 0.97 (d, J=3.58 Hz, 9H), 1.35 (td, J=7.38 Hz and J=2.46 Hz, 3H), 1.48 (m, 6H), 1.96 (m, 2H), 3.05 (s, 3H), 3.85 (m, 2H), 4.19 (m, 2H), 6.93 (d, J=11.43 Hz, 1H), 7.25 (m, 1H), 7.60 (m, 1H), 11.4 (brs, 1H), 11.8 (brs, 1H). $^{31}$P NMR (CDCl$_3$, 162 MHz) δ (ppm) 0.41 (s, 1P). MS (ESI, EI$^+$) m/z=513 (MH$^+$). Example 125 is equivalent to Compound IV-151.

Example 126

(S)-5-tert-butyl-1-(3,3-dimethyl-butyl)-3-(1-ethoxy-1-oxo)-1,4-dihydro-7-methyl-2,4,5-triaza-phospha naphtalen-3-yl-4-hydroxy-1,5-dihydropyrrol-2-one

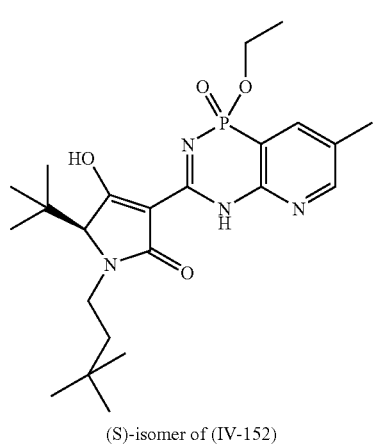

(S)-isomer of (IV-152)

Example 126 was synthesized from intermediate 210 and intermediate 77 following the procedure as described for example 44. Example 126 was a white solid. Example 126 was characterized by the following spectroscopic data: $^1$H NMR (CDCl$_3$, 400 MHz) δ (ppm) 0.86 (s, 9H), 1.02 (s, 9H), 1.23 (m, 4H), 1.64 (m, 1H), 2.36 (s, 3H), 3.37 (m, 1H), 3.59-3.83 (m, 2H), 4.11 (m, 2H), 8.13 (brs, 1H), 8.54 (brs, 1H), 11.64 (brs, 1H). $^{31}$P NMR (CDCl$_3$, 162 MHz) δ (ppm) 1.78 (s, 1P). MS (ESI, EI$^+$) m/z=463 (MH$^+$). Example 126 is equivalent to (S)-isomer of Compound IV-152.

Example 127

(S)-{3-[5-tert-butyl-1-(2,2-dimethyl-butyl)-4-hydroxy-2-oxo-2,5-dihydro-pyrrol-3-yl]-1-(2-benzyloxy-ethyl)-1-oxo-1,4-dihydro-benzo[1,2,4]phosphadiazin-7-yl}-methanesulfonamide

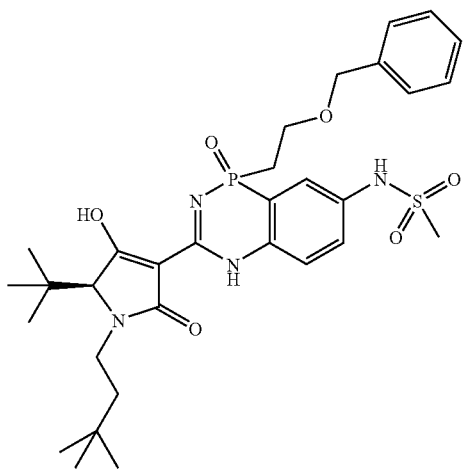

(S)-isomer of (IV-153)

Example 127 was synthesized from intermediate 216 and intermediate 26 following the procedure as described for example 44. Example 127 was an off-white solid. Example 127 was characterized by the following spectroscopic data: $^1$H NMR (CDCl$_3$, 400 MHz) δ (ppm) 0.95 (s, 9H), 1.09 (s, 9H), 1.38-1.41 (m, 1H), 1.58 (m, 1H), 2.52-2.56 (m, 2H), 2.86-2.88 (m, 3H), 3.15-3.18 (m, 1H), 3.48 (m, 1H), 3.84-3.90 (m, 3H), 4.53-4.58 (m, 2H), 7.03-7.56 (m, 8H), 11.47 (m, 1H). $^{31}$P NMR (CDCl$_3$, 162 MHz) δ (ppm) 13.64-14.35 (4s, 1P). MS (ESI, EI$^+$) m/z=631 (MH$^+$). Example 127 is equivalent to (S)-isomer of Compound IV-153.

Example 128

(S)-{3-[5-tert-butyl-1-(2,2-dimethyl-butyl)-4-hydroxy-2-oxo-2,5-dihydro-pyrrol-3-yl]-1-(2-hydroxyethyl)-1-oxo-1,4-dihydro-benzo[1,2,4]phosphadiazin-7-yl}-methanesulfonamide

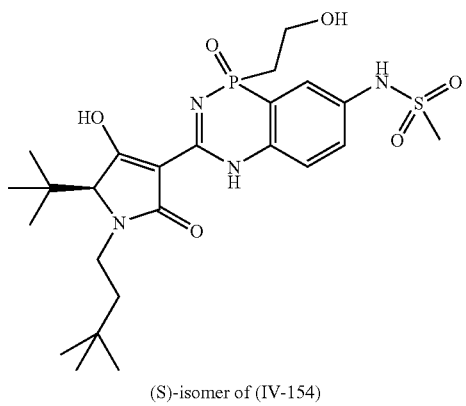

(S)-isomer of (IV-154)

Example 128 was synthesized from example 5084 following the procedure as described for intermediate 216. Example 128 was a beige solid. Example 128 was characterized by the following spectroscopic data: $^1$H NMR (CDCl$_3$, 400 MHz) δ (ppm) 0.95 (s, 9H), 1.09 (s, 9H), 1.38-1.41 (m, 1H), 1.58 (m, 1H), 2.86-2.88 (m, 3H), 3.15-3.18 (m, 1H), 3.48 (m, 1H), 3.84-3.90 (m, 3H), 4.53-4.58 (m, 2H), 7.12-7.56 (m, 3H), 11.47 (m, 1H). $^{31}$P NMR (CDCl$_3$, 162 MHz) δ (ppm) 13.64-14.35 (4s, 1P). MS (ESI, EI$^+$) m/z=541 (MH$^+$). Example 128 is equivalent to (S)-isomer of Compound IV-154.

Example 129

(S)-{3-[5-tert-butyl-1-(2,2-dimethyl-butyl)-4-hydroxy-2-oxo-2,5-dihydro-pyrrol-3-yl]-1-ethyl-1-oxo-1,4-dihydro-benzo[1,2,4]phosphadiazin-7-yl}-methanesulfonamide

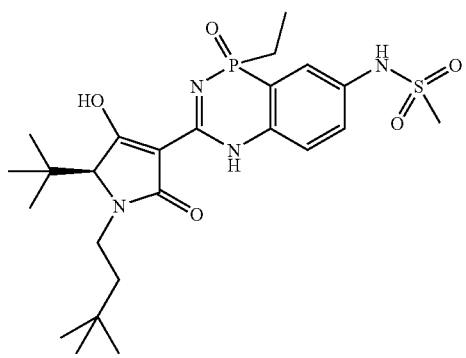

(S)-isomer of (IV-155)

Example 129 was synthesized from intermediate 220 and intermediate 26 following the procedure as described for example 44. Example 129 was an off-White solid. Example 129 was characterized by the following spectroscopic data: $^1$H NMR (CDCl$_3$, 400 MHz) δ (ppm) 0.95 (s, 9H), 1.09 (s, 9H), 1.10-1.12 (1,3H), 1.38-1.41 (m, 1H), 1.58 (m, 1H), 2.86-2.88 (m, 2H), 3.02 (s, 3H), 3.15-3.18 (m, 1H), 3.48 (m, 1H), 3.84-3.90 (m, 1H), 7.12-7.14 (m, 1H), 7.62 (m, 2H), 11.47 (m, 1H). $^{31}$P NMR (CDCl$_3$, 162 MHz) δ (ppm) 19.81-20.43 (m, 1P). MS (ESI, EI$^+$) m/z=525 (MH$^+$). Example 129 is equivalent to (S)-isomer of Compound IV-155.

Example 130

(S)—N-{3-[5-tert-butyl-1-(2,2-dimethyl-butyl)-4-hydroxy-2-oxo-2,5-dihydro-pyrrol-3-yl]-1-(benzyloxy-methyl)-1-oxo-1,4-dihydro-benzo[1,2,4]phosphadiazin-7-yl}-methanesulfonamide

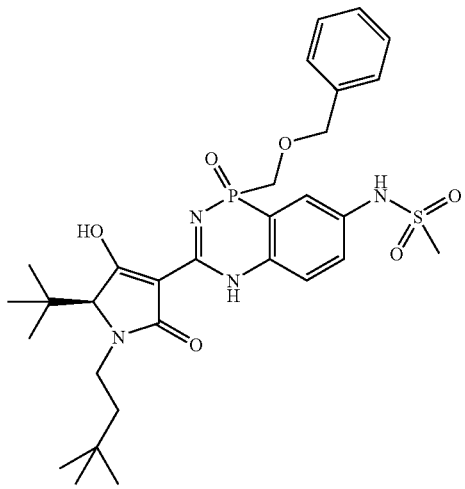

(S)-isomer of (IV-157)

Example 130 was synthesized from intermediate 226 and intermediate 77 following the procedure as described for example 44 and was a yellowish resin. Example 130 was characterized by the following spectroscopic data: $^1$H NMR (CDCl$_3$, 400 MHz) δ (ppm) 0.95 (s, 9H), 1.10 (s, 9H), 1.38-1.41 (m, 1H), 1.58 (m, 1H), 2.98 (s, 3H), 3.15-3.18 (m, 1H), 3.48 (m, 1H), 3.97 (m, 1H), 4.11 (m, 2H), 4.47 (m, 2H), 7.04 (m, 3H), 7.24 (m, 2H), 7.68 (m, 2H), 8.20 (m, 1H), 11.65 (m, 1H). MS (ESI, EI$^+$) m/z=617 (MH$^+$). Example 130 is equivalent to (S)-isomer of compound IV-157.

Example 131

(S)—N-{3-[5-tert-butyl-1-(2,2-dimethyl-butyl)-4-hydroxy-2-oxo-2,5-dihydro-pyrrol-3-yl]-1-(hydroxymethyl)-1-oxo-1,4-dihydro-benzo[1,2,4]phosphadiazin-7-yl}-methanesulfonamide

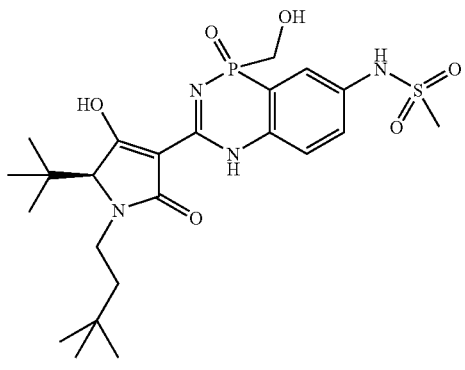

(S)-isomer of (IV-158)

Example 131 was synthesized from example 130 following the procedure as described for example 128 and was an orange resin. Example 131 was characterized by the following spectroscopic data: $^1$H NMR (CDCl$_3$, 400 MHz) δ (ppm) 0.83 (2s, 9H), 1.08 (2s, 9H), 1.22 (m, 1H), 1.38-1.41 (m, 1H), 2.98 (s, 3H), 3.15-3.18 (m, 1H), 3.48 (m, 1H), 3.97 (m, 1H), 4.11 (m, 2H), 7.04 (m, 1H), 7.30 (m, 2H), 8.80 (m, 1H), 11.65 (m, 1H). $^{31}$P NMR (CDCl$_3$, 162 MHz) δ (ppm) 14.12-15.59 (m, 1P). MS (ESI, EI$^+$) m/z=527 (MH$^+$). Example 131 is equivalent to (S)-isomer of compound IV-158.

Example 132

(S)-{3-[5-tert-butyl-1-(2,2-dimethyl-butyl)-4-hydroxy-2-oxo-2,5-dihydro-pyrrol-3-yl]-1-ethyl-1-oxo-1,4-dihydro-benzo[1,2,4]phosphadiazin-7-yl}-methanesulfonamide

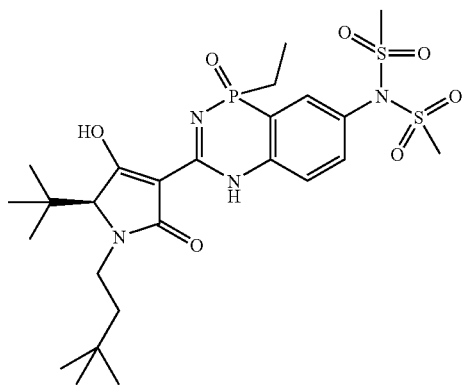

(S)-isomer of (IV-159)

Example 132 was synthesized from intermediate 227 and intermediate 77 following the procedure as described for example 44 and was a yellowish resin. Example 132 was characterized by the following spectroscopic data: $^1$H NMR (CDCl$_3$, 400 MHz) δ (ppm) 0.95 (s, 9H), 1.08 (s, 9H), 1.10-1.12 (m, 3H), 1.38-1.41 (m, 1H), 1.58 (m, 1H), 2.21-2.32 (m, 2H), 3.15-3.22 (m, 1H), 3.40 (m, 6H), 3.70 (m, 1H), 3.93-3.99 (m, 1H), 7.18-7.23 (m, 1H), 7.54-7.58 (m, 1H), 7.73-7.77 (m, 1H), 10.87 (brs, 1H), 11.64 (m, 1H). $^{31}$P NMR (CDCl$_3$, 162 MHz) δ (ppm) 19.81-20.43 (4s, 1P). MS (ESI, EI$^+$) m/z=603 (MH$^+$). Example 132 is equivalent to (S)-isomer of compound IV-159.

Example 133

(S)-3-[5-tert-butyl-1-(3,3-dimethylbutyl)-4-hydroxy-2-oxo-2,5-dihydro-pyrrol-3-yl]-1-ethoxy-1-oxo-benzo-1,2,4-phosphadiazine-6-carboxylic acid amide

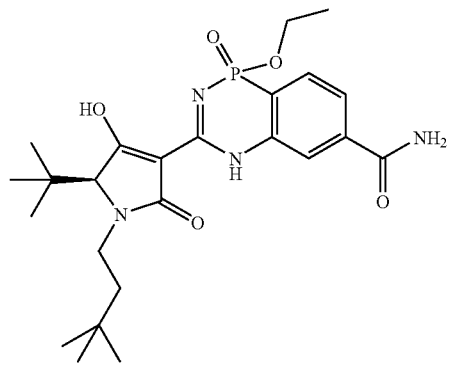

(S)-isomer of (IV-160)

Example 133 was synthesized from intermediate 229 and intermediate 77 following the procedure as described for example 44 and was a beige powder. Example 133 was characterized by the following spectroscopic data: $^1$H NMR (CDCl$_3$, 400 MHz) δ (ppm) 0.95 (s, 9H), 1.09 (s, 9H), 1.33-1.37 (m, 4H), 1.58-1.61 (m, 1H), 3.15-3.21 (m, 1H), 3.49-3.51 (m, 1H), 3.94-4.00 (m, 1H), 4.17-4.19 (m, 2H), 7.67-7.71 (m, 2H), 7.84-7.87 (m, 1H), 11.67-11.82 (m, 1H). $^{31}$P NMR (CDCl$_3$, 162 MHz) δ (ppm) −0.09-0.26 (4s, 1P). MS (ESI, EI$^+$) m/z=491 (MH$^+$). Example 133 is equivalent to (S)-isomer of compound IV-160.

Example 134

(S)-{3-[5-tert-butyl-4-hydroxy-2-oxo-2,5-dihydro-pyrrol-3-yl]-1-ethoxy-1-oxo-benzo-1,2,4-phosphadiazin-7-yl}-methanesulfonamide

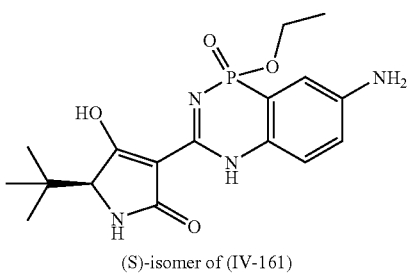

(S)-isomer of (IV-161)

Example 134 was synthesized from intermediate 231 and intermediate 26 following the procedure as described for example 44 and was a white solid. Example 134 was characterized by the following spectroscopic data: $^1$H NMR (CDCl$_3$, 400 MHz) δ (ppm) 1.05 (s, 9H), 1.36-1.39 (m, 3H), 3.05 (s, 1H), 3.59 (m, 1H), 3.61 (s, 1H), 4.19-4.24 (m, 2H), 5.56 (s, 1H), 7.09-7.23 (m, 2H), 7.61-7.65 (m, 2H), 11.67-

11.82 (m, 2H). $^{31}$P NMR (CDCl$_3$, 162 MHz) δ (ppm) –0.09-0.26 (4s, 1P). MS (ESI, EI$^+$) m/z=457 (MH$^+$). Example 134 is equivalent to (S)-isomer of compound IV-161.

Example 135

(S)—N-{3-[5-tert-butyl-1-(3,3-dimethylbutyl)-4-hydroxy-2-thioxo-2,5-dihydro-pyrrol-3-yl]-1-ethoxy-1-thioxo-benzo-1,2,4-phosphadiazin-7-yl}-methane-sulfonamide

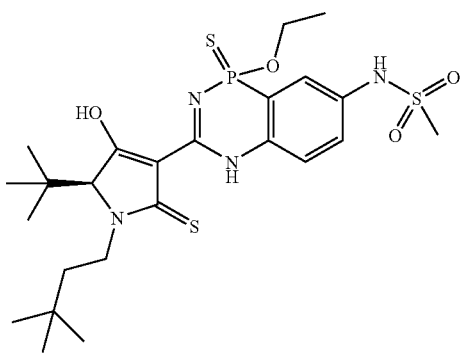

(S)-isomer of (IV-162)

Example 44 (1.25 mmol) and Lawesson's reagent (0.125 mmol) in toluene (1 ml) were stirred at 120° C. for 7 hours. The reaction mixture was concentrated under reduced pressure and purified by preparative HPLC (Water/Acetonitrile 70/30) to give example 135, which was a yellow solid. Example 135 was characterized by the following spectroscopic data: $^1$H NMR (CDCl$_3$, 400 MHz) δ (ppm) 0.95-0.97 (m, 9H), 1.10-1.12 (m, 9H), 1.26-1.30 (m, 3H), 1.33-1.52 (m, 2H), 3.06 (s, 3H), 3.50 (m, 1H), 3.61 (s, 1H), 4.14-4.29 (m, 2H), 4.67-4.75 (m, 1H), 6.51 (s, 1H), 7.16-7.19 (m, 1H), 7.58-7.67 (m, 2H), 12.02 (s, 1H). $^{31}$P NMR (CDCl$_3$, 162 MHz) δ (ppm) 48.18-48.34-48.53-48.59 (4s, 1P). MS (ESI, EI$^+$) m/z=573 (MH$^+$). Example 135 is equivalent to (S)-isomer of compound IV-162.

Example 136

(S)-3-[5-tert-butyl-1-(3,3-dimethyl-butyl)-4-hydroxy-2-oxo-2,5-dihydro-1H-pyrrol-3-yl]-1-hydroxy-1-oxo-1,4-dihydro-benzo[1,2,4]-phosphadiazin-7-yl-carboxylic acid amide

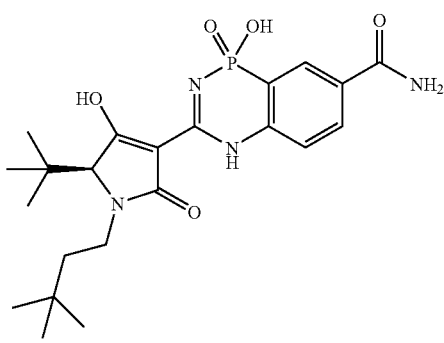

(S)-isomer of (IV-163)

Intermediate 233 (0.05 mmol) and intermediate 77 (0.057 mmol) in solution in pyridine (250 μl) were stirred under microwave irradiations at 200° C. for 30 min. A solution of HCl 1N and EtOAc were added. Organics were dried over Na$_2$SO$_4$, filtered and concentrated under reduced pressure. The crude material was used as it in the next step. Example 136 was a brown oil and was equivalent to (S)-isomer of compound IV-163.

Example 137

(S)-3-[5-tert-butyl-1-(3,3-dimethyl-butyl)-4-ethoxy-2-oxo-2,5-dihydro-1H-pyrrol-3-yl]-1-hydroxy-1-oxo-1,4-dihydro-benzo[1,2,4]-phosphadiazin-7-yl-carboxylic acid amide

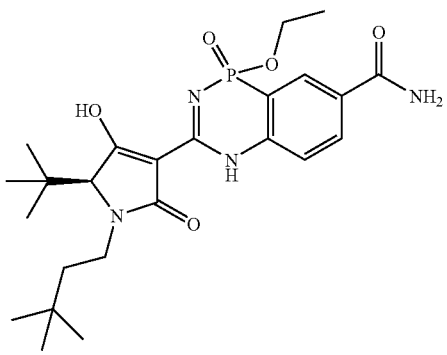

(S)-isomer of (IV-164)

A solution of example 136 (0.06 mmol) in DCM (2 ml) was added to oxalyl chloride (8 μl) in anhydrous DMF (5 μl) at 0° C. The mixture was stirred at room temperature for 1 h30. Anh EtOH (380 μl) was then added and the mixture was let to stir at room temperature for 2 hours. Solvents were evaporated and the crude material was purified by semi-preparative HPLC to yield example 137, which was a white solid. Example 137 was characterized by the following spectroscopic data: $^1$H NMR (DMSO-d$_6$, 400 MHz) δ (ppm)) 0.89 (m, 9H), 1.02 (m, 9H), 1.27 (td, J=5 Hz and J=11.77 Hz, 1H), 1.59-1.71 (m, 1H), 3.74-3.84 (m, 2H), 7.47-7.65 (m, 3H), 10.08 (brs, 1H), 11.37-11.50 (m, 1H). $^{31}$P NMR (DMSO-d$_6$, 162 MHz) δ (ppm) 1.66 (s, 1P), 1.78 (s, 1P). MS (ESI, EI$^+$) m/z=491 (MH$^+$). Example 137 is equivalent to (S)-isomer of compound IV-164.

Example 138

(S)-3-[5-tert-butyl-1-(3,3-dimethyl-butyl)-4-ethoxy-2-oxo-2,5-dihydro-1H-pyrrol-3-yl]-1-hydroxy-1-oxo-1,4-dihydro-benzo[1,2,4]-phosphadiazin-5-yl-carboxylic acid amide

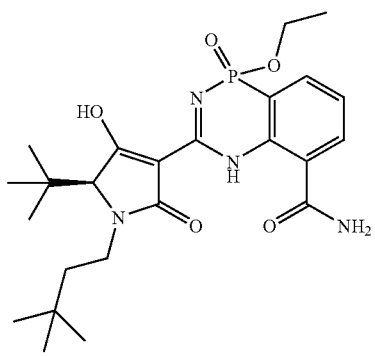

(S)-isomer of (IV-165)

Example 138 was synthesized from intermediate 236 and intermediate 77 following the procedure as described for example 44 and was a white solid. Example 138 was characterized by the following spectroscopic data: $^1$H NMR (CDCl$_3$, 400 MHz) δ (ppm)) 0.91 (m, 9H), 1.07 (m, 9H), 1.32 (t, J=6.35 Hz, 3H), 1.31 (m, 1H), 1.50 (m, 1H), 3.09-3.17 (m, 1H), 3.42-3.50 (m, 1H), 3.98 (brs, 1H), 4.12-4.15 (m, 2H), 6.17-6.40 (brs, 2H), 7.32 (m, 1H), 7.87-7.98 (m, 2H), 11.75 (brs, 1H), 13.37 (brs, 1H). $^{31}$P NMR (DMSO-d$_6$, 162 MHz) δ (ppm) 1.66 (s, 1P), 1.78 (s, 1P). MS (ESI, EI$^+$) m/z=491 (MH$^+$). Example 138 is equivalent to (S)-isomer of compound IV-165.

Example 139

(S)-5-cyclobutyl-1-(3,3-dimethyl-butyl)-3-(1-ethoxy-7-methanesulfonamyl-1-oxo-1,4-dihydro-1-benzo[1,2,4]phosphadiazin-3-yl)-4-hydroxy-1,5-dihydropyrrol-2-one

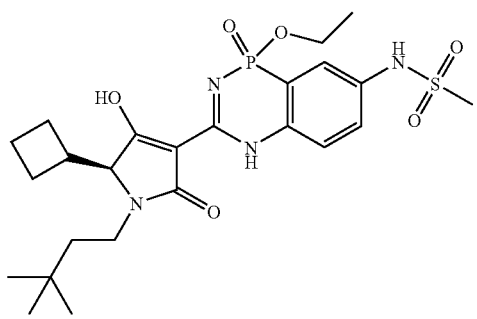

(S)-isomer of (IV-127)

Example 139 was synthesized from Cyanocarbonyl-(3,3-dimethyl-butyl)-amino]-cyclobutyl-acetic acid methyl ester (obtained from L-cyclobutylglycine following the procedures as described for intermediate 120) following the procedure as described for example 44. Example 139 was a white solid. Example 139 was characterized by the following spectroscopic data: $^1$H NMR (CDCl$_3$, 400 MHz) δ (ppm) 0.96 (s, 9H), 1.30-1.42 (m, 4H), 1.49-1.59 (m, 1H), 1.80-2.16 (m, 5H), 2.22-2.35 (m, 1H), 2.60-2.76 (m, 1H), 3.04 (s, 3H), 3.71-3.88 (m, 2H), 4.11-4.22 (m, 2H), 7.12-7.20 (m, 1H), 7.47-7.57 (m, 1H), 7.59-7.68 (in 2H), 11.52-11.60 (m, 1H). $^{31}$P NMR (DMSO-d$_6$, 162 MHz) δ (ppm) 0.53 (m, 1P); MS (ESI, EI$^+$) m/z=539 (MH$^+$). Example 139 is equivalent to (S)-isomer of Compound IV-127.

Example 140

(S)-5-tert-butyl-1-(3-methoxy-4-fluoro-3-methylbenzyl)-3-(1-ethoxy-7-methanesulfonamyl-1-oxo-1,4-dihydro-1-benzo[1,2,4]phosphadiazin-3-yl)-4-hydroxy-1,5-dihydropyrrol-2-one

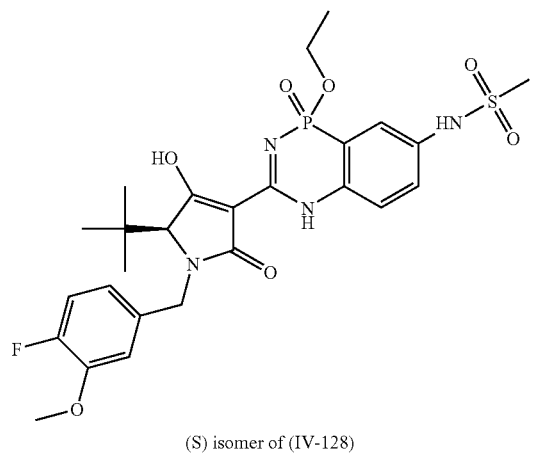

(S) isomer of (IV-128)

Example 140 was synthesized from intermediate 26 and intermediate 238 following the procedure as described for example 44 and was an off white solid. Example 140 was characterized by the following spectroscopic data: $^1$H NMR (CDCl$_3$, 400 MHz) δ (ppm) 1.07 (s, 9H), 1.34-1.40 (m, 3H), 3.04 (s, 3H), 3.33-3.39 (m, 1H), 3.85-3.86 (m, 3H) 4.15-4.29 (m, 3H), 5.19-5.23 (m, 1H), 6.66-6.70 (m, 1H), 6.75-6.84 (m, 1H), 6.98-7.04 (m, 1H) 7.16-7.22 (m, 1H), 7.64-7.68 (m, 2H), 7.75-7.81 (m, 1H), 11.52 (d, J=3.48 Hz, 0.5H), 11.79 (d, J=3.48 Hz, 0.5H). $^{31}$P NMR (CDCl$_3$, 162 MHz) δ (ppm) 0.56-0.81 (q, 1P). $^{19}$F NMR (CDCl$_3$, 376 MHz) δ (ppm) −136.74-136.53 (q, 1F). MS (ESI, EI$^+$) m/z=595 (MH$^+$). Example 140 is equivalent to (S)-isomer of Compound IV-128.

Example 141

(S)-5-tert-butyl-1-(3,4-difluoro-3-methylbenzyl)-3-(1-ethoxy-7-methanesulfonamyl-1-oxo-1,4-dihydro-1-benzo[1,2,4]phosphadiazin-3-yl)-4-hydroxy-1,5-dihydropyrrol-2-one

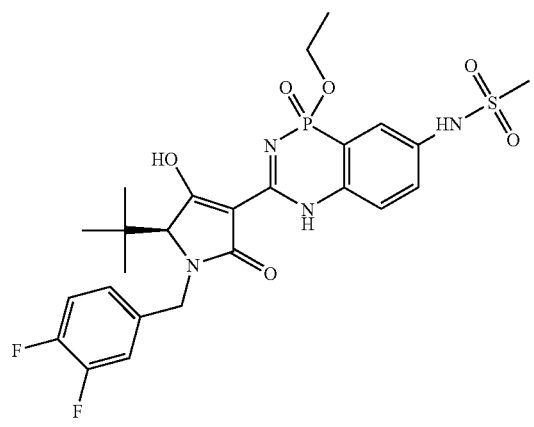

(S)-isomer of (IV-129)

Example 142 was synthesized from intermediate 26 and intermediate 240 following the procedure as described for example 44, and was an off white solid. Example 141 was characterized by the following spectroscopic data: $^1$H NMR (CDCl$_3$, 400 MHz) δ (ppm) 1.06 (s, 9H), 1.34-1.38 (m, 3H), 3.05 (s, 3H), 3.31-3.37 (m, 1H), 4.18-4.31 (m, 3H), 5.16-5.30 (m, 1H), 6.90-6.93 (m, 1H), 6.99-7.03 (m, 1H), 7.08-7.26 (m, 2H), 7.65-7.68 (m, 2H), 7.78 (s, 1H), 11.48 (d, J=3.48 Hz, 0.5H), 11.79 (d, J=3.48 Hz, 0.5H). $^{31}$P NMR (CDCl$_3$, 162 MHz) δ (ppm) 0.52-0.68 (q, 1P). $^{19}$F NMR (CDCl$_3$, 376 MHz) δ (ppm) −139.32-139.19 (q, 1F), −136.79-136.55 (m, 1F). MS (ESI, EI$^+$) m/z=583 (MH$^+$). Example 141 is equivalent to (S)-isomer of Compound IV-129.

Example 142

(S)-5-tert-butyl-1-(3-methylbenzyl)-3-(1-ethoxy-7-methanesulfonamyl-1-oxo-1,4-dihydro-1-benzo[1,2,4]phosphadiazin-3-yl)-4-hydroxy-1,5-dihydropyrrol-2-one

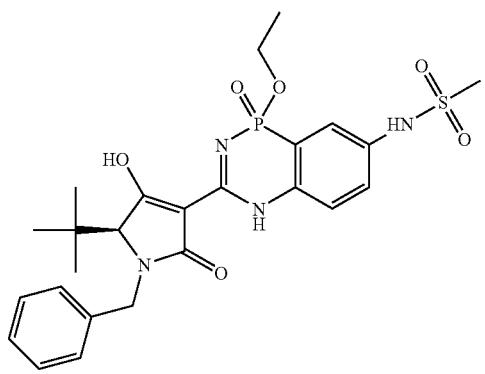

(S)-isomer of (IV-130)

Example 142 was synthesized from intermediate 26 and intermediate 242 following the procedure as described for example 44 and was an off white solid. Example 142 was characterized by the following spectroscopic data: $^1$H NMR (CDCl$_3$, 400 MHz) δ (ppm) 1.07 (s, 9H), 1.33-1.37 (m, 3H), 3.04 (s, 3H), 3.33-3.38 (m, 1H), 4.18-4.23 (m, 3H), 5.34-5.46 (m, 1H), 7.13-7.18 (m, 3H), 7.26-7.33 (m, 3H), 7.64-7.69 (m, 2H), 7.75-7.90 (m, 1H), 11.56 (d, J=3.48 Hz, 0.5H), 11.79 (d, J=3.48 Hz, 0.5H). $^{31}$P NMR (CDCl$_3$, 162 MHz) δ (ppm) 0.39-0.60 (m, 1P). MS (ESI, EI$^+$) m/z=547 (MH$^+$). Example 142 is equivalent to (S)-isomer of Compound IV-130.

Example 143

HCV Polymerase Assay

The HCV polymerase assay was performed in 96-well streptavidin-coated microtiter plates (Pierce) using 50 nM HCV genotype 1b polymerase (strain J4) from Replizyme, 15 µM bromo-UTP, 1 µg/ml 5'-biotynilated oligo (rU12), 1 µg/ml poly(rA) in 20 mM Tris-HCl pH 7.5, 5 mM MgCl$_2$, 0.5 µg/ml BSA, 1 mM DTT, 0.02 U/µl RNasin, 5% DMSO and 25 mM KCL. The 60-µl reaction was incubated at 35° for 60 minutes and terminated by adding 20 µL 0.5 M EDTA pH 8.0. The BrUTP incorporated onto the biotinylated primer was quantified by ELISA using a peroxidase-labeled anti-BrdU monoclonal antibody (Roche) and TMB (Sigma) substrate and the plates were read at 630 nm with the Tecan Sunrise Stectrophotometer. The compounds were routinely solubilised at a concentration of 15 mM in DMSO and tested at a variety of concentrations in assay buffer containing a final DMSO concentration of 5%. The IC$_{50}$ values were determined from the percent inhibition versus concentration data using a sigmoidal non-linear regression analysis based on four parameters with Tecan Magellan software. The biological results are summarized in Table 2 (IC$_{50}$).

Example 144

HCV Replicon Assay

General procedure: Huh-7 cells containing HCV Con1 subgenomic replicon (GS4.1 cells) were grown in Dulbecco's Modified Eagle Medium (DMEM) supplemented with 10% fetal bovine serum (FBS), 2 mM L-glutamine, 110 mg/L sodium pyruvate, 1× non-essential amino acids, 100 U/mL penicillin-streptomycin, and 0.5 mg/mL G418 (Invitrogen). For dose-response testing, the cells were seeded in 96-well plates at 7.5×10$^3$ cells/well in a volume of 50 µL, and incubated at 37° C./5% CO$_2$. Three hours after plating, 50 µL of ten 2-fold serial dilutions of compounds (highest concentration, 75 µM) were added, and cell cultures were incubated at 37° C./5% CO$_2$ in the presence of 0.5% DMSO. Alternatively, compounds were tested at a single concentration of 15 µM. In all cases, Huh-7 cells lacking the HCV replicon served as negative control. The cells were incubated in the presence of compounds for 72 hours after which they were monitored for expression of the NS4A protein by enzyme-linked immunosorbent assay (ELISA). For this, the plates were then fixed for 1 min with acetone/methanol (1:1, v/v), washed twice with phosphate-buffered saline (PBS), 0.1% Tween 20, blocked for 1 hour at room temperature with TNE buffer containing 10% FBS and then incubated for 2 hours at 37° C. with the anti-NS4A mouse monoclonal antibody A-236 (ViroGen) diluted in the same buffer. After washing three times with PBS, 0.1% Tween 20, the cells were incubated 1 hour at 37° C. with anti-mouse immunoglobulin G-peroxidase conjugate in TNE, 10% FBS. After washing as described above, the reaction was developed with O-phenylenediamine (Zymed). The reaction was stopped after 30 min with 2 N H$_2$SO$_4$, and absorbance was read at 492 nm using Sunrise Tecan spectrophotometer. EC$_{50}$ values were determined from the % inhibition versus concentration data using a sigmoidal non-linear regression analysis based on four parameters with Tecan Magellan software. When screening at a single concentration, the results were expressed as % inhibition at 15 µM. The biological results are summarized in Table 1 (EC$_{50}$ and CC$_{50}$).

TABLE 1
| Compound | EC$_{50}$ (μM) | CC$_{50}$ (μM) | Comment |
|---|---|---|---|
| 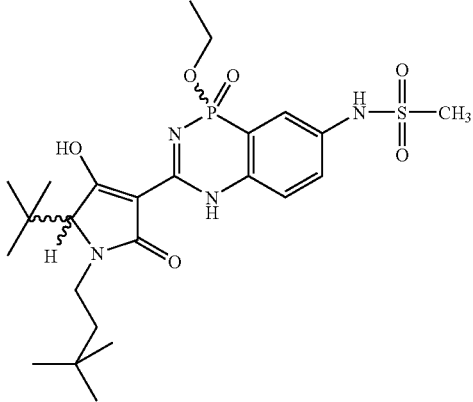 (IV-125) | 0.00109<br>0.00180 | >75<br>>75 | 60.5% viability<br>62% viability |
| 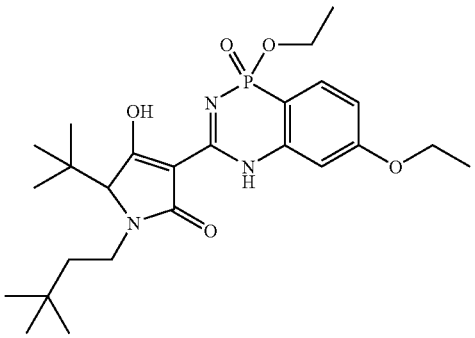 (IV-156) | 7.38794<br>8.03056 | 31.96<br>35.87827 | —<br>— |
| 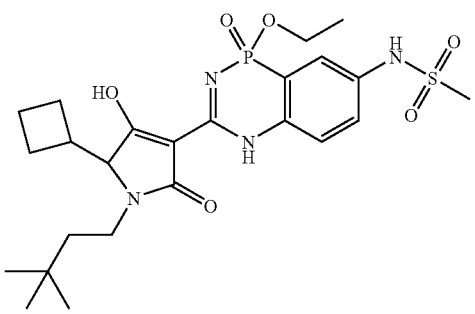 (IV-127) | 0.46836<br>0.30506 | >75<br>>75 | 64.4% viability<br>64% viability |

TABLE 1-continued
| Compound | EC$_{50}$ (μM) | CC$_{50}$ (μM) | Comment |
|---|---|---|---|
| 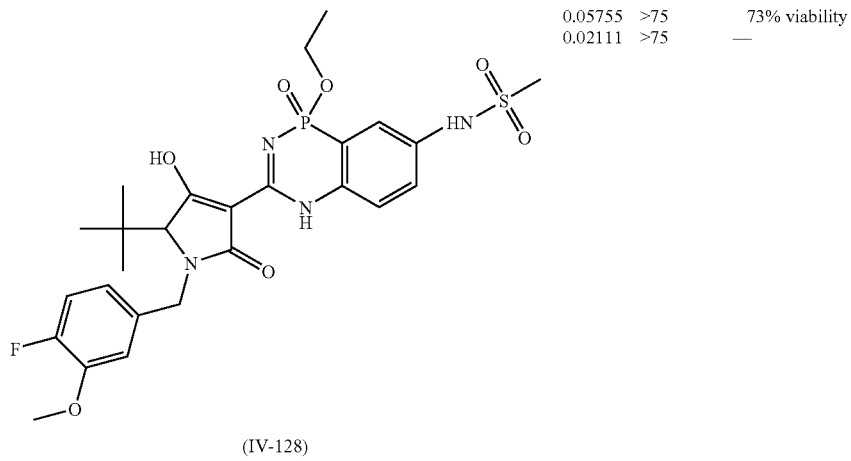 (IV-128) | 0.05755<br>0.02111 | >75<br>>75 | 73% viability<br>— |
| 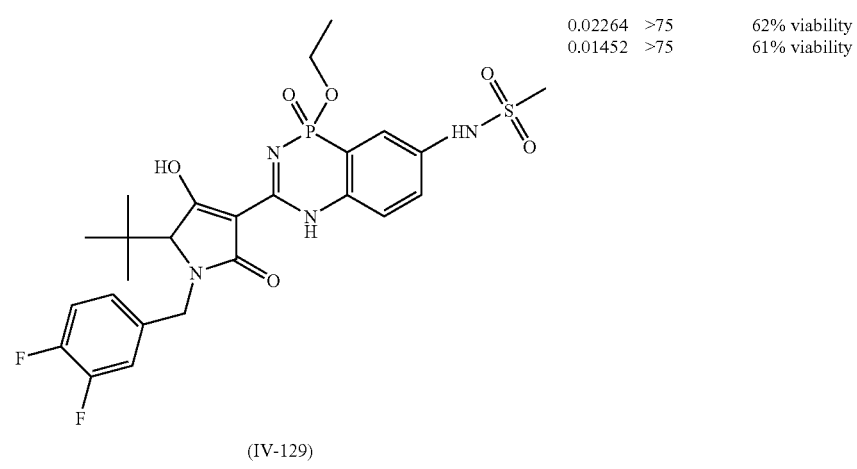 (IV-129) | 0.02264<br>0.01452 | >75<br>>75 | 62% viability<br>61% viability |

In some embodiments, provided herein are individual diastereoisomers of compound IV-50 (equivalent to Example 60A) and they are Compound IV-50A, IV-50B, IV-50C, or IV-50D as shown below:

(IV-50A)
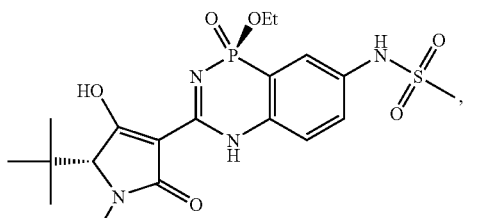

(IV-50B)
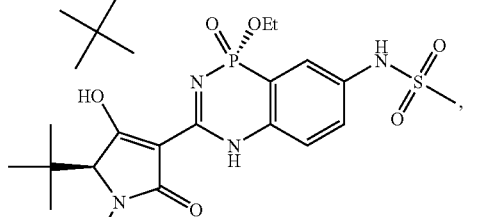

(IV-50C)
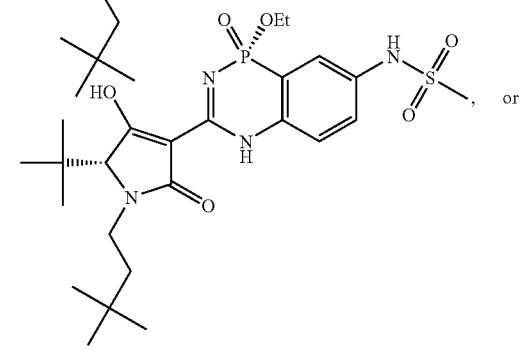

, or (IV-50D)
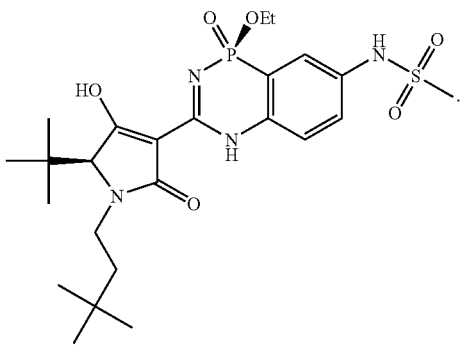

HCV polymerase assays using HCV genotypes 1a and 1b polymerases were conducted on Compound IV-50 and its four stereoisomers (i.e., Compound IV-50A, IV-50B, IV-50C, and IV-50D), following similar procedures as described in Example 134 above. Results are summarized in Table 2 ($IC_{50-1a}$ and $IC_{50-1b}$).

HCV Replicon assay using genotype 1b was also conducted on Compound IV-50 and its four stereoisomers (i.e., Compound IV-50A, IV-50B, IV-50C, and IV-50D), following similar procedures as described in Example 135 above. Results are summarized in Table 2 ($EC_{50-1b}$ and $CC_{50}$) below.

The therapeutic index (TI) and the 1a/1b FC were analyzed. Results are shown in Table 2 below.

TABLE 2

| Compound | $IC_{50-1b}$ (μM) | $IC_{50-1a}$ (μM) | $EC_{50-1b}$ (μM) | $CC_{50}$ (μM) | TI | 1a/1b FC |
|---|---|---|---|---|---|---|
| (IV-50) | 0.012 | 0.061 | 0.0065 | >75 | >11500 | 5 |
| Compound IV-50 diastereoisomer 1 | 0.7 | — | 1.39 | >75 | >54 | — |
| Compound IV-50 diastereoisomer 2 | 0.0055 | 0.015 | 0.0018 | >75 | >41600 | 3 |
| Compound IV-50 diastereoisomer 3 | 2.17 | — | 5.83 | >75 | >13 | — |
| Compound IV-50 diastereoisomer 4 | 0.0145 | — | 0.568 | >75 | >132 | — |

Example 145

In Vitro Inhibition of HCV Wild-Type Polymerases of Different Genotypes

The stereoisomer 2 of compound IV-50 was further analyzed for its ability to inhibit the in vitro polymerase activity of HCV wild-type polymerases of different genotypes.

The polymerase enzymes employed in this Example were either expressed and purified by the sponsor or purchased as research-only reagents from commercial sources. The protein expression constructs used in this study encode the 65 kDa HCV NS5B protein of genotype 1b (strain Con-1) in a standard bacterial expression system used to generate recombinant polymerase enzymes.

Recombinant HCV polymerase of genotypes 1a, 2a and 3a were purchased from Replizyme Ltd, York, UK with the following details:
1. HCV NS5B genotype 1a (H77) C-term Δ-21; lot# RZ10972
2. HCV NS5B genotype 2a (J6) C-term Δ-21; lot# RZ10950
3. HCV N5SB genotype 3a C-term Δ-21; lot# RZ10846

Generation of HCV 1b Polymerases

Carboxyterminally hexa-histidine tagged wild-type and site-directed mutant (SDM) HCV polymerase enzymes were expressed and purified to 85-90% purity from E. coli BL21 (DE3) cells utilizing a single step nickel affinity chromatography procedure. Briefly, a HisTrap HP column (GE Healthcare Life Sciences) was used for capture of the tagged protein. After a linear imidazole gradient elution (100 to 500 mM) the protein-containing fractions were pooled. Proteins were then concentrated at 4° C. in an Amicon Ultra-5 filtration unit, which contains a membrane with a molecular weight cutoff of 30 kDa (Millipore) as recommended by the manufacturer, and then exchanged into enzyme storage buffer (20% glycerol, 10 mM DTT, 25 mM Tris-HCl pH 7.4, 300 mM NaCl, 0.4 mM Pefabloc) using PD10 desalting columns (GE Healthcare Life Sciences). Enzymes were stored at −80° C.

Preparation of Compound Solutions

The stocks of the stereoisomer 2 of compound IV-50 were prepared as 10 mM solutions in nuclease-free water and stored in small aliquots at −20° C. For assays to determine how the stereoisomer 2 of compound IV-50 inhibits the in vitro polymerization activity of HCV NS5B enzymes, serial dilutions of the stereoisomer 2 of compound IV-50 were prepared in an aqueous 5 μM ATP solution. For the HCV NS5B reactions, two-fold serial dilutions of the stereoisomer 2 of compound IV-50 yielded final drug test concentrations of 20 mM to 9.77 nM. For assays to determine the inhibitory constant ($K_I$) for the interaction between drug and enzyme, and to determine the Michaelis-Menten constant ($K_M$) for the interaction between natural substrate (GTP) and enzyme, the stereoisomer 2 of compound IV-50 was prepared in 5 μM CTP solution to yield final drug test concentrations of 1,000, 500, 250 and 125 nM.

HCV Polymerase Assays for $IC_{50}$ Determinations

These assays measured the inhibitory effect of drug on the incorporation of [$^{33}$P]-labeled guanosine monophosphate (GMP) into trichloroacetic acid (TCA) precipitable material. Radiolabeled product was collected by filtration onto 96-well filter plates and quantitated by liquid scintillation counting. Synthetic RNA oligonucleotides were used as template for the synthesis of a complementary RNA strand.

Ninety-six-well flexible plates containing the test article were prepared as follows: 10 μL of the serially-diluted stereoisomer 2 of compound IV-50 in 5 μM ATP was transferred to triplicate wells in adjacent columns. Plates were kept on ice prior to enzyme addition. Ten μL of 500 mM EDTA was added to column 1 of the assay plate to determine the background radioactivity. Ten μL of 5 μM ATP was added to columns 2 and 3 of the assay plate for the no-drug control. Reaction cocktail was prepared in bulk on ice; to start the reactions 40 μL of reaction cocktail was added to each well of the assay. Thus, the final reaction volume was 50 μL. Final concentrations of all reagents in reactions were listed in Table 3 below.

TABLE 3

| Reagent | Concentration |
| --- | --- |
| Sodium glutamate | 20 mM |
| Magnesium chloride | 4 mM |
| Manganese chloride | 1 mM |
| Dithiothreitol | 10 mM |
| Triton X-100 | 0.1% |
| RNase inhibitor | 5 units/reaction |
| Bovine serum albumin | 50 μg/mL |
| ATP | 1 μM |
| CTP | 1 μM |
| UTP | 1 μM |
| GTP | 50 nM |
| α-[$^{33}$P]GTP | 0.1 μCi/reaction |
| RNA template | 30 nM |
| HCV polymerase | ~11-350 nM |
| the stereoisomer 2 of compound IV-50 | variable, as described |
| Nuclease-free water | to final volume of 50 μL |

The reactions were incubated at 30° C. for 2 hours and terminated by the addition of 50 mL precipitation solution (22.5% TCA, 25 mM sodium pyrophosphate, ice cold), followed by precipitation on ice for at least 20 minutes. Plates were harvested on a Packard Unifilter Harvester (Perkin Elmer Life Sciences) using GF/B filter plates (Perkin Elmer Life Sciences) pre-rinsed with 0.1 M sodium pyrophosphate. Plates were washed extensively with deionized water followed by an ethanol wash to aid drying. Plates were allowed to air dry, followed by addition of MicroScint-O (35 μL per well; Perkin Elmer Life Sciences). Plates were counted on the Packard TopCount Liquid Scintillation counter (Perkin Elmer Life Sciences). $IC_{50}$ values were calculated from single-site dose response curves by best-fit equations determined with XLfit 4.1 software. Results are shown in Table 4 below.

TABLE 4

| Enzyme | $N^a$ | Mean $IC_{50}^b$ ± $SD^c$ (nM) |
| --- | --- | --- |
| HCV 1a | 2 | 29.79 ± 3.37 |
| HCV 1b | 2 | 17.62 ± 4.71 |
| HCV 2a | 2 | >1,000 |
| HCV 3a | 2 | >1,000 |
| HCV 4a | 2 | >1,000 |

$^a$N = number of independent experiments
$^b$IC50 = 50% inhibitory concentration
$^c$SD = standard deviation

Example 146

In Vitro Inhibition of Wild-Type and Mutant HCV 1b Polymerases

The stereoisomer 2 of compound IV-50 was further analyzed for its in vitro inhibition activity of wild-type and mutant polymerases. The polymerase enzymes employed in this Example were either expressed and purified by the sponsor or purchased as research-only reagents from commercial sources. The protein expression constructs used in this study encode the 65 kDa HCV NS5B protein of genotype 1b (strain Con-1) in a standard bacterial expression system used to generate recombinant polymerase enzymes. Site-directed HCV pol plasmids carrying a single amino acid substitution were generated by site-directed mutagenesis of the wild-type constructs using a commercial mutagenesis kit as recommended by the manufacturer. The expression constructs utilized in this example were:

1. HCV genotype 1b wild-type polymerase (with a deletion of the 21 carboxyterminal amino acids) cloned into NheI/XhoI restriction sites of expression vector pET21a (Amp$^r$). Clone number 9-15.
2. HCV 1b S282T polymerase contains a single serine-to-threonine substitution at residue 282 within the B domain of the NS5B gene in same expression vector.

$IC_{50}$ values were calculated according to the same procedures as described in Example 145 above. Results are shown in Table 5 below.

TABLE 5

| Enzyme | N$^a$ | Mean IC50$^b$ ± SD$^c$ (nM) | Fold resistance$^d$ |
|---|---|---|---|
| HCV wild-type | 4 | 5.6 ± 1.2 | 1 |
| HCV S282T | 4 | 9.8 ± 3.5 | 1.7 ± 0.3 |
| HCV C316Y | 4 | 748.9 ± 101.1 | 140.7 ± 43.4 |
| HCV S365T | 4 | 11.5 ± 2.9 | 2.0 ± 0.2 |
| HCV M414T | 4 | 16.2 ± 2.6 | 3.0 ± 0.8 |
| HCV M423T | 4 | 5.3 ± 0.6 | 1.0 ± 0.1 |
| HCV Y448H | 4 | 39.6 ± 6.8 | 7.4 ± 2.3 |

$^a$N = number of independent experiments
$^b$IC50 = 50% inhibitory concentration
$^c$SD = standard deviation
$^d$Fold resistance was calculated first for each individual experiment; then the mean fold resistance value ± standard deviation was derived by calculating the mean of the fold-resistance values from the individual experiments.

Example 147

HCV Polymerase Assays for Determination of Kinetic Parameters

These assays calculated biochemical properties describing the interaction between the stereoisomer 2 of compound IV-50 and wild-type HCV 1b polymerases ($K_I$), and the interaction between natural substrate GTP and HCV ($K_M$). The assays measured the incorporation of α-[$^{33}$P]GMP into TCA precipitable material at several fixed concentrations of drug (0, 125, 250, 500 and 1,000 nM) and variable concentrations of GTP. The radiolabeled product was collected by filtration onto 96-well filter plates, and then quantitated by liquid scintillation counting. Synthetic RNA oligonucleotides as described above were employed as template for the synthesis of a complementary RNA strand. The RNA oligonucleotide HHB01 was employed as template for the synthesis of a complementary RNA strand.

Assays were performed in 96-well flexible plates. Plates and reagents were kept on ice during preparation. Each assay condition was performed in triplicate in each experiment. Results were the mean of at least three independent experiments.

Ten μL of the stereoisomer 2 of compound IV-50 in 125 μM CTP was added to reaction plates at fixed concentrations in three adjacent columns. Final reaction concentrations of drug in the HCV 1b assays were 0, 125, 250, 500 and 1,000 nM. Ten μL of 500 mM EDTA was added to the first three columns in the reaction plate to determine background radioactivity. GTP solution consisting of 50 μM unlabeled GTP containing 20 μCi of α-[$^{33}$P] GTP per nanomole of unlabeled GTP was prepared in 125 μM CTP. This GTP stock was then serially diluted in 125 μM CTP. Ten μL of the serial GTP dilutions were added to the appropriate reaction wells. Final concentrations of GTP in reactions were 10 μM, 5 μM, 1 μM, 200 nM, 100 nM, 50 nM, 20 nM and 10 nM. The reaction cocktail was prepared in bulk on ice, and 30 μL aliquots were added to each reaction well in the assay plate, for a final reaction volume of 50 μL. Final concentrations of all reagents in reactions were listed in Table 7 below.

TABLE 6

| Reagent | Concentration |
|---|---|
| Sodium glutamate | 20 mM |
| Magnesium chloride | 4 mM |
| Manganese chloride | 1 mM |
| Dithiothreitol | 10 mM |
| Triton X-100 | 0.1% |
| RNase inhibitor | 5 units/reaction |
| Bovine serum albumin | 50 μg/mL |
| ATP | 50 μM |
| CTP | 50 μM |
| UTP | 50 μM |
| GTP | variable, as described |
| α-[$^{33}$P]GTP | varies with GTP dilution |
| RNA template | 14 nM |
| HCV polymerase | 30-100 nM |
| the stereoisomer 2 of compound IV-50 | fixed concentrations, as described |
| Nuclease-free water | to final volume of 50 μL |

Reactions were incubated at 30° C. for 60 minutes and terminated by the addition of 50 μL precipitation solution (22.5% TCA, 25 mM sodium pyrophosphate, ice cold), followed by precipitation on ice for at least 20 minutes. Plates were harvested on a Packard Unifilter Harvester (Perkin Elmer Life Sciences) using CF/B filter plates (Perkin Elmer Life Sciences) pre-rinsed with 0.1 M sodium pyrophosphate. Plates were washed extensively with deionized water followed by an ethanol wash to aid drying. Plates were allowed to air dry, followed by addition of MicroScint-O (35 μL per well; Perkin Elmer Life Sciences). Plates were counted on the Packard Top Count Liquid Scintillation counter (Perkin Elmer Life Sciences). Triplicate data from each experiment were first imported into Microsoft Excel to average and subtract out background radioactivity. Then, Lineweaver-Burk plots were generated to determine if data fit a model of competitive inhibition.

Averaged data for each experiment were then input to GraphPad Prism 5.00 (GraphPad Software, San Diego, Calif., USA) and fit to a competitive inhibition model of enzyme kinetics using a standard formula. A family of data curves was produced from each experiment, with data derived at each concentration of drug generating one curve within the family. All curves from an experiment were solved simultaneously. Global best-fit values for $K_M$ and $K_I$ were calculated from each family of curves. $K_M$ and $K_I$ were calculated from the equations: $K_{M,\,observed} = K_M \times (1+[I]/K_I)$ and $V_{=Vmax} \times [GTP]/(K_{M,\,observed}+[GTP])$ where $K_M$ is the Michaelis-Menten constant for the natural substrate GTP; $K_{M,\,observed}$ is the apparent $K_M$ in a reaction containing drug; [I] is the concentration of inhibitory drug (the stereoisomer 2 of compound IV-50); $K_I$ is the inhibitory constant for the drug; V is the velocity as measured by radioactivity counts; $V_{max}$ is the maximal (calculated) velocity, and [GTP] is the concentration of GTP.

The mean calculated $K_I$ of the stereoisomer of compound IV against wild-type HCV 1b polymerase (determined from 3 independent experiments) was 40.01±8.77 mM.

Example 148

In Vitro Activity Against Human DNA-Dependent DNA Polymerases

The stereoisomer 2 of compound IV-50 was further analyzed for its in vitro activity against human DNA-dependent DNA polymerases.

Preparation of Compound Solutions

The compound was prepared from a 10 mM aqueous stock solution. Three-fold serial dilutions ranging from 50 to 0.39 µM (pol alpha and beta) or 100 to 0.78 µM (pol gamma) were prepared in dilution buffer (10% glycerol/1 mM DTT/50 mM Tris-HCl pH 7.6/100 µg/mL BSA/25% DMSO). Actinomycin D (the control group, 2 mM stock solution in 25% ethanol) was run in parallel on each plate. Dilution buffer for human polymerase γ consisted of 50 mM Tris-HCl pH 7.8, 10% glycerol, 1 mM EDTA, 1 mM 2-mercaptoethanol, 0.01% NP-40, 0.23 M KCl.

Human Cellular DNA Polymerase Alpha and Beta Assays

These assays measured the incorporation of α-[$^{33}$P]dGMP into TCA precipitable material that was collected by filtration onto glass fiber plates and quantitated by liquid scintillation counting. Activated (DNase I-treated) calf thymus DNA served as the incorporation template. 96-well flexible plates containing the test compound in water were prepared on ice by adding 10 µL of the serial dilutions of the test compound and controls to triplicate wells in adjacent columns. Ten µL of enzyme dilution buffer containing 20 mM EDTA was transferred to column 1 for determination of background radioactivity. Ten µL of enzyme dilution buffer was pipetted into each well of columns 2 and 3 for the no drug control. Actinomycin D (Act. D) was used as control inhibitor. Actinomycin D was titrated from 40 to 0.31 µM in triplicate. Reaction cocktail was prepared on ice according to the scheme outlined below. To start the reaction, 40 µL of reaction cocktail was added to each well, and plates were then incubated at 30° C. for 60 minutes. Final concentrations of all reagents in reactions were listed in Table 8 below.

TABLE 7

| Reagent | Concentration |
| --- | --- |
| Tris-HCl, pH 7.6 | 50 mM |
| Magnesium chloride | 5 mM |
| Dithiothreitol | 1 mM |
| Glycerol | 10% |
| Bovine serum albumin | 100 µg/mL |
| Activated calf thymus DNA | 50 µg/mL |
| dCTP | 5 µM |
| dATP | 5 µM |
| dTTP | 5 µM |
| dGTP | 50 nM |
| α-[$^{33}$P]dGTP | 0.25 µCi/reaction |
| DNA polymerase α or β | 0.1 or 0.5 units |
| the stereoisomer 2 of compound IV-50 or act. D | variable, as described |
| Nuclease-free water | to final volume of 50 µL |

The reactions were stopped by adding 50 µL of stop solution (22.5% TCA/25 mM sodium pyrophosphate). The products were allowed to precipitate for 20 minutes while on ice. Plates were harvested on a Packard Unifilter Harvester using GF/B filter plates pre-wetted with 0.1 M sodium pyrophosphate. Plates were washed extensively with deionized water followed by 3 ethanol (EtOH) washes. Plates were allowed to air dry for 15 minutes prior to the addition of MicroScint-O (30 µL/well); plates were sealed and then counted using a Packard Topcount Liquid Scintillation Counter. $IC_{50}$ values were calculated from dose response curves by best-fit equations with XLfit software.

Human Cellular DNA Polymerase Gamma

This assay utilized the same test principle and incorporation template as outlined in the preparation for "human cellular DNA polymerase alpha and beta assays" above; the assay measured the incorporation of α-[$^{33}$P]dAMP into TCA-precipitable material that was collected by filtration onto glass fiber plates and quantitated by liquid scintillation counting. Activated (DNase I-treated) calf thymus DNA served as the incorporation template.

96-well flexible plates containing test compound in water were prepared on ice by transferring 10 µL of the serially diluted compound and control drug to triplicate wells in adjacent columns. Compound dilution buffer consisted of 50 mM Tris-HCl pH 7.8, 10% glycerol, 1 mM EDTA, 1 mM 2-mercaptoethanol, 0.01% NP-40, 0.23 M KCl. Ten µL of enzyme dilution buffer+20 mM EDTA were added to column 1; this column served as negative control to determine background radioactivity. Ten µL of enzyme dilution buffer was transferred to columns 2 and 3 for the no-drug control. Act. D was used as control inhibitor. Act. D was titrated from 40 to 0.31 µM in triplicate. Reaction cocktail was prepared as outlined below; 40 µL of reaction cocktail were added to each well on ice. Plates were incubated at 30° C. for 1 hour. Final concentrations of all reagents in reactions were listed in Table 9 below.

TABLE 8

| Reagent | Concentration |
| --- | --- |
| Tris-HCl, pH 7.8 | 50 mM |
| Magnesium chloride | 6.25 mM |
| Dithiothreitol | 1 mM |
| Glycerol | 10% |
| Bovine serum albumin | 100 µg/mL |
| Activated calf thymus DNA | 50 µg/mL |
| dCTP | 6.25 µM |
| dGTP | 6.25 µM |
| dTTP | 6.25 µM |
| dATP | 0.3125 µM |
| α-[$^{33}$P]dATP | 0.1 µCi/reaction |
| DNA polymerase γ | 0.64 units |
| the stereoisomer 2 of compound IV-50 or act. D | variable, as described |
| Nuclease-free water | to final volume of 50 µL |

The reactions were stopped by adding 50 µL of stop solution (22.5% TCA/25 mM sodium pyrophosphate). The products were allowed to precipitate for 20 minutes while on ice. Plates were harvested on a Packard Unifilter Harvester using GF/B filter plates pre-wetted with 0.1 M sodium pyrophosphate. Plates were washed extensively with deionized water followed by 3 washes with EtOH. Plates were allowed to air dry for 15 minutes prior to the addition of Microscint-O (30 µL/well), plates were sealed and then counted using the Packard Topcount Liquid Scintillation Counter. $IC_{50}$ values were calculated from dose response curves utilizing best-fit equations determined by XLfit 4.1 software.

The test article (the stereoisomer 2 of compound IV-50) and the control drug actinomycin D (act. D) were assayed for in vitro inhibition of cellular human polymerases alpha, beta and gamma as described above. These DNA-dependent DNA polymerases are central to the replication of chromosomal (alpha and beta) or mitochondrial (gamma) DNA. As key enzymes in cellular DNA synthesis it is important that their function remains unimpaired in the presence of novel drug candidates such as the stereoisomer 2 of compound IV-50. Dose-dependent inhibition of human DNA polymerases alpha, beta and gamma was measured in two independent experiments. Results are shown in Table 10 below.

TABLE 9

Mean $IC_{50}$ Values (μM) ± Standard Deviation[a]

| Compound | N[b] | human DNA polymerase alpha | human DNA polymerase beta | human DNA polymerase gamma |
|---|---|---|---|---|
| the stereoisomer 2 of compound IV-50 | 2 | >100 | >100 | >100 |
| Actinomycin D | 2 | 22.5 ± 20.2 | 11.6 ± 6.8 | 10.8 ± 1.8 |

[a]$IC_{50}$ = effective concentration that inhibits enzyme activity by 50% in vitro.
[b]N = number of independent experiments performed for each polymerase Example 149

In Vitro Activity Against Human DNA-Dependent RNA Polymerase II

The stereoisomer 2 of compound IV-50 was further analyzed for its in vitro activity against human DNA-dependent RNA polymerase II.
Method
A nuclear extract in vitro transcription kit (HeLaScribe) was used as the source for human RNA polymerase II. The transcription reactions were performed as recommended by the manufacturer in the presence or absence of test compound. Aliquots of the stopped reactions were analyzed by denaturing agarose gel electrophoresis and PhosphorImaging.
Compound Solutions
The stereoisomer 2 of compound IV-50 was assayed at a single concentration of 100 μM. Lyophilized triphosphates were reconstituted in RNase-free water at 10 mM and stored at −20° C. in small aliquots. Actinomycin D was used as a control at a concentration of 100 μM.
RNA Polymerase II Transcription Assay
Transcription reactions were set up according to the manufacturer's protocol. Final concentrations of reagents were listed as Table 11 below.

TABLE 10

| Reagent | Concentration |
|---|---|
| HeLaScribe Nuclear Extract | 8 units[a] |
| HeLaScribe Nuclear Extract 1× Transcription Buffer[b] | 11-x μL (where x is the volume of the extract) |
| Magnesium chloride | 3 mM |
| CMV transcription template DNA | 400 ng |
| ATP | 400 μM |
| CTP | 400 μM |
| UTP | 400 μM |
| GTP | 16 μM |
| α-[33P]GTP | 0.1 μCi/reaction |
| Compound or control inhibitor | variable |
| Water, RNase-free | to final volume of 25 μL |

[a]One unit is defined as the amount of extract required for the incorporation of 50 fmole of nucleotides into a 363-nucleotide runoff transcript generated from the CMV immediate early promoter fragment per hour at 30° C. under standard assay conditions.
[b]HeLaScribe Nuclear Extract 1X Transcription Buffer contains 20 mM HEPES (pH 7.9 at 25° C.), 100 mM KCl, 0.2 mM EDTA, 0.5 mM DTT, and 20% glycerol.

Reactions were incubated at −30° C. for 60 minutes. To decrease variability, HeLa Extract Stop Solution (0.3 M Tris-HCl pH 7.4 at 25° C., 0.3 M sodium acetate, 0.5% SDS, 2 mM EDTA, 3 μg/mL tRNA) was warmed to 25° C. for 60 minutes and vigorously mixed. Reactions were terminated by adding 175 μL of the prewarmed stop solution to each transcription reaction. RNA was extracted once with 200 μL phenol:chloroform:isoamyl alcohol, mixed vigorously and centrifuged at 14,000×g for 5 minutes. The aqueous phase was transferred to a fresh tube. Excess α-[33P]GTP was removed from the reactions by exchange chromatography using PD10 desalting columns (Roche Biochemicals) as suggested by the manufacturer. Radiolabeled RNA transcription products were concentrated by ethanol precipitation. Samples were allowed to precipitate at −80° C. overnight. Samples were centrifuged at 14,000×g for 10 minutes at 4° C. Supernatants were carefully removed, and 10 μL of denaturing RNA sample buffer (formaldehyde gel loading dye, Applied Biosystems) was used to resuspend the pellets. RNA samples were denatured for 15 minutes at 65° C., and then analyzed on a 1% denaturing formaldehyde agarose gel. The RNA samples were blotted onto a positively charged nylon membrane for 3 hours at room temperature via capillary transfer in Transfer Buffer (Applied Biosystems kit component). Dried membranes were exposed to a PhosphorImager screen (GE Healthcare Life Sciences) overnight at room temperature, then scanned (Storm 860, GE Healthcare Life Sciences) and quantitated with ImageQuant software (GE Healthcare Life Sciences).

In this example, in vitro specificity testing of the stereoisomer 2 of compound IV-50 was extended to eukaryotic RNA polymerase II. Transcription of genetic information is carried out by DNA-dependent RNA polymerases. In the eukaryotic cell nucleus there are three transcriptional enzymes: RNA polymerase I that transcribes ribosomal RNA genes, RNA polymerase III that transcribes tRNA and small nuclear RNA (snRNA) genes, and lastly RNA polymerase II (Pol II) which is the key enzyme in the eukaryotic messenger RNA (mRNA) transcription machinery. Pol II catalyzes the transcription of DNA to synthesize precursors of mRNA as well as most snRNAs and microRNAs. It consists of 12 subunits forming a 550 kDa complex. Pol II is the most studied type of eukaryotic RNA polymerase. A wide range of transcription factors are required for it to bind to its promoters and initiate transcription.

Since purified mammalian RNA polymerase II is not readily available, a HeLa nuclear extract in vitro transcription system, which supports accurate transcription initiation by RNA polymerase II (Dignam, Lebovitz, and Roeder 1983), was used in this study. The HeLaScribe Nuclear Extract in vitro Transcription System contained all of the necessary components for in vitro generation of 363-nucleotide run-off transcripts from a CMV immediate early promoter.

Following the manufacturer's recommendation reactions were carried out as described above. Actinomycin D was used as positive control inhibitor, which is better known as a DNA polymerase inhibitor but was found in this study to limit in vitro transcription by RNA pol II at high concentrations. [33P]-radiolabeled run-off transcripts were partially purified, and then analyzed on a denaturing formaldehyde-agarose gel. RNA products were transferred onto a nylon membrane, which was exposed to a PhosphorImager screen (GE Healthcare Life Sciences) and visualized on a Storm 860 PhosphorImager (GE Healthcare Life Sciences). Band intensities were quantified using ImageQuant software (GE Healthcare Life Sciences). Results are shown in Table 12 below.

TABLE 11

| Sample | N[a] | Percent of positive control[b] |
|---|---|---|
| Positive (no drug) control | 1 | 100 |
| Negative (no enzyme) control | 1 | 3.5 |
| Actinomycin D (100 µM) | 1 | 5.7 |
| The stereoisomer 2 of compound IV-50 (100 µM) | 1 | 98.4 |

[a]N = Number of independent experiments performed
[b]numbers represent mean values ± standard deviation

Example 150

Selectivity In Vitro Against Human Cellular Polymerases

The stereoisomer 2 of compound IV-50 was further analyzed for its selectivity in vitro against human cellular polymerases. Results are shown in Table 16 below.

TABLE 11

| Enzyme | $EC_{50}$ (µM) |
|---|---|
| Human Polymerase alpha | >100 |
| Human Polymerase beta | >100 |
| Human Polymerase gamma | >100 |

Example 151

Other Biological Characteristics of Compound IV-50 Diatereoisomer 2

Several other biological characteristics of the diatereoisomer 2 of compound IV-50 were analyzed, including loss of activity against HCV genotypes 1a, 2a, 3a, and 4a polymerases, and the selectivity index. Table 18 shows a summary of the biological characteristics of compound IV-50 diastereoisomer 2 compared with their respective target values.

TABLE 17

| Performance | Value |
|---|---|
| $IC_{50-1b}$ HCV Polymerase | 2-9 nM |
| Loss of activity against: | |
| 1a Polymerase: | 1.7 fold |
| 2a Polymerase: | >56 fold |
| 3a Polymerase: | >56 fold |
| 4a Polymerase: | >56 fold |
| $EC_{50-1b}$ HCV replicon: | 1.8-3.0 nM |
| $CC_{50}$ | >100 µM |
| Selectivity Index | >33,000 |

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A compound of Formula IV':

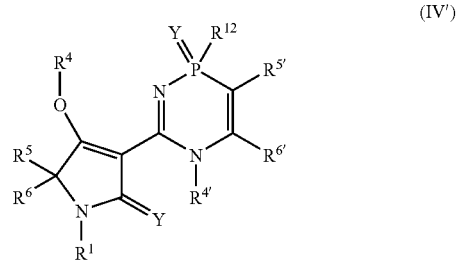

(IV')

or a single enantiomer, a mixture of an enantiomeric pair, an individual diastereomer, a mixture of diastereomers, or any tautomeric form thereof; or a pharmaceutically acceptable salt or prodrug thereof, wherein:

$R^1$ is H, alkyl, arylalkyl, heteroarylalkyl, —$NR^{10}SO_2R^8$, —$OR^8$, —$NR^8R^9$, —$C(O)R^8$, —$C(O)NR^8R^9$, —$C(O)OR^8$, aryl, alkenyl, alkynyl, heterocyclylalkyl, sulfonyl, or heteroaryl;

$R^4$ is H, alkyl, aryl-$CH_2$—, —$NR^8R^9$, —$C(O)R^8$, —$C(O)NR^8R^9$, —$C(O)OR^8$, sulfonyl, aryl, arylalkyl, alkenyl, alkynyl, heterocyclylalkyl or heteroaryl;

$R^{4'}$ is H, alkyl, aryl-$CH_2$—, —$NR^8R^9$, —$C(O)R^8$, —$C(O)NR^8R^9$, —$C(O)OR^8$, sulfonyl, aryl, arylalkyl, alkenyl, alkynyl, heterocyclylalkyl or heteroaryl;

$R^5$ is H, halogen, —$NR^{10}SO_2R^8$, —$OR^8$, —$NR^8R^9$, —$C(O)R^8$, —$C(O)NR^8R^9$, —$C(O)OR^8$, alkyl, aryl, or heteroaryl, or $R^4$ and $R^5$ together form a part of a 3-8 membered heterocycloalkyl ring;

$R^6$ is H, halogen, —$NR^{10}SO_2R^8$, —$OR^8$, —$NR^8R^9$, —$C(O)R^8$, —$C(O)NR^8R^9$, —$C(O)OR^8$, alkyl, aryl, or heteroaryl, or $R^5$ and $R^6$ together form a part of a 3-8 membered cycloalkyl or heterocycloalkyl ring;

$R^{5'}$ is H, halogen, cyano, nitro, —$NR^{10}SO_2R^8$, —$OR^8$, —$NR^8R^9$, —$C(O)R^8$, —$C(O)NR^8R^9$, —$C(O)OR^8$, alkyl, aryl, heteroaryl, —$NR^8R^{10}$, alkenyl, or alkynl;

$R^{6'}$ is H, halogen, cyano, nitro, —$NR^{10}SO_2R^8$, —$OR^8$, —$NR^8R^9$, —$C(O)R^8$, —$C(O)NR^8R^9$, —$C(O)OR^8$, alkyl, aryl, or heteroaryl, or $R^{5'}$ and $R^{6'}$ together form a part of a 3-8 membered, aryl ring;

$R^{12}$ is F, —$OR^8$, —$SR^8$, —$NR^8R^9$, alkyl, or aryl;

each $R^8$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, $C_{1-6}$ alkyl-$C_{3-7}$ cycloalkylene, or $C_{1-10}$ alkyl-siloxyl;

each $R^9$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or $R^8$ and $R^9$ together with the N atom to which they are attached form heterocyclyl;

each $R^{10}$ is independently H, alkyl, aryl, sulfonyl, $C(O)R^8$, $C(O)OR^8$ or $C(O)NR^8R^9$; and each Y is independently O or S, wherein each alkyl, aryl, arylalkyl, heteroaryl, alkenyl, alkynyl, cycloalkyl, heterocyclyl, sulfonyl, or alkyl-cycloalkyl is optionally substituted.

2. The compound of claim 1, wherein each pair of $R^{5'}$ and $R^{6'}$ together independently forms a benzo ring having formula (A):

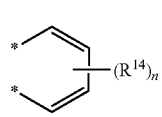

(A)

where each * is a bond;

each $R^{14}$ is independently H, halogen, alkyl, alkenyl, alkynyl, aryl, heterocyclyl, heteroaryl, cyano, nitro, OH, —$NR^{10}SO_2R^8$, —$OR^8$, —$NR^8R^9$, —$C(O)R^8$, $C(O)NR^8R^9$, —$OCH_2C(O)NR^8R^9$, —$C(O)OR^8$, —O—($C_1$-$C_6$ hydroxyalkyl), —O—($C_1$-$C_6$ alkoxy), —O—($C_1$-$C_6$ alkylene)-cyano, —O—($C_1$-$C_6$ alkylene)-$C(O)R^{9'}$, —$OCHR^{9'}C(O)O$—$R^8$, —$OCHR^{9'}C(O)NHOH$, —O—($C_1$-$C_6$ alkyl)-$C(O)NR^8R^9$, —O—($C_1$-$C_6$ alkylene)-$NR^{9'}C(O)R^8$, —O—($C_1$-$C_6$ alkylene)-$NR^{9'}C(O)OR^8$, —O—($C_1$-$C_6$ alkylene)-$NR^{9'}C(O)NR^8R^9$, —$OCHR^{9'}C(O)NR^8R^9$, —O—($C_1$-$C_6$ alkylene)-$S(O)R^{9'}$, —O—($C_1$-$C_6$ alkyl)-$S(O)_2R^{9'}$, —O—($C_1$-$C_6$ alkylene)-$S(O)_2NR^8R^9$, —O—($C_1$-$C_6$ alkylene)-$NR^{9'}S(O)_2NR^8R^9$, —O—($C_1$-$C_6$ alkylene)-$NR^{9'}S(O)_2R^8$—O—($C_1$-$C_6$ alkylene)-$S(O)_2R^{9'}$—O—($C_1$-$C_6$ alkylene)-$NR^8R^9$, —($C_1$-$C_6$ alkylene)-$S(O)_2R^8$, —($C_1$-$C_6$ alkylene)-$S(O)_2NR^8R^9$, —($C_1$-$C_6$ alkylene)-$S(O)R^8$, —($C_1$-$C_6$ alkylene)-$C(O)R^8$, —($C_1$-$C_6$ alkylene)-$C(O)NR^8R^9$, —($C_1$-$C_6$ alkylene)-$NR^{9'}C(O)R^8$, —($C_1$-$C_6$ alkylene)-$NR^{9'}S(O)_2R^8$, —($C_1$-$C_6$ alkylene)-$NR^{9'}C(O)OR^8$, —($C_1$-$C_6$ alkylene)-$NR^{9'}C(O)NR^8R^9$, —($C_1$-$C_6$ alkylene)-$NR^{9'}S(O)_2NR^8R^9$, —($C_1$-$C_6$ alkylene)-$C(O)OR^8$, —($C_1$-$C_6$ alkylene)-$NR^8R^9$, —$NR^8C(O)R^9$, —$NR^{9'}S(O)_2NR^8R^9$, —$NR^{9'}S(O)_2NR^8R^{10}$, —$S(O)R^{9'}$, —$S(O)_2R^{9'}$, or —$S(O)_2NR^8R^9$;

each $R^{9'}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; and n is an integer from 1 to 4.

3. The compound of claim 1, wherein each pair of $R^5$ and $R^6$ together independently forms a part of a 3-8 membered cycloalkyl, aryl, heterocycloalkyl or heteroaryl ring.

4. The compound of claim 2, wherein the compound of Formula IV' has formula I'':

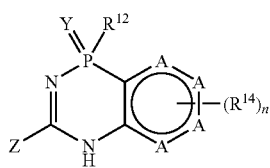

(I'')

wherein each A is independently $CR^{18}$;

$R^{18}$ is a bond, H, halogen, —$NR^{10}SO_2R^8$, —($C_1$-$C_6$ alkylene)-$NR^{9'}S(O)_2NR^8R^9$, —($C_1$-$C_6$ alkylene)-$NR^{9'}S(O)_2NR^8R^{10}$, —($C_1$-$C_6$ alkylene)-$NR^{9'}S(O)_2R^8$, —$OR^8$, —$NR^8R^9$, —$C(O)R^8$, —$C(O)NR^8R^9$, —$C(O)OR^8$, alkyl, aryl, or heteroaryl; and Z has the following structure:

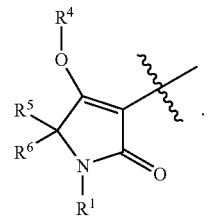

5. A compound of Formula IV:

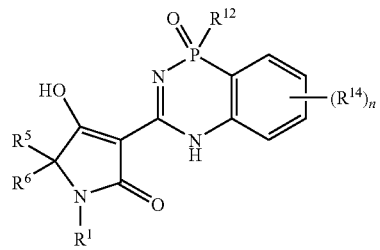

(IV)

or a single enantiomer, a mixture of an enantiomeric pair, an individual diastereomer, a mixture of diastereomers, or any tautomeric form thereof; or a pharmaceutically acceptable salt or prodrug thereof, wherein $R^1$ is H, alkyl, arylalkyl, heteroarylalkyl, —$NR^{10}SO_2R^8$, —$OR^8$, —$NR^8R^9$, —$C(O)R^8$, —$C(O)NR^8R^9$, —$C(O)OR^8$, aryl, alkenyl, alkynyl, heterocyclylalkyl, sulfonyl, or heteroaryl;

$R^5$ is H, halogen, —$NR^{10}SO_2R^8$, —$OR^8$, —$NR^8R^9$, —$C(O)R^8$, —$C(O)NR^8R^9$, —$C(O)OR^8$, alkyl, aryl, or heteroaryl;

$R^6$ is H, halogen, —$NR^{10}SO_2R^8$, —$OR^8$, —$NR^8R^9$, —$C(O)R^8$, —$C(O)NR^8R^9$, —$C(O)OR^8$, alkyl, aryl, or heteroaryl, or $R^5$ and $R^6$ together form a part of a 3-8 membered cycloalkyl or heterocycloalkyl ring;

$R^{12}$ is –$OR^8$, —$SR^8$, —$NR^8R^9$, alkyl, or aryl;

each $R^{14}$ is independently H, halogen, alkyl, alkenyl, alkynyl, aryl, heterocyclyl, heteroaryl, cyano, nitro, OH, —$NR^{10}SO_2R^8$, —$OR^8$, —$NR^8R^9$, —$C(O)R^8$, $C(O)NR^8R^9$, —$OCH_2C(O)NR^8R^9$, —$C(O)OR^8$, —O—($C_1$-$C_6$ hydroxyalkyl), —O—($C_1$-$C_6$ alkoxy), —O—($C_1$-$C_6$ alkylene)-cyano, —O—($C_1$-$C_6$ alkylene)-$C(O)R^{9'}$, —$OCHR^{9'}C(O)O$—$R^8$, —$OCHR^{9'}C(O)NHOH$, —O—($C_1$-$C_6$ alkyl)-$C(O)NR^8R^9$, —O—($C_1$-$C_6$ alkylene)-$NR^{9'}C(O)R^8$, —O—($C_1$-$C_6$ alkylene)-$NR^{9'}C(O)OR^8$, —O—($C_1$-$C_6$ alkylene)-$NR^{9'}C(O)NR^8R^9$, —$OCHR^{9'}C(O)NR^8R^9$, —O—($C_1$-$C_6$ alkylene)-$S(O)R^{9'}$, —O—($C_1$-$C_6$ alkyl)-$S(O)_2R^{9'}$, —O—($C_1$-$C_6$ alkylene)-$S(O)_2NR^8R^9$, —O—($C_1$-$C_6$ alkylene)-$NR^{9'}S(O)_2NR^8R^9$, —O—($C_1$-$C_6$ alkylene)-$NR^{9'}S(O)_2R^8$—O—($C_1$-$C_6$ alkylene)-$S(O)_2R^{9'}$—O—($C_1$-$C_6$ alkylene)-$NR^8R^9$, —($C_1$-$C_6$ alkylene)-$S(O)_2R^8$, —($C_1$-$C_6$ alkylene)-$S(O)_2NR^8R^9$, —($C_1$-$C_6$ alkylene)-$S(O)R^8$, —($C_1$-$C_6$ alkylene)-$C(O)R^8$, —($C_1$-$C_6$ alkylene)-$C(O)NR^8R^9$, —($C_1$-$C_6$ alkylene)-$NR^{9'}C(O)R^8$, —($C_1$-$C_6$ alkylene)-$NR^{9'}S(O)_2R^8$, —($C_1$-$C_6$ alkylene)-$NR^{9'}C(O)OR^8$, —($C_1$-$C_6$ alkylene)-$NR^{9'}C(O)NR^8R^9$, —($C_1$-$C_6$ alkylene)-$NR^{9'}S(O)_2NR^8R^9$, —($C_1$-$C_6$ alkylene)-$C(O)OR^8$, —($C_1$-$C_6$ alkylene)-$NR^8R^9$, —$NR^8C(O)R^9$, —$NR^{9'}S(O)_2NR^8R^9$, —$NR^{9'}S(O)_2NR^8R^{10}$, —$S(O)R^{9'}$, —$S(O)_2R^{9'}$, or —$S(O)_2NR^8R^9$;

n is an integer from 1 to 4;

each $R^8$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, heterocyclyl, $C_{1-6}$ alkyl-$C_{3-7}$ cycloalkylene, or $C_{1-10}$ alkyl-siloxyl;

each $R^9$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or $R^8$ and $R^9$ together with the N atom to which they are attached form heterocyclyl;

each $R^{9'}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or $R^8$ and $R^9$ together with the N atom to which they are attached form heterocyclyl; and each $R^{10}$ is independently H, alkyl, aryl, sulfonyl, $C(O)R^8$, $C(O)OR^8$ or $C(O)NR^8R^9$, wherein each alkyl, aryl, arylalkyl, heteroaryl, alkenyl, alkynyl, cycloalkyl, heterocyclyl, sulfonyl, or alkyl-cycloalkyl is optionally substituted.

6. The compound of claim 5 according to Formula IVa:

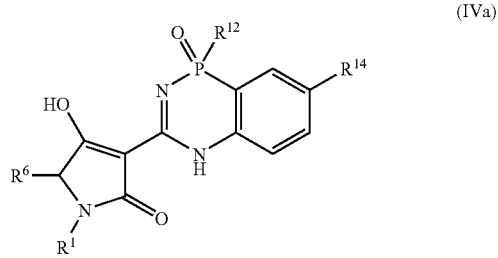

(IVa)

or a single enantiomer, a mixture of an enantiomeric pair, an individual diastereomer, a mixture of diastereomers, or any tautomeric form thereof; or a pharmaceutically acceptable salt or prodrug thereof.

7. The compound of claim 6, wherein the compound has the structure of Formula IVa.

8. The compound of claim 5, wherein each alkyl, aryl, arylalkyl, heteroaryl, alkenyl, alkynyl, cycloalkyl, heterocyclyl, or alkyl-cycloalkyl is unsubstituted.

9. The compound of claim 5, wherein $R^1$ is $C_{1-6}$ alkyl.

10. The compound of claim 9, wherein $R^1$ is 3,3-dimethylbutyl.

11. The compound of claim 5 wherein $R^6$ is hydrogen or halogen.

12. The compound of claim 5, wherein $R^6$ is tert-butyl.

13. The compound of claim 5, wherein $R^{12}$ is $C_{1-6}$ alkoxy.

14. The compound of claim 13, wherein $R^{12}$ is methoxy.

15. The compound of claim 13, wherein $R^{12}$ is ethoxy.

16. The compound of claim 5, wherein $R^{12}$ is $NH_2$.

17. The compound of claim 5, wherein $R^{12}$ is OH.

18. The compound of claim 5, wherein $R^{14}$ is hydrogen.

19. The compound of claim 5, wherein $R^{14}$ is —$NHSO_2R^8$.

20. The compound of claim 19, wherein $R^8$ is $C_{1-6}$ alkyl.

21. The compound of claim 20, wherein $R^8$ is methyl.

22. The compound of claim 5, wherein $R^1$ is 3,3-dimethylbutyl; $R^6$ is tert-butyl; $R^{12}$ is methoxy, ethoxy, fluoro, $NH_2$ or OH; and $R^{14}$ is hydrogen or —$NHSO_2Me$.

23. The compound of claim 5 according to the following formula:

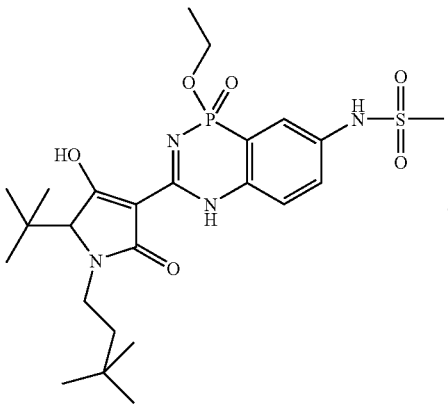

24. The compound of claim 23 according to the following formula:

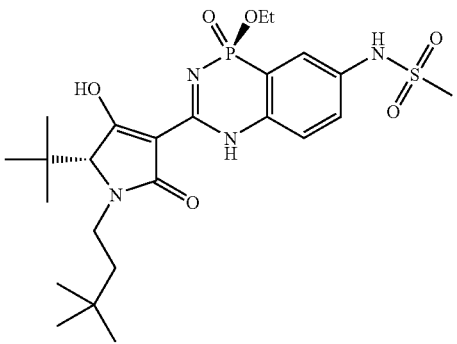

25. The compound of claim 23 according to the following formula:

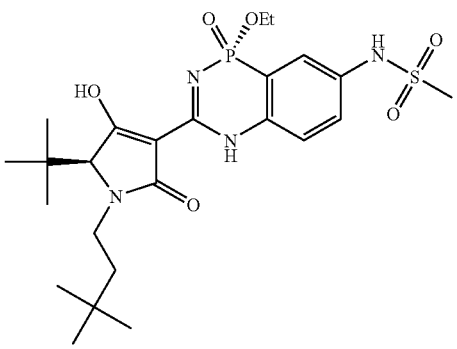

26. The compound of claim 23 according to the following formula:
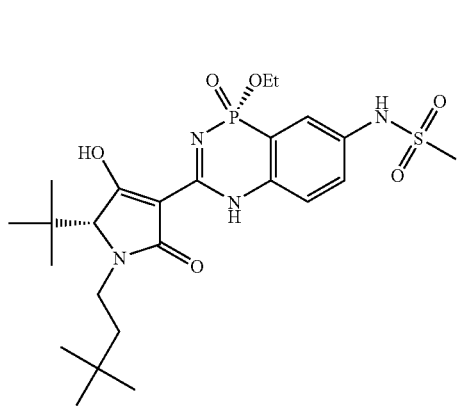
27. The compound of claim 23 according to the following formula:
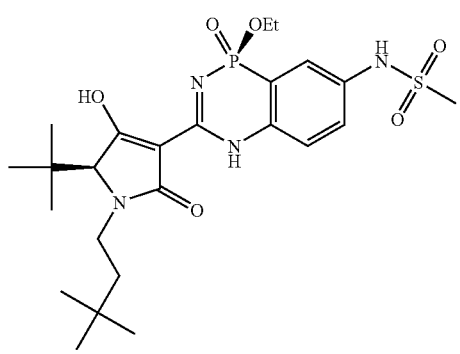
28. The compound of claim 5 according to the following formula:
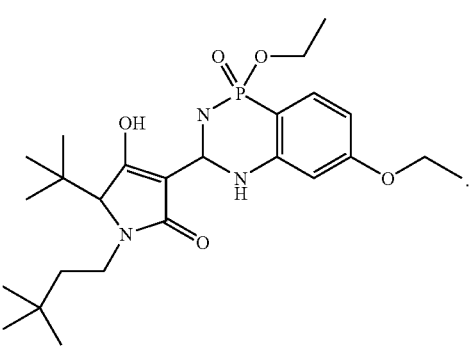
29. The compound of claim 5 according to the following formula:
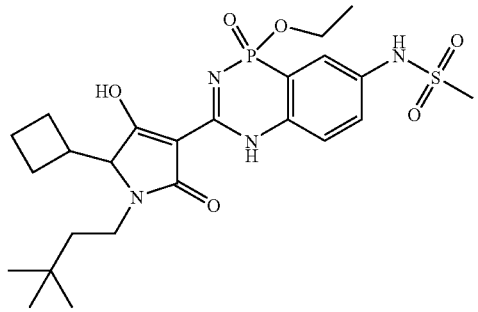
30. The compound of claim 5 according to the following formula:
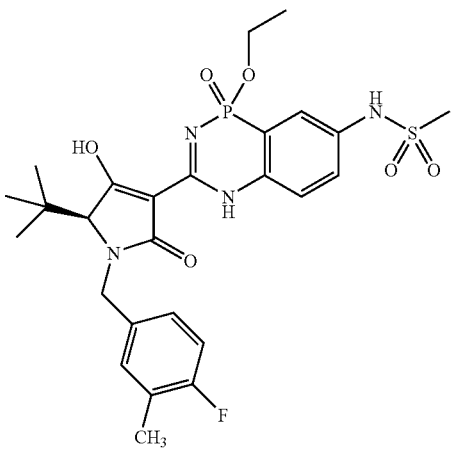
31. The compound of claim 5 according to the following formula:
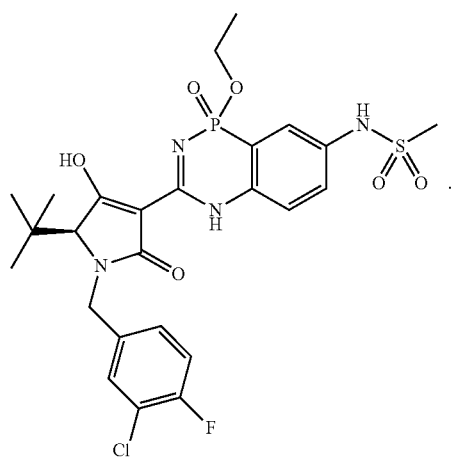

32. The compound of claim 5 according to the following formula:

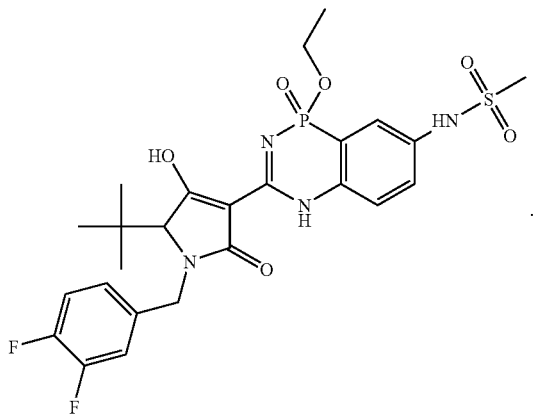

33. A pharmaceutical composition comprising the compound of claim 1 and one or more pharmaceutically acceptable carriers.

34. The pharmaceutical composition of claim 33, further comprising a second antiviral agent.

35. The pharmaceutical composition of claim 34, wherein the second antiviral agent is selected from the group consisting of an interferon, ribavirin, an interleukin, an NS3 protease inhibitor, a cysteine protease inhibitor, a phenathrenequinone, a thiazolidine, a benzanilide, a helicase inhibitor, a polymerase inhibitor, a nucleotide analogue, a nucleoside analogue, a liotoxin, acerulenin, an antisense phosphorothioate oligodeoxynucleotide, an inhibitor of IRES-dependent translation, and a ribozyme.

36. The pharmaceutical composition of claim 35, wherein the second antiviral agent is an interferon.

37. The pharmaceutical composition of claim 36, wherein the interferon is selected from the group consisting of pegylated interferon alpha 2a, interferon alphcon-1, natural interferon, albuferon, interferon beta-1a, omega interferon, interferon alpha, interferon gamma, interferon tau, interferon delta, and interferon gamma-1b.

38. The pharmaceutical composition of claim 33, wherein the composition is formulated for single dose administration.

39. The pharmaceutical composition of claim 33, wherein the composition is formulated as an oral, parenteral, or intravenous dosage form.

40. The pharmaceutical composition of claim 39, wherein the oral dosage form is a tablet or capsule.

41. The pharmaceutical composition of claim 33, wherein the compound is administered in a dose of about 0.5 milligram to about 1,000 milligram daily.

42. A method for treating an HCV infection, which comprises administering the compound of claim 1.

43. A method for treating an HCV infection, which comprises administering the pharmaceutical composition of claim 33.

44. The method of claim 42, wherein the method comprises administering a second antiviral agent, in combination or alternation.

45. The method of claim 43, wherein the method comprises administering a second antiviral agent, in combination or alternation.

46. The method of claim 44, wherein the second antiviral agent is selected from the group consisting of an interferon, ribavirin, amantadine, an interleukin, a NS3 protease inhibitor, a cysteine protease inhibitor, a phenathrenequinone, a thiazolidine, a benzanilide, a helicase inhibitor, a polymerase inhibitor, a nucleotide analogue, a nucleoside analogue, a liotoxin, acerulenin, an antisense phosphorothioate ologodeoxynucleotide, an inhibitor of IRES-dependent translation, and a ribozyme.

47. The method of claim 45, wherein the second antiviral agent is selected from the group consisting of an interferon, ribavirin, amantadine, an interleukin, a NS3 protease inhibitor, a cysteine protease inhibitor, a phenathrenequinone, a thiazolidine, a benzanilide, a helicase inhibitor, a polymerase inhibitor, a nucleotide analogue, a nucleoside analogue, a liotoxin, acerulenin, an antisense phosphorothioate ologodeoxynucleotide, an inhibitor of IRES-dependent translation, and a ribozyme.

48. The method of claim 44, wherein the second antiviral agent is an interferon.

49. The method of claim 45, wherein the second antiviral agent is an interferon.

50. The method of claim 48, wherein the interferon is selected from the group consisting of pegylated interferon alpha 2a, interferon alphcon-1, natural interferon, albuferon, interferon beta-1a, omega interferon, interferon alpha, interferon gamma, interferon tau, interferon delta, and interferon gamma-1b.

51. The method of claim 49, wherein the interferon is selected from the group consisting of pegylated interferon alpha 2a, interferon alphcon-1, natural interferon, albuferon, interferon beta-1a, omega interferon, interferon alpha, interferon gamma, interferon tau, interferon delta, and interferon gamma-1b.

52. A method for inhibiting replication of a virus in a host, which comprises contacting the host with the compound of claim 1.

53. A method for inhibiting replication of a virus in a host, which comprises contacting the host with the pharmaceutical composition of claim 33.

54. The method of claim 52, wherein the host is a human.

55. The method of claim 53, wherein the host is a human.

56. A method for inhibiting replication of a virus, which comprises contacting the virus with the compound of claim 1.

57. A method for inhibiting replication of a virus, which comprises contacting the virus with the pharmaceutical composition of claim 33.

58. A method for inhibiting the activity of a polymerase, which comprises contacting the polymerase with the compound of claim 1.

59. A method for inhibiting the activity of a polymerase, which comprises contacting the polymerase with the pharmaceutical composition of claim 33.

60. The method of claim 58, wherein the polymerase is an HCV NS5B polymerase.

61. The method of claim 59, wherein the polymerase is an HCV NS5B polymerase.

* * * * *